(12) United States Patent
Chong et al.

(10) Patent No.: US 6,569,878 B1
(45) Date of Patent: May 27, 2003

(54) SUBSTITUTED 4-AMINO-THIAZOL-2-YL COMPOUNDS AS CYCLIN-DEPENDENT KINASE INHIBITORS

(75) Inventors: Wesley K. M. Chong, Encinitas, CA (US); Shao Song Chu, Encinitas, CA (US); Lin Li, San Diego, CA (US); Rohit K. Duvadie, San Diego, CA (US); Yi Yang, San Diego, CA (US); Wei Xiao, San Diego, CA (US)

(73) Assignee: Agouron Pharmaceuticals Inc., San Diego, CA (US)

(*) Notice: Subject to any disclaimer, the term of this patent is extended or adjusted under 35 U.S.C. 154(b) by 0 days.

(21) Appl. No.: 09/179,744

(22) Filed: Oct. 27, 1998

Related U.S. Application Data

(60) Provisional application No. 60/063,634, filed on Oct. 27, 1997, and provisional application No. 60/063,666, filed on Oct. 28, 1997.

(51) Int. Cl.[7] .................... A61K 31/425; C07D 419/00; C07D 277/04; C07D 401/00; C07D 243/08
(52) U.S. Cl. ................... 514/370; 514/218; 514/255; 514/326; 544/360; 544/367; 546/208; 546/209; 548/191; 548/194; 540/575
(58) Field of Search ................... 514/218, 255, 514/326, 370; 540/575; 544/360, 367; 546/208, 209; 548/191, 194

(56) References Cited

U.S. PATENT DOCUMENTS

| | | | |
|---|---|---|---|
| 3,530,161 A | 9/1970 | Hull ........................ 260/454 |
| 4,086,239 A | 4/1978 | Fancher ................... 260/306.8 |
| 4,269,978 A | 5/1981 | Petitpierre ................ 544/133 |
| 4,649,146 A | 3/1987 | Takaya et al. ............... 514/307 |
| 5,189,049 A | 2/1993 | Frehel et al. ............... 514/371 |
| 5,262,409 A | 11/1993 | Margolis et al. ............ 514/183 |
| 5,424,400 A | 6/1995 | Smith ........................ 530/350 |
| 5,441,880 A | 8/1995 | Beach et al. ................ 435/193 |
| 5,443,962 A | 8/1995 | Draetta et al. ............... 435/29 |
| 5,449,755 A | 9/1995 | Roberts et al. ............. 530/350 |
| 5,472,985 A | 12/1995 | Grainger et al. ............ 514/651 |
| 5,473,056 A | 12/1995 | Ivey-Hoyle et al. ........ 530/358 |
| 5,484,710 A | 1/1996 | Reed et al. ................. 435/69.1 |
| 5,496,831 A | 3/1996 | Alexander-Bridges et al. ........................ 514/290 |
| 5,514,571 A | 5/1996 | Riabowol ................ 435/172.3 |
| 5,532,167 A | 7/1996 | Cantley et al. .............. 436/89 |
| 5,543,291 A | 8/1996 | Keyomarsi et al. ............ 435/6 |
| 5,571,523 A | 11/1996 | Lee et al. ................... 424/423 |
| 5,596,079 A | 1/1997 | Smith et al. ................ 530/328 |
| 5,599,681 A | 2/1997 | Epstein et al. ............. 435/7.23 |
| 5,599,844 A | 2/1997 | Grainger et al. ............ 514/651 |
| 5,620,963 A | 4/1997 | Cook et al. ................... 514/44 |
| 5,621,082 A | 4/1997 | Xiong et al. ................ 530/350 |
| 5,624,819 A | 4/1997 | Skolnick et al. ........... 435/69.1 |
| 5,625,031 A | 4/1997 | Webster et al. ............. 530/300 |
| 5,629,407 A | 5/1997 | Xiong et al. ............. 530/387.1 |
| 5,631,156 A | 5/1997 | Xiong et al. ............. 435/252.3 |
| 5,637,471 A | 6/1997 | Artavanis-Tsakonas et al. ........................ 435/7.23 |
| 5,733,920 A | 3/1998 | Mansuri et al. ............. 514/337 |
| 2002/0025976 A1 * | 2/2002 | Chu et al. ................... 514/370 |

FOREIGN PATENT DOCUMENTS

| | | |
|---|---|---|
| DE | 2259220 | 6/1973 |
| DE | 3804531 | 8/1989 |
| EP | 0666270 | 8/1995 |
| WO | WO 9220642 | 11/1992 |
| WO | WO 9515758 | 6/1995 |
| WO | WO 9639145 | 12/1996 |
| WO | WO 9716447 | 5/1997 |
| WO | WO 9716452 | 5/1997 |
| WO | WO 9742949 | 11/1997 |
| WO | WO 9804536 | 2/1998 |
| WO | WO 9805336 | 2/1998 |
| WO | WO 9817662 | 4/1998 |
| WO | WO 9833798 | 8/1998 |

OTHER PUBLICATIONS

Ando et al., "Role of the Pyrrolidine Ring of Proline in Determining the Substrate Specificity of cdc2 Kinase or cdk5," *J. Biochem*, 122, 409–414 (1997).

Aoyama et al., "New Methods and Reagents in Organic Synthesis. 17. Trimethylsilydiazomethane ($TMSCHN_2$) as a Stable and Safe Substitute for Hazardous Diazomethane. Its Application to the Arndt–Eistert Synthesis," *Chem. Pharm. Bull.*, 29(11), 3249–3255 (1981).

Aspinall, "A Synthesis of Monoketopiperazines," *J. Am. Chem. Soc.*, 62, 1202–1204 (1940).

Baker et al., "Mechanism of Aromatic Side–chain Reactions, with Special Reference to the Polar Effects of Substituents. Part X. Physical and Chemical Evidence relating to the Polar Effect of o–Methyl Substituents in Derivatives of the Type $C_6H_2Me_3.CO.CH_2R$," *J. Chem. Soc.*, 796–802 (1941).

(List continued on next page.)

*Primary Examiner*—Richard L. Raymond
*Assistant Examiner*—Tamthom N. Troung
(74) *Attorney, Agent, or Firm*—Bryan C. Zielinski; Joseph F. Reidy; Wendy Lei Hsu

(57) ABSTRACT

Pharmaceutical compositions containing effective amounts of CDK-inhibiting diaminothiazole compounds of the following formula (where $R^1$ and $R^2$ are as defined in the specification) or their salts, or prodrugs or active metabolites of such compounds or salts, are useful for treating disorders and diseases such as cancer:

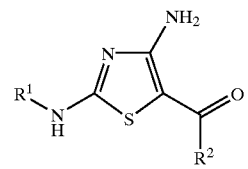

In preferred embodiments, $R^1$ and $R^2$ are independently unsubstituted or substituted carbocyclic or heterocyclic aryl ring structures. Compounds where $R^2$ is ortho-substituted aryl are especially potent inhibitors of CDKs such as CDK4.

20 Claims, No Drawings

OTHER PUBLICATIONS

Beach et al., "Dipole Moments of Some N–Phenyl–substituted Derivatives of Pyrrolidine, Piperidine, Morpholine, and Thiomorpholine," *J. Chem. Soc. Perkin Trans. II*, 217–221 (1984).

Binu et al., "Synthesis and Cyclization of 1–(N–Nitroamidino)Thioreas to 2,4–Diaminothiazoles," *OPPI Briefs*, 30 (1), 93–96 (1998).

Boev et al.,"Synthesis and Antimicrobial Activity of 5(6)–Isothiocyanatobenzaloles," *Pharm. Chem. J. Engl. Transl.*, 24(11), 818–822 (1991).

Breslin et al., "Synthesis and Anti–HIV–1 Activity of 4,5, 6,7–Tetrahydro–5–methylimidazo–[4,5,1–jk][1,4] benzodiazepin–2(1H)–one(TIBO) Derivatives. 3," *J. Med. Chem.*, 38, 771–793 (1995).

Cain et al., "Potential Antitumor Agents. 23. 4'–(9–Acridinylamino)alkanesulfonanilide Congeners Bearing Hydrophilic Functionality," *J. Med. Chem.*, 20 (8), 987–996 (1977).

Cale et al., "Benzo– and Pyrido–1,4–oxazepin–5–ones and thiones: Synthesis and Structure–Activity Relationships of a New Series of $H_1$ Antihistamines," *J. Med. Chem.*, 32, 2178–2199 (1989).

Chapman et al., "Some o–substituted NN–dimethyl–2–halogeno–2–phenethylamines," *J. Chem. Soc. (C)*, 1202–1206 (1971).

Chu et al., "Synthesis and antibacterial activity of novel 6–fluoro–7–(gem–disubstituted piperazine–1–yl)–quinolines," *Can. J. Chem.*, 70, 1328–1337 (1992).

Connolly et al., "Discovery and Structure–Activity Studies of a Novel Series of Pyrido[2,3–d]Pyrimidine Tyrosine Kinase Inhibitors," *Bioorg. Med. Chem. Letters*, 7(18), 2415–2420 (1997).

Cousseau et al., "Tetrabutylammonium and Polymer–Supported Dihydrogentrifluoride: New Reagents for the Hdyrofluorination of Activated Acetylenic Bonds," *Bull. Soc. Chim. Fr.*, 6, 910–915 (1986).

Croce et al., "Selective α–Chlorination of Acetylpyrroles," *Synthesis*, 212–213 (1990).

Davies et al., "The Synthesis and Properties of 2:4–Diaminothiazoles," 3491–3494 (1950).

del Agua et al., "Bromothiophene Reactions. I. FriedelCrafts Acylation," *J. Het. Chem.*, 18, 1345–1347 (1981).

DelSal et al., "Cell Cycle and Cancer: Critical Events at the G1 Restriction Point," *Critical Review in Oncogenesis*, 7(1&2), 127–142 (1996).

de Silva et al., "Luminescence and Charge Transfer. Part 3. The Use of Chromophores with ICT (Internal Charge Transfer) Excited States in the Construction of Fluorescent PET (Photoinduced Electron Transfer) pH Sensors and Related Absorption pH Sensors with Aminoalkyl Side Chains," *J. Chem Soc. Perkin Trans.* 2, 1611–1616 (1993).

Flaig et al., "Synthesis of N–Substituted 2,4–Diaminothiazoles and their Salts," *Heterocycles*, 45 (5), 875–886 (1997).

Flores et al., "Analysis of the CDKN2A, CDKN2B and CDK4 genes in 48 Australian melanoma kindreds," *Oncogene*, 15, 2999–3005 (1997).

Galstukhova et al., "Synthesis of Thiourea Derivatives VI. 1–(2–methylmercapto–5–pyrimidinyl)–3–arylthiourea," 5, 6, 1121–1124 (1969).

Gewald et al.,"4–Amino–thiazole," *J. Prakt. Chem.*, 35, 97–104 (1967).

Gewald, "Heterocyclen aus CH–aciden Nitrilen. VI. Reaktion won methylenaktiven nitrilen mit Senfölen und Schwefel," *J. Prakt. Chem.*, 32, 26–30 (1966).

Gewald et al., "Zur chemie der 4–aminothiazolin–2–thione," *Monatschefte für Chemie*, 112, 1393–1404 (1981).

Ginzburg et al., "Synthesis of Benzimidazole Derivatives Containing the Bis(β–chloroethyl)amino group," *J. Gen. Chem. USSR (Engl. Transl.)*, 30, 591–593 (1960).

Gray et al., "Exploiting Chemical Libraries, Structure, and Genomics in the Search for Kinase Inhibitors," *Science*, 281, 533–538 (1998).

Grant et al., "Crystal Structure–Based Design of cyclin Dependent Kinase Inhibitors," *Proc. Amer. Assoc. Cancer Res*, 39, Abstract 1207 (1998).

Hall et al., "Genetic Alterations of Cyclins, Cyclin–Dependent Kinases, and Cdk Inhibitors in Human Cancer," *Advances in Cancer Research*, 68, 67–108 (1996).

Harper, "Cyclin Dependent Kinase Inhibitors," *Cancer Surveys*, 29, 91–107 (1997).

Jeffrey et al., "Mechanism of CDK activation revealed by the structure of a cyclinA–CDK2 complex," *Nature*, 376, 313–320 (1995).

Joshua et al., "Mass Spectral Studies of 3,5–Diamino–1,2, 4–thiadiazoles," *Aust. J. Chem.*, 30, 563–568 (1977).

Kamb et al., "A Cell Cycle Regulator Potentially Invovled in Genesis of Many Tumor Types," *Science*, 264, 436–440 (1994).

Kamb, "Cell–cycle Regulators and Cancer," *TIG*, 11(4), Review (1995).

Katz et al., "Head–to–Tail Assemblies of Dipolar, Piperazine–Linked Chromophores: Synthesis, X–ray Structure, and Dielectric Characterization," *J. Am. Chem. Soc.*, 111, 7554–7557 (1989).

Khanna et al., "1,2–Diarylpyrroles as Potent and Selective Inhibitors of Cyclooxygenase–2," *J. Med. Chem.*, 40, 1619–1633 (1997).

Kuroboshi et al., "A Facile Synthesis of Trifluoromethylamines by Oxidative Desulfurization–Fluorination of Dithiocarbamates," *Tetrahedron Lett.*, 33(29), 4177–4178 (1992).

Kurzer, "Thiadiazoles. Part II. 3:5–Diamino–1:2:4–thiadiazole and its 5–Alkyl Homologues," 2288–2295 (1955).

Kutney et al., "Synthesis in the Pyridine Series, III. The Synthesis of New 3,5–Dimethyl–4–Substituted Pyridines. Steric Effects as an aid to Synthesis," *Canadian Journal of Chemistry*, 41, 695–702 (1963).

LaMattina et al., "Synthesis of 1H–5–Acetyl–2–alkylimidazoles," *J. Org. Chem.*, 48, 897–898 (1983).

Loda et al., "Increased proteasome–dependent degradation of the cyclin–dependent kinase inhibitor p27 in aggresive colorectal carcinomas," 3(2), 231–234 (1997).

Lukas et al., "Cylin E–induced S phase without activation of the pRb/E2F pathway," *Genes and Development*, 1479–1492 (1997).

Lutz et al., "Antimalarials. α–Phenyl–β–Dialkylamino Alcohols," *J. Org. Chem.*, 12, 617–703 (1947).

Martvon et al., "Isothiocyanates. XXXIX. Synthesis, infrared and ultraviolet spectra of some phenyl isothiocyanates having a heterocyclic substituent," *Chem. Zvesti.*, 27(6), 808–810 (1973).

McKee et al., "p–Substituted Phenyl Isothiocyanates and Some Related Thioureas," *J. Am. Chem. Soc.*, 68, 2506–2507 (1946).

Meijer et al., "Chemical Inhibitors of Cyclin–Dependent Kinases," *Methods in Enzymol*, 283, 113–128 (1997).

Menasse et al., "Uber 2,4–Di($\alpha$–pyridyl)–thiazol," *Helvetica Chimica Acta*, 38, 1289–1291 (1955).

Mlotkowska et al., "Reactions of 2,4– and 2,6–Dichlorophenacylidene Halides with Trialkylphosphites in Protic Solvents. Direct Evidence for the 'Enolate Anion' Pathway," *Polish Journal of Chemistry*, 55, 631–642 (1981).

Morgan, "Cyclin–Dependent Kinases: Engines. Clocks, and Microprocessors," *Annu. Rev. Cell Dev. Biol.*, 13, 261–291 (1997).

Mosman, "Rapid Colorimetric Assay for Cellular Growth and Survival: Application to Proliferation and Cytotoxicity Assays," *Journal of Immunological Methods*, 65, 55–63 (1983).

Nasmyth, "Viewpoint: Putting the Cell Cycle in Order," *Science*, 274, 1643–1677 (1996).

Nesterov et al., "Cyclization of Nitriles XXIV. Reactions of Cyanamide Derivatives of Thiocarbamic Acids with Cyanothioacetamide. Crystal Structure of 2–Allylamino–4–Amino–5–Benzoyl–1,3–Thiazole," 762–770 (1988).

Nobori et al., "Deletions of the cyclin–dependent kinase–4 inhibitor gene in multiple human cancers," *Nature*, 368, 753–756 (1994).

Ochiai et al., "Synthesis von diathiazolyl–(4.5')–und 4–[imidazolyl–(5)]–thiazol–derivaten," *Chem. Ber.*, 73, 28–32 (1940).

Ohno et al., "Synthesis and Structure–Activity Rleationships of New (5R,8R,10R)–Ergoline Derivatives with Antihypertensive or Dopaminergic Activity," *Chem. Pharm. Bul.*, 42(7), 1463–1473 (1994).

Rajasekharan et al., "Studies on the Synthesis of 5–Acyl–2, 4–diaminothiazoles from Amidinothioureas," *Synthesis*, Papers, 353–355 (1986).

Ratouis et al., "Synthesis and Pharmacological Study of New Piperazine Derivatives. II. Phenethylpiperazines," *J. Med. Chem.*, 8, 104–107 (1965).

Reynolds et al., "o–Nitroacetophenone ," *Org. Syn. Coll. vol. IV*, 708–710 (1963).

Rifkind et al., "Induced Differentiation, the Cell Cycle, and the Treatment of Cancer," *Pharmacol. Ther.*, 69(2), 97–102 (1996).

Rosenblatt et al., "Purification and Crystallization of Human Cyclin–dependent Kinase 2," *J. Med. Biol.*, 230, 1317–1319 (1993).

Ruetz et al., "Effect of CGP 60474 on Cyclin Dependent Kinases (cdks), Cell Cycle Progression and Onset of Apoptosis in Normal and Transformed Cells," *Proc. Amer. Assoc. Cancer Res.*, 39, Abstract 3796 (1998).

Schow et al., "Synthesis and Activity of 2,6,9–Trisubstituted Purines," *Bioorganic & Medicinal Chemistry Letters*, 7(21), 2697–2702 (1997).

Sedlacek et al., "Flavopiridol (L86 8275; NSC 649890), a new kinase inhibitor for tumor therapy," *International Journal of Oncology*, 9, 1143–1168 (1996).

Sheaff et al., "Cyclin E–CDK2 is a regulator of p27$^{Kip1}$," *Genes & Development*, 11, 1464–1478 (1997).

Slotta et al., "über Guanyl–thioharstoffe I," *Jaharg.*, 63, 208–222 (1930).

Spinelli et al., "Linear Free Energy ortho–Correlations in the Thiophen Series. Part I. The Kinetics of Piperidinodebromination of Some 2–Bromo–3–X–5–nitro–thiophenes in Methanol," *J.C.S. Perkins II*, 620–622 (1975).

Swanson et al., "Specific Covalent Labeling of Cytochrome P–450$_{CAM}$ with 1–(4–Azidophenyl)imidazole, an Inhibitor-derived Photoaffinity Probe for P–450 Heme Proteins," *J. Biol. Chem.*, 254(15), 7238–7246 (1979).

Swenton et al., "Intramolecular Anodic Carbon–Carbon Bond–Forming Reactions of Oxidized Phenol Intermediates Leading to Spirodienones. Structural Effects on Reactivity and Evidence for a Phenoxonium Ion Intermediate," *J. Org. Chem.*, 58, 3308–3316 (1993).

Sych et al., "Thiazolocyanines. IX. The Synthesis of Thiazolocyanines from Derivatives of Thiazole with Heterocyclic Residues as Substituents," *J. Gen. Chem. USSR*, 32, 970–975 (1962).

Venuti et al., "Inhibitors of Cyclic AMP phosphodiesterase. 3. Synthesis and Biological Evaluation of Pyrido and Imidazolyl Analogues of 1,2,3,5–tetrahydro–2–oxoimidazo[2, 1–b]quinazoline," *J. Med. Chem.*, 31, 2136–2145 (1988).

Vesely et al., "Inhibition of cyclin–dependent kinases by purine analogues," *Eur. J. Biochem.*, 224, 771–786 (1994).

Wang et al., "Photochemistry of Intramolecular Charge Transfer Excited States in Donor–Acceptor–Substituted Diamines," *J. Phys. Chem.*, 99, 6876–6888 (1995).

Webster, "The Therapeutic potential of targeting the cell cycle," *Exp. Opin. Invest. Drugs*, 865–887 (1998).

Ganapathi et al., "Chemistry of the Thiazoles. Part III. Synthesis of Thiazole Derivatives Unsubstituted in Position 2: An Evaluation of Various Possible Methods," *Indian Academy of Science*, 362–378 (1945).

Imuta et al., "Product Stereospecificity in the Microbial Reduction of $\alpha$–Haloaryl Ketones," *J. Org. Chem.*, 45, 3352–3355 (1980).

Jenardanan et al., "1–(N–Arylthiocarbamoyl)Amidino–3, 5–Dimethyl Pyrazoles–Preparation and Use in Heterocycle Synthesis," *Synthetic Communications*, 27(19), 3457–3462 (1997).

King et al., "Selective Bromination with Copper(II) Bromide," *J. Org. Chem.*, 3459–3461 (1964).

Kurzer, "Thiadiazoles. Part III. 3–Amino–5–arylamino– and 3:5–Di(aralkylamino)–1:2:4–thiadiazoles," 455, 2345–2352 (1956).

Meyer et al., "CGP 60474, A Protein Kinase Inhibitor with Potent Antitumor Activity in vivo at Well Tolerated Doses," *Proc. Amer. Assoc. Cancer Res.*, 39, Abstract 3794 (1998).

* cited by examiner

SUBSTITUTED 4-AMINO-THIAZOL-2-YL COMPOUNDS AS CYCLIN-DEPENDENT KINASE INHIBITORS

CROSS-REFERENCE TO RELATED APPLICATIONS

This regular application claims priority to U.S. Provisional Application No. 60/063,634, filed Oct. 27, 1997, and U.S. Provisional Application No. 60/063,666, filed Oct. 28, 1997.

FIELD OF THE INVENTION

This invention is directed to pharmaceutical compositions containing aminothiazole compounds for inhibiting cyclin-dependent kinases (CDKs), such as CDK1, CDK2, CDK4, and CDK6. The invention is also directed to the therapeutic or prophylactic use of pharmaceutical compositions containing such compounds and to methods of treating malignancies and other disorders by administering effective amounts of such compounds.

BACKGROUND OF THE INVENTION

Uncontrolled cell proliferation is the insignia of cancer. Cell proliferation in response to various stimuli is manifested by a deregulation of the cell division cycle, the process by which cells multiply and divide. Tumor cells typically have damage to the genes that directly or indirectly regulate progression through the cell division cycle.

CDKs constitute a class of enzymes that play critical roles in regulating the transitions between different phases of the cell cycle, such as the progression from a quiescent stage in $G_1$ (the gap between mitosis and the onset of DNA replication for a new round of cell division) to S (the period of active DNA synthesis), or the progression from $G_2$ to M phase, in which active mitosis and cell-division occur. See, e.g., the articles compiled in *Science*, vol. 274 (1996), pp. 1643–1677; and *Ann. Rev. Cell Dev. Biol.*, vol. 13 (1997), pp. 261–291. CDK complexes are formed through association of a regulatory cyclin subunit (e.g., cyclin A, B1, B2, D1, D2, D3, and E) and a catalytic kinase subunit (e.g., cdc2 (CDK1), CDK2, CDK4, CDK5, and CDK6). As the name implies, the CDKs display an absolute dependence on the cyclin subunit in order to phosphorylate their target substrates, and different kinase/cyclin pairs function to regulate progression through specific portions of the cell cycle.

The D cyclins are sensitive to extracellular growth signals and become activated in response to mitogens during the $G_1$ phase of the cell cycle. CDK4/cyclin D plays an important role in cell cycle progression by phosphorylating, and thereby inactivating, the retinoblastoma protein (Rb). Hypophosphorylated Rb binds to a family of transcriptional regulators, but upon hyperphosphorylation of Rb by CDK4/cyclin D, these transcription factors are released to activate genes whose products are responsible for S phase progression. Rb phosphorylation and inactivation by CDK4/cyclin D permit passage of the cell beyond the restriction point of the $G_1$ phase, whereupon sensitivity to extracellular growth or inhibitory signals is lost and the cell is committed to cell division. During late $G_1$, Rb is also phosphorylated and inactivated by CDK2/cyclin E, and recent evidence indicates that CDK2/cyclin E can also regulate progression into S phase through a parallel pathway that is independent of Rb phosphorylation (see Lukas et al., "Cyclin E-induced S Phase Without Activation of the pRb/E2F Pathway," *Genes and Dev.*, vol. 11 (1997), pp. 1479–1492).

The progression from $G_1$ to S phase, accomplished by the action of CDK4/cyclin D and CDK2/cyclin E, is subject to a variety of growth regulatory mechanisms, both negative and positive. Growth stimuli, such as mitogens, cause increased synthesis of cyclin D1 and thus increased functional CDK4. By contrast, cell growth can be "reined in," in response to DNA damage or negative growth stimuli, by the induction of endogenous inhibitory proteins. These naturally occurring protein inhibitors include $p21^{WAF1/CIP1}$, $p27^{KIP1}$, and the $p16^{INK4}$ family, the latter of which inhibit CDK4 exclusively (see Harper, "Cyclin Dependent Kinase Inhibitors," *Cancer Surv.*, vol. 29 (1997), pp. 91–107). Aberrations in this control system, particularly those that affect the function of CDK4 and CDK2, are implicated in the advancement of cells to the highly proliferative state characteristic of malignancies, such as familial melanomas, esophageal carcinomas, and pancreatic cancers (see, e.g., Hall and Peters, "Genetic Alterations of Cyclins, Cyclin-Dependent Kinases, and CDK Inhibitors in Human Cancer," *Adv. Cancer Res.*, vol. 68 (1996), pp. 67–108; and Kamb et al., "A Cell Cycle Regulator Potentially Involved in Genesis of Many Tumor Types," *Science*, vol. 264 (1994), pp. 436–440). Over-expression of cyclin D1 is linked to esophageal, breast, and squamous cell carcinomas (see, e.g., DelSal et al., "Cell Cycle and Cancer: Critical Events at the $G_1$ Restriction Point," *Critical Rev. Oncogenesis*, vol. 71 (1996), pp. 127–142). Genes encoding the CDK4-specific inhibitors of the p16 family frequently have deletions and mutations in familial melanoma, gliomas, leukemias, sarcomas, and pancreatic, non-small cell lung, and head and neck carcinomas (see Nobori et al., "Deletions of the Cyclin-Dependent Kinase-4 Inhibitor Gene in Multiple Human Cancers," *Nature*, vol. 368 (1994), pp. 753–756). Amplification and/or overexpression of cyclin E has also been observed in a wide variety of solid tumors, and elevated cyclin E levels have been correlated with poor prognosis. In addition, the cellular levels of the CDK inhibitor p27, which acts as both a substrate and inhibitor of CDK2/cyclin E, are abnormally low in breast, colon, and prostate cancers, and the expression levels of p27 are inversely correlated with the stage of disease (see Loda et al., "Increased Proteasome-dependent Degradation of the Cyclin-Dependent Kinase Inhibitor p27 in Aggressive Colorectal Carcinomas," *Nature Medicine*, vol. 3 (1997), pp. 231–234). The p21 proteins also appear to transmit the p53 tumor-suppression signal to the CDKs; thus, the mutation of p53 in approximately 50% of all human cancers may indirectly result in deregulation of CDK activity.

The emerging data provide strong validation for the use of compounds inhibiting CDKs, and CDK4 and CDK2 in particular, as anti-proliferative therapeutic agents. Certain biomolecules have been proposed for this purpose. For example, U.S. Pat. No. 5,621,082 to Xiong et al. discloses nucleic acid encoding an inhibitor of CDK6, and European Patent Publication No. 0 666 270 A2 describes peptides and peptide mimetics that act as inhibitors of CDK1 and CDK2. Several small molecules have been identified as CDK inhibitors (for a recent review, see Webster, "The Therapeutic Potential of Targeting the Cell Cycle," *Exp. Opin. Invest, Drugs*, vol. 7 (1998), pp. 865–887). The flavone flavopiridol displays modest selectivity for inhibition of CDKs over other kinases, but inhibits CDK4, CDK2, and CDK1 equipotently, with $IC_{50}$s in the 0.1–0.3 $\mu$M range. Flavopiridol is currently in Phase II clinical trials as an oncology chemotherapeutic (Sedlacek et al., "Flavopiridol (L86-8275; NSC 649890), A New Kinase Inhibitor for Tumor Therapy," *Int. J. Oncol.*, vol. 9 (1996), pp. 1143–1168). Analogs of flavopiridol are the subject of other publications, for example, U.S. Pat. No. 5,733,920 to Mansuri et al. (International Publication No. WO 97/16447) and International Publication Nos. WO 97/42949, and WO 98/17662. Results with purine-based derivatives are described in Schow et al., *Bioorg. Med. Chem. Lett.*, vol. 7 (1997), pp. 2697–2702; Grant et al., *Proc. Amer. Assoc. Cancer Res*,. vol. 39 (1998), Abst. 1207; Legravend et al., *Bioorg. Med. Chem. Lett.*, vol. 8 (1998), pp. 793–798; Gray et al., *Science*, vol. 281 (1998), pp. 533–538; and Furet et al., *216th ACS Natl. Mtg.* (Aug. 23–27, 1998, Boston), Abst MEDI-218. In addition, the following publications disclose certain pyrimidines that inhibit cyclin-dependent kinases and growth-factor mediated kinases: International Publication No. WO 98/33798; Ruetz et al., *Proc. Amer. Assoc. Cancer Res*,. vol. 39 (1998), Abst. 3796; and Meyer et al., *Proc. Amer. Assoc. Cancer Res.*, vol. 39 (1998), Abst. 3794.

There is still a need, however, for small-molecule compounds that may be readily synthesized and are potent inhibitors of one or more CDKs or CDK/cyclin complexes. Because CDK4 may serve as a general activator of cell division in most cells, and because complexes of CDK4/cyclin D and CDK2/cyclin E govern the early $G_1$ phase of the cell cycle, there is a need for effective and specific inhibitors of CDK4 and/or CDK2 for treating one or more types of tumors.

SUMMARY OF THE INVENTION

Accordingly, one object of the invention is to attain compounds and drug compositions that inhibit the activity of one or more CDKs, such as CDK2, CDK4, and/or CDK6, or cyclin complexes thereof. A further object is to provide an effective method of treating cancer indications through CDK inhibition, preferably through inhibition of CDK4 or CDK4/D-type cyclin complexes and/or CDK2 or CDK2/E-type cyclin complexes. Another object is to achieve pharmaceutical compositions containing compounds effective to block the transition of cancer cells into their proliferative phase. These and other objects and advantages of the invention, which will become apparent in light of the detailed description below, are achieved through cell-cycle control agents of the invention described below.

In one general aspect, the invention relates to pharmaceutical compositions comprising:
(a) a cell-cycle control agent selected from:
  (i) compounds of the Formula I:

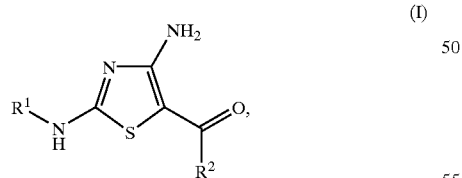

(I)

wherein:
  $R^1$ is a substituted or unsubstituted group selected from: $C_{1-6}$-alkyl (e.g., methyl, ethyl, propyl, isopropyl, butyl, isobutyl, sec-butyl, or tert-butyl); $C_{1-6}$-alkenyl; $C_{1-6}$-alkynyl; $C_{1-6}$-alkoxyl; $C_{1-6}$-alcohol; carbocyclic or heterocyclic cycloalkyl, which may be monocyclic or fused or non-fused polycyclic (e.g., cyclopropyl, cyclobutyl, cyclopentyl, cyclohexyl) or heterocycloalkyl, which may be monocyclic or fused or non-fused polycyclic (e.g., pyrrolidinyl, piperidinyl, morpholinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); carbonyl (e.g., carboxyl, ester, aldehyde, or ketone); ether; ($C_{1-6}$-alkyl)-carbonyl; ($C_{1-6}$-alkyl)-aryl; ($C_{1-6}$-alkyl)-cycloalkyl; ($C_{1-6}$-alkyl)-($C_{1-6}$-alkoxyl); aryl-($C_{1-6}$-alkoxyl); thioether (e.g., aryl-S-aryl, cycloalkyl-S-aryl, cycloalkyl-S-cycloalkyl, or dialkyl sulfide); thiol; and sulfonyl; and $R^2$ is a substituted or unsubstituted: carbocyclic or heterocyclic, monocyclic or fused or non-fused polycyclic, ring structure;

where each optional substituent for $R^1$ and $R^2$ is independently a halogen (e.g., chloro, iodo, bromo, or fluoro); oxygen (=O); haloalkyl (e.g., trifluoromethyl); $C_{1-6}$-alkyl; $C_{1-6}$-alkenyl; $C_{1-6}$-alkynyl; hydroxyl; $C_{1-6}$-alkoxyl; carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether; imine; cyano; amido; phosphonato; phosphine; carboxyl; thiocarbonyl; sulfonyl; sulfonamide; ketone; aldehyde; or ester;

(ii) pharmaceutically acceptable salts of compounds of the Formula I; and
(iii) prodrugs and pharmaceutically active metabolites of compounds of the Formula I or pharmaceutically acceptable salts thereof; and
(b) a pharmaceutically acceptable carrier.

In a further general aspect, the invention relates to pharmaceutical compositions comprising:
(a) a cell-cycle control agent selected from:
  (i) compounds of the Formula I:

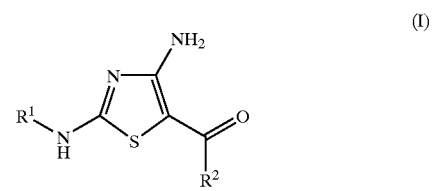

(I)

wherein:
R¹ is selected from:

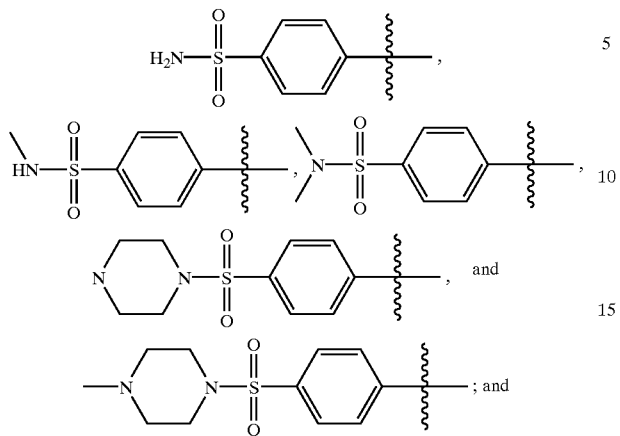

R² is a substituted or unsubstituted: carbocyclic or heterocyclic, monocyclic or fused or non-fused polycyclic, ring structure; where each optional substituent for R² is independently a halogen (e.g., chloro, iodo, bromo, or fluoro); oxygen (═O); haloalkyl (e.g., trifluoromethyl); $C_{1-6}$-alkyl; $C_{1-6}$-alkenyl; $C_{1-6}$-alkynyl; hydroxyl; $C_{1-6}$-alkoxyl; carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether; imine; cyano; amido; phosphonato; phosphine; carboxyl; thiocarbonyl; sulfonyl; sulfonamide; ketone; aldehyde; or ester;

(ii) pharmaceutically acceptable salts of compounds of the Formula I; and (iii) prodrugs and pharmaceutically active metabolites of compounds of the Formula I or pharmaceutically acceptable salts thereof; and (b) a pharmaceutically acceptable carrier.

Such compositions are useful as inhibitors of mammalian CDK/cyclin complexes, insect CDK, or fungal CDK complexes. Such compositions are also useful for controlling proliferation, differentiation, and/or apoptosis. Thus, in one general aspect the invention is directed to pharmaceutical compositions containing pharmaceutically effective amounts of cell-cycle control agents.

In a preferred embodiment, the invention is directed to potent cell-cycle control agents where R² in Formula I is an ortho-substituted aryl ring structure (e.g., o-substituted phenyl). Particularly preferred among such agents are those in which R² is an o-disubstituted phenyl.

The invention further relates to methods of using cell-cycle control agents for treating diseases or disorders mediated by CDK inhibition, especially those mediated by CDK4 and/or CDK2 inhibition. More particularly, the invention is directed to methods of treating malignancies or cancer-type disorders by administering a pharmaceutical composition comprising a cell-cycle control agent. Additionally, the invention relates to the use of cell-cycle control agents to prevent or treat mycotic infections.

Other aspects, advantages, and preferred features of the invention will become apparent from the detailed description below.

DETAILED DESCRIPTION AND PREFERRED EMBODIMENTS OF THE INVENTION

In one general embodiment, the invention relates to pharmaceutical compositions each comprising:

(a) an amount of a cell-cycle control agent effective to inhibit a CDK, the cell-cycle control agent being:
(i) a compound of the Formula I:

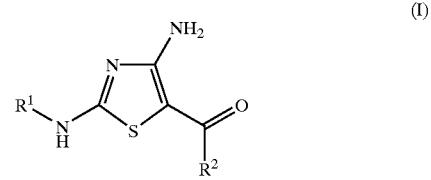

(I)

wherein:
R¹ is a substituted or unsubstituted group selected from: $C_{1-6}$-alkyl; $C_{1-6}$-alkenyl; $C_{1-6}$-alkynyl; $C_{1-6}$-alkoxyl; carbocylic or heterocyclic, monocyclic or fused or non-fused polycyclic, cycloalkyl; carbocyclic or heterocyclic, monocyclic or fused or non-fused polycyclic, aryl; carbonyl; ether; ($C_{1-6}$-alkyl)-carbonyl; ($C_{1-6}$-alkyl)-aryl; ($C_{1-6}$-alkyl)-cycloalkyl; ($C_{1-6}$-alkyl)-($C_{1-6}$-alkoxyl); aryl-($C_{1-6}$-alkoxyl); thioether; thiol; and sulfonyl; and R² is a substituted or unsubstituted, carbocyclic or heterocyclic, monocyclic or fused or non-fused polycyclic, ring structure;

where each optional substituent for R¹ and R² is independently a halogen; haloalkyl; $C_{1-6}$-alkyl; $C_{1-6}$-alkenyl; $C_{1-6}$-alkynyl; hydroxyl; $C_{1-6}$ alkoxyl; amino; nitro; thiol; thioether; imine; cyano; amido; phosphonato; phosphine; carboxyl; thiocarbonyl; sulfonyl; sulfonamide; ketone; aldehyde; or ester;

(ii) a pharmaceutically acceptable salt of a compound of the Formula I; or (iii) a prodrug or pharmaceutically active metabolite of a compound of the Formula I or a pharmaceutically acceptable salt thereof; and (b) a pharmaceutically acceptable carrier.

In another general embodiment, each optional substituent for R¹ and R² may be independently selected from, in addition to the above-identified groups, the following groups: oxygen; carbocyclic or heterocyclic, monocyclic or fused or non-fused polycyclic, cycloalkyl; and carbocyclic or heterocyclic, monocyclic or fused or non-fused polycyclic, aryl. Such substituents may optionally be further substituted with a substituent selected from such groups.

Examples for the moiety R¹ include substituted or unsubstituted aryl and alkyl, such as phenyl, pyridyl, benzimidazole, benzyl, and $C_{1-6}$-alkyl. In a preferred embodiment, these groups have one or more substituents selected from: halogen; oxygen; haloalkyl; $C_{1-6}$-alkyl; cycloalkyl; heterocycloalkyl; aryl; hydroxyl; $C_{1-6}$ alkoxyl;

amino; nitro thioether; cyano; amido; carboxyl; sulfonamido; ketone; aldehyde; and ester.

Other preferred moieties for $R^1$ are phenyl groups substituted by an alkylamine or pyridine group having optional substituents selected from the group described in the above paragraph for $R^1$. The alkylamine substitutent may be a 5- to 7-membered heterocycloalkyl optionally containing, in addition to the nitrogen ring atom, one or more heteroatoms selected from N, O and S.

Examples of such preferred $R^1$ groups include phenyl substituted in the para position with a heterocycloalkyl, for example piperidinyl, piperazinyl, thiazinyl, or morpholinyl, or a pyridyl group. The following are examples of preferred $R^1$ groups:

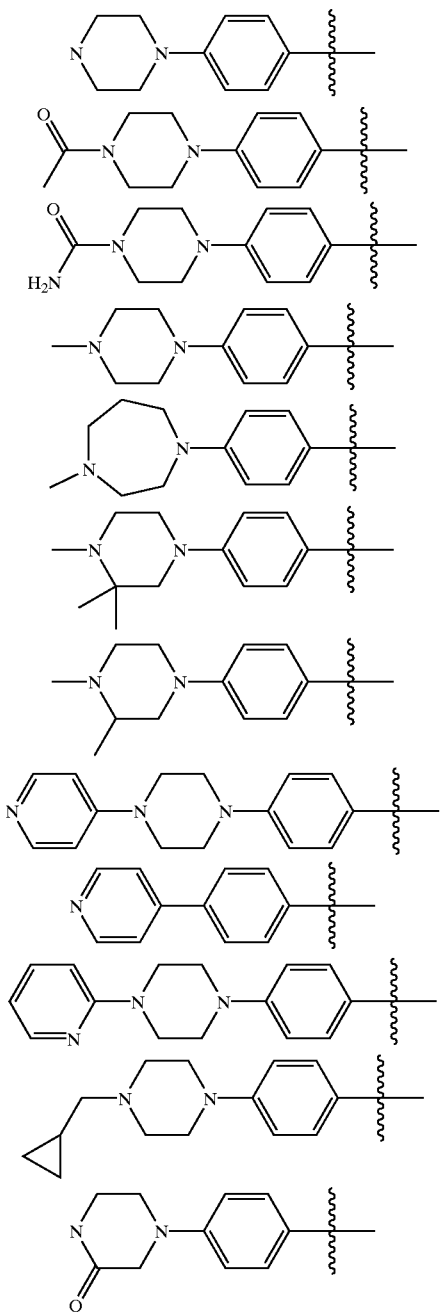

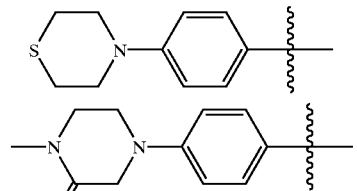

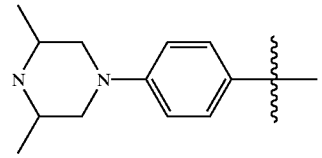

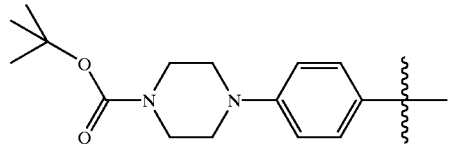

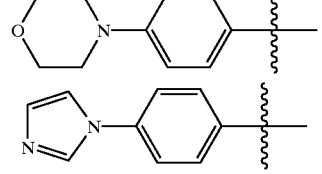

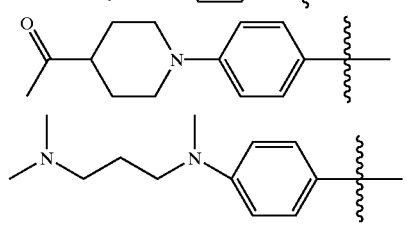

Other particularly preferred $R^1$ groups include phenyl groups substituted with carbonyl or sulfonamide moieties, wherein the carbonyl carbon and sulfonamide nitrogen are optionally further substituted. The following are examples of preferred $R^1$ groups:

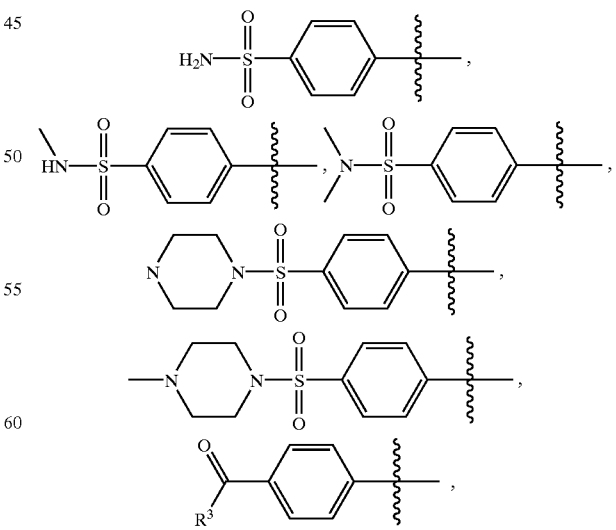

where $R^3$ is selected from $C_1$–$C_6$ alkyl, $C_1$–$C_6$ alkoxy, aryl, aryloxy, and amine.

Other preferred examples for the moiety $R^1$ include substituted or unsubstituted phenyl, alkylbenzyl, alkyl, benzyl carboxyl ester, benzyloxyphenyl, dimethylaminophenyl, pyridinyl, phenethyl, alkylcarboxyl, alkylpiperidinyl, phenylamino, cyclohexyl, benzylcarboxylalkyl, benzylnitro, phenyl-alkoxyl, ethyl benzoate, benzyl carboxyl, alkylbenzoimidazole, benzoimidazole, benzyldimethylamino, pyridinyl-sulfanyl, cyanobenzyl, and phenyl sulfamyl.

In preferred embodiments, $R^2$ in Formula I is a bulky group such as a substituted or unsubstituted carbocyclic or heterocyclic monocycle, or a substituted or unsubstituted fused or non-fused carbocyclic or heterocyclic polycycle. More preferably, $R^2$ is a substituted (carbo or poly)-(monocycle or polycycle); even more preferably, $R^2$ is such a cyclic ring structure bearing a substituent at the position adjacent or vicinal to the point of attachment (to the core structure).

For example, preferred species for $R^2$ include an ortho-substituted aromatic ring structure such as o-substituted phenyl or thienyl, or a 1,2-substituted cycloalkyl or cycloalkenyl ring structure such as 2-substituted cyclopent-1-enyl. Particularly preferred examples for the moiety $R^2$ include substituted or unsubstituted: o-halophenyl (e.g., o-fluorophenyl, o-chlorophenyl, o-iodophenyl, or o-bromophenyl), o-nitrophenyl, o-aminophenyl, o-$C_{1-6}$-alkylphenyl, o-$C_{1-6}$-alkoxyphenyl (e.g., o-methoxyphenyl or o-ethoxyphenyl), o-$C_{1-6}$-alkoxybenzothiophenyl), o-methylthiophenyl, benzonitrile, and carboxybenzyl. Particularly preferred examples for the moiety $R^2$ also include ortho-disubstituted aryls, for example, 2,6-dihalophenyl (e.g., 2,6-difluorophenyl) and 2-halo-6-trifluoromethylphenyl (e.g., 2-fluoro-6-trifluoromethylphenyl). Compounds of the Formula I where $R^2$ is a 1,2-substituted cyclic ring structure, optionally having one or more additional substituents, such as an ortho-substituted aryl having another substituent at the para position, have been surprisingly found to be potent CDK inhibitors.

Particularly preferred examples of compounds of Formula I include:

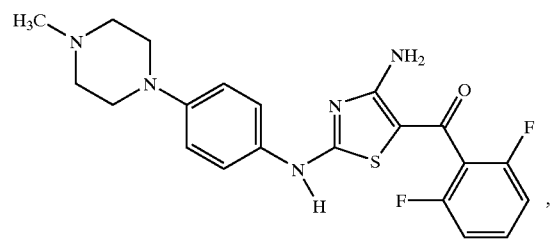

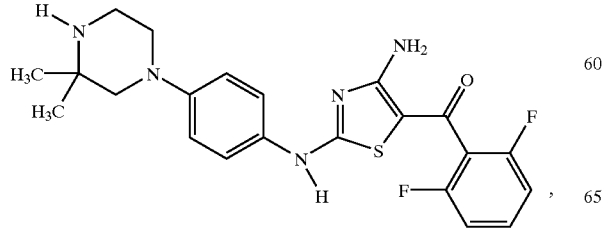

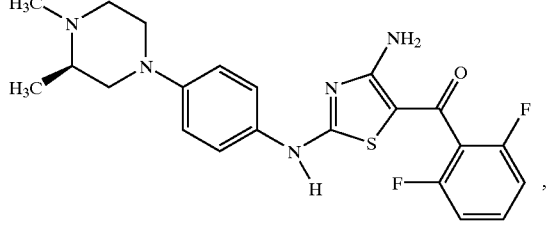

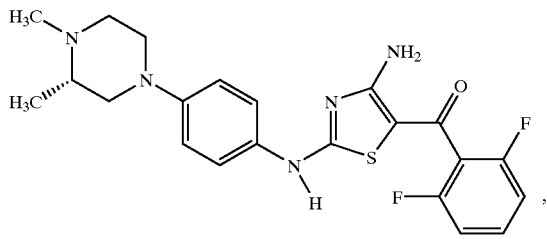

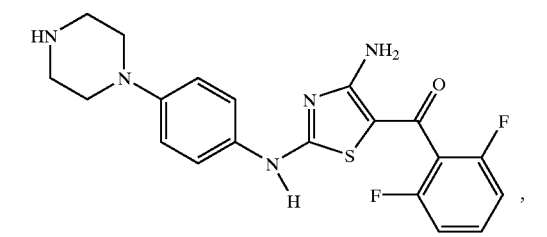

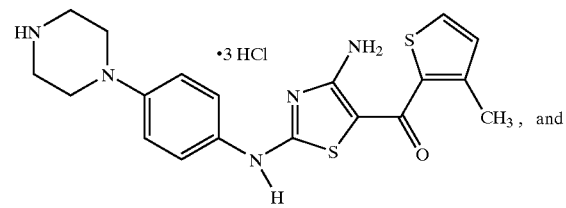

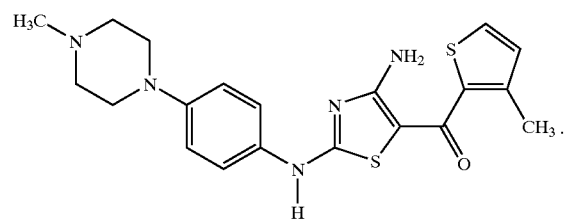

Other particularly preferred examples of compounds of Formula I include:

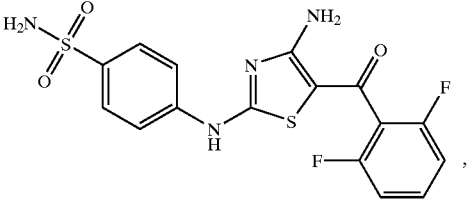

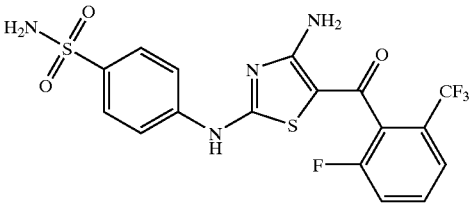

-continued

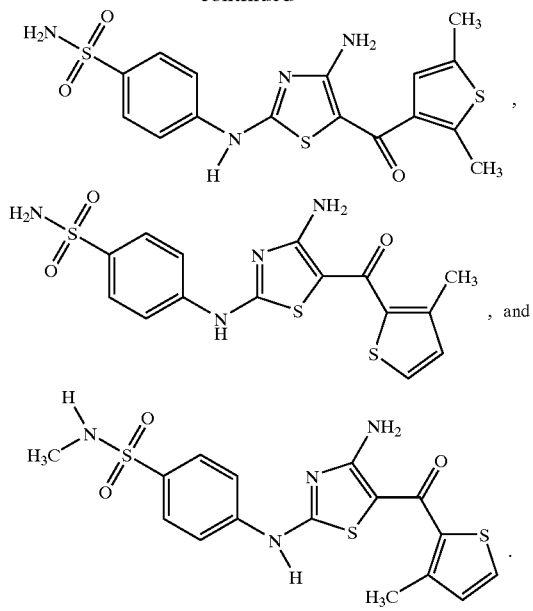

Pharmaceutical compositions according to the invention may, alternatively or in addition to a compound of the Formula I, comprise as an active ingredient a pharmaceutically acceptable salt of a compound of the Formula I, or a prodrug or pharmaceutically active metabolite of such a compound or salt. Such compounds, salts, prodrugs, and metabolites are sometimes referred to herein collectively as "cell-cycle control agents."

Compositions in accordance with the invention inhibit the kinase activity of CDK/cyclin complexes, such as those active in the $G_0$ or $G_1$ stage of the cell cycle, e.g., CDK2, CDK4, and/or CDK6 complexes. Preferred compositions of the invention contain cell-cycle control agents having an inhibition constant against CDK4 or a CDK4/D-type cyclin complex of about 1 $\mu$M or less, more preferably of about 500 nM or less, even more preferably of about 200 nM or less, and most preferably of about 100 nM or less. Especially preferred compounds of the invention include those having a CDK4/cyclin D3 inhibition constant ($K_i$ CDK4/D3) of about 100 nM or less. Other preferred compositions of the invention contain cell-cycle control agents having an inhibition constant against CDK2 or a CDK2/E-type cyclin complex of about 1 $\mu$M or less, more preferably of about 500 nM or less, even more preferably of about 200 nM or less, and most preferably of about 100 nM or less.

Certain compounds of the Formula I may exist in various stereoisomeric or tautomeric forms. The present invention encompasses all such CDK-inhibiting compounds, including active compounds in the form of essentially pure enantiomers, racemic mixtures, and tautomers.

The term "pharmaceutically acceptable" means pharmacologically acceptable and substantially non-toxic to the subject being administered the cell-cycle control agent. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from organic bases such as carbonates, bicarbonates, amines, benzylamines, piperidines, and pyrrolidines.

The term "prodrug" refers to a metabolic precursor of a compound of the Formula I (or a salt thereof) that is pharmaceutically acceptable. A prodrug may be inactive when administered to a subject but is converted in vivo to an active compound of the Formula I. The term "active metabolite" refers to a metabolic product of a compound of the Formula I that is pharmaceutically acceptable and effective. Prodrugs and active metabolites of compounds of the Formula I may be determined using techniques known in the art.

Cell-cycle control agents in accordance with the invention are useful as pharmaceuticals for treating proliferative disorders in mammals, especially humans, marked by unwanted proliferation of endogenous tissue. Compounds of the Formula I may be used for treating subjects having a disorder associated with excessive cell proliferation, e.g., cancers, psoriasis, immunological disorders involving undesired proliferation of leukocytes, and restenosis and other smooth-muscle disorders. Furthermore, such compounds may be used to prevent de-differentiation of post-mitotic tissue and/or cells.

Pharmaceutical compositions or preparations of the invention comprise a pharmaceutically acceptable carrier and an effective amount of at least one cell-cycle control agent. The term "effective amount" means an amount that significantly inhibits proliferation and/or prevents de-differentiation of a eukaryotic cell, e.g., a mammalian, insect, plant, or fungal cell, and is effective for the indicated utility, e.g., specific therapeutic treatment.

The specific dosage amount of a cell-cycle control agent being administered to obtain therapeutic or inhibitory effects, of course, may be determined in a manner known in the art according to the particular circumstances surrounding the case, including, e.g., the specific agent being administered, the route of administration, the condition being treated, and the subject or host being treated. An exemplary total daily dose of a cell-cycle control agent, which may be administered in single or multiple doses, contains a dosage level of from about 0.01 mg/kg body weight to about 50 mg/kg body weight.

The cell-cycle control agents of the invention may be administered by any of a variety of suitable routes, such as orally, rectally, transdermally, subcutaneously, intravenously, intramuscularly, or intranasally. The cell-cycle control agents are preferably formulated into compositions suitable for the desired routes before being administered.

A pharmaceutical composition or preparation according to the invention comprises an effective amount of a cell-cycle control agent and a pharmaceutically acceptable carrier, such as a diluent or excipient for the agent. When the carrier serves as a diluent, it may be a solid, semi-solid, or liquid material acting as a vehicle, excipient, or medium for the active ingredient(s). Compositions according to the invention may be made by admixing the active ingredient(s) with a carrier, or diluting it with a carrier, or enclosing or encapsulating it within a carrier, which may be in the form of a capsule, sachet, paper container, or the like. Exemplary ingredients, in addition to one or more cell-cycle control agents and any other active ingredients, include Avicel (microcrystalline cellulose), starch, lactose, calcium sulfate dihydrate, terra alba, sucrose, talc, gelatin, agar, pectin, acacia, magnesium stearate, stearic acid, peanut oil, olive oil, glyceryl monostearate, Tween 80 (polysorbate 80), 1,3-butanediol, cocoa butter, beeswax, polyethylene glycol, propylene glycol, sorbitan monostearate, polysorbate 60, 2-octyldodecanol, benzyl alcohol, glycine, sorbic acid, potassium sorbate, disodium hydrogen phosphate, sodium chloride, and water.

The compositions may be prepared in any of a variety of forms suitable for the desired mode of administration. For example, pharmaceutical compositions may be prepared in the form of tablets, pills, powders, lozenges, sachets, cachets, elixirs, suspensions, emulsions, solutions, syrups, aerosols (as solids or in liquid media), ointments (e.g., containing up to 10% by weight of a cell-cycle control agent), soft-gel and hard-gel capsules, suppositories, sterile injectable solutions, sterile packaged powders, and the like.

A pharmaceutical composition according to the invention comprises a cell-cycle control agent and, optionally, one or more other active ingredients, such as a known antiproliferative agent that is compatible with the cell-cycle control agent and suitable for the indication being treated. In a preferred embodiment, a pharmaceutical composition of the invention includes an effective amount of a cell-cycle control agent of the Formula I as an active ingredient.

Compounds in accordance with the invention may be prepared in manners analogous to those specifically described below, with the lettered example prefixes (i.e., A, B, C, D, E, F, G, H, J, K, L, M and N) designating general synthesis schemes.

EXAMPLES

Example A(1)

(4-Amino-2-phenylamino-thiazol-5-yl)-(3-nitrophenyl)-methanone

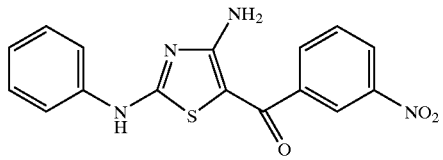

Following the procedure of Gewald et al., *J. Prakt. Chem.*, vol. 35 (1967), pp. 97–104, sodium (188 mg, 8.20 mmol) was carefully dissolved in methanol (9 mL) at 0° C. and allowed to warm to ambient temperature. The resultant solution was added portionwise to a mixture of cyanamide (345 mg, 8.20 mmol) and phenyl isothiocyanate (0.98 mL, 8.2 mmol), whereupon heat evolved. 2-Bromo-3'-nitroacetophenone (2.00 g, 8.2 mmol) was added, and the resultant mixture stirred overnight at ambient temperature. The mixture was diluted with water (150 mL). A yellow-brown solid was filtered off, rinsed with water and a small amount of ether, dried under vacuum, and recrystallized from ethanol to give 2.17 g (52% yield) of the title compound in the form of dark brown crystals, melting point (mp) 186–187° C.

$^1$H NMR (DMSO-d$_6$): δ 10.95 (1H, s), 8.44 (1H, t, J=1.9 Hz), 8.54–8.22 (2H, bs), 8.34 (1H, ddd, J=8.2, 1.9, 0.9 Hz), 8.12 (1H, ddd, J=8.2, 1.9, 0.9 Hz), 7.78 (1H, t, J=8.2 Hz), 7.62 (2H, d, J=7.8 Hz), 7.36 (2H, t, J=7.8 Hz), 7.09 (1H, t, J=7.8 Hz).

ESIMS (MH$^+$): 341.

Anal. Calcd. for C$_{16}$H$_{12}$N$_4$O$_3$S.EtOH: C, 55.94; H, 4.70; N, 14.50; S, 8.30. Found: C, 55.96; H, 4.73; N, 14.40; S, 8.29.

Example A(2)

(4-Amino-2-phenylamino-thiazol-5-yl)-(4-nitrophenyl)-methanone

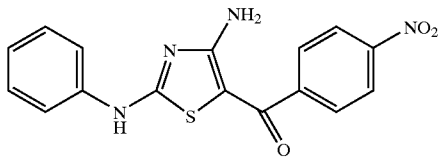

The title compound was prepared in a manner analogous to that described for Example A(1). Phenyl isothiocyanate and 2-bromo-4'-nitro-acetophenone gave, after recrystallization from ethanol, 3.06 g (55% yield) of red-brown crystals, mp 162–164° C.

$^1$H NMR (DMSO-d$_6$): δ 10.91 (1H, s), 8.38 (2H, bs), 8.30 (2H, d, J=8.7 Hz), 7.90 (2H, d, J=8.7 Hz), 7.59 (2H, d, J=7.5 Hz), 7.36 (2H, t, J=7.5 Hz), 7.10 (1H, d, J=7.5 Hz).

FABMS (MH$^+$): 341.

Anal. Calcd. for C$_{16}$H$_{12}$N$_4$O$_3$S: C, 56.46; H, 3.55; N, 16.46; S, 9.42. Found: C, 56.54; H, 3.54; N, 16.52; S, 9.42.

Example A(3)

[4-Amino-2-(pyridin-3-ylamino)-thiazol-5-yl]-phenyl-methanone

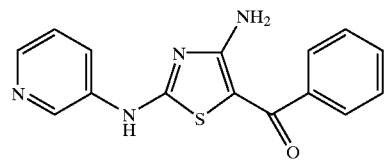

The title compound was prepared in a manner similar to that described for Example A(1). Pyridin-3-yl isothiocyanate and phenacyl chloride provided, after recrystallization from ethanol, 4.1 g (75% yield) of yellow crystals, mp 227–229° C.

$^1$H NMR (DMSO-d$_6$): δ 10.95 (1H, s), 8.82 (1H, d, J=2.5 Hz), 8.28 (1H, dd, J=4.7, 1.2 Hz), 8.23 (2H, bs), 8.12 (1H, ddd, J=8.4, 2.8, 1.6 Hz), 7.68 (1H, d, J=6.9 Hz), 7.66 (1H, d, J=7.8 Hz), 7.54–7.44 (3H, m), 7.39 (1H, dd, J=8.4, 4.7 Hz).

HRFABMS: Calcd. for C$_{15}$H$_{13}$N$_4$OS (MH$^+$): 297.0810. Found: 297.0815.

Anal. Calcd. for C$_{15}$H$_{12}$N$_4$OS.EtOH: C, 59.63; H, 5.30; N, 16.36; S, 9.36. Found: C, 59.62; H, 5.32; N, 16.43; S, 9.41.

Example A(4)

(4-Amino-2-phenylamino-thiazol-5-yl)-pyridin-2-yl-methanone

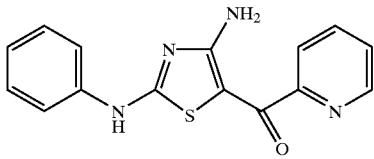

The title compound was prepared in a manner similar to that described for Example A(1). Phenyl isothiocyanate and 2-(2-bromoacetyl)pyridine (see Menassé et al., *Helv. Chim. Acta*, vol. 38 (1955), pp. 1289–1291; Imuta et al., *J. Org. Chem.*, vol. 45 (1980), pp. 3352–3355) gave, after recrystallization from 95% ethanol, 510 mg (71% yield) of brown needles, mp 181.5–183.0° C.

$^1$H NMR (DMSO-d$_6$): δ 10.75 (1H, s), 8.92 (1H, bs), 8.66 (1H, ddd, J=5.11.8, 1.2 Hz), 8.22 (1H, bs), 8.13 (1H, dt, J=7.5, 1.2 Hz), 8.01 (1H, dt, J=7.5, 1.8 Hz), 7.69 (2H, dd, J=7.5, 1.2 Hz), 7.54 (1H, ddd, J=7.5, 5.1, 1.2 Hz), 7.36 (2H, t, J=7.5 Hz), 7.07 (1H, dt, J=7.5, 1.2 Hz).

HRFABMS: Calcd. for C$_{15}$H$_{13}$N$_4$OS (MH$^+$): 297.0810. Found: 297.0818.

Anal. Calcd. for C$_{15}$H$_{12}$N$_4$OS.H$_2$O: C, 57.31; H, 4.49; N, 17.82; S, 10.20. Found: C, 57.31; H, 4.46; N, 17.80; S, 10.14.

Example A(5)

Ethyl 4-[4-Amino-5-(2-nitro-benzoyl)-thiazol-2-ylamino]-benzoate

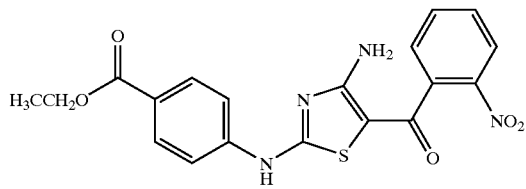

The title compound was prepared in a manner analogous to that used in Example A(1). 4-Carboethoxy-phenyl isothiocyanate and 2-bromo-2'-nitro-acetophenone gave, after recrystallization from ethanol, 1.2 g (59% yield) of yellow crystalline powder, mp 262–265° C.

$^1$H NMR (DMSO-d$_6$): δ 11.08 (1H, s), 8.12 (2H, bs), 8.08 (1H, d, J=8.7 Hz), 7.93 (2H, d, J=8.7 Hz), 7.82 (1H, dt, J=7.2, 1.2 Hz), 7.77–7.66 (3H, m), 7.73 (1H, d, J=8.7 Hz), 4.28 (2H, q, J=7.2 Hz), 1.30 (3H, t, J=7.2 Hz).

ESIMS (MH$^+$): 413.

Anal. Calcd. for C$_{19}$H$_{18}$N$_4$O$_3$S: C, 55.33; H, 3.91; N, 13.58; S, 7.77. Found: C, 55.22; H, 3.86; N, 13.48; S, 7.67.

Example A(6)

[4-Amino-2-(2-methyl-1H-benzoimidazol-6-ylamino)-thiazol-5-yl]-(2-nitro-phenyl)-methanone

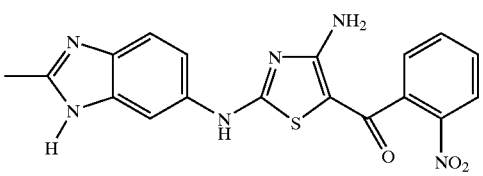

The title compound was prepared in a similar manner to that described in Example A(1). 6-Isothiocyanato-2-methyl-1H-benzoimidazole (see Galley et al., German Patent Publication DE 2259220 (1973); C.A. No. 478781 (1973)) and 2-bromo-2'-nitro-acetophenone gave, after recrystallization from ethanol, 1.2 g (62% yield) of brown crystals, mp 190.0–192.5° C.

$^1$H NMR (DMSO-d$_6$): δ 12.20 (1H, bs), 10.76 (1H, s), 8.10–8.76 (3H, m), 7.76 (1H, t, J=7.0 Hz), 7.70–7.58 (3H, m), 7.40 (1H, d, J=8.4 Hz), 7.13 (1H, dd, J=8.4, 1.6 Hz), 2.44 (3H, s).

FABMS (MH$^+$): 395.

Anal. Calcd. for C$_{18}$H$_{14}$N$_6$O$_3$S.H$_2$O: C, 52.42; H, 3.91; N, 20.38; S, 7.77. Found: C, 52.29; H, 3.89; N, 20.31; S, 7.86.

Example A(7)

[4-Amino-2-(4-iodo-phenylamino)-thiazol-5-yl]-(2-nitro-phenyl)-methanone

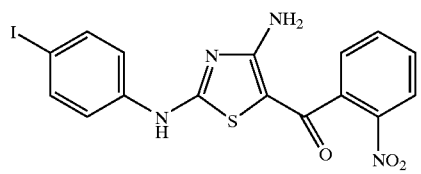

The title compound was prepared analogously to Example A(1). 4-Iodophenyl isothiocyanate and 2-bromo-2'-nitro-acetophenone provided 7.9 g (88% yield) of orange-red powder, mp 182–184° C.

$^1$H NMR (DMSO-d$_6$): δ 10.89 (1H, s), 8.20 (1H, s), 8.50 (1H, d, J=8.7 Hz), 7.80 (1H, dd, J=8.7, 6.2 Hz), 7.72–7.62 (4H, m), 7.41 (2H, d, J=8.7 Hz).

FABMS (MH$^+$): 467.

Anal. Calcd. for C$_{16}$H$_{11}$N$_4$O$_3$SI: C, 41.21; H, 2.38; N, 12.02; S, 6.88; I, 27.22. Found: C, 41.34; H, 2.46; N, 12.07; S, 7.02; I, 27.35.

Example A(8)

[4-Amino-2-(4-nitro-phenylamino)-thiazol-5-yl]-phenyl-methanone

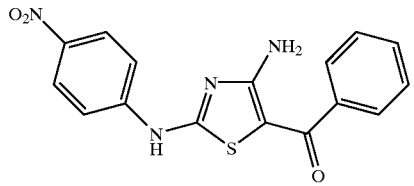

The title compound was prepared in a manner analogous to that described for Example A(1). 4-Nitrophenyl isothiocyanate and phenacyl chloride furnished 2.5 g (60% yield) of solid, mp 280.0–281.5° C.

$^1$H NMR (DMSO-$d_6$): δ 11.38 (1H, s), 8.30–8.18 (2H, bs), 8.23 (2H, d, J=9.3 Hz), 7.87 (2H, d, J=9.3 Hz), 7.69 (2H, dd, J=7.8, 1.6 Hz), 7.56–7.44 (3H, m).

FABMS (MH$^+$): 341.

Anal. Calcd. for $C_{16}H_{12}N_4O_3S$: C, 56.46; H, 3.55; N, 16.46; S, 9.42. Found: C, 56.40; H, 3.49; N, 16.40; S, 9.41.

Example A(9)

[4-Amino-2-(1H-benzoimidazol-6-yl-amino)-thiazol-5-yl]-(2-nitro-phenyl)-methanone

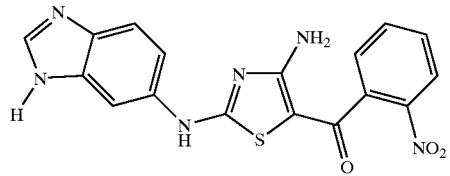

The title compound was prepared in a manner similar to that described for Example A(1). 6-Isothiocyanato-1H-benzoimidazole (see Boev et al., *Pharm. Chem. J.* (*Engl. Transl*), vol. 24 (1990), pp. 818–822) and 2-bromo-2'-nitro-acetophenone afforded, after recrystallization from ethanol/methanol, 1.5 g (83% yield) of red-brown amorphous powder, mp 249–255° C.

$^1$H NMR (DMSO-$d_6$): δ 12.50 (1H, bs), 10.84 (1H, s), 8.20 (1H, s), 8.60 (2H, bs), 8.03 (1H, d, J=8.1 Hz), 7.88–7.78 (1H, m), 7.76 (1H, d, J=7.5 Hz), 7.66 (1H, t, J=7.5 Hz), 7.65 (1H, s), 7.55 (1H, d, J=8.7 Hz), 7.21 (1H, d, J=8.7 Hz).

FABMS (MH$^+$): 381.

Anal. Calcd. for $C_{17}H_{12}N_6O_3S$: C, 53.68; H, 3.18; N, 22.09; S, 8.43. Found: C, 53.69; H, 3.14; N, 21.99; S, 8.39.

Example A(10)

[4-Amino-2-(4-methoxy-phenylamino)-thiazol-5-yl]-(2-nitro-phenyl)-methanone

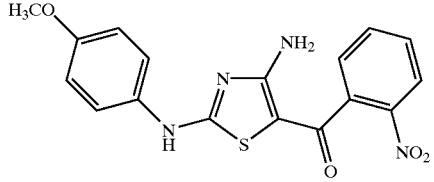

The title compound was prepared in a manner similar to that described for Example A(1). 4-Methoxy-phenyl isothiocyanate and 2-bromo-2'-nitro-acetophenone provided, after recrystallization from aqueous ethanol, 562 mg (43% yield) of brown-red crystals, mp 185–188° C.

$^1$H NMR (DMSO-$d_6$): δ 10.65 (1H, s), 8.25 (2H, bs), 8.20 (1H, d, J=7.5 Hz), 7.77 (1H, t, J=7.5 Hz), 7.66 (1H, t, J=7.5 Hz), 7.62 (1H, d, J=7.5 Hz), 7.41 (2H, d, J=8.7 Hz), 6.92 (2H, d, J=8.7 Hz), 3.72 (3H, s).

FABMS (M+Na$^+$): 393.

Anal. Calcd. for $C_{17}H_{14}N_4O_4S$: C, 55.13; H, 3.81; N, 15.13; S, 8.66. Found: C, 55.08; H, 3.83; N, 15.11; S, 8.56.

Example A(11)

[4-Amino-2-(pyridin-3-ylamino)-thiazol-5-yl]-(2-nitro-phenyl)-methanone

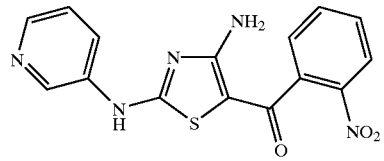

The title compound was prepared as essentially described for Example A(1). Pyridin-3-yl isothiocyanate and 2-bromo-2'-nitro-acetophenone afforded, after column chromatography with 5% MeOH/CH$_2$Cl$_2$, 750 mg (42% yield) of yellow solid, mp 143.5–146.0° C.

$^1$H NMR (DMSO-$d_6$): δ 10.95 (1H, bs), 8.62 (1H, s), 8.19 (1H, dd, J=4.7, 1.3 Hz), 8.08–7.86 (4H, m), 7.76 (1H, td, J=8.3, 0.9 Hz), 7.66 (1H, dd, J=8.4, 1.3 Hz), 7.62 (d, J=7.5 Hz), 7.31 (1H, dd, J=8.4, 4.7 Hz).

FABMS (MH$^+$): 342.

Anal. Calcd. for $C_{15}H_{11}N_5O_3S \cdot 0.5H_2O \cdot 0.4EtOH$: C, 51.46; H, 3.94; N, 18.99; S, 8.69. Found: C, 51.86; H, 3.88; N, 19.24; S, 8.88.

Example A(12)

4-Amino-2-(1H-benzoimidazol-6-ylamino)-thiazole-5-carboxylic Acid Methyl Ester

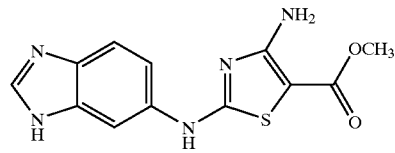

The title compound was prepared essentially as described for Example A(1). 6-Isothiocyanato-1H-benzoimidazole (see Boev et al., *Pharm. Chem. J.* (*Engl. Transl*). vol. 24 (1990), pp. 818–822) and methyl bromoacetate gave in 63% yield a yellow solid, mp 266–267° C.

$^1$H NMR (DMSO-d$_6$): δ 12.37 (1H, bs), 10.52 (1H, s), 8.15 (1H, s), 7.92 (1H, s), 7.52 (1H, d, J=8.7 Hz), 7.23 (1H, dd, J=8.7, 1.9 Hz), 6.89 (2H, bs), 3.62 (3H, s).

FABMS (MH$^+$): 250.

Anal. Calcd. for C$_{11}$H$_{11}$N$_3$O$_2$S.0.15EtOH: C, 49.87; H, 4.05; N, 23.64; S, 10.82. Found: C, 49.94; H, 3.94; N, 23.41; S, 10.79.

Example A(13)

[4-Amino-2-(p-tolylamino)-thiazol-5-yl]-(2,4-dimethoxyphenyl)-methanone

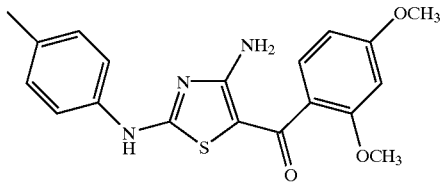

The title compound was prepared in a manner similar to that described for Example A(1). p-Tolyl isothiocyanate and 2-bromo-2',4'-dimethoxyacetophenone gave, after recrystallization from MeOH/CHCl$_3$, 78 mg (24% yield) of a yellow solid, mp 215–216° C.

$^1$H NMR (DMSO-d$_6$): δ 10.51 (1H, s), 7.88 (2H, bs), 7.41 (2H, d, J=8.4 Hz), 7.16 (2H, d, J=8.4 Hz), 7.12 (2H, d, J=8.4 Hz), 6.58 (1H, d, J=2.2 Hz), 6.52 (1H, dd, J=8.4, 2.2 Hz), 3.78 (3H, s), 3.74 (3H, s), 2.24 (3H, s).

IR (KBr): 3279, 2959, 1606, 1515, 1432, 1306, 1284, 1209, 1157, 1124, 1032 cm$^{-1}$.

Anal. Calcd. for C$_{19}$H$_{19}$N$_3$O$_3$S: C, 61.77; H, 5.18; N, 11.37; S, 8.68. Found: C, 61.69; H, 5.16; N, 11.33; S, 8.79.

Example A(14)

[4-Amino-2-(p-tolylamino)-thiazol-5-yl]-(2,4-dimethylphenyl)-methanone

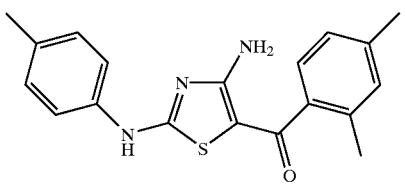

The title compound was prepared in a manner similar to that described for Example A(1). p-Tolyl isothiocyanate and 2-bromo-2',4'-dimethylacetophenone gave, after recrystallization from MeOH/CHCl$_3$, 65 mg (33% yield) of a yellow crystals, mp 220–221° C.

$^1$H NMR (DMSO-d$_6$): δ 10.58 (1H, s), 7.99 (2H, bs), 7.39 (2H, d, J=8.1 Hz), 7.17 (2H, d, J=7.8 Hz), 7.13 (2H, d, J=8.1 Hz), 7.04 (1H, s), 7.00 (1H, d, J=7.8 Hz), 2.73 (3H, s), 2.24 (3H, s), 2.22 (3H, s).

IR (KBr): 3266, 2921, 1612, 1598, 1546, 1518, 1431 cm$^{-1}$.

Anal. Calcd. for C$_{19}$H$_{19}$N$_3$OS: C, 67.63; H, 5.68; N, 12.45; S, 9.50. Found: C, 67.70; H, 5.73; N, 12.47; S, 9.62.

Example B

[4-Amino-2-(p-tolylamino)-thiazole-5-carbonyl]-phenyl Benzoate

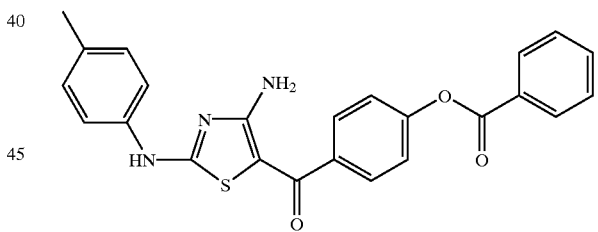

An intermediate, S-(4-Benzoyloxyphenylacetyl)-N'-cyano-N"-p-tolyl-isothiourea, was first prepared following a procedure in Gewald et al., *J. Prakt. Chem*, vol. 35 (1967), pp. 97–104. Sodium (6.7 mg, 0.29 mmol) was carefully dissolved in methanol (0.5 mL) and allowed to cool to ambient temperature. To the resultant solution was added p-tolyl isothiocyanate (43 mg, 0.29 mmol) and cyanamide (12 mg, 0.29 mmol). After 1 hour, 4-bromoacetylphenyl benzoate (92 mg, 0.29 mmol) was added, and the resultant mixture was stirred overnight at ambient temperature. The mixture was then diluted with water (10 mL). The resulting tan solid was filtered off, rinsed with water and a small amount of ether, dried under vacuum, and recrystallized from ethanol/CHCl$_3$ to give an initial crop of 63 mg (51% yield) of S-(4-benzoyloxyphenylacetyl)-N'-cyano-N"-p-tolyl-isothiourea (as white needles):

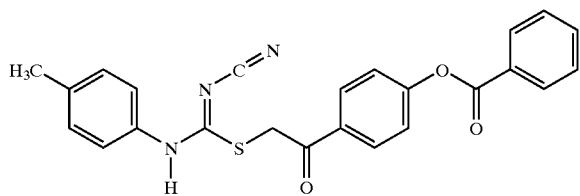

$^1$H NMR (DMSO-d$_6$): δ 8.10–8.04 (2H, m), 7.72 (1H, ddd, J=7.5, 1.8, 1.8 Hz), 7.67–7.54 (4H, m), 7.20 (2H, d, J=8.7 Hz), 7.03 (4H, dd, J=11.2, 8.7 Hz), 4.10 (1H, d, J=12.1 Hz), 3.77 (1H, d, J=12.1 Hz), 2.19 (3H, s).

From the intermediate the title compound was prepared as follows. Crude S-(4-benzoyloxyphenylacetyl)-N'-cyano-N''-p-tolyl-isothiourea (0.29 mmol) and triethylamine (101 μL, 0.73 mmol) in ethyl acetate (1 mL) was heated at reflux for 2 hours, then allowed to cool to ambient temperature, and concentrated in vacuo to a crude solid, which crystallized from MeOH/CHCl$_3$ in successive crops to afford 67 mg (54% yield) of yellow needles, mp 245–247° C.

$^1$H NMR (DMSO-d$_6$): δ 10.71 (1H, s), 8.34–8.11 (4H, m), 7.80–7.72 (3H, m), 7.66–7.57 (2H, m), 7.46 (2H, d, J=8.1 Hz), 7.38 (2H, d, J=8.4, Hz), 7.16 (2H, d, J=8.4 Hz), 2.26 (3H, s).

IR (KBr): 3451, 3332, 3026, 1732, 1597, 1522, 1444, 1264, 1206, 1164, 1062, 708 cm$^{-1}$.

HRFABMS: Calcd. for C$_{24}$H$_{19}$N$_3$O$_3$SCs (M+Cs$^+$): 562.0201. Found: 562.0184.

Anal. Calcd. for C$_{24}$H$_{19}$N$_3$O$_3$S: C, 67.12; H, 4.46; N, 9.78; S, 7.47. Found: C, 66.90; H, 4.43; N, 9.70; S, 7.50.

Example C(1)

4-[4-Amino-5-(4-methoxy-benzoyl)-thiazol-2-ylamino]-benzoic Acid Methyl Ester

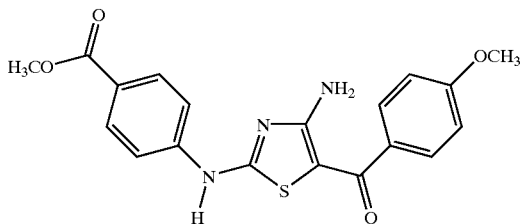

To a mixture of 4-methoxycarbonylphenyl isothiocyanate (82 mg, 0.5 mmol) and cyanamide (23 mg, 0.55 mmol) in acetonitrile (5 mL), a solution of potassium tert-butoxide (61 mg, 0.55 mmol) in tert-butanol (5 mL) was added. After 30 minutes at ambient temperature, 2-bromo-4'-methoxy-acetophenone (115 mg, 0.5 mmol) was added. After 2 hours at ambient temperature, the reaction mixture was diluted with water (50 mL). The product was collected by filtration, rinsed with water and ethyl ether, and dried under vacuum to furnish a yellow solid, 172 mg (90% yield).

$^1$H NMR (DMSO-d$_6$): δ 8.00 (2H, d, J=8.2 Hz), 7.84 (2H, d, J=8.2 Hz), 7.72 (2H, d, J=8.2 Hz), 7.10 (2H, d, J=8.2 Hz), 3.90 (6H, s).

FABMS (MH+): 384.

Anal. Calcd. for C$_{19}$H$_{17}$N$_3$O$_4$S.0.5H$_2$O: C, 57.36; H, 4.71; N, 10.56; S, 8.06. Found: C, 56.97; H, 4.74; N, 10.51; S, 8.07.

Example C(2)

[4-Amino-2-(4-benzyloxy-phenylamino)-thiazol-5-yl]-(4-methoxy-phenyl)-methanone

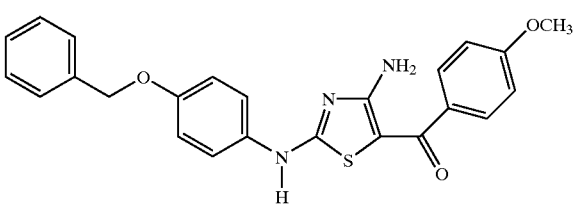

The title compound was prepared in a manner like that described for Example C(1). 4-Benzyloxy-phenyl isothiocyanate and 2-bromo-4'-methoxy-acetophenone gave a yellow-brown solid in 85% yield, mp 222–224° C.

$^1$H NMR (DMSO-d$_6$): δ 7.70 (2H, d, J=8.2 Hz), 7.58–7.34 (7H, m), 7.06 (4H, dd, J=7.5, 1.2 Hz), 5.18 (2H, s), 3.94 (3H, s).

FABMS (MH$^+$): 432.

Anal. Calcd. for C$_{24}$H$_{21}$N$_3$O$_3$S: C, 66.80; H, 4.91; N, 9.74; S, 7.43. Found: C, 66.86; H, 4.91; N, 9.76; S, 7.53.

Example C(3)

[4-Amino-2-(4-dimethylamino-phenylamino)-thiazol-5-yl]-(4-methoxy-phenyl)-methanone

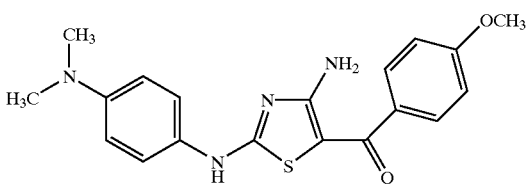

The title compound was prepared similarly as described for Example C(1) from 4-dimethylamino-phenyl isothiocyanate and 2-bromo-4'-methoxy-acetophenone to give the product as a yellow solid in 85% yield, mp 178–180° C.

$^1$H NMR (DMSO-d$_6$): δ 7.70 (2H, d, J=8.2 Hz), 7.34 (2H, d, J=8.2 Hz), 7.00 (2H, d, J=8.6 Hz), 6.80 (2H, d, J=8.6), 3.94 (3H, s), 2.94 (6H, s).

Anal. Calcd. for C$_{19}$H$_{20}$N$_4$O$_2$S: C, 61.94; H, 5.47; N, 15.21; S, 8.70. Found: C, 62.22; H, 5.48; N, 15.03; S, 8.58.

Example C(4)

[4-Amino-2-(4-dimethylamino-phenylamino)-thiazol-5-yl]-(2-nitro-phenyl)-methanone

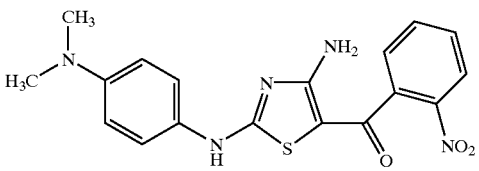

The title compound was prepared in a manner analogous to that described for Example C(1). 4-Dimethylamino-phenyl isothiocyanate and 2-bromo-2'-nitro-acetophenone furnished a yellow solid in 90% yield, mp >195° C. (decomp.).

¹H NMR (DMSO-d₆): δ 8.06 (2H, bs), 7.76 (2H, m), 7.27 (2H, bs), 6.74 (2H, d, J=9.0 Hz), 3.38 (6H, s).

FABMS (MH⁺): 384.

Anal. Calcd. for C₁₈H₁₇N₅O₃S.0.5CH₃CN: C, 56.49; H, 4.62; N, 19.07; S, 7.94. Found: C, 56.71; H, 4.64; N, 19.09; S, 7.88.

Example C(5)

(4-Amino-2-phenethylamino-thiazol-5-yl)-(2-nitro-phenyl)-methanone

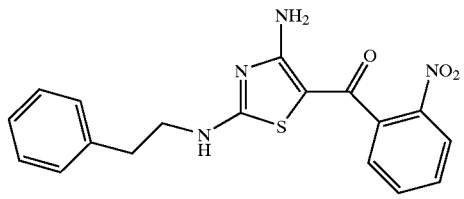

The title compound was prepared essentially as described for Example C(1). Phenethyl isothiocyanate and 2-bromo-2'-nitro-acetophenone provided an amorphous yellow solid in 90% yield, mp 75.0–81.5° C. (decomp.).

¹H NMR (DMSO-d₆): δ 8.67 (1H, bs), 8.00 (1H, d, J=8.1 Hz), 7.80 (2H, bs), 7.75 (1H, t, J=7.5 Hz), 7.65 (1H, t, J=7.5 Hz), 7.58 (1H, d, J=6.5 Hz), 7.04–7.32 (5H, m), 3.50 (2H, bs), 2.82 (2H, t, J=7.2 Hz).

FABMS (MH⁺): 369.

Anal. Calcd. for C₁₈H₁₆N₄O₃S.0.1H₂O.0.1C₆H₁₄: C, 58.97; H, 4.68; N, 14.79; S, 8.46. Found: C, 58.97; H, 4.78; N, 14.54; S, 8.37.

Example C(6)

Methyl 2(S)-[4-Amino-5-(4-nitro-benzoyl)-thiazol-2-ylamino]-butyrate

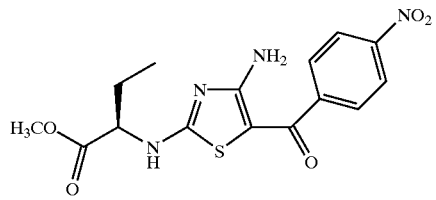

The title compound was prepared in a manner similar to that described for Example C(1). Methyl 2(S)-isothiocyanato-butyrate and 2-bromo-4'-nitro-acetophenone afforded an amorphous red-brown solid in 89% yield.

¹H NMR (CDCl₃): δ 8.28 (2H, d, J=8.2 Hz), 7.86 (2H, J=8.2 Hz), 3.94 (3H, s), 4.32 (1H, bs), 2.12 (1H, m), 1.88 (1H, m), 0.96 (3H, t, J=6.4 Hz).

FABMS (MH⁺): 365.

Example C(7)

[4-Amino-2-((4-dimethylaminophenyl)amino)-thiazol-5-yl]-(3-methyl-benzo[b]thiophen-2-yl)-methanone

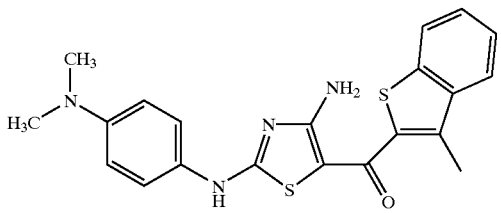

The title compound was prepared essentially as described for Example C(1). 4-Dimethylaminophenyl isothiocyanate and 2-(2-bromoacetyl)-3-methyl-benzo[b]thiophene gave, after recrystallization from ethanol, 210 mg (92% yield) of yellow powder, mp 123–126° C.

¹H NMR (DMSO-d₆): δ 10.50 (1H, s), 8.20 (2H, bs), 7.96 (1H, ddd, J=5.0, 5.0, 1.9 Hz), 7.82 (1H, ddd, J=4.1, 4.1, 1.7 Hz), 7.44 (2H, ddd, J=9.0, 4.5, 4.5 Hz), 7.26 (2H, d, J=8.5 Hz), 6.69 (2H, d, J=9.0 Hz), 2.84 (6H, s).

FABMS (MH⁺): 409.

Anal. Calcd. for C₂₁H₂₀N₄OS₂.0.5H₂O.0.5MeOH: C, 59.56; H, 5.35; N, 12.92; S, 14.79. Found: C, 59.87; H, 5.39; N, 12.86; S, 14.69.

Example C(8)

[4-Amino-2-(1H-benzoimidazol-6-ylamino)-thiazol-5-yl]-(3-methyl-benzo[b]thiophen-2-yl)-methanone

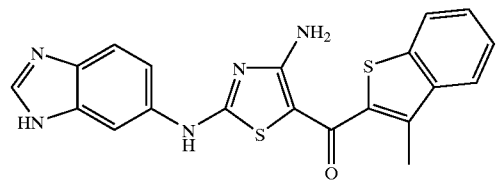

The title compound was prepared in a manner like that described for Example C(1). 6-Isothiocyanato-1H-benzoimidazole (see Boev et al., Pharm. Chem. J. (Engl. Transl)., vol. 24 (1990), pp. 818–822) and 2-(2-bromoacetyl)-3-methyl-benzo[b]thiophene provided 160 mg (53% yield) of yellow powder, mp 235–240° C.

¹H NMR (DMSO-d₆): δ 12.50 (1H, s), 10.9 (1H, s), 8.28 (2H, bs), 8.19 (1H, s), 8.20–7.93 (1H, m), 7.93–8.00 (2H, m), 7.56 (1H, d, J=8.7 Hz), 7.50–7.40 (2H, m), 7.25 (1H, d, J=8.7 Hz), 2.49 (3H, s).

FABMS (MH⁺): 406.

Anal. Calcd. for C₂₀H₁₅N₅OS₂.0.5H₂O: C, 57.95; H, 3.89; N, 16.90; S, 15.47. Found: C, 57.98; H, 3.88; N, 17.06; S, 15.55.

Example C(9)

[4-Amino-2-(5-chloro-3-methyl-benzo[b]thiophen-2-ylamino)-thiazol-5-yl]-(4-dimethylamino-phenyl)-methanone

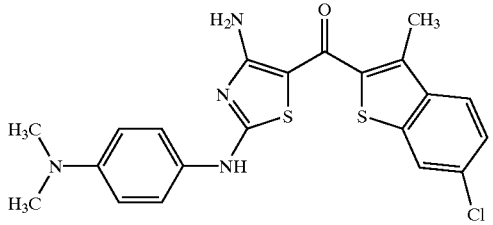

The title compound was prepared essentially as described for Example C(1). 4-Dimethylaminophenyl isothiocyanate and 2-(2-bromoacetyl)-5-chloro-3-methyl-benzo[b]thiophene provided 54% yield of yellow powder, mp 265–268° C.

$^1$H NMR (DMSO-$d_6$): δ 10.60 (1H, s), 8.04 (2H, bs), 8.00 (1H, d, J=8.7 Hz), 7.88 (1H, d, J=1.8 Hz), 7.46 (1H, dd, J=8.7, 1.8 Hz), 7.34–7.20 (2H, m), 6.68 (2H, d, J=9.0 Hz), 2.85 (6H, s), 2.43 (3H, s).

FABMS (MH$^+$): 443/445.

Anal. Calcd. for $C_{21}H_{19}N_4OS_2Cl$: C, 56.94; H, 4.32; N, 12.65; S, 14.48; Cl, 8.00. Found: C, 56.82; H, 4.39; N, 12.42; S, 14.42; Cl, 8.17.

Example C(10)

[4-Amino-2-(1H-benzoimidazol-6-yl-amino)-thiazol-5-yl]-(5-chloro-3-methyl-benzo[b]thiophen-2-yl)-methanone

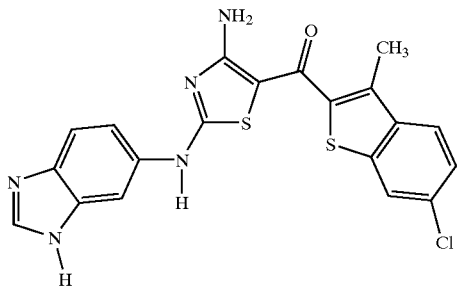

The title compound was prepared in a similar manner as that described for Example C(1). 6-Isothiocyanato-1H-benzoimidazole (see Boev, et al., *Pharm. Chem. J. (Engl. Transl.)*, vol. 24 (1990), pp. 818–822) and 2-(2-bromoacetyl)-5-chloro-3-methyl-benzo[b]thiophene provided 59% yield of yellow powder, mp 275–280° C.

$^1$H NMR (DMSO-$d_6$): δ 12.44 (1H, s), 10.86 (1H, s), 8.30 (2H, bs), 8.18 (1H, s), 8.02 (1H, d, J=8.4 Hz), 7.90 (1H, d, J=2.0 Hz), 7.86 (1H, bs), 7.55 (1H, d, J=8.4 Hz), 7.45 (1H, dd, J=8.7, 2.0 Hz), 7.25 (1H, d, J=8.7 Hz), 2.46 (3H, s).

ESIMS (MH$^+$): 440/442.

Anal. Calcd. for $C_{20}H_{14}N_5OS_2Cl \cdot 1.0H_2O$: C, 52.45; H, 3.52; N, 15.29; S, 14.00; Cl, 7.74. Found: C, 52.61; H, 3.60; N, 15.15; S, 14.12; Cl, 7.81.

Example C(11)

[4-Amino-2-(benzo[1,3]dioxol-5-yl-amino)-thiazol-5-yl]-(2-nitro-phenyl)-methanone

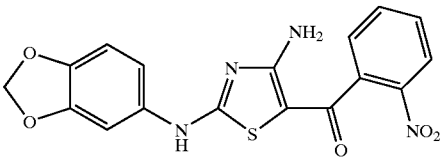

The title compound was prepared analogously to Example C(1). 3,4-Methylenedioxyphenyl isothiocyanate and 2-bromo-2'-nitro-acetophenone provided a yellow solid in 73% yield, mp 200.0–202.5° C.

$^1$H NMR (DMSO-$d_6$): δ$_6$ 10.69 (1H, s), 8.04 (2H, bs), 8.03 (1H, d, J=7.8 Hz), 7.78 (1H, dd, J=7.8, 6.5 Hz), 7.67 (1H, dd, J=7.2, 6.5 Hz), 7.63 (1H, d, J=7.2 Hz), 7.28 (1H, s), 6.89 (1H, d, J=8.9 Hz), 6.85 (1H, d, J=8.9 Hz), 6.00 (2H, s).

FABMS (MH$^+$): 385.

Anal. Calcd. for $C_{17}H_{12}N_4O_5S$: C, 53.12; H, 3.15; N, 14.58; S, 8.34. Found: C, 53.02; H, 3.20; N, 14.39; S, 8.27.

Example C(12)

[4-Amino-2-(4-methoxy-phenylamino)-thiazol-5-yl]-(2-iodo-phenyl)-methanone

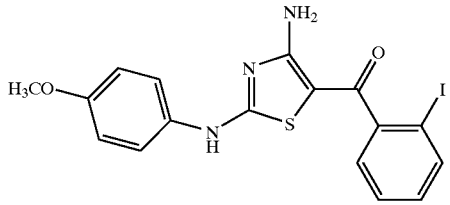

2-Bromo-2'-iodoacetophenone, which has the structural formula

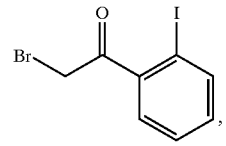

was first prepared as follows. According to a procedure of King et al., *J. Org. Chem*, vol. 29 (1964), pp. 3459–3461, to a solution of 2'-iodoacetophenone (3.54 g, 14.4 mmol) in EtOAc was added copper(II)bromide (6.34 g, 28.8 mmol), and the resulting mixture was heated at reflux for 90 minutes. The mixture was allowed to cool, and the solid was filtered off and rinsed with EtOAc. The filtrate was concentrated, providing 4.60 g (98% yield) of 2-bromo-2'-iodoacetophenone as a yellow oil, which matched previously reported material (Lutz et al., *J. Org. Chem.*, vol. 12 (1947), p. 617).

The title compound was next prepared essentially as described for Example C(1). 4-Methoxyphenyl isothiocyanate and 2-bromo-2'-iodoacetophenone provided a yellow solid in 71% yield, mp 187–190° C.

$^1$H NMR (DMSO-$d_6$): δ 10.56 (1H, s), 8.03 (2H, bs), 7.85 (1H, d, J=7.5 Hz), 7.32–7.48 (3H, m), 7.29 (1H, dd, J=7.5, 1.6 Hz), 7.12 (1H, td, J=7.5, 1.6 Hz), 6.90 (2H, d, J=9.0 Hz), 3.51 (3H, s).

FABMS (MH+): 452.

Anal. Calcd. for $C_{17}H_{14}N_3O_2SI.0.05C_6H_6.0.2EtOH$: C, 45.78; H, 3.36; N, 9.05; S, 6.90; I, 27.33. Found: C, 46.06; H, 3.54; N, 9.09; S, 7.04; I, 27.62.

Example C(13)

[4-Amino-2-(4-nitro-phenylamino)-thiazol-5-yl]-(2-nitro-phenyl)-methanone

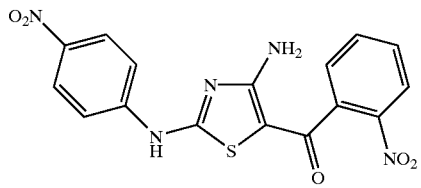

The title compound was prepared in a manner similar to that described for Example C(1). 4-Nitrophenyl isothiocyanate and 2-bromo-2'-nitroacetophenone provided a yellow solid in 45% yield, mp 266.0–268.2° C.

$^1$H NMR (DMSO-$d_6$): δ 10.80 (1H, s), 8.23 (2H, d, J=9.4 Hz), 8.15 (2H, bs), 8.08 (1H, d, J=8.1 Hz), 7.84 (2H, d, J=9.4 Hz), 7.83 (1H, t, J=7.5 Hz), 7.75–7.66 (2H, m).

FABMS (MH+): 386.

Anal. Calcd. for $C_{16}H_{11}N_5O_5S$: C, 49.87; H, 2.88; N, 18.17; S, 8.32. Found: C, 49.83; H, 2.90; N, 18.10; S, 8.27.

Example C(14)

(4-Amino-2-cyclohexylamino-thiazol-5-yl)-(2-nitro-phenyl)-methanone

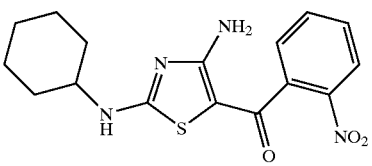

The title compound was prepared analogously to Example C(1). Cyclohexyl isothiocyanate and 2-bromo-2'-nitroacetophenone provided a yellow solid in 45% yield, mp 116–118° C.

$^1$H NMR (DMSO-$d_6$): δ 8.62 (1H, bs), 8.00 (1H, d, J=8.1 Hz), 7.97 (2H, bs), 7.75 (1H, dd, J=8.1, 7.5 Hz), 7.64 (1H, dd, J=8.1, 7.5 Hz), 7.59 (1H, d, J=7.5 Hz), 3.62 (1H, bs), 1.94–1.78 (2H, m), 1.73–1.60 (2H, m), 1.58–1.46 (1H, m), 1.32–1.02 (5H, m).

FABMS (MH+): 347.

Anal. Calcd. for $C_{16}H_{18}N_4O_3S.0.7H_2O$: C, 53.53; H, 5.45; N, 15.61; S, 8.93. Found: C, 53.79; H, 5.24; N, 15.44; S, 8.93.

Example C(15)

[4-Amino-2-(4-isopropyl-phenylamino)-thiazol-5-yl]-(2-nitro-phenyl)-methanone

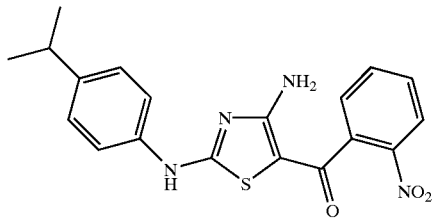

The title compound was prepared essentially as described for Example C(1). Isopropyl isothiocyanate and 2-bromo-2'-nitroacetophenone provided a yellow solid in 58% yield, mp 202.5–205.0° C.

$^1$H NMR (DMSO-$d_6$): δ 10.74 (1H, s), 8.05 (2H, bs), 8.03 (1H, d, J=7.5 Hz), 7.78 (1H, dt, J=7.5, 1.3 Hz), 7.71–7.60 (2H, m), 7.41 (2H, d, J=8.3 Hz), 7.20 (2H, d, J=8.3 Hz), 2.83 (1H, heptet, J=6.9 Hz), 1.16 (6H, d, J=6.9 Hz).

FABMS (MH+): 383.

Anal. Calcd. for $C_{19}H_{18}N_4O_3S$: C, 59.67; H, 4.74; N, 14.65; S, 8.38. Found: C, 59.62; H, 4.77; N, 14.56; S, 8.43.

Example C(16)

{4-Amino-2-[2-(4-chloro-phenyl)-ethylamino]-thiazol-5-yl}-(2-nitro-phenyl)-methanone

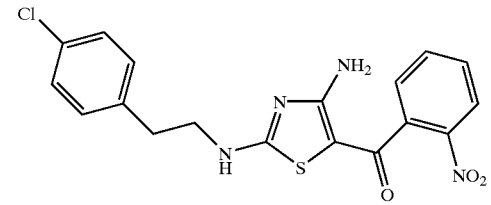

The title compound was prepared in a manner similar to that described for Example C(1). 4-Chlorophenethyl isothiocyanate and 2-bromo-2'-nitroacetophenone provided a yellow solid in 61% yield, mp 117–120° C.

$^1$H NMR (DMSO-$d_6$): δ 8.74 (1H, bs), 8.00 (1H, d, J=8.1 Hz), 7.95 (2H, bs), 7.75 (1H, td, J=7.5, 1.2 Hz), 7.64 (2H, td, J=8.1, 1.6 Hz), 7.57 (1H, dd, J=7.5, 1.2 Hz), 7.33 (2H, d, J=8.4 Hz), 7.23 (2H, d, J=8.4 Hz), 3.60–3.35 (2H, m), 2.81 (2H, t, J=6.8 Hz)

FABMS (MH+): 403.

Anal. Calcd. for $C_{18}H_{15}N_4O_3SCl.0.5EtOH$: C, 5 3.5 8; H, 4.26; N, 13.16; S, 7.5 3; Cl, 8.32. Found: C, 53.63; H, 4.33; N, 13.22; S, 7.47; Cl, 8.45.

Example C(17)

[4-Amino-2-(4-diethylamino-phenylamino)-thiazol-5-yl]-(2-nitro-phenyl)-methanone

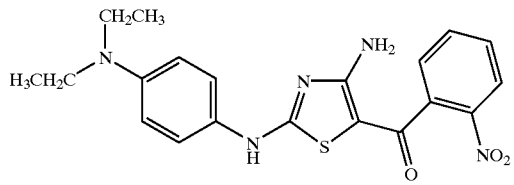

The title compound was prepared in a manner like that described for Example C(1). 4-Diethylaminophenyl isothiocyanate and 2-bromo-2'-nitroacetophenone provided a yellow solid in 63% yield, mp 202.5–205.0° C.

$^1$H NMR (DMSO-d$_6$): δ 10.45 (1H, s), 8.01 (1H, d, J=8.1 Hz), 7.97 (2H, bs), 7.75 (1H, dd, J=8.1, 7.8 Hz), 7.64 (1H, dd, J=8.1, 7.8 Hz), 7.59 (1H, d, J=7.8 Hz), 7.18 (2H, d, J=9.0 Hz), 6.61 (2H, d, J=9.0 Hz), 3.28 (4H, q, J=7.2 Hz), 1.05 (6H, t, J=7.2 Hz).

FABMS (MH$^+$): 412.

Anal. Calcd. for C$_{20}$H$_{21}$N$_5$O$_3$S: C, 58.38; H, 5.14; N, 17.02; S, 7.79. Found: C, 58.28; H, 5.20; N, 16.77; S, 7.94.

Example C(18)

[4-Amino-2-(4-diethylamino-phenylamino)-thiazol-5-yl]-(4-nitro-phenyl)-methanone

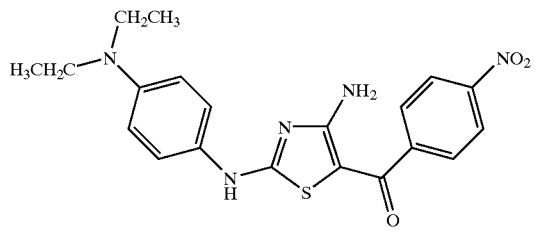

The title compound was prepared in a manner analogous to that described for Example C(1). 4-Diethylaminophenyl isothiocyanate and 2-bromo-4'-nitroacetophenone provided a yellow solid in 63% yield, mp 220–221° C.

$^1$H NMR (DMSO-d$_6$): δ 10.51 (1H, s), 8.42 (2H, bs), 8.26 (2H, d, J=12.0 Hz), 7.84 (2H, d, J=12.0 Hz), 7.22 (2H, d, J=9.0 Hz), 6.63 (2H, d, J=9.0 Hz), 3.26 (4H, q, J=6.8 Hz), 1.05 (6H, t, J=6.8 Hz).

FABMS (MH$^+$): 412.

Anal. Calcd. for C$_{20}$H$_{21}$N$_5$O$_3$S: C, 58.38; H, 5.14; N, 17.02; S, 7.79. Found: C, 58.23; H, 5.16; N, 16.94; S, 7.86.

Example C(19)

[4-Amino-2-(1H-benzoimidazol-6-ylamino)-thiazol-5-yl]-(3-methyl-thiophen-2-yl)-methanone

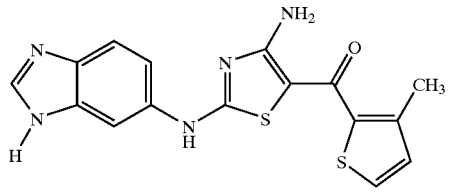

The title compound was prepared essentially in the manner described for Example C(1). 6-Isothiocyanato-1H-benzoimidazole (see Boev et al., *Pharm. Chem. J.* (*Engl. Transl*)., vol. 24 (1990), pp. 818–822) and 2-(2-bromoacetyl)-3-methyl-thiophene (U.S. Pat. No. 5,189,049; an acetyl brominated with copper(II)bromide according to a procedure from King, et al., *J. Org. Chem.*, Vol. 29 (1964), pp. 3459–3461; representative procedure in Example C(19)) provided 67% yield of yellow powder, mp 285–287° C.

$^1$H NMR (DMSO-d$_6$): δ 12.60 (1H, bs), 10.78 (1H, s), 8.23 (1H, s), 8.17 (2H, bs), 7.93 (1H, s), 7.56 (1H, d, J=8.7 Hz), 7.55 (1H, d, J=5.0 Hz), 7.27 (1H, dd, J=8.7, 1.9 Hz), 6.60 (1H, d, J=5.0 Hz), 2.36 (3H, s).

FABMS (MH$^+$): 356.

Anal. Calcd. for C$_{16}$H$_{13}$N$_5$OS$_2$.0.6H$_2$O: C, 52.47; H, 3.91; N, 19.12; S, 17.51. Found: C, 52.50; H, 3.90; N, 19.10; S, 17.71.

Example C(20)

[4-Amino-2-(1H-benzoimidazol-6-ylamino)-thiazol-5-yl]-(2,4-dimethyl-phenyl)-methanone

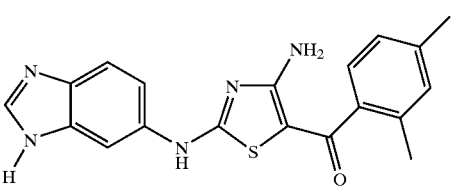

The title compound was prepared in a manner similar to that described for Example C(1). 6-Isothiocyanato-1H-benzoimidazole (see Boev et al., *Pharm. Chem. J.* (*Engl. Transl.*), vol. 24 (1990), pp. 818–822) and 2-bromo-2',4'-dimethylacetophenone provided 77% yield of yellow powder, mp 290–292° C.

$^1$H NMR (DMSO-d$_6$): δ 12.43 (1H, bs), 10.65 (1H, s), 8.18 (1H, s), 8.00 (2H, bs), 7.80 (1H, s), 7.54 (1H, d, J=8.7 Hz), 7.20 (1H, d, J=8.7 Hz), 7.16 (1H, d, J=7.5 Hz), 7.03 (1H, s), 6.99 (1H, d, J=7.5 Hz), 2.26 (3H, s), 2.22 (3H, s).

FABMS (MH$^+$): 364.

Anal. Calcd. for C$_{19}$H$_{17}$N$_5$OS: C, 62.79; H, 4.71; N, 19.27; S, 8.82. Found: C, 62.50; H, 4.78; N, 19.22; S, 8.72.

Example C(21)

[4-Amino-2-(pyridin-3-ylamino)-thiazol-5-yl]-(2,4-dimethyl-phenyl)-methanone

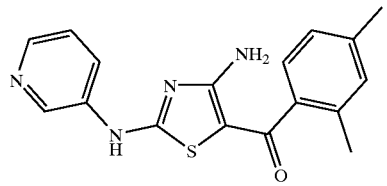

The title compound was prepared in a manner similar to that described for Example C(1). 3-Pyridyl-isothiocyanate and 2-bromo-2',4'-dimethylacetophenone provided 63% yield of yellow powder, mp 200–202° C.

$^1$H NMR (DMSO-d$_6$): δ 10.82 (1H, s), 8.76 (1H, d, J=2.5 Hz), 8.25 (1H, d, J=4.1 Hz), 8.06 (1H, d, J=8.4 Hz), 8.04 (2H, bs), 7.36 (1H, dd, J=8.4, 4.1 Hz), 7.21 (1H, d, J=7.5 Hz), 7.06 (1H, s), 7.02 (1H, d, J=7.5 Hz), 2.28 (3H, s), 2.23 (3H, s).

FABMS (MH$^+$): 325.

Anal. Calcd. for C$_{17}$H$_{16}$N$_4$OS: C, 62.94; H, 4.97; N, 17.27; S, 9.88. Found: C, 62.86; H, 5.03; N, 17.17; S, 9.95.

Example C(22)

3-[4-Amino-5-(2-cyano-benzoyl)-thiazol-2-ylamino]-benzonitrile

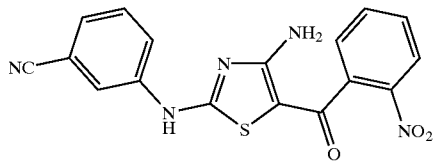

The title compound was prepared essentially as described for Example C(1). 3-Cyanophenyl isothiocyanate and 2-bromo-2'-nitro-acetophenone furnished an orange solid in 94% yield, mp 235–236° C.

$^1$H NMR (DMSO-d$_6$): δ 8.26 (1H, bs), 8.06 (1H, d, J=8.0 Hz), 7.8 (1H, t, J=7.0 Hz), 7.74–7.64 (3H, m), 7.58–7.48 (2H, m).

IR (KBr): 3460, 3307, 3271, 3083, 2214, 1625, 1601, 1525 cm$^{-1}$.

Anal. Calcd. For C$_{17}$H$_{11}$N$_5$O$_3$S: C, 55.80; H, 3.03; N, 19.17; S, 8.78. Found: C, 55.70; H, 3.05; N, 19.01; S, 8.73.

Example C(23)

[4-Amino-2-(3-methoxy-propylamino)-thiazol-5-yl]-(2-nitro-phenyl)-methanone

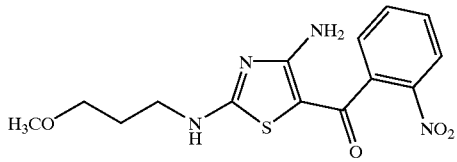

The title compound was prepared analogously to Example C(1). 3-Methoxypropyl isothiocyanate and 2-bromo-2'-nitro-acetophenone furnished a yellow solid in 90% yield, mp 170–172° C.

$^1$H NMR (DMSO-d$_6$): δ 8.02–7.92 (2H, m), 7.4 (1H, t, J=7.0 Hz), 7.68–7.56 (2H, m), 3.38–3.22 (7H, m), 1.78–1.66 (2H, m).

Anal. Calcd. for C$_{14}$H$_{16}$N$_4$O$_4$S: C, 49.99; H, 4.79; N, 16.66; S, 9.53. Found: C, 50.04; H, 4.81; N, 16.69; S, 9.61.

Example C(24)

1-{4-[4-Amino-5-(2-nitro-benzoyl)-thiazol-2-ylamino]-phenyl}-ethanone

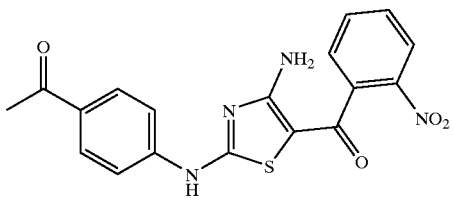

The title compound was prepared in a manner similar to Example C(1). 4-Acetylphenyl isothiocyanate and 2-bromo-2'-nitro-acetophenone furnished a yellow solid in 87% yield, mp 264–265° C.

$^1$H NMR (DMSO-d$_6$): δ 8.06 (1H, d, J=8.0 Hz), 7.92 (2H, d, J=9.0 Hz), 7.84–7.78 (1H, m), 7.73–7.64 (4H, m), 2.42 (3H, s).

IR (KBr): 3389, 3248, 1690, 1655, 1537, 1472, 1420, 1273 cm$^{-1}$.

Anal. Calcd. for C$_{18}$H$_{14}$N$_4$O$_4$S: C, 56.54; H, 3.69; N, 14.65; S, 8.39. Found: C, 56.39; H, 3.73; N, 14.44; S, 8.31.

Example C(25)

{4-Amino-2-[4-(2-chloro-5-trifluoromethyl-pyridin-2-yl sulfanyl)-phenylamino]-thiazol-5-yl}-(2-nitro-phenyl)-methanone

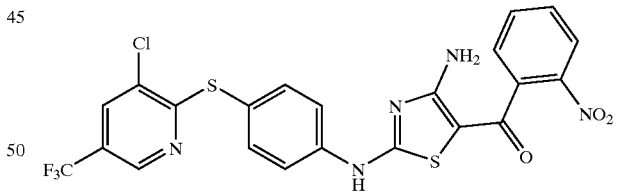

The title compound was prepared in a manner similar to that described for Example C(1). 2-[4-(2-Chloro-5-trifluoromethyl-pyridine-2-yl-sulfanyl)-phenyl] isothiocyanate and 2-bromo-2'-nitro-acetophenone furnished an orange solid in 52% yield, mp 150–152° C.

$^1$H NMR (DMSO-d$_6$): δ 8.65 (1H, bs), 8.38 (1H, bs), 8.06 (2H, d, J=8.0 Hz), 7.80 (1H, t, J=7.0 Hz), 7.74–7.64 (4H, m), 7.54 (2H, d, J=8.0 Hz).

IR (KBr): 3272, 3048, 1596, 1531, 1431, 1320 cm$^{-1}$.

Anal. Calcd. for C$_{22}$H$_{13}$ClF$_3$N$_5$O$_3$S$_2$: C, 47.87; H, 2.37; N, 12.69; S, 11.62; Cl, 6.42. Found: C, 47.79; H, 2.44; N, 12.54; S, 11.70; Cl, 6.52.

Example C(26)

Methyl 3-[4-Amino-5-(2-methoxy-benzoyl)-thiazol-2-ylamino]-benzoate

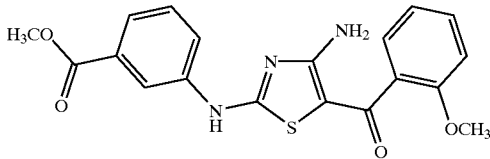

The title compound was prepared essentially as described for Example C(1). 3-Methoxycarbonylphenyl isothiocyanate and 2-bromo-2'-methoxy-acetophenone gave an ivory solid in 59% yield, mp 214–215° C.

$^1$H NMR (DMSO-d$_6$): δ 10.81 (1H, s), 8.12–7.90 (4H, m), 7.62 (1H, ddd, J=7.8, 1.2, 1.2 Hz), 7.49 (1H, t, J=7.9 Hz), 7.39 (1H, ddd, J=8.7, 8.7, 1.7 Hz), 7.25 (1H, dd, J=7.5, 1.9 Hz), 7.09 (1H, d, J=8.4 Hz), 6.98 (1H, ddd, J=7.5, 7.5, 0.6 Hz), 3.85 (3H, s), 3.87 (3H, s).

FABMS (MH$^+$): 327.

IR (KBr): 3473, 3333, 3261, 3092, 1718, 1602, 1527, 1417, 1294 cm$^{-1}$. Anal. Calcd. for C$_{19}$H$_{17}$N$_3$O$_4$S: C, 59.52; H, 4.47; N, 10.96; S, 8.36. Found: C, 59.41; H, 4.46; N, 10.93; S, 8.38.

Example C(27)

{4-Amino-2-[2-(4-chloro-phenyl)-ethylamino]-thiazol-5-yl}-(2-methoxy-phenyl)-methanone

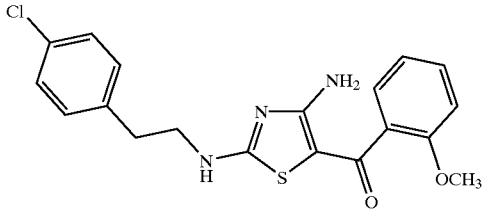

The title compound was prepared in a manner like that described for Example C(1). The product from 4-chlorophenethyl isothiocyanate and 2-bromo-2'-methoxy-acetophenone was extracted with 10% i-PrOH/CHCl$_3$. The resultant solid was washed with Et$_2$O to give an ivory solid in 49% yield, mp 150–151° C.

$^1$H NMR (DMSO-d$_6$): δ 8.53 (2H, bs), 7.87 (1H, bs), 7.39–7.28 (3H, m), 7.23 (2H, d, J=8.4 Hz), 7.17 (1H, dd, J=7.5, 1.6 Hz), 7.03 (1H, d, J=8.4 Hz), 6.93 (1H, t, J=7.5 Hz), 3.88 (3H, s), 3.40 (2H, bs), 2.81 (2H, t, J=7.0 Hz).

FABMS (MH$^+$): 388.

IR (KBr): 3354, 3214, 3166, 3103, 1600, 1578, 1544, 1525, 1462, 1363 cm$^{-1}$.

Anal. Calcd. for C$_{19}$H$_{18}$ClN$_3$O$_2$S: C, 58.83; H, 4.68; N, 10.83; S, 8.27. Found: C, 58.70; H, 4.62; N, 10.75; S, 8.25.

Example C(28)

[4-Amino-2-(pyridin-3-ylamino)-thiazol-5-yl]-(2,4-dichloro-phenyl)-methanone

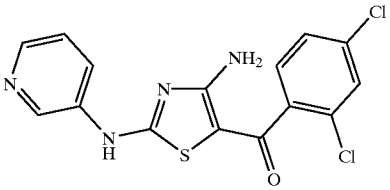

The title compound was prepared in a manner similar to that described for Example C(1). 3-Pyridyl-isothiocyanate and 2,2',4'-trichloroacetophenone gave a yellow solid in 39% yield, mp 209–210° C.

$^1$H NMR (DMSO-d$_6$): δ 10.95 (1H, s), 8.77 (1H, d, J=2.5 Hz), 8.28 (1H, dd, J=4.7, 1.6 Hz), 8.16 (2H, bs), 8.06 (1H, bd, J=9.6 Hz), 7.70 (1H, d, J=1.6 Hz), 7.48 (2H, dd, J=11.5, 8.1 Hz), 7.37 (1H, dd, J=8.4, 4.7 Hz).

FABMS (MH+): 365.

IR (KBr): 3378, 3272, 3175, 3072, 1608, 1586, 1561, 1525, 1424 cm$^{-1}$.

Anal. Calcd. for C$_{15}$H$_{10}$Cl$_2$N$_4$OS.0.9H$_2$O: C, 47.23; H, 3.12; N, 14.69; S, 8.41. Found: C, 47.03; H, 3.09; N, 14.52; S, 8.42.

Example C(29)

[4-Amino-2-(pyridin-3-ylamino)-thiazol-5-yl]-(2-methoxy-phenyl)-methanone

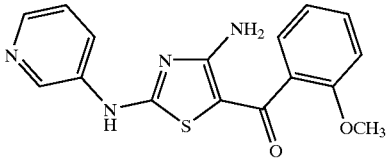

The title compound was prepared in a manner analogous to Example C(1). 3-Pyridyl-isothiocyanate and 2-bromo-2'-methoxy-acetophenone gave an off-white/ivory solid in 67% yield, mp 245–246° C.

$^1$H NMR (DMSO-d$_6$): δ 10.80 (1H, s), 8.77 (1H, d, J=2.8 Hz), 8.25 (1H, dd, J=4.7, 1.2 Hz), 8.07 (1H, ddd, J=8.4, 2.8, 1.6 Hz), 8.00 (2H, bs), 7.44–7.33 (2H, m), 7.24 (1H, dd, J=7.5, 1.6 Hz), 7.09 (1H, d, J=8.1 Hz), 6.98 (1H, t, J=7.5 Hz), 3.76 (3H, s).

FABMS (MH$^+$): 327.

IR (KBr): 3424, 3310, 2971, 1632, 1603, 1526, 1459, 1405 cm$^{-1}$.

Anal. Calcd. for C$_{16}$H$_{14}$N$_4$O$_2$S: C, 58.88; H, 4.32; N, 17.17; S, 9.82. Found: C, 58.84; H, 4.33; N, 17.07; S, 9.90.

Example C(30)

[4-Amino-2-(pyridin-3-ylamino)-thiazol-5-yl]-naphthalen-2-yl-methanone

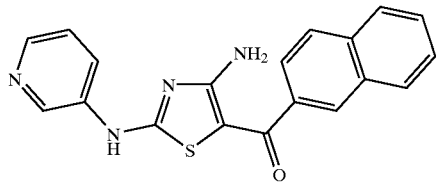

The title compound was prepared essentially as described for Example C(1). 3-Pyridyl-isothiocyanate and 2-bromo-2'-acetonaphthone gave, after recrystallization from EtOH, a yellow solid in 12% yield, mp 242–243° C. (decomp.).

$^1$H NMR (DMSO-d$_6$): δ 10.97 (1H, s), 8.82 (1H, d, J=2.5 Hz), 8.36–8.18 (3H, m), 8.13 (1H, ddd, J=8.4, 4.0, 1.6 Hz), 8.08–7.93 (2H, m), 7.77 (1H, dd, J=8.4, 1.6 Hz), 7.60 (2H, ddd, J=14.3, 10.6, 7.9, 2.2 Hz), 7.39 (1H, dd, J=8.4, 5.0 Hz).

FABMS (MH$^+$): 347.

IR (KBr): 3462, 3316, 3261, 3071, 1623, 1584, 1531, 1421 cm$^{-1}$.

Anal. Calcd. for C$_{19}$H$_{14}$N$_4$OS: C, 65.88; H, 4.07; N, 16.17; S, 9.26. Found: C, 65.80; H, 4.09; N, 16.09; S, 9.34.

Example C(31)

[4-Amino-2-(2-methoxy-benzylamino)-thiazol-5-yl]-(5-chloro-benzofuran-2-yl)-methanone

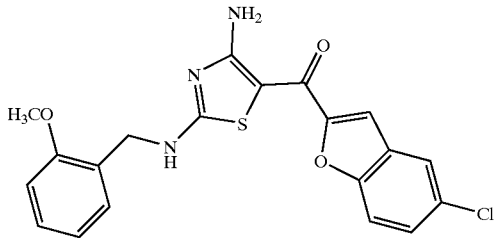

The title compound was prepared in a manner similar to that described for Example C(1). 2-Methoxybenzyl isothiocyanate and 2-bromoacetyl-5-chlorobenzofuran provided 62% yield of yellow powder, mp 241–242° C.

$^1$H NMR (DMSO-d$_6$): δ 9.17 (1H, bs), 8.78 (1H, bs), 8.21 (1H, bs), 7.83 (1H, d, J=2.2 Hz), 7.66 (1H, d, J=9.0 Hz), 7.44 (1H, dd, J=9.0, 2.2 Hz), 7.39 (1H, s), 7.28 (1H, d, J=8.1 Hz), 7.25 (1H, dd, J=7.5, 7.2 Hz), 7.01 (1H, d, J=8.1 Hz), 6.92 (1H, dd, J=7.5, 7.2 Hz), 4.51 (2H, bs), 3.82 (3H, s).

FABMS (MH$^+$): 414/416.

Anal. Calcd. for C$_{20}$H$_{16}$N$_3$O$_3$ClS: C, 58.04; H, 3.90; N, 10.15; S, 7.75; Cl, 8.57. Found: C, 57.97; H, 3.85; N, 10.11; S, 7.85; Cl, 8.63.

Example C(32)

[4-Amino-2-(1H-benzoimidazol-6-ylamino)-thiazol-5-yl]-(2-methoxy-phenyl)-methanone

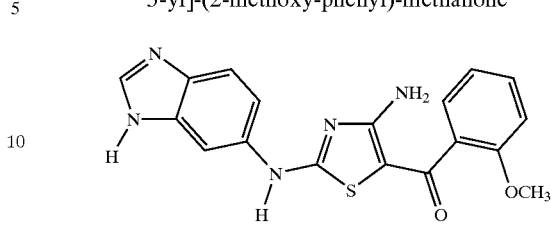

The title compound was prepared in a manner analogous to that described for Example C(1). 6-Isothiocyanato-1H-benzoimidazole (see Boev et al., *Pharm. Chem. J.* (*Engl. Transl.*), vol. 24 (1990), pp. 818–822) and 2-bromo-2'-methoxyacetophenone provided 72% yield of amorphous yellow powder, mp 180–185° C. (decomp.).

$^1$H NMR (DMSO-d$_6$): δ 12.40 (1H, bs), 10.61 (1H, bs), 8.16 (1H, s), 7.94 (2H, bs), 7.83 (1H, bs), 7.53 (1H, d, J=8.4 Hz), 7.36 (1H, ddd, J=8.4, 7.6, 1.6 Hz), 7.24–7.16 (2H, m), 7.05 (1H, d, J=8.1 Hz), 6.95 (1H, dd, J=7.6, 7.2 Hz), 3.74 (3H, s).

FABMS (MH$^+$): 366.

Anal. Calcd. for C$_{18}$H$_{15}$N$_5$O$_2$S.0.5H$_2$O: C, 57.74; H, 4.31; N, 18.71; S, 8.56. Found: C, 57.78; H, 4.29; N, 18.64; S, 8.53.

Example C(33)

4-[4-Amino-5-(2,4-dimethoxy-benzoyl)-thiazol-2-ylamino]-benzenesulfonamide

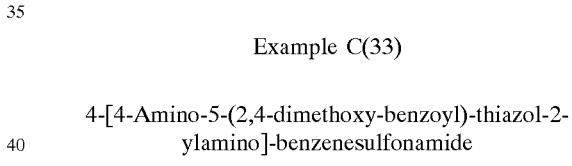

The title compound was prepared essentially as described for Example C(1). 4-Isothiocyanato-benzenesulfonamide and 2-bromo-2',4'-dimethoxyacetophenone provided 75% yield of yellow powder, mp 249–250° C.

$^1$H NMR (DMSO-d$_6$): δ 10.93 (1H, bs), 7.93 (2H, bs), 7.75 (4H, bs), 7.25 (2H, bs), 7.21 (1H, d, J=8.1 Hz), 6.61 (1H, d, J=1.9 Hz), 6.55 (1H, dd, J=8.1, 1.9 Hz), 3.79 (3H, s), 3.76 (3H, s).

FABMS (MH$^+$): 435.

Anal. Calcd. for C$_{18}$H$_{18}$N$_4$O$_5$S$_2$: C, 49.76; H, 4.18; N, 12.89; S, 14.76. Found: C, 49.66; H, 4.15; N, 12.77; S, 14.86.

Example C(34)

Ethyl 4-[4-Amino-2-(4-sulfamoyl-phenylamino)-thiazole-5-carbonyl]-benzoate

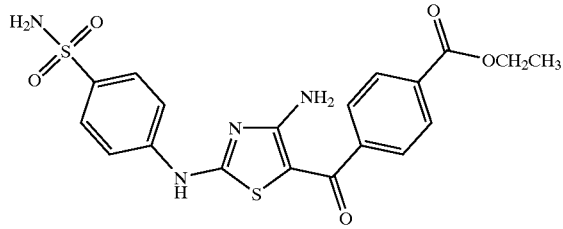

The title compound was prepared substantially as described for Example C(1). 4-Isothiocyanato-benzenesulfonamide and ethyl 4-bromoacetyl-benzoate provided 95% yield of yellow powder, mp 225–227° C.

$^1$H NMR (DMSO-d$_6$): δ 11.16 (1H, s), 8.32 (2H, bs), 8.04 (2H, d, J=8.4 Hz), 7.80 (2H, d, J=8.4 Hz), 7.78 (4H, bs), 7.26 (2H, bs), 4.33 (2H, q, J=7.2 Hz), 1.33 (3H, t, J=7.2 Hz).

FABMS (MH$^+$): 447.

Anal. Calcd. for C$_{19}$H$_{18}$N$_4$O$_5$S$_2$.0.4H$_2$O: C, 50.30; H, 4.18; N, 12.38; S, 14.13. Found: C, 50.11; H, 3.97; N, 12.26; S, 14.14.

Example C(35)

4-[4-Amino-5-(2,4-dimethyl-benzoyl)-thiazol-2-ylamino]-benzenesulfonamide

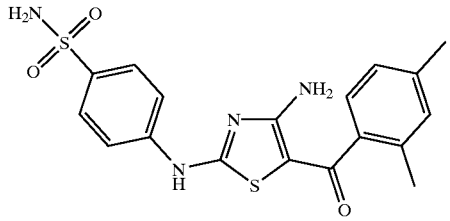

The title compound was prepared essentially as described for Example C(1). 4-Isothiocyanatobenzenesulfonamide and 2-bromo-2',4'-dimethylacetophenone furnished a yellow solid in 75% yield, mp 242–244° C.

$^1$H NMR (DMSO-d$_6$): δ 10.97 (1H, bs), 8.00 (2H, bs), 7.76 (2H, d, J=9.7 Hz), 7.72 (2H, d, J=9.7 Hz), 7.24 (2H, bs), 7.22 (1H, d, J=7.5 Hz), 7.07 (1H, s), 7.03 (1H, d, J=7.5 Hz), 2.29 (3H, s), 2.23 (3H, s).

FABMS (MH$^+$): 403.

Anal. Calcd. for C$_{18}$H$_{18}$N$_4$O$_3$S$_2$: C, 53.71; H, 4.51; N, 13.92; S, 15.93. Found: C, 53.47; H, 4.54; N, 13.69; S, 15.83.

Example C(36)

{4-Amino-2-[4-(2-chloro-5-trifluoromethyl-pyridine-2-yl sulfanyl)-phenylamino]-thiazol-5-yl}-(2,6-dichloro-4-trifluoromethyl-phenyl)-methanone

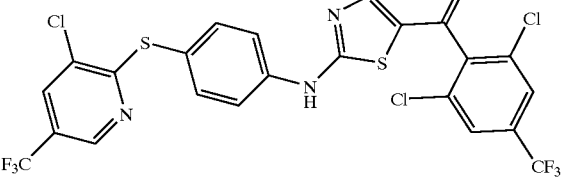

The title compound was prepared essentially as described for Example C(1). 2-[4-(2-Chloro-5-trifluoromethyl-pyridin-2-yl-sulfanyl)-phenyl]isothiocyanate and 2-bromo-2',6'dichloro-4'-trifluoromethyl-acetophenone furnished an orange solid in 52% yield, mp 130–132° C.

$^1$H NMR (DMSO-d$_6$): δ 8.65 (1H, bs), 8.38 (1H, bs), 8.06 (2H, d, J=8.0 Hz), 7.80 (1H, t, J=7.0 Hz), 7.74–7.64 (4H, m), 7.54 (2H, d, J=8.0 Hz).

IR (KBr): 3272, 3048, 1596, 1531, 1431, 1320 cm$^{-1}$.

Anal. Calcd. for C$_{22}$H$_{13}$ClF$_3$N$_5$O$_3$S$_2$: C, 47.87; H, 2.37; N, 12.69; S, 11.62; Cl, 6.42; Found: C, 47.79; H, 2.44; N, 12.54; S, 11.70; Cl, 6.52.

Example C(37)

[4-Amino-2-(1H-benzoimidazol-6-ylamino)-thiazol-5-yl]-(2,6-dichloro-4-trifluoromethyl-phenyl)-methanone

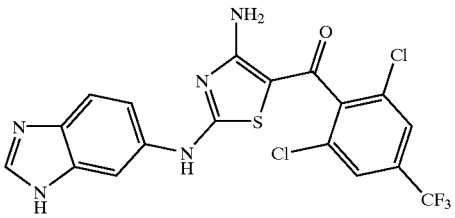

The title compound was prepared in a manner analogous to that described for Example C(1). 6-Isothiocyanato-1H-benzoimidazole (see Boev et al,. *Pharm. Chem J.* (*Engl. Transl.*), vol. 24 (1990), pp. 818–822) and 2-bromo-2',6'-dichloro-4'-trifluoromethyl-acetophenone gave a yellow solid in 56% yield that decomposed at a temperature above 180° C.

$^1$H NMR (DMSO-d$_6$): δ 12.45 (1H, bd, J=16.0 Hz), 11.10–10.80 (1H, m), 8.20 (1H, s), 8.00 (2H, s), 7.70–7.45 (2H, m), 7.20 (1H, d, J=8.0 Hz).

IR (KBr): 3191, 2974, 1619, 1559, 1467, 1309 cm$^{-1}$.

FABMS (MH$^+$): 472.

Anal. Calcd. for C$_{18}$H$_{10}$C$_{12}$F$_3$N$_5$OS.0.6HOAc.0.1CH$_2$Cl$_2$.H$_2$O: C, 45.58; H, 2.95; N, 12.18; S, 5.69; Cl, 13.92. Found: C, 45.70; H, 3.05; N, 12.45; Cl, 13.87.

Example C(38)

4-[4-Amino-5-(2,6-dichloro-4-trifluoromethyl-benzoyl)-thiazol-2-ylamino]-benzenesulfonamide

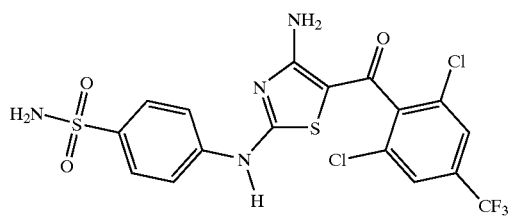

The title compound was prepared essentially as described for Example C(1). 4-Isothiocyanatobenzenesulfonamide and 2-bromo-2',6'-dichloro-4'-(trifluoromethyl)acetophenone furnished, after recrystallization from EtOH/H$_2$O and drying via benzene azeotrope, a yellow solid in 46% yield, mp 294–296° C.

$^1$H NMR (DMSO-d$_6$): δ 8.10 (1H, s), 8.05 (2H, s) 7.77 (4H, dd, J=9.0, 14.0 Hz).

HRFABMS: Calcd. for C$_7$H$_{12}$Cl$_2$F$_3$N$_4$O$_3$S$_2$ (MH$^+$): 510.9680. Found: 510.9697.

Anal. Calcd. for C$_{17}$H$_{11}$Cl$_2$F$_3$N$_4$O$_3$S$_2$.0.1H$_2$O.C$_6$H$_6$: C, 40.28; H, 2.51; N, 10.30; S, 11.97; Cl, 13.51. Found: C, 40.58; H, 2.28; N, 10.75; S, 12.31; Cl, 13.61.

Example C(39)

Phenyl 4-[4-Amino-2-(4-sulfamoyl-phenylamino)-thiazole-5-carbonyl]-benzoate

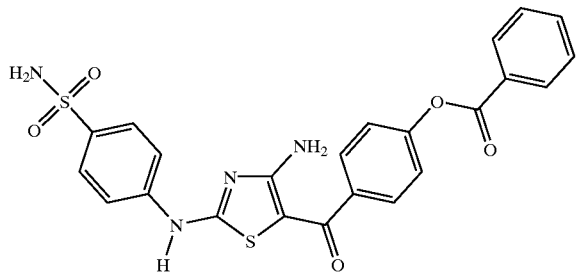

The title compound was prepared in a manner analogous to that used in Example C(1). 4-Isothiocyanato-benzenesulfonamide and 4-(bromoacetyl)-phenyl benzoate provided a yellow solid in 77% yield, mp >300° C.

$^1$H NMR (DMSO-d$_6$): δ 11.13 (1H, s), 8.26 (2H, bs), 8.15 (2H, dd, J=7.2, 1.6 Hz), 7.83–7.73 (7H, m), 7.66–7.59 (2H, m), 7.41 (2H, d, J=6.9 Hz), 7.27 (2H, s).

HRFABMS (MH$^+$): Calcd.: 495.0797. Found: 495.0812.

Anal. Calcd. for C$_{23}$H$_{18}$N$_4$O$_5$S$_2$.0.2H$_2$O: C, 55.45; H, 3.72; N, 11.25; S, 12.87. Found: C, 55.34; H, 3.592; N, 11.01; S, 12.88.

Example C(40)

[4-Amino-2-(4-methoxy-phenylamino)-thiazol-5-yl]-(4-methyl-1H-imidazol-5-yl)-methanone

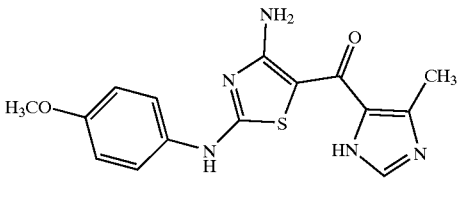

5-Bromoacetyl-4-methyl-1H-imidazole, which has the structural formula

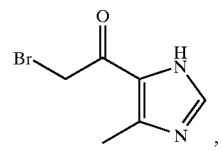

was first prepared as follows. Bromine (0.40 mL, 7.77 mmol) was added dropwise to a solution of 5-acetyl-4-methyl-1H-imidazole (964 mg, 7.77 mmol; LaMattina et al, J. Org. Chem., vol. 48 (1983), pp. 897–898) in HOAc (20 mL). After two days, the HOAc was removed in vacuo and the residue partitioned with CH$_2$Cl$_2$ and sat. aq. NaHCO$_3$. The organic layer was washed with brine, dried over Na$_2$SO$_4$, and evaporated to provide a light brown solid, 625 mg (40% yield), which was used without further purification.

$^1$H NMR (DMSO-d$_6$): δ 12.65 (1H, bs), 7.67 (1H, s), 4.62 (2H, s), 2.44 (3H, s).

The title compound was prepared in a manner analogous to that used in Example C(1). 4-Methoxy-phenyl isothiocyanate and 5-bromoacetyl-4-methyl-1H-imidazole provided a yellow powder in 57% yield, mp 248–50° C.

$^1$H NMR (DMSO-d$_6$): δ 12.28 (1H, bs), 10.21 (1H, s), 8.00 (2H, bs), 7.56 (1H, s), 7.49 (2H, d, J=9.0 Hz), 6.94 (2H, d, J=9.0 Hz), 3.75 (3H, s), 2.50 (3H, s).

HRFABMS (M+Na$^+$): Calcd.: 352.0844. Found: 352.0840.

Anal. Calcd. for C$_{15}$H$_{15}$N$_5$O$_2$S.0.5H$_2$O: C, 53.24; H, 4.77; N, 20.70; S, 9.48. Found: C, 53.43; H, 4.78; N, 20.54; S, 9.38.

Example C(41)

[4-Amino-2-(4-imidazol-1-yl-phenylamino)-thiazol-5-yl]-(2,4-dimethyl-phenyl)-methanone

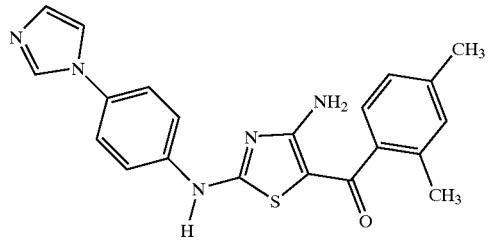

1-(4-Isothiocyanato-phenyl)-1H-imidazole, which has the structural formula

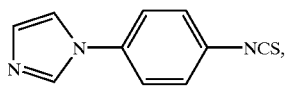

was first prepared as follows. To a solution of 1-(4-aminophenyl)-1H-imidazole (1.00 g, 6.30 mmol; Venuti et al, *J. Med. Chem.*, vol. 31 (1988), pp. 2136–2145) in acetone (10 mL) at 0° C. was simultaneously added a solution of thiophosgene (580 μL, 7.6 mmol) in acetone (15 mL) and a solution of 25% aq. $Na_2CO_3$ (15 mL). The mixture was stirred at 0° C. for 0.5 hour and allowed to warm to room temperature over 1.5 hour. The acetone was removed under reduced pressure and the residue diluted with $H_2O$. The cream-colored precipitate was filtered off, washed with $H_2O$, and dried under high vacuum to give 1.20g (95% crude yield) of a light tan solid, which was used without further purification.

$^1$H NMR (DMSO-$d_6$): δ 8.33 (1H, s), 7.81 (1H, s), 7.76 (2H, d, J=8.8 Hz), 7.61 (2H, d, J=8.8 Hz), 7.12 (1H, s).

The title compound was prepared in a manner like that described for Example C(1). 1-(4-Isothiocyanato-phenyl)-1H-imidazole and 2-bromo-2',4'-dimethyl-acetophenone provided a yellow solid in 14% yield, mp 180.0–180.5° C.

$^1$H NMR (DMSO-$d_6$): δ 10.80 (1H, s), 8.10 (1H, s), 8.02 (1H, bs), 7.68 (2H, d, J=7.5 Hz), 7.58 (2H, d, J=9.0 Hz), 7.20 (1H, d, J=7.8 Hz), 7.10–7.00 (2H, m), 2.28 (3H, s), 2.24 (3H, s).

IR (KBr): 3393, 3119, 2925, 1612, 1566, 1524, 1425 cm$^{-1}$.

FABMS (MH$^+$): 390.

Anal. Calcd. for $C_{21}H_{19}N_5OS.0.2H_2O$: C, 64.17; H, 4.97; N, 17.82; S, 8.16. Found: C, 64.14; H, 4.98; N, 17.68; S, 8.21.

Example C(42)

[4-Amino-2-(4-imidazol-1-yl-phenylamino)-thiazol-5-yl]-(3-methyl-thiophen-2-yl)-methanone

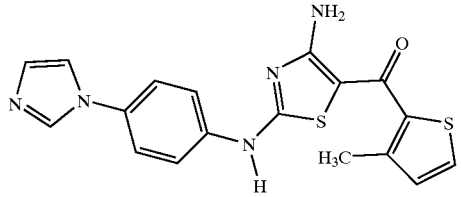

The title compound was prepared in a manner like that described for Example C(1). 1-(4-Isothiocyanato-phenyl)-1H-imidazole (from Example C(41)) and 2-bromoacetyl-3-methyl-thiophene (from Example C(19)) provided a yellow solid in 83% yield, mp >300° C.

$^1$H NMR (DMSO-$d_6$): δ 10.98 (1H, s), 8.25 (1H, s), 8.18 (1H, bs), 7.77 (1H, s), 7.72 (2H, J=6.5 Hz), 7.65 (1H, s), 7.62 (2H, J=4.7), 7.10 (1H, s), 6.98 (1H, d, J=5.0 Hz), 2.28 (3H, s).

IR (KBr): 3402, 3278, 3103, 2982, 1609, 1523, 1422, 1306 cm$^{-1}$.

Anal. Calcd. for $C_{17}H_{16}N_5OS_2$: C, 56.67; H, 3.96; N, 18.36; S, 16.81. Found: C, 56.38; H, 4.06; N, 18.13; S, 16.67.

Example C(43)

[4-Amino-2-(1H-benzimidazol-5-ylamino)-thiazol-5-yl]-(1-methyl-1H-pyrrol-2-yl)-methanone

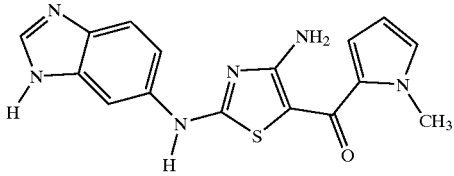

The title compound was prepared in a manner analogous to that used in Example C(1). 6-Isothiocyanato-1H-benzoimidazole (see Boev et al., *Pharm. Chem. J.* (*Engl. Transl*)., vol. 24 (1990), pp. 818–822) and 2-chloroacetyl-N-methyl-pyrrole (Croce et al., *Synthesis* (1990), pp. 212–213) provided a yellow solid in 42% yield, mp 284–285° C.

$^1$H NMR (DMSO-$d_6$): δ 12.43 (1H, bs), 10.65 (1H, bs), 8.18 (1H, s), 7.94 (3H, bs), 7.55 (1H, d, J=8.7 Hz), 7.27 (1H, dd, J=8.7, 1.9 Hz), 6.92 (1H, m), 6.62 (1H, dd, J=3.7, 2.1 Hz), 6.04 (1H, dd, J=4.1, 2.1 Hz), 3.80 (3H, s).

HRFABMS (MH$^+$): Calcd.: 339.1028. Found: 339.1024.

Anal. Calcd. for $C_{16}H_{14}N_6OS.0.3H_2O$: C, 55.90; H, 4.28; N, 24.45; S, 9.33. Found: C, 56.08; H, 4.28; N, 24.46; S, 9.33.

Example C(44)

1-{4-[4-Amino-5-(3-methyl-thiophene-2-carbonyl)-thiazol-2-ylamino]-phenyl}-ethanone

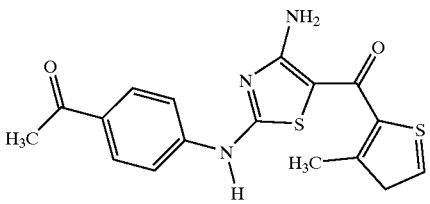

The title compound was prepared essentially as described for Example C(1). 4-Acetylphenyl isothiocyanate and 2-bromoacetyl-3-methyl-thiophene (from Example C(19)) gave a yellow solid in 89% yield, mp 171–2° C.

$^1$H NMR (DMSO-$d_6$): δ 11.14 (1H, s), 8.22 (2H, bs), 7.95 (2H, d, J=9.0 Hz), 7.76 (2H, d, J=9.0 Hz), 7.62 (1H, d, J=5.0 Hz), 7.00 (1H, d, J=5.0 Hz), 2.53 (3H, s), 2.39 (3H, s).

IR (KBr): 3618, 3354, 3254, 3178, 3072, 1651, 1599, 1524, 1403, 1355, 1318, 1275, 1170 cm$^{-1}$.

FABMS (MH$^+$): 357.

Anal. Calcd for $C_{17}H_{15}N_3O_2S_2.0.5H_2O$: C, 55.72; H, 4.40; N, 11.47; S, 17.50. Found: C, 55.92; H, 4.44; N, 11.51; S, 17.44.

Example C(45)

trans-3RS-Amino-4RS-{4-[4-amino-5-(3-methyl-thiophene-2-carbonyl)-thiazol-2-ylamino]-benzoyl}-dihydro-furan-2-one

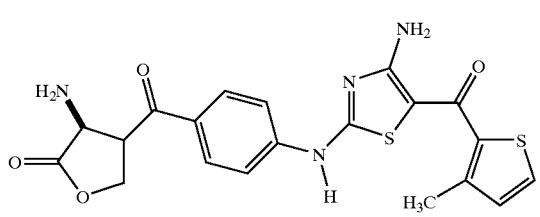

The title compound was prepared essentially as described for Example C(1). The product from 4-isothio-cyanato-benzoyl-DL-homoserine lactone and 2-bromoacetyl-3-methyl-thiophene (from Example C(19)) was extracted into 10% i-PrOH/CHCl₃. Flash column chromatography with 2–3–4–5–6% MeOH/CH₂Cl₂ stepwise gradient gave a yellow solid in 43% yield, mp 162–3° C.

$^1$H NMR (DMSO-d$_6$): δ 11.05 (1H, s), 8.88 (2H, d, J=8.1 Hz), 8.32 (2H, bs), 7.85 (2H, d, J=9.0 Hz), 7.74 (2H, d, J=9.0 Hz), 7.61 (1H, d, J=5.0 Hz), 6.99 (1H, d, J=5.0 Hz), 4.73 (1H, q, J=9.3 Hz), 4.40 (1H, ddd, J=10.8, 8.7, 2.0 Hz), 4.26 (1H, ddd, J=10.2, 8.7, 6.7 Hz).

IR (KBr): 3413, 3284, 3084, 1773, 1637, 1608, 1524, 1413, 1313, 1254, 1181 cm⁻¹.

FABMS (MH⁺): 443.

Anal. Calcd for C₂₀H₁₈N₄O₄S₂.0.4H₂O: C, 53.41; H, 4.21; N, 12.46; S, 14.26. Found: C, 53.56; H, 4.28; N, 12.30; S, 14.43.

Example C(46)

Ethyl 3RS-[4-Amino-5-(3-methyl-thiophene-2-carbonyl)-thiazol-2-ylamino]-butyrate

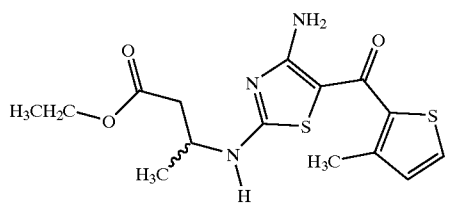

The title compound was prepared essentially as described for Example C(1). The product from ethyl dl-3-isothiocyanato-butyrate and 2-bromoacetyl-3-methyl-thiophene (from Example C(19)) was extracted with 10% i-PrOH/CHCl₃. Flash column chromatography with 3% MeOH/CH₂Cl₂ gave a yellow solid in 45% yield, mp 129–30° C.

$^1$H NMR (DMSO-d$_6$): δ 8.61 (1H, d, J=7.8 Hz), 8.08 (2H, bs), 7.53 (1H, d, J=5.0 Hz), 6.94 (1H, d, J=5.0 Hz), 4.05 (2H, q, J=7.2 Hz), 2.33 (3H, s), 1.22–1.12 (6H, m).

IR (KBr): 3307, 3213, 3160, 2976, 1737, 1618, 1586, 1526, 1423, 1349, 1215, 1183, 1091 cm⁻¹.

FABMS (MH⁺): 353.

Anal. Calcd for C₁₅H₁₉N₃O₃S₂: C, 50.97; H, 5.42; N, 11.89; S, 18.14. Found: C, 50.81; H, 5.39; N, 11.72; S, 17.97.

Example C(47)

4-[4-Amino-5-(4-methyl-thiazole-5-carbonyl)-thiazol-2-ylamino]-benzenesulfonamide

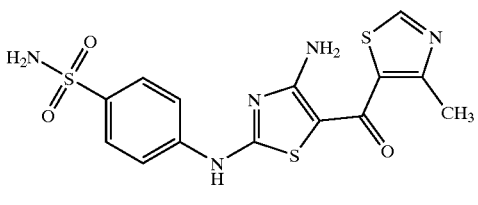

5-Bromoacetyl-4-methyl-thiazole, which has the structural formula

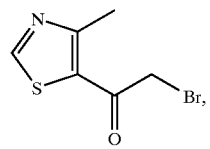

was prepared as described in Sych et al., *J. Gen. Chem. USSR*, vol. 32 (1962), pp. 970–975. Bromine (0.75 mL, 7.77 mmol) was added dropwise into the solution of 1-(4-methyl-thiazol-5-yl)-ethanone (2.05 mg, 14.5 mmol; Ganapathi et al., *Proc.-Indian Acad. Sci. Sect. A*, vol. 22 (1945), pp. 362–378) in HOAc (3 mL). The mixture was stirred at 85° C. for 1.5 hours and turned into yellow cake. HOAc (3 mL) was added, and after 1.5 hours, allowed to cool. The HOAc was removed in vacuo and the residue partitioned between CH₂Cl₂ and sat aq NaHCO₃. The organic layer was washed with brine, dried over Na₂SO₄, and evaporated to give a black solid, 1.3 g (41% yield), which was used without further purification.

$^1$H NMR (CDCl₃): δ 8.85 (1H, s), 4.28 (2H, s), 2.81 (3H, s).

The title compound was prepared in a manner analogous to that used in Example C(1). 4-Isothiocyanato-benzenesulfonamide and 5-bromoacetyl-4-methyl-thiazole provided a brown solid in 31% yield, mp 265–266° C.

$^1$H NMR (DMSO-d$_6$): δ 11.18 (1H, s), 9.08 (1H, s), 8.30 (2H, bs), 7.78 (4H, bs), 7.72 (2H, bs), 2.55 (3H, s).

Anal. Calcd. for C₁₆H₁₃N₅O₃S₃: C, 42.52; H, 3.31; N, 17.11; S, 24.32. Found: C, 42.28; H, 3.33; N, 17.15; S, 24.52.

Example C(48)

4-[4-Amino-5-(3-methyl-thiophene-2-carbonyl)-thiazol-2-ylamino]-benzenesulfonamide

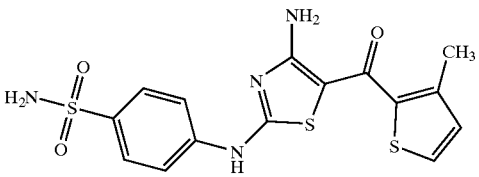

The title compound was prepared in a manner analogous to that used in Example C(1). 4-Isothiocyanato-benzenesulfonamide and 2-bromoacetyl-3-methyl-thiophene (from Example C(19)) provided a yellow solid in 69% yield, mp 284.5–286.0° C.

¹H NMR (DMSO-d₆): δ 11.11 (1H, s), 8.20 (2H, bs), 7.80 (2H, d, J=10.7 Hz), 7.76 (2H, d, J=10.7 Hz), 7.61 (1H, d, J=5.0 Hz), 7.26 (2H, s), 6.90 (1H, d, J=5.0 Hz), 2.38 (3H, s).

Anal. Calcd. for $C_{15}H_{14}N_4O_3S_3$: C, 45.67; H, 3.58; N, 14.20; S, 24.39. Found: C, 45.52; H, 3.58; N, 14.04; S, 24.36.

Example C(49)

4-[4-Amino-5-(3-methyl-benzo[b]thiophene-2-carbonyl)-thiazol-2-ylamino]-benzenesulfonamide

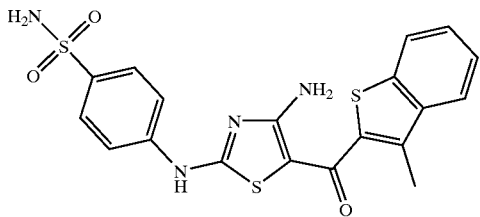

The title compound was prepared in a manner analogous to that used in Example C(1). 4-Isothiocyanato-benzenesulfonamide and 2-(2-bromoacetyl)-3-methyl-benzo[b]thiophene provided a yellow powder in 73% yield, mp 274.0–275.5° C.

¹H NMR (DMSO-d₆): δ 11.17 (1H, bs), 8.33 (2H, bs), 8.04–7.97 (1H, m), 7.90–7.84 (1H, m), 7.78 (4H, bs), 7.51–7.44 (2H, m), 7.27 (2H, s), 2.52 (3H, s).

Anal. Calcd. for $C_{19}H_{16}N_4O_3S_3$: C, 51.33; H, 3.63; N, 12.60; S, 21.64. Found: C, 51.19; H, 3.67; N, 12.31; S, 21.37.

Example C(50)

4-[4-Amino-5-(2,5-dimethyl-thiophene-3-carbonyl)-thiazol-2-ylamino]-benzenesulfonamide

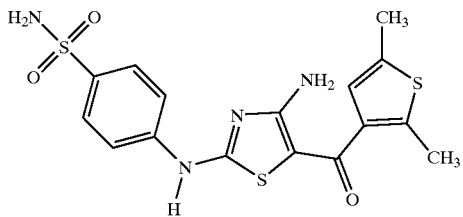

3-Bromoacetyl-2,5-dimethyl-thiophene, which has the structural formula

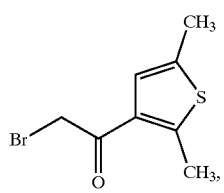

was prepared in a manner analogous to 2-bromo-2'-iodoacetophenone for Example C(12). 3-Acetyl-2,5-dimethylthiophene (6.83 g, 44.3 mmol) provided 10.1 g (98% yield) of yellow oil, which was used without further purification.

¹H NMR (CDCl₃): δ 7.22 (1H, s), 4.64 (2H, s), 2.58 (3H, s), 2.36 (3H, s).

The title compound was prepared in a manner analogous to that used in Example C(1). 4-Isothiocyanato-benzenesulfonamide and 3-bromoacetyl-2,5-dimethyl-thiophene provided a yellow powder in 69% yield, mp 263–5° C.

¹H NMR (DMSO-d₆): δ 11.02 (1H, s), 8.05 (2H, bs), 7.76 (4H, s), 7.25 (2H, s), 6.87 (1H, s), 2.43 (3H, s), 2.38 (3H, s).

Anal. Calcd. for $C_{16}H_{16}N_4O_3S_3$: C, 47.04; H, 3.95; N, 13.71; S, 23.55. Found: C, 47.01; H, 3.92; N, 13.62; S, 23.47.

Example C(51)

4-[4-Amino-5-(2-oxo-1,2,3,4-tetrahydro-quinoline-6-carbonyl)-thiazol-2-ylamino]-benzenesulfonamide

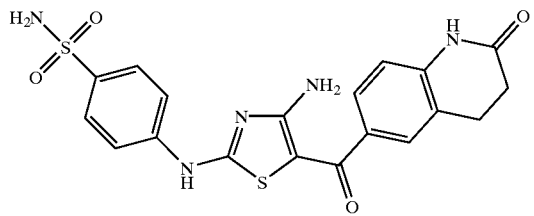

The title compound was prepared essentially as described for Example C(1). 4-Isothiocyanato-benzenesulfonamide and 6-(bromoacetyl)-2-oxo-1,2,3,4-tetrahydroquinoline gave a grey-yellow solid in 48% yield, mp 300–305° C.(d).

¹H NMR (DMSO-d₆): δ 11.08 (1H, s), 10.32 (1H, s), 8.17 (2H, bs), 7.82–7.70 (4H, m), 7.58–7.45 (3H, m), 7.27 (1H, s), 6.90 (1H, d, J=8.1 Hz), 2.93 (4H, t, J=7.7 Hz).

IR (KBr): 3266, 3193, 3069, 1679, 1597, 1525, 1434, 1365, 1317, 1153 cm⁻¹.

HRFABMS. Calcd. for $C_{19}H_{18}N_5O_4S_2$ (MH⁺): 444.0800. Found: 444.0816.

Anal. Calcd for $C_{19}H_{17}N_5O_4S_2 \cdot 0.6$MeOH: C, 50.88; H, 4.23; N, 15.13; S, 13.86. Found: C, 51.02; H, 4.00; N, 15.00; S, 13.60.

Example C(52)

[4-Amino-2-(1H-benzoimidazol-6-ylamino)-thiazol-5-yl]-(2,6-dichloro-phenyl)-methanone

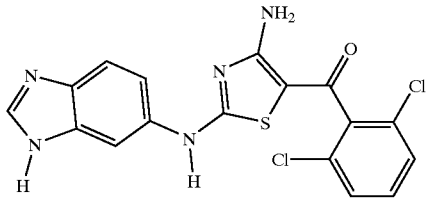

2-Bromo-2',6'-dichloro-acetophenone, which has the structural formula

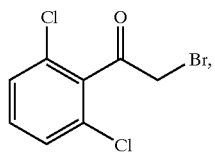

was prepared as follows. To 2',6'-dichloroacetophenone (1.0 g, 5.30 mmol) in HOAc (5 mL) was added dropwise bromine (272 μl, 5.30 mmol). The mixture was heated at 90° C. for 1 hour, then diluted with ice-water and partitioned between ether and sat aq NaHCO₃. The organic layer was washed with brine, dried over MgSO₄, concentrated and azeotroped with heptane twice, to obtain 1.41 g (100% yield) of a light yellow oil, which matched by ¹H NMR and IR previously described (see Mlotkowska et al., *Pol. J. Chem.*, vol. 55 (1981), pp. 631–642) and was used without further purification.

¹H NMR (CDCl₃): δ 7.39–7.33 (3H, m), 4.23 (2H, s).

The title compound was prepared in a manner analogous to that used in Example C(1). 6-Isothiocyanato-1H-benzoimidazole (see Boev et al., *Pharm. Chem. J. (Engl. Transl).*, vol. 24 (1990), pp. 818–822) and 2-bromo-2',6'-dichloro-acetophenone (from Example C(52)) provided a yellow solid in 47% yield, mp 203–208° C.

¹H NMR (DMSO-d₆): δ 12.47 (1H, d, J=17.7 Hz), 10.83 (1H, d, J=16.5 Hz), 8.22–7.80 (3H, m), 8.18 (1H, s), 7.76–7.36 (5H, m), 7.19 (1H, d, J=8.4 Hz).

Anal. Calcd. for C₁₇H₁₂N₅OSCl₂: C, 50.51; H, 2.74; N, 17.32; S, 7.93; Cl, 17.54. Found: C, 50.32; H, 2.78; N, 17.11; S, 7.91; Cl, 17.75.

Example C(53)

{4-Amino-2-[4-(1H-imidazol-2-yl)-phenylamino]-thiazol-5-yl}-(2,6-dichloro-4-trifluoromethyl-phenyl)-methanone

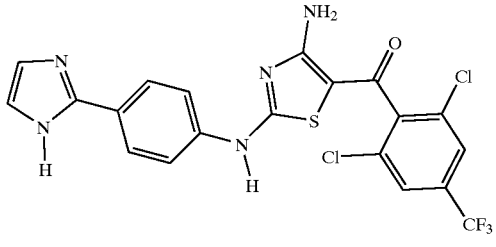

2-(4-Nitro-phenyl)-1H-imidazole, which has the structural formula

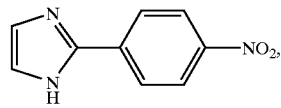

was first prepared as follows. To a solution of 2-phenylimidazole (5.00 g, 34.7 mmol) in conc. H₂SO₄ (20 mL) at 0° C. was added a solution of conc. HNO₃ (2.2 mL, 35 mmol) in conc. H₂SO₄ (5 mL). The resultant brown mixture was stirred at 0° C. for 2 hours and quenched with crushed-ice. A pale white precipitate formed, which was filtered. The filtrate was brought to pH 9 with 2N NaOH. A yellow precipitate formed, which was filtered off, washed with H₂O, and recrystallized from boiling MeOH to give 3.0 g (46% yield) of a yellow solid. This crude product was used without any further purification.

¹H NMR (MeOH-d₄): δ 8.34 (2H, d, J=9.0 Hz), 8.08 (2H, d, J=9.0 Hz), 7.26 (2H, s).

4-(1H-Imidazol-2-yl)-aniline, which has the structural formula

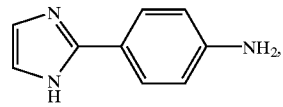

was next prepared as follows. To a suspension of 2-(4-nitro-phenyl)-1H-imidazole (1.5 g, 7.93 mmol) in absolute ethanol (30 mL) was added 10% Pd—C (250 mg). The resultant mixture was stirred under an atmosphere of H₂ for 5 hours. The mixture was filtered through a pad of Celite. The filtrate was concentrated under reduced pressure to afford 1.20 g (95% in crude yield) of a red gum, which was used without further purification.

2-(4-Isothiocyanato-phenyl)-1H-imidazole, which has the structural formula

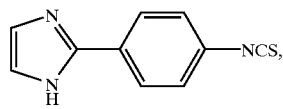

was prepared in a manner analogous to 1-(4-isothiocyanato-phenyl)-1H-imidazole for Example C(41). 4-(1H-Imidazol-2-yl)-aniline gave a pale-brown solid, which recrystallized from CHCl₃ in 85% yield, and was used without any further purification.

¹H NMR (MeOH-d₄): δ 7.88 (4H, bd, J=7.8 Hz), 7.58 (2H, s).

The title compound was prepared in a manner like that described for Example C(1). 2-(4-Isothiocyanato-phenyl)-1H-imidazole and 2-bromo-2',6'-dichloro-4'-trifluoromethyl-acetophenone gave, after purification via preparative thin layer chromatography with MeOH:CHCl₃ (8:92) as eluant, a yellow solid in 21% yield, mp 195–197° C.

¹H NMR (DMSO-d₆): δ 11.0 (1H, s), 8.18 (1H, s), 8.02 (2H, s), 7.88 (2H, d, J=8.7 Hz), 7.62 (2H, d, J=8.1 Hz), 7.12 (2H, bs).

IR (KBr): 3400, 2929, 1610, 1527, 1426, 1310 cm⁻¹.

HRFABMS: Calcd. for C₂₀H₁₃Cl₂F₃N₅OS (MH⁺): 498.0170. Found: 498.0183.

Anal. Calcd. for C₂₀H₁₂Cl₂F₃N₅OS.H₂O: C, 46.52; H, 2.73; N, 13.56; Cl, 13.73; S, 6.21. Found: C, 46.45; H, 2.78; N, 13.40; Cl, 13.73, S, 6.11.

Example C(54)

[4-Amino-2-(4-morpholin-4-yl-phenylamino)-thiazol-5-yl]-(2,4-dimethyl-phenyl)-methanone

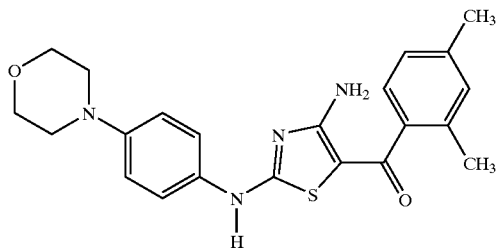

4-(4-Isothiocyanato-phenyl)-morpholine, which has the structural formula

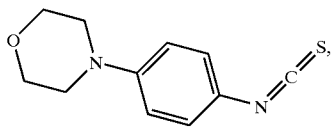

was made as follows. To 4-morpholinoaniline (2.0 g, 11.2 mmol) and triethylamine (5.01 mL, 35.9 mmol) in THF (200 mL) at 0° C. was added dropwise thiophosgene (1.03 mL, 13.5 mmol). The mixture stirred at ambient temperature overnight, and then was partitioned between ether and water. The ether layer was washed with water and brine, dried over $MgSO_4$, and concentrated to give 2.46 g (99%) of dark brown solid.

$^1$H NMR (CDCl$_3$): δ 7.15 (2H, d, J=9.3 Hz), 6.87 (2H, d, J=9.3 Hz), 3.80 (4H, t, J=5.0 Hz), 3.19 (4H, t, J=5.0 Hz).

The title compound was prepared in a manner analogous to that used in Example C(1). 4-(4-Isothiocyanato-phenyl)-morpholine and 2-bromo-2',4-dimethylacetophenone provided a yellow solid in 28% yield, mp 253–254.5° C.

$^1$H NMR (DMSO-d$_6$): δ 10.44 (1H, s), 7.98 (2H, bs), 7.31 (2H, d, J=9.0 Hz), 7.14 (1H, d, J=7.8 Hz), 7.02 (1H, s), 6.99 (1H, d, J=7.8 Hz), 6.90 (2H, d, J=9.0 Hz), 3.70 (4H, t, J=4.7 Hz), 3.04 (4H, t, J=4.7 Hz), 2.26 (3H, s), 2.20 (3H, s).

Anal. Calcd. for $C_{22}H_{24}N_4O_2S$: C, 64.68; H, 5.92; N, 13.71; S, 7.85. Found: C, 64.49; H, 5.97; N, 13.64; S, 7.93.

Example C(55)

[4-Amino-2-(4-morpholin-4-yl-phenylamino)-thiazol-5-yl]-(2,6-dichloro-phenyl)-methanone

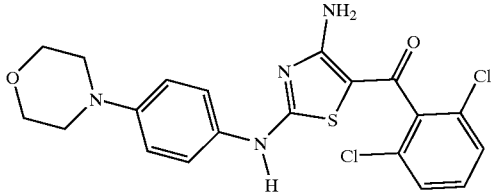

The title compound was prepared in a manner analogous to that used in Example C(1). 4-(4-Isothiocyanato-phenyl)-morpholine (from Example C(54)) and 2-bromo-2',6'-dichloro-acetophenone (from Example C(52)) provided a yellow solid in 9% yield, mp 245–247° C.

$^1$H NMR (DMSO-d$_6$): δ 10.58 (1H, s), 8.02 (2H, bs), 7.52 (2H, d, J=7.3 Hz), 7.41 (1H, m), 7.30 (2H, d, J=9.0 Hz), 6.92 (2H, d, J=9.0 Hz), 3.72 (4H, dd, J=5.0, 4.2 Hz), 3.06 (4H, dd, J=5.0, 4.2 Hz).

Anal. Calcd. for $C_{20}H_{18}N_4O_2SCl$: C, 53.46; H, 4.04; N, 12.47; S, 7.14; Cl, 15.78. Found: C, 53.39; H, 4.04; N, 12.47; S, 7.21; Cl, 15.71.

Example C(56)

Ethyl 4-[4-Amino-5-(2,6-dichloro-benzoyl)-thiazol-2-ylamino]-benzoate

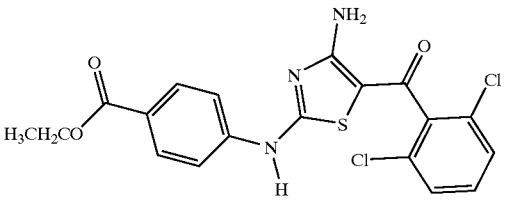

The title compound was prepared in a manner analogous to that used in Example C(1). 4-Ethoxycarbonylphenyl isothiocyanate and 2-bromo-2',6'-dichloro-acetophenone (from Example C(52)) provided an amorphous yellow solid in 48% yield.

$^1$H NMR (DMSO-d$_6$): δ 11.13 (1H, s), 8.15 (2H, bs), 7.92 (2H, d, J=8.7 Hz), 7.70 (2H, d, J=8.7 Hz), 7.58–7.40 (3H, m), 4.27 (2H, q, J=7.0 Hz), 1.29 (3H, t, J=7.0 Hz).

Anal. Calcd. for $C_{19}H_{15}N_3O_3SCl_2$: C, 52.30; H, 3.47; N, 9.63; S, 7.35; Cl, 16.25. Found: C, 52.20; H, 3.42; N, 9.63; S, 7.44; Cl, 16.26.

Example C(57)

[4-Amino-2-(1H-benzoimidazol-6-ylamino)-thiazol-5-yl]-(2,4,6-trimethyl-phenyl)-methanone

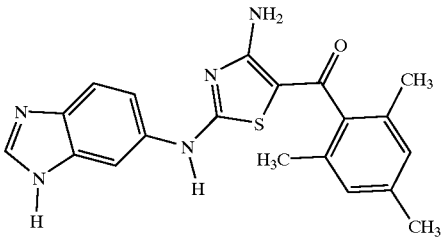

2-Bromo-2',4',6'-trimethyl-acetophenone, which has the structural formula

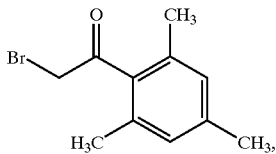

was prepared in a manner analogous to 2-bromo-2'-iodo-acetophenone, see Example C(12). 2,4,6-trimethylacetophenone (1.50 g, 9.25 mmol) provided 2.26 g (100%) of clear oil, which was used without further purification.

$^1$H NMR (CDCl$_3$): δ 6.87 (2H, s), 4.27 (2H, s), 2.22 (9H, s).

The title compound was prepared in a manner analogous to that used in Example C(1). 6-Isothiocyanato-1H-benzoimidazole (see Boev et al., *Pharm. Chem. J. (Engl. Transl).*, vol. 24 (1990), pp. 818–822) and 2-bromo-2',4',6'-trimethyl-acetophenone provided a yellow powder in 26% yield, that decomposed above 185° C.

$^1$H NMR (DMSO-d$_6$): δ 12.42 (1H, bs), 10.66 (1H, bs), 8.17 (1H, s), 7.96 (2H, bs), 7.75 (1H, bs), 7.44 (1H, bs), 7.16 (1H, d, J=8.7 Hz), 6.82 (2H, s), 2.21 (3H, s), 2.11 (6H, s).

HRFABMS (MH+): Calcd.: 378.1389. Found: 378.1381.

Anal. Calcd. for C_{20}H_{19}N_5OS.0.3H_2O: C, 62.74; H, 5.16; N, 18.29; S, 8.37. Found: 62.96; H, 5.14; N, 18.24; S, 8.35.

Example C(58)

[4-Amino-2-(1H-benzoimidazol-6-ylamino)-thiazol-5-yl]-(2,3,6-trimethyl-phenyl)-methanone

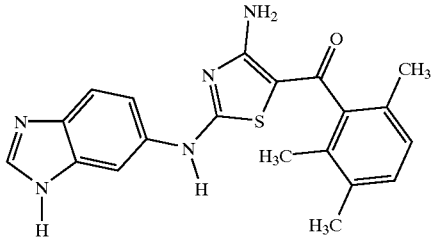

2-Bromo-2',3',6'-trimethyl-acetophenone, which has the structural formula

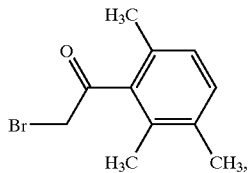

was prepared in a manner analogous to 2-bromo-2'-iodo-acetophenone for Example C(12). 2',3',6'-trimethylacetophenone (1.50 g, 9.25 mmol) provided 2.10 g (93%) of clear oil, which was used without further purification.

The title compound was prepared in a manner analogous to that used in Example C(1). 6-Isothiocyanato-1H-benzoimidazole (see Boev et al., *Pharm. Chem. J. (Engl. Transl).*, vol. 24 (1990), pp. 818–822) and 2-bromo-2',3',6'-trimethyl-acetophenone provided a yellow powder in 70% yield, that decomposed above 196° C.

1H NMR (DMSO-d_6): δ 12.41 (1H, bs), 10.65 (1H, bs), 8.17 (1H, s), 7.96 (2H, bs), 7.70 (1H, bs), 7.52 (1H, bs), 7.17 (1H, dd, J=8.4, 1.9 Hz), 6.82 (2H, s), 2.11 (9H, s).

Anal. Calcd. for C_{20}H_{19}N_5OS: C, 63.64; H, 5.07; N, 18.55; S, 8.50. Found: C, 63.40; H, 5.17; N, 18.37; S, 8.36.

Example C(59)

[4-Amino-2-(4-sulfamoyl-phenylamino)-thiazol-5-yl]-(3,5-dimethyl-pyridin-4-yl)-methanone

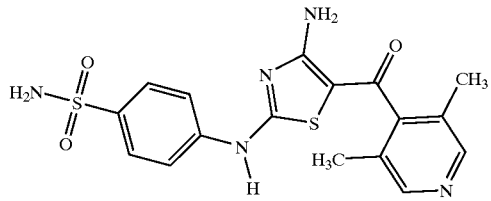

4-(Bromoacetyl)-3,5-dimethylpyridine hydrobromide, which has the structural formula

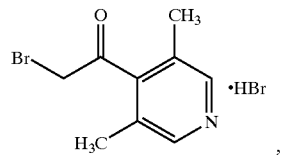

was first prepared as follows. 4-Acetyl-3,5-dimethylpyridine (500 mg, 3.36 mmol; Kutney et al., *Can. J. Chem.*, vol. 41 (1963), pp. 695–702) was dissolved in 30% HBr in acetic acid (1 mL), heated to 70° C., and treated with a mixture of bromine (0.17 mL, 3.36 mmol) in 30% HBr in acetic acid (0.5 mL). After 2 hours, the mixture was allowed to cool to ambient temperature and ether (8 mL) was added. The resultant precipitate was filtered off, rinsed with ether (2×), and dried to afford 1.03 g (100%) of a purple solid, mp 222–225° C., that was used without further purification.

The title compound was prepared essentially as described for Example C(1). 4-Isothiocyanato-benzenesulfonamide and 4-(bromoacetyl)-3,5-dimethylpyridine hydrobromide provided a tan solid, which was purified via column chromatography with 10% MeOH/CHCl_3 and crystallized from MeOH to obtain 35 mg (51%) of amorphous yellow solid.

1H NMR (DMSO-d_6): δ 11.09 (1H, s), 8.32 (2H, s), 8.18 (2H, bs), 7.74 (4H, dd, J=11.5, 9.3 Hz), 7.27 (2H, s), 2.15 (6H, s).

IR (KBr): 3378, 3342, 3260, 3160, 1625, 1594, 1560, 1518, 1443, 1342, 1160 cm$^{-1}$.

HRFABMS: Calcd. for C_{17}H_{18}N_5O_3S_2 (MH+): 404.0851. Found: 404.0840.

Anal. Calcd for C_{17}H_{17}N_5O_3S_2.0.4H_2O.0.3MeOH: C, 49.44; H, 4.56; N, 16.66; S, 15.26. Found: C, 49.13; H, 4.31; N, 16.61; S, 15.10.

Example C(60)

[4-Amino-2-(1H-benzoimidazol-6-ylamino)-thiazol-5-yl]-(2,6-dimethyl-phenyl)-methanone

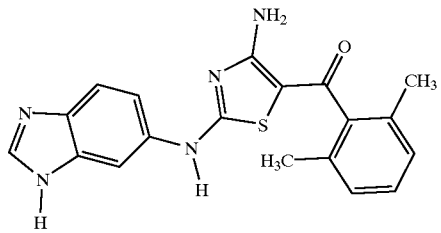

2',6'-Dimethylacetophenone, which has the structural formula

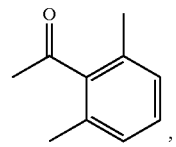

was prepared according to a procedure for o-nitroacetophenone (Reynolds et al, *Org. Syn. Coll.*, vol. IV (1963), pp. 708–710). 2,6-Dimethylbenzoic acid (3.00 g, 20.0 mmol) provided 2.56 g (86% yield) of yellow oil, which was used without further purification.

$^1$H NMR (CDCl$_3$): δ 7.16 (1H, t, J=7.2 Hz), 7.02 (2H, d, J=7.2 Hz), 2.48 (3H, s), 2.55 (6H, s).

2-Bromo-2',6'-dimethyl-acetophenone, which has the structural formula

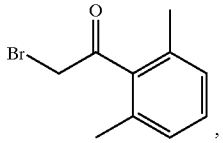

was prepared in a manner analogous to 2-bromo-2'-iodo-acetophenone, see Example C(12). 2',6'-dimethylacetophenone (1.50 g, 10.1 mmol) provided 2.04 g (89% yield) of clear oil, which was used without further purification.

$^1$H NMR (CDCl$_3$): δ 7.21 (1H, t, J=7.2 Hz), 7.05 (2H, t, J=7.2 Hz), 4.29 (2H, s), 2.26 (6H, s).

The title compound was prepared in a manner analogous to that used in Example C(1). 6-Isothiocyanato-1H-benzoimidazole (see Boev et al., *Pharm. Chem. J. (Engl. Transl).*, vol. 24 (1990), pp. 818–822) and 2-bromo-2',6'-dimethyl-acetophenone provided a yellow solid in 71% yield, that decomposed above 185° C.

$^1$H NMR (DMSO-d$_6$): δ 12.41 (1H, bs), 10.67 (1H, bs), 8.17 (1H, s), 7.99 (2H, s), 7.60 (1H, s), 7.52 (1H, s), 7.17 (1H, dd, J=8.7, 1.9 Hz), 7.12 (1H, d, J=7.1 Hz), 7.02 (1H, d, J=7.5 Hz), 2.15 (6H, s).

HRFABMS (MH$^+$): Calcd.: 364.1232. Found: 364.1227.

Anal. Calcd. for C$_{19}$H$_{17}$N$_5$OS.0.3CH$_3$OH: C, 62.14; H, 4.92; N, 18.77; S, 8.60. Found: C, 62.43; H, 5.15; N, 18.91; S, 8.60.

Example C(61)

[4-Amino-2-(1H-benzoimidazol-6-ylamino)-thiazol-5-yl]-(2-methyl-6-nitro-phenyl)-methanone

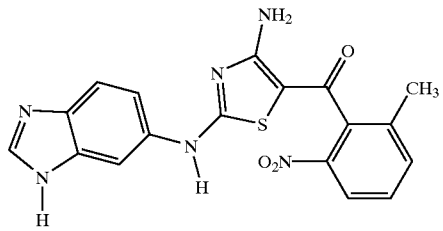

2'-Methyl-6'-nitro-acetophenone, which has the structural formula

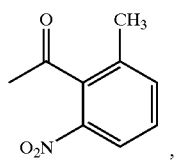

was prepared according to a procedure for o-nitro-acetophenone (see Reynolds et al, *Org. Syn. Coll.*, vol. IV, (1963), pp. 708–710). 2-Methyl-6-nitrobenzoic acid (15.0 g, 82.8 mmol) provided 14.7 g (99% yield) of yellow oil, which was used without further purification.

$^1$H NMR (CDCl$_3$): δ 8.04 (1H, d, J=8.4 Hz), 7.55 (1H, d, J=7.5 Hz), 7.44 (1H, dd, J=8.4, 7.5 Hz), 2.56 (3H, s), 2.35 (3H, s).

2-Bromo-2'-methyl-6'-nitro-acetophenone, which has the structural formula

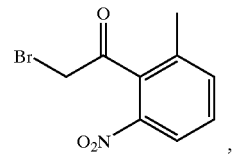

was prepared in a manner analogous to 5-bromoacetyl-4-methyl-1H-imidazole Example C(40). Crude 2'-methyl-6'-nitro-acetophenone (1.56 g, 8.72 mL) furnished a white solid, 2.17 g (97% yield), that was used without further purification.

$^1$H NMR (CDCl$_3$): δ 8.11 (1H, d, J=7.8 Hz), 7.62 (1H, d, J=7.8 Hz), 7.52 (1H, d, t=7.8 Hz), 4.33 (2H, s), 2.40 (3H, s).

The title compound was prepared in a manner analogous to that used in Example C(1). 6-Isothiocyanato-1H-benzoimidazole (see Boev et al., *Pharm. Chem. J. (Engl. Transl).*, vol. 24 (1990), pp. 818–822) and 2-bromo-2'-methyl-6'-nitro-acetophenone provided a brown solid in 32% yield, mp 198–201° C.

$^1$H NMR (DMSO-d$_6$): δ 12.40 (1H, bs), 10.78 (1H, bs), 8.17 (1H, d, J=10.6 Hz), 8.00 (2H, bs), 7.92 (2H, d, J=8.4 Hz), 7.68 (1H, d, J=7.5 Hz), 7.62–7.44 (2H, m), 7.19 (1H, d, J=7.5 Hz), 2.30 (3H, s).

HRFABMS (MH$^+$): Calcd.: 395.0926. Found: 395.0920.

Anal. Calcd. for C$_{18}$H$_{14}$N$_6$O$_3$S.0.5H$_2$O: C, 53.59; H, 3.75; N, 20.83; S, 7.95. Found: C, 53.43; H, 3.67; N, 20.68; S, 7.81.

Example C(62)

[4-Amino-2-(4-morpholin-4-yl-phenylamino)-thiazol-5-yl]-(2,6-dimethyl-phenyl)-methanone

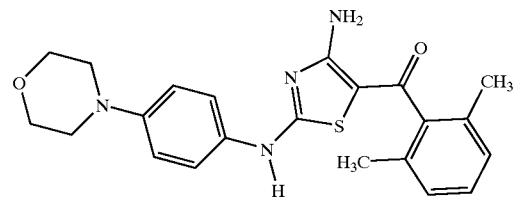

The title compound was prepared in a manner analogous to that used in Example C(1). 4-(4-Isothiocyanato-phenyl)-morpholine (from Example C(54)) and 2-bromo-2',6'-dimethyl-acetophenone (from Example C(60)) provided a brown solid in 23% yield, mp 221–223° C.

$^1$H NMR (DMSO-d$_6$): δ 10.42 (1H, s), 7.95 (2H, bs), 7.30 (2H, d, J=9.0 Hz), 7.18–7.10 (1H, m), 7.02 (2H, d, J=7.5 Hz), 6.91 (2H, d, J=9.0 Hz), 3.72 (4H, t, J=4.8 Hz), 3.05 (4H, t, J=4.8 Hz), 2.16 (6H, s).

HRFABMS (M+): Calcd.: 408.1620. Found: 408.1607.

Anal. Calcd. for C$_{22}$H$_{24}$N$_4$O$_2$S.0.75H$_2$O: C, 62.61; H, 6.09; N, 13.28; S, 7.60. Found: C, 62.64; H, 6.10; N, 13.05; S, 7.55.

Example C(63)

[4-Amino-2-(1H-benzoimidazol-5-yl-amino)-thiazol-5-yl]-(3,5-dichloro-pyridin-4-yl)-methanone

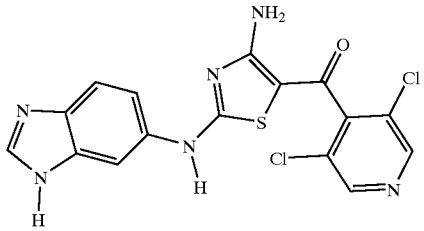

4-Bromoacetyl-3,5-dichloropyridine, which has the structural formula

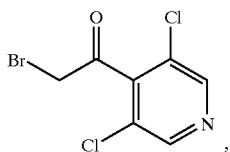

was first prepared as follows. A mixture of 3,5-dichloropyridine-4-carboxylic acid (4.00 g, 20.9 mmol; Cale et al., *J. Med. Chem.*, vol. 32 (1989), pp. 2178–2199), benzene (20 mL), DMF (0.4 mL), and thionyl chloride (3.80 mL, 52.0 mmol) was heated at reflux for 60 min, allowed to cool to ambient temperature, concentrated in vacuo, suspended in ether (20 mL), and cautiously treated with a solution of trimethylsilyldiazomethane (25 mL of 2.0 M in hexanes). After 72 hours, 48% HBr (18 mL) was carefully added dropwise over 20 min, initially with vigorous gas evolution. After 30 min, the mixture was made alkaline carefully with NaHCO$_3$ and extracted with ether. The ethereal layers were dried over Na$_2$SO$_4$ and evaporated to give an orange oil, which was purified via column chromatography with 50% CH$_2$Cl$_2$/hex eluant to separate 2.50 g (51%) of 3,5-dichloropyridine-4-carbonyl chloride as a yellow oil, providing desired product, 2.00 g (36%) of pale yellow crystals that darkened at ambient temperature, which was used without further purification.

NMR (CDCl$_3$): δ 8.58 (2H, s), 4.37 (2H, s).

Anal. Calcd for C$_7$H$_4$BrCl$_2$NO.0.02C$_6$H$_{14}$: C, 31.60; H, 1.59; N, 5.18. Found: C, 31.92; H, 1.59; N, 5.24.

The title compound was prepared essentially as described for Example C(1). 6-Isothiocyanato-1H-benzoimidazole (see Boev et al., *Pharm. Chem. J.* (*Engl. Transl*)., vol. 24 (1990), pp. 818–822) and 4-(bromoacetyl)-3,5-dichloropyridine gave a product that was extracted into 10% MeOH/CHCl$_3$ and column chromatography with same to furnish a yellow amorphous solid, 198 mg (55%). An analytical sample precipitated from EtOH, mp 235–240° (d).

$^1$H NMR (CD$_3$OD): δ 8.60 (2H, s), 8.18 (1H, s), 7.98 (1H, bs), 7.58 (1H, d, J=9.0 Hz), 7.30 (1H, dd, J=1.2, 8.7 Hz).

IR (KBr): 3183, 1608, 1544, 1461, 1427, 1355 cm$^{-1}$.

HRFABMS: Calcd. for C$_{16}$H$_{11}$Cl$_2$N$_6$OS (MH$^+$): 405.0092. Found: 405.0079.

Anal. Calcd for C$_{16}$H$_{10}$Cl$_2$N$_6$OS.1.1H$_2$O: C, 45.21; H, 2.89; N, 19.77; Cl, 16.68; S, 7.54. Found: C, 45.49; H, 2.59; N, 19.64; Cl, 16.62; S, 7.43.

Example C(64)

2S-[4-Amino-2-(1H-benzoimidazol-5-yl-amino)-thiazole-5-carbonyl]-N-carbobenzyloxy-pyrrolidine

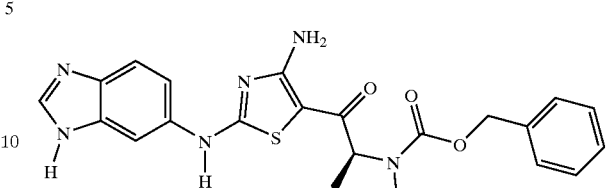

2S-Bromoacetyl-N-carbobenzyloxy-pyrrolidine, which has the structural formula

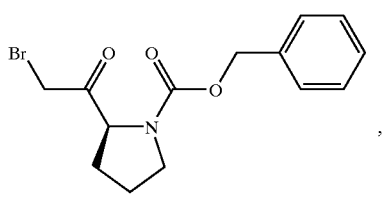

was first prepared as follows. The acid chloride of N-carbobenzyloxy-L-proline (1.20 g, 4.80 mmol) was made according to Aoyama et al. *Chem. Pharm. Bull.*, vol. 29 (1981), pp. 3249–3255, with oxalyl chloride and a catalytic amount of DMF. To a solution of the crude acid chloride in THF (5 mL) and MeCN (5 mL) at 0° C. was carefully added dropwise a solution of trimethylsilyldiazomethane (5.0 mL of 2.0 M in hex), and initially vigorous gas evolution occurred. The resultant red suspension was allowed to warm and stirred at ambient temperature overnight. The brown mixture was then cooled to 0° C., cautiously treated with a mixture of 47% HBr (4.1 mL) and ether (10 mL), and initially vigorous gas evolution ensued. The mixture was allowed to warm to ambient temperature over 1 h, then made alkaline with satd aq NaHCO$_3$ (20 mL), and extracted with EtOAc (2×20 mL). The combined organic layers were dried over Na$_2$SO$_4$ and evaporated to give a brown oil, 1.57 g (100%), which was used without further purification.

NMR (CDCl$_3$): δ 7.44–7.24 (5H, m), 4.34 (1H, d, J=15.6 Hz), 4.27 (1H, d, J=15.6 Hz).

The title compound was prepared essentially as described for Example C(1). 6-Isothiocyanato-1H-benzoimidazole (see Boev et al., *Pharm. Chem. J.* (*Engl. Transl*)., vol. 24 (1990), pp. 818–822) and 2S-bromoacetyl-N-carbobenzyloxy-pyrrolidine provided a solid that was precipitated from iPrOH/hex twice to give a yellow amorphous solid, 154 mg (54%), mp 150–1650° (d).

$^1$H NMR (DMSO-d$_6$): δ 12.40 (1H, d, J=7.8 Hz), 10.68 (1H, d, J=19.3 Hz), 8.20 (1H, d, J=10.6 Hz), 8.10–7.70 (2H, m), 7.52 (1H, dd, J=8.7, 34.8 Hz), 7.45–7.05 (5H, m), 5.17–4.80 (2H, m), 4.32 (1H, d, J=4.9 Hz), 4.30–4.18 (1H, bm), 2.33–1.70 (2H, bm).

IR (KBr): 3278, 1686, 1599, 1560, 1421, 1356, 1121 cm$^{-1}$.

HRFABMS: Calcd. for C$_{23}$H$_{23}$N$_6$O$_3$S (MH$^+$): 463.1552. Found: 463.1538.

Anal. Calcd for C$_{23}$H$_{22}$N$_6$O$_3$S.0.1H$_2$O.0.7iPrOH: C, 59.53; H, 5.53; N, 16.60; S, 6.33. Found: C, 59.53; H, 5.53; N, 16.60; S, 6.22.

Example C(65)

2S-[4-Amino-2-(4-sulfamoyl-phenylamino)-thiazole-5-carbonyl]-N-carbobenzyloxy-pyrrolidine

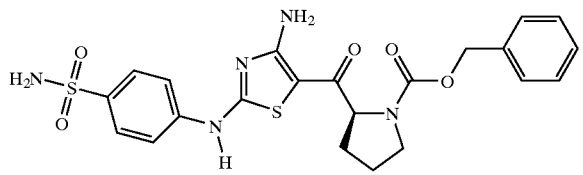

The title compound was prepared essentially as described for Example C(1). 4-Isothiocyanato-benzenesulfonamide and 2S-bromoacetyl-N-carbobenzyloxy-pyrrolidine (see Example C(64)) provided a solid that was purified via column chromatography with 5% MeOH/CHCl$_3$ eluant to give a yellow amorphous solid, 140 mg (46%), mp 150–160° (d).

$^1$H NMR (DMSO-d$_6$): δ 11.05 (1H, d, J=10.0 Hz), 7.98 (2H, bd, J=17.1 Hz), 7.79 (4H, dd, J=12.1, 9.7 Hz), 7.41–7.11 (5H, m), 5.15–4.89 (2H, m), 4.32–4.21 (1H, bm), 3.51–3.40 (2H, bm), 2.35–2.13 (1H, bm), 1.93–1.75 (3H, bm).

IR (KBr): 3288, 1686, 1598, 1550, 1527, 1420, 1157 cm$^{-1}$.

HRFABMS: Calcd. for C$_{22}$H$_{23}$N$_5$O$_5$S$_2$Cs (M+Cs$^+$): 634.0195. Found: 634.0215.

Anal. Calcd for C$_{22}$H$_{23}$N$_5$O$_5$S$_2$·0.3H$_2$O·0.1CHCl$_3$: C, 51.15; H, 4.60; N, 13.50; S, 12.36. Found: C, 51.36; H, 4.63; N, 13.31; S, 12.47.

Example C(66)

[4-Amino-2-(1H-benzoimidazol-6-ylamino)-thiazol-5-yl]-(2-bromo-6-methyl-phenyl)-methanone

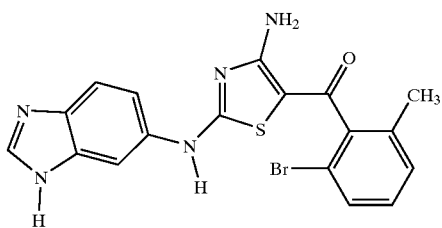

2'-Bromo-6'-methyl-acetophenone, which has the structural formula

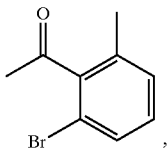

was prepared in a manner analogous to o-nitro-acetophenone (see Reynolds et al., *Org. Syn. Coll*, vol. IV (1963), pp. 708–710). From 2-methyl-6-bromobenzoic acid (3.10 g, 14.4 mmol) was provided 2.45 g (80%) of yellow oil, which matched previously described material by $^1$H NMR (Swenton et al., *J. Org. Chem.*, vol. 58 (1993), pp. 3308–3316) and was used without further purification.

2,2'-Dibromo-6'-methyl-acetophenone, which has the structural formula

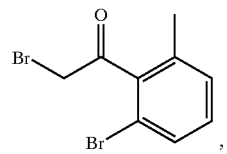

was prepared in a manner analogous to 2-bromo-2'-iodo-acetophenone, see Example C(12). Crude 2'-bromo-6'-methyl-acetophenone (1.00 g, 4.69 mmol) provided 1.48 g of yellow oil, which was used without further purification.

$^1$H NMR (CDCl$_3$): δ 7.44–7.37 (1H, m), 7.21–7.17 (2H, m), 4.42 (2H, s), 2.31 (3H, s).

The title compound was prepared in a manner analogous to that used in Example C(1). 6-Isothiocyanato-1H-benzoimidazole (see Boev et al., *Pharm. Chem. J.* (*Engl. Transl.*)., vol. 24 (1990), pp. 818–822) and 2,2'-dibromo-6'-methyl-acetophenone provided a brown solid in 32% yield, mp 208–210° C.

$^1$H NMR (DMSO-d$_6$): δ 12.43 (1H, bs), 10.74 (1H, bs), 8.18 (1H, s), 8.02 (2H, s), 7.75 (1H, bs), 7.44 (1H, bs), 7.44 (1H, d, J=7.5 Hz), 7.28–7.14 (3H, m), 2.22 (3H, s).

ESIMS (MH$^+$): 428/430.

Anal. Calcd. for C$_{18}$H$_{14}$N$_5$OSBr·1.0H$_2$O: C, 48.44; H, 3.61; N, 15.69; S, 7.18; Br, 17.90. Found: C, 48.54; H, 3.69; N, 15.57; S, 7.11; Br, 17.88.

Example C(67)

[4-Amino-2-(1H-benzoimidazol-6-ylamino)-thiazol-5-yl]-(3-methyl-biphenyl-2-yl)-methanone

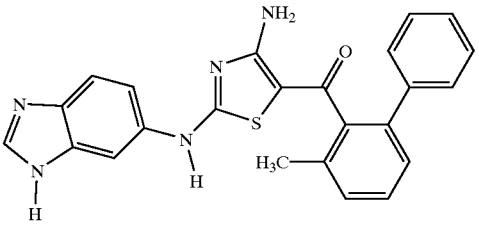

1-(3-Methyl-biphenyl-2-yl)-ethanone, which has the structural formula

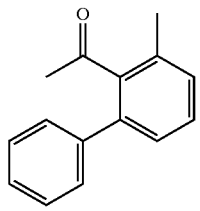

was prepared in the following manner. To 2'-bromo-6'-methyl-acetophenone (from Example C(66); 760 mg, 3.58 mmol) and Pd(OAc)$_2$ (114 mg) in DMF (38 mL) at 0° C. under Ar° was added in succession phenylboronic acid (495 mg) and 2M aq Na$_2$CO$_3$ (1.6 mL). The mixture was heated at 90° C. for 3 hours, then diluted with water (50 mL), and extracted with ether (2×100 mL). The ethereal extracts were concentrated to a crude product, which was purified via column chromatography with 2–5% ether/hexane stepwise gradient to obtain 670 mg (89% yield) of yellow oil, used without further purification.

$^1$H NMR (CDCl$_3$): δ 7.44–7.31 (5H, m), 7.25–7.19 (2H, m), 7.16–7.09 (1H, m), 2.33 (3H, s), 1.93 (3H, s).

2-Bromoacetyl-3-methyl-biphenyl, which has the structural formula

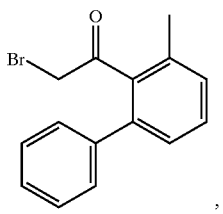

was prepared in a manner analogous to 2-bromo-2'-iodo-acetophenone, see Example C(12). Crude 1-(3-methyl-biphenyl-2-yl)-ethanone (295 mg, 1.40 mmol) provided 413 mg of yellow oil, which was used without further purification.

$^1$H NMR (CDCl$_3$): δ 7.48–7.18 (8H, m), 4.42 (2H, s), 2.38 (3H, s).

The title compound was prepared in a manner analogous to that used in Example C(1). 6-Isothiocyanato-1H-benzoimidazole (see Boev et al., *Pharm. Chem. J. (Engl. Transl).*, vol. 24 (1990), pp. 818–822) and 2-bromoacetyl-3-methyl-biphenyl provided a yellow solid in 49% yield, mp 184–190° C.

$^1$H NMR (DMSO-d$_6$): δ 8.13 (1H, s), 7.87 (1H, s), 7.53 (1H, d, J=8.7 Hz), 7.46–7.39 (2H, m), 7.38–7.15 (7H, m), 2.35 (3H, s).

HRFABMS (M+): Calcd.: 426.1389. Found: 426.1374.

Anal. Calcd. for C$_{24}$H$_{19}$N$_5$OS.1.0H$_2$O.0.3CH$_3$CN: C, 64.82; H, 4.84; N, 16.29; S, 7.03. Found: C, 64.88; H, 4.69; N, 16.40; S, 7.28.

Example C(68)

[4-Amino-2-(4-methoxy-benzylamino)-thiazol-5-yl]-(2,5-dimethyl thiophen-3-yl)-methanone

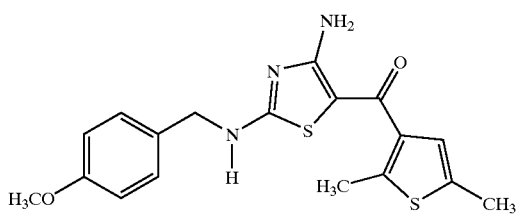

The title compound was prepared in a manner like that described for Example C(1). 3-Bromoacetyl-2,5-dimethyl-thiophene (from Example C(52)) and 1-(2-isothiocyanato-ethyl)-4-methoxy-benzene provided a white solid in 72% yield, mp 175° C.

$^1$H NMR (DMSO-d$_6$): δ 6.88 (2H, d, J=8.7 Hz), 6.74 (2H, d, J=8.7 Hz), 6.41 (1H, s), 6.24 (1H, s), 4.88 (2H, s), 3.78 (3H, s), 2.40 (3H, s), 1.98 (3H, s).

IR (KBr): 3311, 2920, 1663, 1552, 1514, 1244 cm$^{-1}$.

FABMS (MH+): 380.

Anal. Calcd. for C$_{18}$H$_{19}$N$_3$O$_2$S$_2$: C, 57.88; H, 5.13; N, 11.25; S, 17.17. Found: C, 57.97; H, 5.11; N, 11.33; S, 17.28.

Example C(69)

{4-Amino-2-[4-morpholin-4-yl-phenylamino]-thiazol-5-yl}-(3,5-dichloro-pyridin-4-yl)-methanone

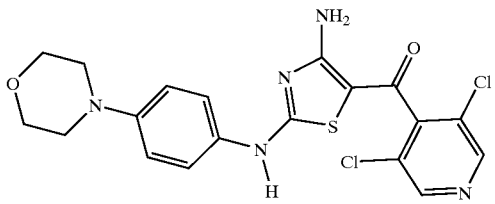

The title compound was prepared in a manner analogous to that used in Example C(1). 4-(4-Isothiocyanato-phenyl)-morpholine (from Example C(54)) and 4-bromoacetyl-3,5-dichloro-pyridine (from Example C(63)) provided a yellow solid in 58% yield, mp 291.5–292.5° C.

$^1$H NMR (DMSO-d$_6$): δ 10.75 (1H, s), 8.71 (2H, s), 8.32 (1H, bs), 8.01 (1H, bs), 7.30 (2H, bs), 6.92 (2H, d, J=9.0 Hz), 3.70 (4H, t, J=4.5 Hz), 3.05 (4H, t, J=4.5 Hz).

FABMS (MH+): 450/452;

Anal. Calcd. for C$_{19}$H$_{17}$N$_5$O$_2$SCl$_2$: C, 50.67; H, 3.80; N, 15.55; S, 7.12, Cl, 15.74. Found: C, 50.55; H, 3.83; N, 15.29; S, 6.95, Cl, 15.47.

Example C(70)

{4-Amino-2-[4-(4-methyl-piperazin-1-yl)-phenylamino]-thiazol-5-yl}-(3,5-dichloro-pyridin-4-yl)-methanone

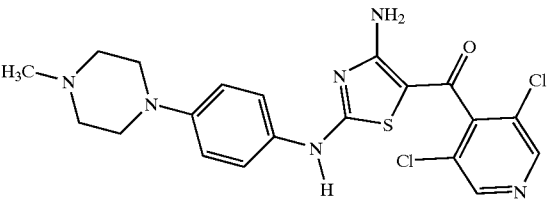

1-Methyl-4-(4-nitro-phenyl)-piperazine, which has the structural formula

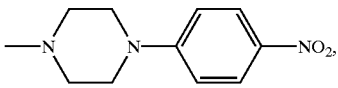

was first prepared as follows. A mixture of 1-methyl-piperazine (4.00 g, 39.9 mmol) and 1-chloro-4-nitro-benzene (3.14 g, 20.0 mmol) was heated to 80° C. for 24 hours, allowed to cool, and diluted with H$_2$O. The aqueous layer was extracted with MeOH:CH$_2$Cl$_2$ (20:80; 4×50 mL). The combined organic layers were dried over MgSO$_4$, filtered, concentrated under reduced pressure, and recrystallized from ethanol to afford 3.2 g (75% yield) of a yellow solid, which matched previously reported material by $^1$H NMR (de Silva et al., *J. Chem. Soc. Perkin Trans.* 2, vol. 9 (1993), pp. 1611–1616) and was used without further purification.

4-(4-Methyl-piperazin-1-yl)-aniline, which has the structural formula

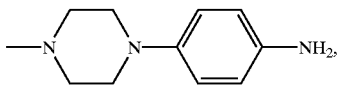

was next prepared as follows. To a suspension of 1-methyl-4-(4-nitro-phenyl)-piperazine (2 g, 9.02 mmol) in absolute ethanol (30 mL) was added 10% Pd—C (250 mg). The resultant mixture was stirred under an atmosphere of $H_2$ for 5 hours, then filtered through a pad of Celite. The filtrate was concentrated under reduced pressure to afford 1.7 g (99% yield) of a brown solid, which was used without further purification.

$^1$H NMR (CDCl$_3$): δ 6.81 (2H, d, J=8.8 Hz), 6.62 (2H, d, J=8.8 Hz), 3.42 (2H, bs), 3.15 (4H, t, J=5.0 Hz), 2.68 (4H, t, J=5.0 Hz), 2.40 (3H, s).

1-(4-Isothiocyanato-phenyl)-4-methyl-piperazine, which has the structural formula

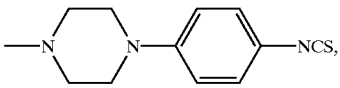

was prepared in a manner analogous to 1-(4-isothio-cyanato-phenyl)-1H-imidazole for Example C(41). 4-(4-Methyl-piperazin-1-yl)-aniline provided 1.7 g (83% yield) of a cream-colored solid, mp 118–120° C. (lit. 120–122° C., Galstuckova et al., *J. Org. Chem. USSR* (*Engl. Transl.*), vol. 5 (1969), pp. 1121–1124), which was used without further purification. IR spectrum matched that reported by Martvon et al., *Chem. Zvesti*, vol. 27 (1973), pp. 808–810.

$^1$H NMR (CDCl$_3$): δ 7.20 (2H, d, J=9.0 Hz), 6.82 (2H, d, J=9.0 Hz), 3.20 (4H, dd, J=5.0, 4.7 Hz), 2.52 (4H, dd, J=5.0, 4.7 Hz), 2.24 (3H, s).

Anal. Calcd. for C$_{12}$H$_{15}$N$_3$S: C, 61.77; H, 6.48; N, 18.01; S, 13.69. Found: C, 61.51; H, 6.56; N, 17.86; S, 13.69.

The title compound was prepared in a manner like that described for Example C(1). 1-(4-Isothiocyanato-phenyl)-4-methyl-piperazine and 4-bromoacetyl-3,5-dichloro-pyridine (from Example C(63)) gave a crude solid, which after recrystallization with EtOH/H$_2$O, provided a 40 mg (23% yield) of a pale brown solid, mp 150–151° C.

$^1$H NMR (DMSO-d$_6$): δ 10.78 (1H, s), 8.70 (1H, s), 8.00–8.41 (2H, m), 7.24 (2H, bs), 6.88 (2H, d, J=9.0 Hz), 3.08 (4H, dd, J=5.0, 4.7 Hz), 2.40 (4H, dd, J=5.0, 4.7 Hz), 2.20 (3H, s).

IR (KBr): 3395, 2925, 1618, 1546, 1514, 1426, 1240 cm$^{-1}$.

HRFABMS: Calcd. for C$_{20}$H$_{21}$Cl$_2$N$_6$OS (MH$^+$): 463.0875. Found: 563.0861.

Anal. Calcd. for C$_{20}$H$_{20}$N$_6$OSCl$_2$.0.6H$_2$O.0.1EtOH.0.05CHCl$_3$: C, 50.20; H, 5.06; N, 16.22; S, 6.19, Cl, 14.71. Found: C, 50.34; H, 5.11; N, 16.53; S, 6.43; Cl, 14.74.

Example C(71)

{4-Amino-2-[4-(4-methyl-piperazin-1-yl)-phenylamino]-thiazol-5-yl}-(2,6-dichloro-phenyl)-methanone

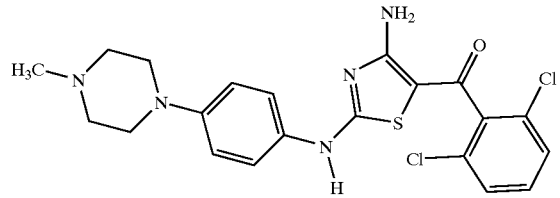

The title compound was prepared in a manner like that described for Example C(1). 1-(4-Isothiocyanato-phenyl)-4-methyl-piperazine (from Example C(70)) and 2-bromo-2',6'-dichloro-acetophenone (from Example C(52)) gave, after recrystallization with H$_2$O/EtOH/CH$_2$Cl$_2$, 2.2 g (64% yield) of a yellow solid, mp 160–162° C.

$^1$H NMR (DMSO-d$_6$): δ 10.60 (1H, s), 8.00 (2H, bs), 7.20–7.41 (4H, m), 6.88 (2H, d, J=9.0 Hz), 3.08 (4H, dd, J=5.0, 4.7 Hz), 2.40 (4H, dd, J=5.0, 4.7 Hz), 2.18 (3H, s).

IR (KBr): 3394, 3164, 2942, 2810, 1610, 1546, 1427, 1242 cm$^{-1}$.

HRFABMS: Calcd. for C$_{21}$H$_{22}$Cl$_2$N$_5$OS (MH$^+$): 462.0922. Found: 462.0906.

Anal. Calcd. for C$_{21}$H$_{21}$N$_5$OSCl$_2$.0.5H$_2$O.1EtOH.0.1CH$_2$Cl$_2$: C, 52.75; H, 5.40; N, 13.32; S, 6.10, Cl, 14.83. Found: C, 53.06; H, 5.37; N, 13.51; S, 6.26; Cl, 14.63.

Example C(72)

[4-Amino-2-(1H-benzoimidazol-6-ylamino)-thiazol-5-yl]-(3,5-dibromo-thiophen-2-yl)-methanone

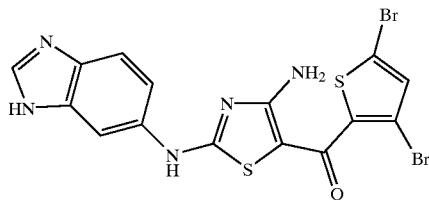

2-Acetyl-3,5-dibromo-thiophene, which has the structural formula

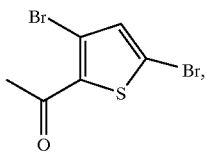

was first prepared as follows. To a solution of 2,4-dibromothiophene (2.0 g, 8.27 mmol) and acetyl chloride (0.82 mL, 11.6 mmol) in ether (3 mL) was added portion-wise AlCl$_3$ (1.5 g, 11.2 mmol). After 4 hours, another portion of acetyl chloride and AlCl$_3$ were added, the mixture was refluxed for 1 hour and allowed to cool. The reaction was carefully quenched with ice and extracted with ether. The ethereal layers were decolorized with activated carbon, dried over MgSO$_4$, passed through a pad of silica gel, and concentrated to give 1.8 g (77% yield) of dark brown oil, which had a ¹H NMR spectrum that matched previously described, see del Agua et al, *J. Heterocycl. Chem.*, vol. 18 (1981), pp. 1345–1347, and was used without further characterization.

2-Bromoacetyl-3,5-dibromo-thiophene, which has the structural formula

was next prepared in a manner analogous to 2-bromo-2'-iodo-acetophenone, see Example C(12). 2-Acetyl-3,5-dibromo-thiophene (220 mg, 0.77 mmol) provided 295 mg of dark brown solid, which was used without further purification.

¹H NMR (CDCl₃): δ 7.13 (1H, s), 4.54 (2H, s).

Finally, the title compound was prepared in a manner analogous to that used in Example C(1). 6-Isothiocyanato-1H-benzoimidazole (see Boev et al., *Pharm. Chem J.* (*Engl. Transl*)., vol. 24 (1990), pp. 818–822) and 2-bromoacetyl-3,5-dibromo-thiophene provided a dark brown solid in 50% yield, mp 261–264° C.

¹H NMR (DMSO-d₆): δ 12.50 (1H, bs), 10.94 (1H, s), 8.27 (2H, bs), 8.21 (1H, s), 7.87 (1H, bs), 7.57 (1H, d, J=8.7 Hz), 7.36 (1H, s), 7.24 (1H, d, J=8.7 Hz).

HRFABMS (MH⁺): Calcd.: 499.8673. Found: 499.8686.

Anal. Calcd. for C₁₅H₉N₅OS₂Br₂.0.5H₂O: C, 35.45; H, 1.98; N, 13.78; S, 12.62; Br, 31.45. Found: C, 35.37; H, 1.73; N, 13.52; S, 12.75; Br, 31.25.

Example C(73)

4-[4-Amino-5-(3,5-dibromo-thiophene-2-carbonyl)-thiazol-2-ylamino]-benzenesulfonamide

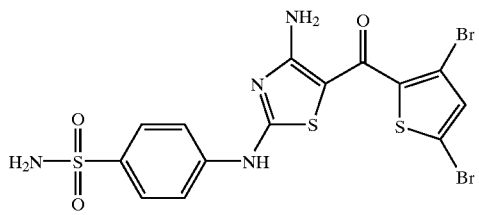

The title compound was prepared in a manner analogous to that used in Example C(1). 4-Isothiocyanato-benzenesulfonamide and 2-bromoacetyl-3,5-dibromo-thiophene (from Example C(72)) provided a yellow powder in 41% yield, mp 254–255° C.

¹H NMR (DMSO-d₆): δ 11.24 (1H, s), 8.31 (2H, bs), 7.77 (4H, s), 7.40 (1H, s), 7.28 (2H, s).

FABMS (MH⁺): 536/538/540.

Anal. Calcd. for C₁₄H₁₀N₄O₃S₃Br₂: C, 31.24; H, 1.87; N, 10.41; S, 17.87; Br, 29.69. Found: C, 31.08; H, 1.90; N, 10.16; S, 17.69; Br, 29.96.

Example C(74)

[4-Amino-2-(1H-benzoimidazol-6-ylamino)-thiazol2-5-yl]-(1,5-dimethyl-1H-imidazol-4-yl)-methanone

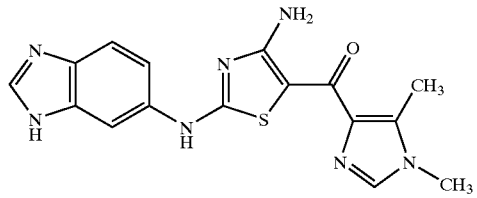

1,5-Dimethyl-1H-imidazole-4-carboxylic acid, which has the structural formula

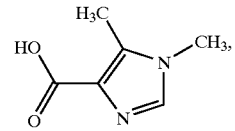

was first made as follows. A fresh solution of NaOH (3.86 g, 96.5 mmol) in water (20 mL) was added to a solution of ethyl 1,5-dimethyl-1H-imidazole-4-carboxylate (5.39 g, 32.0 mmol; Ohno et al, *Chem. Pharm. Bull.*, vol. 42 (1994), pp. 1463–1473) in EtOH (20 mL). After 5 hours, the mixture was cooled to 0° C., and acidified with 38% HCl to pH 3–4. The resultant white solid was filtered off, washed with small amount of cold EtOH:H₂O (1:1), and dried under high vacuum to give 3.51 g (78%) of white solid, which was used without further purification.

¹H NMR (D₂O): δ 8.49 (1H, s), 3.73 (3H, s), 2.46 (3H, s).

Anal. Calcd. for C₆H₈N₂O₂: C, 51.42; H, 5.75; N, 19.99. Found: C, 51.52; H, 5.78; N, 19.98.

1,5-Dimethyl-1H-imidazole-4-carboxylic acid N-methoxy-N-methyl-amide, which has the structural formula

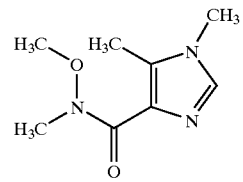

was next prepared as follows. To a mixture of 1,5-dimethyl-1H-imidazole-4-carboxylic acid (2.01 g, 14.4 mmol) in DMF (20 mL) was added O-(7-azabenzotriazol-1-yl)-N,N,N',N'-tetramethyluronium hexafluorophosphate (HATU; 6.00 g, 15.8 mmol) and diisopropylethylamine (7.5 mL, 43 mmol). After 5 min., to the resultant clear solution was added N,O-dimethylhydroxylamine hydrochloride (1.54 g, 15.79 mmol). After 1 hour, the resultant yellow solution was partitioned between CHCl₃ and water. The separated organic layer was washed with water and brine, dried over K₂CO₃, concentrated, and dried under high vacuum to provide 1.88 g (72% yield) of light brown solid, which was used without further purification.

¹H NMR (CDCl₃): δ 7.36 (1H, s), 3.81 (3H, s), 3.56 (3H, s), 3.47 (3H, s), 2.45 (3H, s).

1-(1,5-Dimethyl-1H-imidazol-4-yl)-ethanone, which has the structural formula

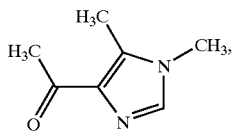

was prepared as follows. To a solution of crude 1,5-dimethyl-1H-imidazole-4-carboxylic acid N-methoxy-N-methyl-amide (1.69 g, 9.21 mmol) in THF (55 mL) at −78° C. was added dropwise 1.4 M CH$_3$MgBr in ether (8.55 mL, 12.0 mmol). The mixture was allowed to warm to ambient temperature over one hour, then quenched with 1N HCl, basified to pH 9 with 1N NaOH, concentrated under reduced pressure to remove the THF, and extracted with EtOAc (200 mL). The organic layer was separated, dried over K$_2$CO$_3$, and evaporated to furnish 1.2 g (94% yield) of yellow solid, which was used without further purification.

$^1$H NMR (CDCl$_3$): δ 7.35 (1H, s), 3.57 (3H, s), 2.55 (3H, s), 2.53 (3H, s).

2-Bromo-1-(1,5-dimethyl-1H-imidazol-4-yl)-ethanone, which has the structural formula

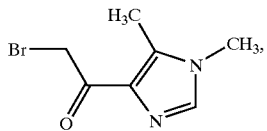

was next prepared as follows. To 1-(1,5-dimethyl-1H-imidazol-4-yl)-ethanone (464 mg, 3.36 mmol) in HOAc (8.5 mL) at 0° C. was added dropwise bromine (173 μl, 3.36 mmol). After 36 hours at ambient temperature, crude 2-bromo-1-(1,5-dimethyl-1H-imidazol-4-yl)-ethanone hydrobromide salt was filtered off as a brown solid, which was successively washed with a minimal amount of water and ether, dissolved in CHCl$_3$, cooled to 0° C., treated with NaHCO$_3$, and concentrated under reduced pressure below 40° C. to obtain 719 mg (99% yield) of yellow oil, which was used without further purification.

$^1$H NMR (DMSO-d$_6$): δ 8.40 (1H, s), 4.68 (2H, s), 3.66 (3H, s), 2.67 (3H, s).

The title compound was finally prepared in a manner analogous to that used in Example C(1). 6-Isothiocyanato-1H-benzoimidazole (see Boev et al., *Pharm. Chem. J.* (*Engl. Transl*)., vol. 24 (1990), pp. 818–822) and 2-bromo-1-(1,5-dimethyl-1H-imidazol-4-yl)-ethanone provided a dark brown solid in 15% yield, mp 275.5–277° C.

$^1$H NMR (DMSO-d$_6$): δ 12.42 (1H, s), 10.42 (1H, s), 8.16 (1H, s), 7.94 (1H, bs), 7.61–7.30 (2H, m), 7.26 (1H, dd, J=8.4, 1.9 Hz), 3.54 (3H, s), 2.51 (3H, s).

HRFABMS (MH$^+$): Calcd.: 354.1137. Found: 354.1132.

Anal. Calcd. for C$_{16}$H$_{15}$N$_7$OS.0.5H$_2$O.0.8CH$_3$OH: C, 52.00; H, 4.99; N, 25.27; S, 8.26. Found: C, 52.27; H, 4.81; N, 25.06; S, 8.12.

Example C(75)

[4-Amino-2-(4-morpholin-4-yl-phenylamino)-thiazol-5-yl]-(2,6-dichloro-3-nitro-phenyl)-methanone

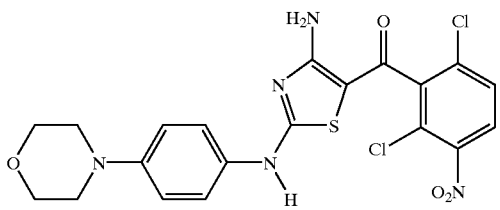

2-Bromo-2',6'-dichloro-3'-nitro-acetophenone, which has the structural formula

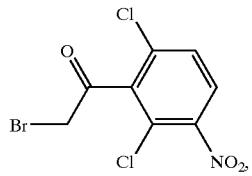

was first prepared as follows. To a solution of 2',6'-dichloro-3'-nitro-acetophenone (1.3 g, 5.6 mmol; Breslin, et al., *J. Med. Chem.*, vol. 38 (1995), pp. 771–793) in glacial acetic acid (5 mL) at ambient temperature was added bromine (352 μL, 6.83 mmol). The resulting mixture was heated to 80° C. for 1 hour, allowed to cool, and diluted with ether. The organic layer was washed with ice-cold H$_2$O (25 mL), sat aq. NaHCO$_3$ (3×25 mL), and brine (25 mL), dried over MgSO$_4$, and concentrated under reduced pressure to give 1.7 g (97% in crude yield) of a yellow oil, which was used without further purification.

$^1$H NMR (CDCl$_3$): δ 7.98 (1H, d, J=8.7 Hz), 7.38 (1H, d, J=8.7 Hz), 4.40 (2H, s).

The title compound was prepared in a manner like that described for Example C(1). 2-Bromo-2',6'-dichloro-3'-nitro-acetophenone and 4-(4-isothiocyanato-phenyl)-morpholine (from Example C(54)) gave a crude solid, which after purification by flash column chromatography with hexane/EtOAc (70:30) as eluant, provided a dark-brown foam in 52% yield, mp 170–172° C.

$^1$H NMR (DMSO-d$_6$): δ 10.70 (1H, s), 8.30 (1H, s), 8.10 (1H, d, J=9.0 Hz), 7.90 (1H, d, J=8.7 Hz), 7.20–7.30 (2H, m), 6.90 (2H, d, J=9.0 Hz), 3.70 (4H, dd, J=5.0, 4.7 Hz), 3.06 (4H, dd, J=5.0, 4.7 Hz).

IR (KBr): 3289, 2966, 2848, 1634, 1542, 1425, 1343, 1225, 1108 cm$^{-1}$.

HRFABMS: Calcd. for C$_{20}$H$_{17}$Cl$_2$N$_5$O$_4$SNa (M+Na$^+$): 516.0276. Found: 516.0258.

Anal. Calcd. for C$_{20}$H$_{17}$Cl$_2$N$_5$O$_4$S.0.35CHCl$_3$: C, 45.59; H, 3.26; N, 13.06; S, 5.98; Cl, 20.07. Found: C, 45.33; H, 3.37; N, 12.96; S, 5.93; Cl, 20.27.

Example C(76)

4-[4-Amino-5-(1,5-dimethyl-1H-imidazole-4-carbonyl)-thiazol-2-ylamino]-benzenesulfonamide

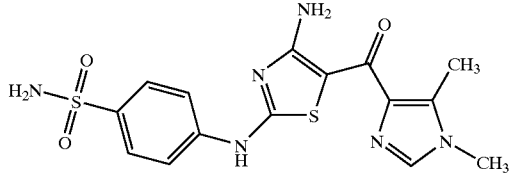

The title compound was prepared in a manner analogous to that used in Example C(1). 4-Isothiocyanato-benzenesulfonamide and 5-bromoacetyl-1,5-dimethyl-1H-imidazole (from Example C(74)) provided a yellow solid in 8% yield, mp 293–294° C.

$^1$H NMR (DMSO-d$_6$): δ 10.80 (1H, s), 7.81 (2H, d, J=9.0 Hz), 7.75 (2H, d, J=9.0 Hz), 7.62 (1H, s), 7.24 (2H, s), 3.56 (3H, s), 2.52 (3H, s).

HRFABMS (M+Na$^+$): Calcd.: 415.0623. Found: 415.0609.

Anal. Calcd. for C$_{15}$H$_{16}$N$_6$O$_3$S$_2$.1.0CH$_3$OH.1.0CHCl$_3$: C, 42.53; H, 4.45; N, 18.26; S, 13.93. Found: C, 42.57; H, 4.41; N, 18.18; S, 14.07.

Example C(77)

[4-Amino-2-(4-morpholin-4-yl-phenylamino)-thiazol-5-yl]-(1,5-dimethyl-1H-imidazol-4-yl)-methanone

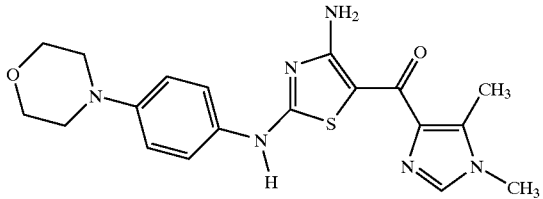

The title compound was prepared in a manner analogous to that used in Example C(1). 4-(4-Isothiocyanato-phenyl)-morpholine (from Example C(54)) and 5-bromoacetyl-1,5-dimethyl-1H-imidazole (from Example C(74)) provided a yellow solid in 12% yield, mp >300° C.

$^1$H NMR (DMSO-d$_6$): δ 10.21 (1H, s), 7.57 (1H, s), 7.42 (2H, d, J=8.8 Hz), 6.94 (2H, d, J=8.8 Hz), 3.72 (4H, t, J=4.7 Hz), 3.54 (3H, s), 3.06 (4H, t, J=4.7 Hz), 2.50 (3H, s).

HRFABMS (M+): Calcd.: 398.1525. Found: 398.1516.

Anal. Calcd. for C$_{19}$H$_{22}$N$_6$O$_2$S.0.2CH$_3$OH.0.2CHCl$_3$: C, 54.34; H, 5.41; N, 19.60; S, 7.48. Found: C, 54.63; H, 5.27; N, 19.56; S, 7.47.

Example C(78)

[4-Amino-2-(1H-benzoimidazol-6-ylamino)-thiazol-5-yl]-(3-methyl-5-nitro-thiophen-2-yl)-methanone

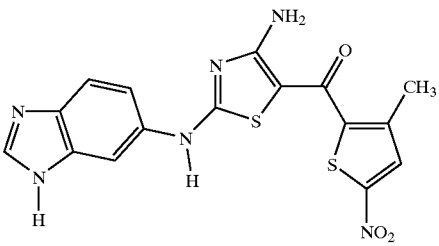

2-Acetyl-3-methyl-5-nitro-thiophene, which has the structural formula

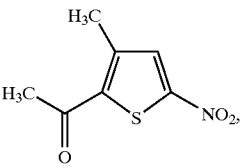

was first prepared as follows. 2-Bromo-3-methyl-5-nitro-thiophene (5.17 g, 23.3 mmol; Spinelli et al, *J. Chem. Soc. Perkin Trans.* 2, (1975), pp. 620–622), tributyl(1-ethoxyvinyl)tin(IV) (8.65 mL, 25.6 mmol), and dichlorobis(triphenylphosphine)palladium(II) (163 mg, 0.23 mmol) in toluene (10.5 mL) was heated under Ar° at 100° C. for 2.5 hours. 5% aq HCl (78 mL) was added, and the mixture stirred at 60° C. for 15 min., then partitioned with ether and water. The organic layer was separated, dried over MgSO$_4$, and concentrated to a residue that was dissolved in ether (130 mL). 1,8-Diazabicyclo[5.4.0]undec-7-ene (DBU; 2.2 eq) and a 0.1M solution of iodine in ether was added dropwise until color persisted for several seconds. The resultant solution was passed through a short column of silica gel and concentrated in vacuo to give 3.74 g (87% yield) of yellow solid, which was used without further purification.

$^1$H NMR (CDCl$_3$): δ 7.72 (1H, s), 2.58 (3H, s), 2.57 (3H, s).

2-Bromoacetyl-3-methyl-5-nitro-thiophene, which has the structural formula

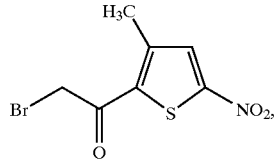

was prepared in a manner analogous to 2-bromo-2'-iodo-acetophenone, see Example C(12). 2-Acetyl-3-methyl-5-nitro-thiophene (230 mg, 1.24 mmol) provided 330 mg of a cloudy yellow oil, which contained a trace amount of dibrominated byproduct by NMR, which was used without further purification.

$^1$H NMR (CDCl$_3$): δ 7.75 (1H, s), 4.28 (2H, s), 2.60 (2H, s).

The title compound was prepared in a manner analogous to that used in Example C(1). 6-Isothiocyanato-1H-benzoimidazole (see Boev et al., *Pharm. Chem. J. (Engl.*

Transl)., vol. 24 (1990), pp. 818–822) and 2-bromoacetyl-3-methyl-5-nitro-thiophene provided a yellow solid in 23% yield, mp >300° C.

¹H NMR (DMSO-d₆): δ 12.50 (1H, d, J=14.3 Hz), 11.01 (1H, bs), 8.40 (2H, bs), 8.21 (1H, s), 8.02 (1H, s), 7.63 (1H, bs), 7.52 (1H, bs), 7.36 (1H, d, J=11.0 Hz), 2.33 (3H, s).

HRFABMS (MH⁺): Calcd.: 401.0491. Found: 401.0474.

Anal. Calcd. for $C_{16}H_{12}N_6O_3S_2 \cdot 0.7H_2O \cdot 0.8CH_3OH$: C, 46.00; H, 3.81; N, 19.16; S, 14.62. Found: C, 45.92; H, 3.50; N, 19.096; S, 14.59.

Example C(79)

[4-Amino-2-(1H-benzoimidazol-6-ylamino)-thiazol-5-yl]-(2,6-difluoro-phenyl)-methanone

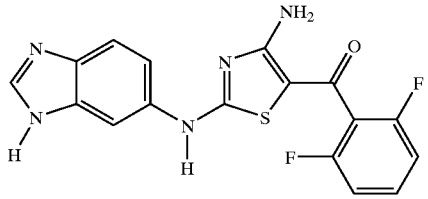

2-Bromo-2',6'-difluoro-acetophenone, which has the structural formula

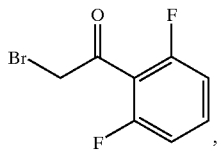

was first prepared in a manner analogous to 2-bromo-2'-iodo-acetophenone, see Example C(12). 2',6'-difluoroacetophenone (703 mg, 4.5 mmol) provided 1.01 g (96% yield) of light yellow oil, which was used without further purification.

¹H NMR (CDCl₃): δ 7.56–7.42 (1H, m), 7.07–6.98 (2H, m), 4.38 (2H, s).

The title compound was prepared in a manner analogous to that used in Example C(1). 6-Isothiocyanato-1H-benzoimidazole (see Boev et al., *Pharm. Chem. J. (Engl. Transl).*, vol. 24 (1990), pp. 818–822) and 2-bromo-2',6'-difluoro-acetophenone provided yellow crystals in 78% yield, mp 194–200° C.

¹H NMR (DMSO-d₆): δ 12.45 (1H, s), 10.86 (1H, s), 8.19 (1H, s), 8.16 (2H, bs), 7.80 (1H, bs), 7.59–7.44 (2H, m), 7.22–7.11 (3H, m).

HRFABMS (MH⁺): Calcd.: 372.0731. Found: 372.0725.

Anal. Calcd. for $C_{17}H_{11}N_5OSF_2 \cdot 0.5H_2O$: C, 53.68; H, 3.18; N, 18.41; S, 8.43. Found: C, 53.73; H, 3.14; N, 18.32; S, 8.53.

Example C(80)

{4-Amino-2-[4-(4-methyl-piperazin-1-yl)-phenylamino]-thiazol-5-yl}-(2,6-difluoro-phenyl)-methanone

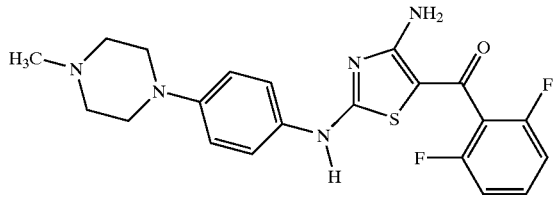

The title compound was prepared in a manner analogous to that used in Example C(1). 1-(4-Isothiocyanato-phenyl)-4-methyl-piperazine (from Example C(70)) and 2-bromo-2',6'-difluoro-acetophenone (from Example C(79)) provided a yellow solid in 71% yield, mp 168–70° C.

¹H NMR (DMSO-d₆): δ 10.62 (1H, s), 8.11 (2H, bs), 7.54–7.43 (1H, m), 7.28 (2H, d, J=7.5 Hz), 7.20–7.10 (2H, m), 6.90 (2H, d, J=9.0 Hz), 3.08 (4H, t, J=4.8 Hz), 2.41 (4H, t, J=4.8 Hz), 2.19 (3H, s).

IR (KBr): 2942, 2809, 1620, 1590, 1546, 1516, 1464, 1429, 1238, 1002 cm⁻¹.

HRFABMS (MH⁺): Calcd.: 430.1513. Found: 430.1502.

Anal. Calcd. for $C_{21}H_{21}N_5OSF_2 \cdot 0.3H_2O$: C, 58.00; H, 5.01; N, 16.10; S, 7.37. Found: C, 57.98; H, 4.92; N, 16.08; S, 7.42.

Example C(81)

({4-Amino-2-[4-(4-methyl-piperazin-1-yl)-phenylamino]-thiazol-5-yl}-(2,6-dichloro-4-trifluoromethyl-phenyl)-methanone

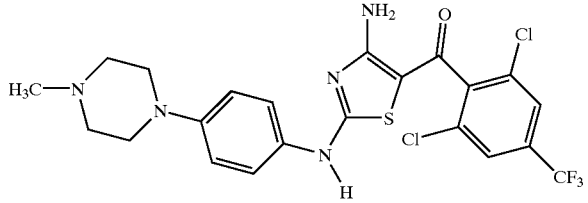

The title compound was prepared in a manner like that described for Example C(1). 1-(4-Isothiocyanato-phenyl)-4-methyl-piperazine (from Example C(70)) and 2-bromo-2',6'-dichloro-4'-trifluoromethyl-acetophenone gave, after recrystallization from EtOAc/hexane, yellow needles in 68% yield, mp 239–240° C.

¹H NMR (DMSO-d₆): δ 8.00 (2H, s), 7.28 (2H, bs), 6.92 (2H, d, J=8.7 Hz), 3.10 (4H, dd, J=5.1, 4.7 Hz), 2.42 (4H, dd, J=5.1, 4.8 Hz), 2.20(3H,s).

IR (KBr): 3377, 3283, 2942, 2813, 1598, 1542, 1513, 1425 cm⁻¹.

FABMS (M+Na⁺): 552.

Anal. Calcd. for $C_{22}H_{20}Cl_2F_3N_5OS \cdot 0.8H_2O \cdot 0.7C_6H_{14}$: C, 52.00; H, 5.23; N, 11.57; S, 5.30, Cl, 11.72. Found: C, 51.94; H, 4.98; N, 11.18; S, 5.20; Cl, 11.48.

Example C(82)

N-{3-[4-Amino-2-(1H-benzoimidazol-6-ylamino)-thiazole-5-carbonyl]-2,4-dichloro-phenyl}-acetamide

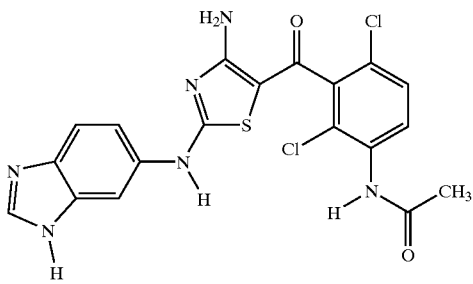

3'-Amino-2',6'-dichloro-acetophenone, which has the structural formula

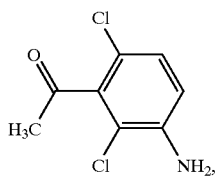

was first prepared as follows. To a solution of $SnCl_2.2H_2O$ (7.70 g, 34.2 mmol) in 6N aq HCl (20 mL) was added 2',6'-dichloro-3'-nitro-acetophenone (4.00 g, 17.1 mmol; Breslin, et al., *J. Med. Chem.*, vol. 38 (1995), pp. 771–793). The resultant mixture was heated at reflux for 5 hours, allowed to cool, and carefully treated with anhydrous $Na_2CO_3$. The resultant white precipitate was filtered off and washed with $CHCl_3$. The organic layer was reserved and the aqueous layer was extracted with $CHCl_3$ (3×50 mL). The combined organic layers were dried over $MgSO_4$, filtered, and concentrated in vacuo to give a black oil, which was purified via flash column chromatography with EtOAc:hexane (20:80) as eluant. In this manner, 2.6 g (75% yield) of a pale brown oil was obtained and used without further purification.

$^1$H NMR ($CDCl_3$): δ 7.08 (1H, d, J=8.7 Hz), 6.70 (1H, d, J=8.7 Hz), 4.12 (2H, bs), 2.56 (3H, s).

N-(3-Acetyl-2,4-dichloro-phenyl)-acetamide, which has the structural formula,

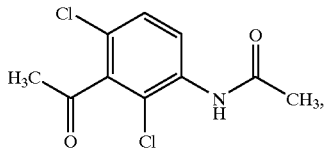

was next prepared as follows. To a solution of 3'-amino-2',6'-dichloro-acetophenone (2.40 g, 11.8 mmol) in glacial acetic acid (25 mL) was added acetic anhydride (5.56 mL, 58.8 mmol). The resultant mixture was heated at reflux for 2 hours, allowed to cool, and diluted with ether (100 mL). The organic layer was washed with $H_2O$ (2×50 mL), dried over $MgSO_4$, concentrated in vacuo, and azeotroped with n-heptane to give 2.3 g of a pale white solid, which was used without further purification.

$^1$H NMR ($CDCl_3$): δ 8.38 (1H, d, J=9.1 Hz), 7.62 (1H, bs), 7.34 (1H, d, J=9.0 Hz), 2.60 (3H, s), 2.22 (3H, s).

N-(3-Bromoacetyl-2,4-dichloro-phenyl)-acetamide, which has the structural formula,

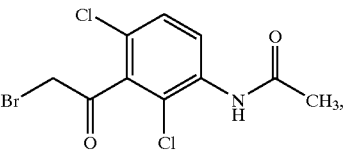

was prepared in a manner analogous to 2-bromo-2',6'-dichloro-3'-nitro-acetophenone for Example C(75). N-(3-Acetyl-2,4-dichloro-phenyl)-acetamide gave a pale brown oil in 100% crude yield, which was used without further purification.

$^1$H NMR ($CDCl_3$): δ 8.48 (1H, d, J=8.7 Hz), 7.60 (1H, bs), 7.38 (1H, d, J=9.0 Hz), 4.40 (2H, s), 2.2 (3H, s).

The title compound was prepared in a manner like that described for Example C(1). 6-Isothiocyanato-1H-benzoimidazole (see Boev et al., *Pharm. Chem. J. (Engl. Transl.)*, vol. 24 (1990), pp. 818–822) and N-(3-bromoacetyl-2,4-dichloro-phenyl)-acetamide gave a product which was purified via flash column chromatography with a stepwise gradient of $MeOH:CH_2Cl_2$ (10:90) to $HOAc:MeOH:CH_2Cl_2$ (1:10:90) to provide a yellow foam in 56% yield, that decomposed above 200° C.

$^1$H NMR (DMSO-$d_6$): δ 9.90 (1H, s), 8.20 (1H, s), 7.84–7.96 (1H, m), 7.68 (1H, d, J=7.4 Hz), 7.58 (1H, d, J=8.8 Hz), 7.24 (1H, d, J=8.4 Hz), 2.20 (3H, s).

IR (KBr): 3295, 1625, 1525, 1425 cm$^{-1}$.

HRFABMS. Calcd. (MH$^+$): 461.0354. Found: 461.0344.

Anal. Calcd. for $C_{19}H_{15}Cl_2N_6O_2S.H_2O.3HOAc$: C, 45.53; H, 4.28; N, 12.74; S, 4.86; Cl, 10.75. Found: C, 45.93 H, 4.08; N, 12.49; S, 4.83; Cl, 10.45.

Example C(83)

[4-Amino-2-(4-morpholin-4-yl-phenylamino)-thiazol-5-yl]-(3-methyl-biphenyl-2-yl)-methanone

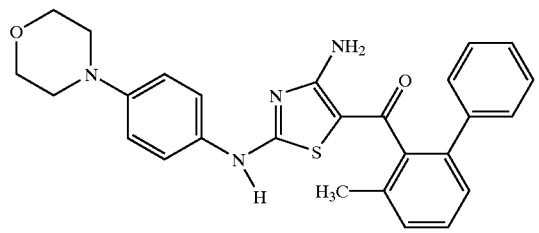

The title compound was prepared in a manner analogous to that used in Example C(1). 4-(4-Isothiocyanato-phenyl)-morpholine (from Example C(54)) and 2-bromoacetyl-3-methyl-biphenyl (from Example C(67)) provided a yellow solid in 29% yield, mp 125–35° C.

$^1$H NMR (DMSO-$d_6$): δ 10.40 (1H, s), 7.86 (2H, s), 7.42–7.24 (9H, m), 7.19 (1H, d, J=7.5 Hz), 6.93 (2H, d, J=8.7 Hz), 3.73 (4H, t, J=4.4 Hz), 3.07 (4H, t, J=4.4 Hz), 2.26 (3H, s).

HRFABMS (M$^+$): Calcd.: 471.1855. Found: 471.1839.

Anal. Calcd. for $C_{27}H_{26}N_4O_2S.1.0CF_3CO_2H$: C, 59.58; H, 4.66; N, 9.58; S, 5.48. Found: C, 59.41; H, 5.01; N, 9.26; S, 5.18.

Example C(84)

[4-Amino-2-(4-morpholin-4-yl-phenylamino)-thiazol-5-yl]-(2-bromo-6-methyl-phenyl)-methanone

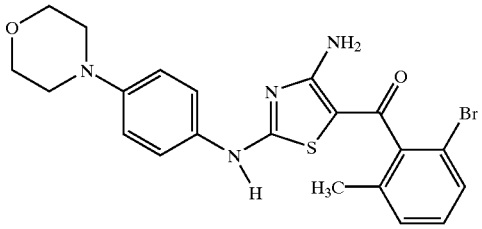

The title compound was prepared in a manner analogous to that used in Example C(1). 4-(4-Isothiocyanato-phenyl)-morpholine (from Example C(54)) and 2,2'-dibromo-6'-methyl-acetophenone (from Example C(66)) provided a crude solid, which was triturated with MeOH/CHCl$_3$ to furnish a yellow solid in 22% yield, mp 105–125° C.

$^1$H NMR (DMSO-d$_6$): δ 10.57 (1H, s), 8.01 (2H, bs), 7.46 (1H, d, J=7.5 Hz), 7.39–7.18 (4H, m), 6.96 (2H, d, J=8.7 Hz), 3.74 (4H, t, J=4.7 Hz), 3.09 (4H, t, J=4.7 Hz), 2.20 (3H, s).

HRFABMS (MH$^+$): Calcd.: 73.0647/475. Found: 473.0657/475.

Anal. Calcd. for C$_{21}$H$_{21}$N$_4$O$_2$SBr.0.7MeOH.0.6CHCl$_3$: C, 47.60; H, 4.37; N, 9.98; S, 5.71. Found: C, 47.95; H, 4.05; N, 9.77; S, 5.51.

Example C(85)

4-[4-Amino-5-(2,6-difluoro-benzoyl)-thiazol-2-ylamino]-benzenesulfonamide

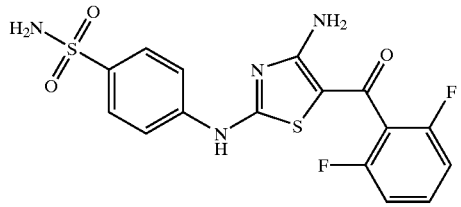

The title compound was prepared in a manner analogous to that used in Example C(1). 4-Isothiocyanato-benzenesulfonamide and 2-bromo-2',6'-difluoro-acetophenone (from Example C(79)) provided light yellow crystals in 69% yield, mp 258–260° C.

$^1$H NMR (DMSO-d$_6$): δ 11.20 (1H, s), 8.20 (2H, bs), 7.79 (2H, d, J=9.0 Hz), 7.74 (2H, d, J=9.0 Hz), 7.61–7.49 (1H, m), 7.26 (2H, s), 7.22 (1H, d, J=7.9 Hz), 7.19 (1H, d, J=8.0 Hz).

IR (KBr): 3310, 1622, 1599, 1547, 1525, 1467, 1425, 1410, 1318, 1156 cm$^{-1}$.

HRFABMS (MH$^+$): Calcd.: 411.0397. Found: 411.0410.

Anal. Calcd. for C$_{16}$H$_{12}$N$_4$O$_3$S$_2$F$_2$.0.7CH$_3$OH: C, 46.34; H, 3.45; N, 12.94; S, 14.82. Found: C, 46.19; H, 3.12; N, 12.83; S, 14.94.

Example C(86)

N-(3-{4-Amino-2-[4-(4-methyl-piperazin-1-yl)-phenylamino]-thiazole-5-carbonyl}-2,4-dichloro-phenyl)-acetamide

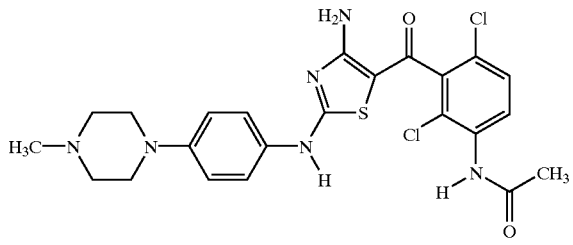

The title compound was prepared in a manner like that described for Example C(1). 1-(4-Isothiocyanato-phenyl)-4-methyl-piperazine (from Example C(70)) and N-(2-bromoacetyl-3-chloro-phenyl)-acetamide (from Example C(82)) gave, after recrystallization with EtOH/CHCl$_3$, 60 mg (13% yield) of a yellow solid, mp 195–197° C.

$^1$H NMR (DMSO-d$_6$): δ 10.62 (1H, s), 9.62 (1H, s), 7.90 (1H, bs), 7.78 (1H, dd, J=8.9, 4.4 Hz), 7.47 (1H, d, J=8.8 Hz), 7.30 (2H, bs), 6.92 (2H, d, J=9.1 Hz), 3.08 (4H, dd, J=5.1, 4.6 Hz), 2.42 (4H, dd, J=5.1, 4.6 Hz), 2.18 (3H, s), 2.08 (3H, s).

IR (KBr): 3260, 3025, 2801, 1666, 1613, 1525, 1437, 1382, 1299 cm$^{-1}$.

HRFABMS. Calcd. (M+Na$^+$): 541.0956. Found: 541.0970.

Anal. Calcd. for C$_{23}$H$_{24}$Cl$_2$N$_6$O$_2$S.0.5H$_2$O.0.4EtOH: C, 52.27; H, 5.05; N, 15.37; S, 4.86, Cl, 12.97. Found: C, 52.13; H, 5.09; N, 15.13; S, 5.78; Cl, 12.96.

Example C(87)

{4-Amino-2-[4-(4-methyl-piperazin-1-yl)-phenylamino]-thiazol-5-yl}-3-methyl-thiophen-2-yl-methanone

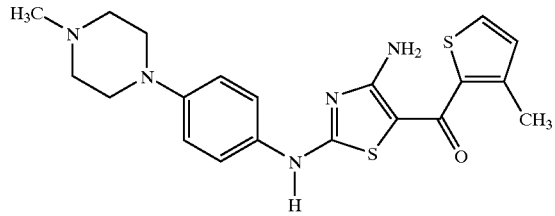

The title compound was prepared in a manner like that described for Example C(1). 1-(4-Isothiocyanato-phenyl)-4-methyl-piperazine (from Example C(70)) and 2-bromoacetyl-3-methyl-thiophene (from Example C(1 9)) gave, after recrystallization with EtOH/CHCl$_3$, a dark yellow solid in 75% yield, mp 237.0–237.5° C.

$^1$H NMR (DMSO-d$_6$): δ 10.50 (1H, s), 8.10 (1H, bs), 7.56 (1H, d, J=5.0 Hz), 7.38 (2H, d, J=8.8 Hz), 6.96 (3H, m), 3.10 (4H, dd, J=5.1, 4.7 Hz), 2.45 (4H, dd, J=4.9, 4.7 Hz), 2.38 (3H, s), 2.24 (3H, s).

IR (KBr): 3484, 3319, 2943, 2809, 1593, 1546, 1414 cm$^{-1}$.

HRFABMS. Calcd. (MH$^+$): 414.1422. Found: 414.1408.

Anal. Calcd: C$_{20}$H$_{23}$N$_5$OS$_2$.3H$_2$O: C, 57.34; H, 5.68; N, 16.72; S, 15.31. Found: C, 57.01; H, 5.72; N, 16.41; S, 15.34.

Example C(88)

trans-3RS-Amino-4RS-{4-[4-amino-5-(3,5-dichloropyridine-4-carbonyl)-thiazol-2-ylamino]-benzoyl}-dihydro-furan-2-one

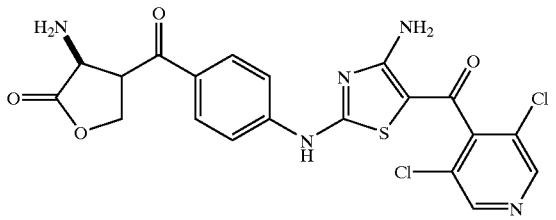

The title compound was prepared essentially as described for Example C(1). 4-Isothiocyanato-benzoyl-DL-homoserine lactone and 4-bromoacetyl-3,5-dichloropyridine (from Example C(63)) gave a product which was purified via column chromatography with 10% MeOH/CHCl$_3$ as eluant to provide an amorphous yellow solid, 203 mg (79%), that decomposed above 150° C.

$^1$H NMR (DMSO-d$_6$): δ 11.17 (1H, s), 8.89 (1H, d, J=8.0 Hz), 8.76 (2H, s), 7.86 (2H, d, J=8.7 Hz), 7.69 (2H, d, J=8.7 Hz), 4.73 (1H, q, J=9.3 Hz), 4.42 (1H, ddd, J=8.9, 8.7, 1.8 Hz), 4.27 (1H, ddd, J=10.0, 8.7, 6.7 Hz).

HRFABMS. Calcd. for C$_{21}$H$_{15}$Cl$_2$N$_5$O$_4$SNa (M+Na$^+$): 514.0120. Found: 514.0133.

IR (KBr): 3284, 1774, 1610, 1524, 1459, 1423, 1348. 1306, 1180 cm$^{-1}$.

Anal. Calcd for C$_{20}$H$_{15}$Cl$_2$N$_5$O$_4$S.0.25H$_2$O.0.6CHCl$_3$: C, 43.52; H, 2.85; N, 12.32; Cl, 23.70; S, 5.64. Found: C, 43.31; H, 2.78; N, 12.46; Cl, 24.07; S, 5.63.

Example C(89)

[4-Amino-2-(1H-benzoimidazol-6-ylamino)-thiazol-5-yl]-(2,6-dichloro-3-nitro-phenyl)-methanone

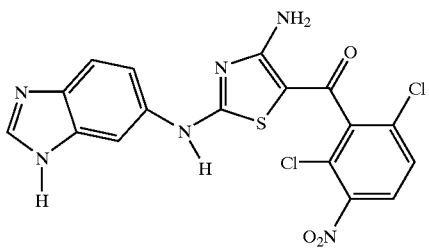

The title compound was prepared in a manner like that described for Example C(1). 2-Bromo-2',6'-dichloro-3'-nitro-acetophenone (from Example C(75)) and 6-isothiocyanato-1H-benzoimidazole (see Boev et al., Pharm. Chem. J. (Engl. Transl.), vol. 24 (1990), pp. 818–822) provided, after column chromatography with 1% HOAc/10% MeOH/CH$_2$Cl$_2$ as eluant, 26% yield of yellow powder, mp 250–252° C.

$^1$H NMR (DMSO-d$_6$): δ 8.18 (1H, s), 8.00 (2H, d, J=8.7 Hz), 7.80 (1H, d, J=8.7 Hz), 7.52 (1H, bd, J=8.1 Hz), 7.24–7.10 (2H, m).

IR (KBr): 3385, 1607, 1500 cm$^{-1}$.

HRFABMS: Calcd. for C$_{17}$H$_{10}$Cl$_2$N$_6$O$_3$S (M-H$^+$): 447.9930. Found: 447.9930.

Anal. Calcd. for C$_{17}$H$_{10}$Cl$_2$N$_6$O$_3$S.0.1H$_2$O.1MeOH.0.7 HOAc.0.1CH$_2$Cl$_2$: C, 43.30; H, 3.35; N, 15.54; S, 5.93, Cl, 14.42. Found: C, 43.26; H, 3.01; N, 14.74; S, 7.14; Cl, 14.74.

Example C(90)

{4-Amino-2-[4-(4-methyl-piperazin-1-yl)-phenylamino]-thiazol-5-yl}-(2,5-dimethyl-thiophen-3-yl)-methanone

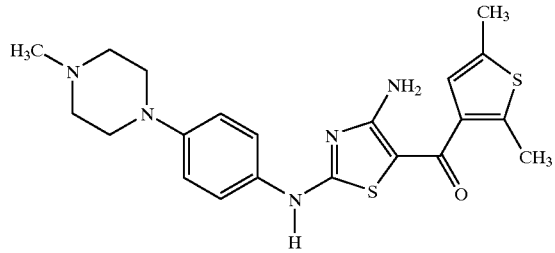

The title compound was prepared in a manner like that described for Example C(1). 3-Bromoacetyl-2,5-dimethyl-thiophene (from Example C(50)) and 1-(4-isothiocyanato-phenyl)-4-methyl-piperazine (from Example C(70)) gave, after purification via flash column chromatography with 5–10% MeOH:CH$_2$Cl$_2$ as stepwise gradient eluant, a yellow solid in 70% yield, mp 205–206° C.

$^1$H NMR (DMSO-d$_6$): δ 10.50 (1H, s), 8.00 (2H, bs), 7.48 (2H, d, J=8.7 Hz ), 6.95 (2H, d, J=8.7 Hz), 6.80 (1H, s), 3.10 (4H, dd, J=5.0, 4.4 Hz), 2.46 (4H, t, J=4.7 Hz), 2.42 (3H, s), 3.38 (3H, s), 2.24 (3H, s).

IR (KBr): 3154, 2944, 2804, 1609, 1543, 1516, 1420, 1296 cm$^{-1}$.

HRFABMS: Calcd. for C$_{21}$H$_{26}$N$_5$OS$_2$ (MH$^+$): 428.1579. Found: 428.1566.

Anal. Calcd. for C$_{21}$H$_{25}$N$_5$OS$_2$.0.7H$_2$O: C, 57.30; H, 6.04; N, 15.91; S, 14.57. Found: C, 57.19; H, 6.06; N, 15.77; S, 14.55.

Example C(91)

[4-Amino-2-(1H-benzoimidazol-6-ylamino)-thiazol-5-yl]-(3-amino-4-bromo-2,6-dichloro-phenyl)-methanone

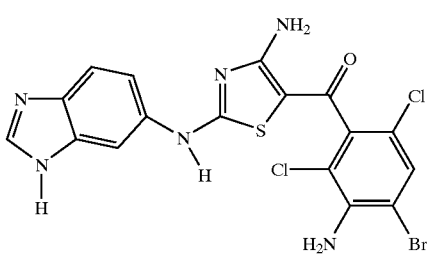

3'-Amino-4'-bromo-2',6'-dichloro-acetophenone, which has the structural formula

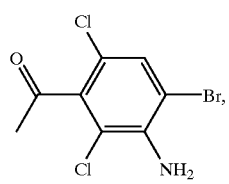

was first prepared as follows. 3'-Amino-2',6'-dichloro-acetophenone (from Example C(82); 2.15 g, 11.3 mmol) in HOAc (8.7 mL) was carefully degassed with argon and cooled to 0° C., bromine was added, and the reaction mixture was then allowed to warm to ambient temperature. After 0.5 hour, the mixture was diluted with ice/water and extracted with ether. The combined ethereal layers were washed with sat aq. NaHCO$_3$ and brine, dried over K$_2$CO$_3$, and evaporated to afford 2.87 g (90%) of brown solid, which was used without further purification.

3'-Amino-2,4'-dibromo-2',6'-dichloro-acetophenone, which has the structural formula

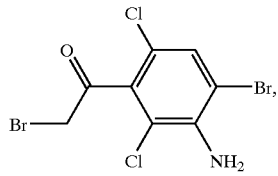

was prepared in a manner analogous to 5-bromoacetyl-4-methyl-1H-imidazole for Example C(40). 3'-Amino-4'-bromo-2',6'-dichloro-acetophenone provided, after column chromatography with a stepwise gradient of 2.5–5% CH$_2$Cl$_2$/hex, 725 mg (22% yield) of white solid, which was used without further purification. Later fractions yielded 33% recovery of starting material.

The title compound was prepared in a manner analogous to that used in Example C(1). 6-Isothiocyanato-1H-benzoimidazole (see Boev et al., *Pharm. Chem. J.* (*Engl. Transl*)., vol. 24 (1990), pp. 818–822) and 3'-amino-2,4'-dibromo-2',6'-dichloro-acetophenone provided light yellow crystals in 34% yield, mp 227–230° C.

$^1$H NMR (DMSO-d$_6$): δ 12.48 (1H, bs), 10.85 (1H, s), 8.22 (1H, s), 8.06 (2H, bs), 7.80 (1H, bs), 7.34 (1H, s), 7.58 (1H, d, J=8.5 Hz), 7.22 (1H, d, J=8.5 Hz), 5.75 (2H, s).

FABMS (MH$^+$): Calcd.: 498.9333. Found: 498.9312.

Anal. Calcd. for C$_{17}$H$_{11}$N$_6$OSCl$_2$Br.0.8H$_2$O: C, 39.83; H, 2.48; N, 16.39; S, 6.26. Found: C, 39.92; H, 2.43; N, 16.26; S, 6.14.

Example C(92)

4-[4-Amino-5-(2,5-dichloro-thiophene-3-carbonyl)-thiazol-2-ylamino]-benzenesulfonamide

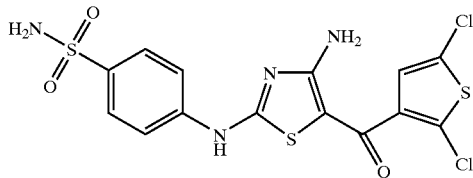

3-Bromoacetyl-2,5-dichloro-thiophene, which has the structural formula

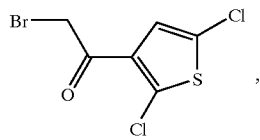

was prepared in a manner analogous to 2-bromo-2'-iodo-acetophenone, see Example C(12): 3-Acetyl-2,5-dichlorothiophene (2.0 g, 10.2 mmol) provided 2.9 g (100% yield) of yellow oil, which was used without further purification.

$^1$H NMR (CDCl$_3$): δ 7.25 (1H, s), 4.40 (2H, s).

The title compound was prepared in a manner analogous to that used in Example C(1). 4-Isothiocyanato-benzenesulfonamide and 3-bromoacetyl-2,5-dichloro-thiophene provided a yellow solid in 65% yield, mp 274–276° C.

$^1$H NMR (DMSO-d$_6$): δ 11.20 (1H, s), 8.24 (2H, bs), 7.80 (4H, s), 7.33 (1H, s), 7.31 (2H, s).

FABMS (MH$^+$): 449/451.

Anal. Calcd. for C$_{14}$H$_{10}$N$_4$O$_3$S$_3$Cl$_2$: C, 37.42; H, 2.24; N, 12.47; S, 21.41; Cl, 15.78. Found: C, 37.56; H, 2.19; N, 12.39; S, 21.29; Cl, 15.71.

Example C(93)

[4-Amino-2-(1H-benzoimidazol-6-ylamino)-thiazol-5-yl]-(2,5-dichloro-thiophen-3-yl)-methanone

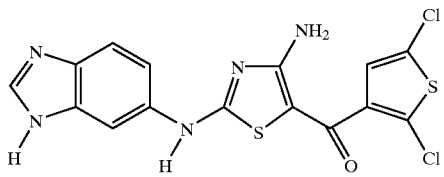

The title compound was prepared in a manner analogous to that used in Example C(1). 6-Isothiocyanato-1H-benzoimidazole (see Boev et al., *Pharm. Chem. J.* (*Engl. Transl*)., vol. 24 (1990), pp. 818–822) and 3-bromoacetyl-2,5-dichloro-thiophene (from Example C(92)) provided, after precipitation with THF, an amorphous yellow solid in 52% yield, mp >300° C.

$^1$H NMR (DMSO-d$_6$): δ 12.52 (1H, bs), 10.89 (1H, s), 8.26 (1H, s), 8.21 (2H, bs), 7.90 (1H, bs), 7.60 (1H, d, J=8.4 Hz), 7.28 (1H, s), 7.27 (1H, d, J=8.4 Hz).

ESIMS (MH$^+$): 410/412.

Anal. Calcd. for C$_{15}$H$_9$N$_5$OS$_2$Cl$_2$.0.1HCl.0.6THF: C, 45.71; H, 3.06; N, 15.32; S, 14.03; Cl, 16.28. Found: C, 45.84; H, 2.83; N, 15.01; S, 14.27; Cl, 16.00.

Example C(94)

{4-Amino-2-[4-(4-methyl-piperazin-1-yl)-phenylamino]-thiazol-5-yl}-(3-methyl-5-nitro-thiophen-2-yl)-methanone

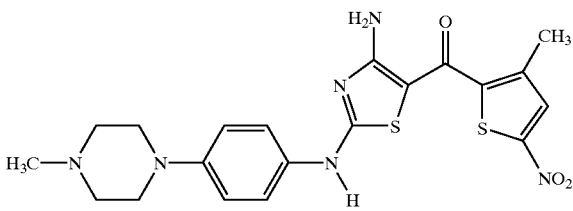

The title compound was prepared in a manner analogous to that used in Example C(1). 1-(4-Isothiocyanato-phenyl)-4-methyl-piperazine (from Example C(70)) and 2-bromoacetyl-3-methyl-5-nitro-thiophene (from Example C(78)) afforded, after precipitation with aqueous EtOH, an amorphous dark brown solid in 64% yield.

$^1$H NMR (DMSO-d$_6$): δ 10.88 (1H, s), 8.38 (2H, bs), 8.04 (1H, s), 7.38 (2H, d, J=9.0 Hz), 6.98 (2H, d, J=9.0 Hz), 3.35 (4H, bs), 3.15 (4H, bs), 2.34 (3H, s), 2.28 (3H, s).

HRFABMS (MH$^+$): Calcd.: 459.1273. Found: 459.1259.

Anal. Calcd. for $C_{21}H_{22}N_6O_3S_2 \cdot 0.8H_2O \cdot 0.2EtOH$: C, 50.81; H, 5.18; N, 17.43; S, 13.30. Found: C, 50.94; H, 4.98; N, 17.13; S, 13.55.

Example C(95)

4-[4-Amino-5-(3-methyl-5-nitro-thiophene-2-carbonyl)-thiazol-2-ylamino]-benzenesulfonamide

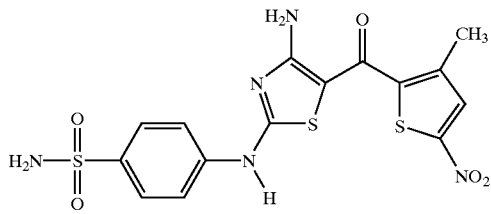

The title compound was prepared in a manner analogous to that used in Example C(1). 4-Isothiocyanato-benzenesulfonamide and 2-bromoacetyl-3-methyl-5-nitro-thiophene (from Example C(78)) provided a dark brown in 38% yield, mp 268–269° C.

$^1$H NMR (DMSO-$d_6$): δ 11.31 (1H, s), 8.46 (2H, bs), 8.08 (1H, s), 7.81 (4H, s), 7.32 (2H, s), 2.38 (3H, s).

Anal. Calcd. for $C_{15}H_{13}N_5O_5S_3$: C, 40.99; H, 2.98; N, 15.94; S, 21.89. Found: C, 41.11; H, 2.95; N, 15.66; S, 21.70.

Example C(96)

(3-Amino-4-bromo-2,6-dichloro-phenyl)-{4-amino-2-[4-(4-methyl-piperazin-1-yl)-phenylamino]-thiazol-5-yl}-methanone

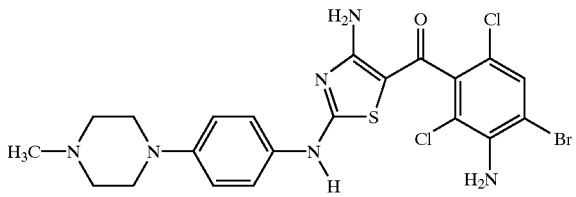

The title compound was prepared in a manner analogous to that used in Example C(1). 1-(4-Isothiocyanato-phenyl)-4-methyl-piperazine (from Example C(70)) and 3'-amino-2,4'-dibromo-2',6'-dichloro-acetophenone (from Example C(91)) provided, after recrystallization from EtOH, a yellow powder in 43% yield, mp 180–182° C.

$^1$H NMR (DMSO-$d_6$): δ 10.61 (1H, s), 8.01 (2H, bs), 7.59 (1H, s), 7.28 (2H, d, J=8.7 Hz), 6.94 (2H, d, J=8.7 Hz), 5.74 (2H, s), 3.11 (4H, bs), 2.45 (4H, bs), 2.23 (3H, s).

HRFABMS (MH$^+$): Calcd.: 555.0136/557/559. Found: 555.0122/557/559.

Anal. Calcd. for $C_{21}H_{21}N_6OSCl_2Br \cdot 0.7H_2O \cdot 0.6EtOH$: C, 44.70; H, 4.39; N, 14.09; S, 5.38. Found: C, 44.84; H, 4.18; N, 13.95; S, 5.27.

Example C(97)

2-[4-(1-Acetyl-piperazin-4-yl)-phenylamino]-4-amino-thiazol-5-yl-(2,6-dichlorophenyl)-methanone

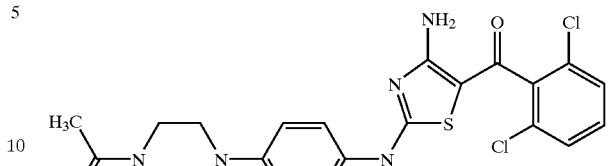

1-Acetyl(4-nitro-phenyl)-piperazine, which has the structural formula

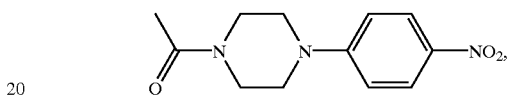

was first prepared in a manner analogous to N-(3-acetyl-2,4-dichloro-phenyl)-acetamide for Example C(82). 1-(4-Nitro-phenyl)-piperazine gave a yellow solid in 83% yield, which matched previously reported material by $^1$H NMR (Katz et al., J. Amer. Chem. Soc., vol. 111 (1989), pp. 7554–7557).

1-Acetyl-4-(4-amino-phenyl)-piperazine, which has the structural formula

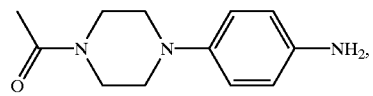

was prepared in a manner analogous to 4-(4-methyl-piperazin-1-yl)-aniline for Example C(82). 1-Acetyl-4-(4-nitro-phenyl)-piperazine gave a pale white powder in 100% crude yield, which was used without any further purification.

$^1$H NMR (CDCl$_3$): δ 6.85 (2H, d, J=8.7 Hz), 6.98 (2H, d, J=8.7 Hz), 3.78 (2H, dd, J=5.3, 5.0 Hz), 3.62 (2H, t, J=5.3, 5.0 Hz), 3.62 (2H, dd, J=5.3, 5.0 Hz), 2.98–3.10 (4H, m), 2.18 (3H, s).

1-Acetyl-4-(4-isothiocyanato-phenyl)-piperazine, which has the structural formula

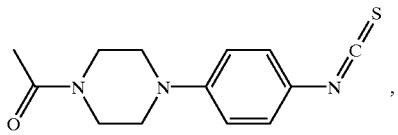

was prepared in a manner analogous to 1-(4-isothiocyanato-phenyl)-1H-imidazole for Example C(41). 1-Acetyl-4-(4-amino-phenyl)-piperazine provided a cream-colored powder in 88% yield.

$^1$H NMR (CDCl$_3$): δ 7.18 (2H, d, J=9.0 Hz), 6.82 (2H, d, J=9.0 Hz), 3.78 (2H, dd, J=5.1, 5.3 Hz), 3.64 (2H, dd, J=4.9, 5.3 Hz), 3.16–3.27 (4H, m), 2.10 (3H, s).

The title compound was prepared in a manner like that described for Example C(1). 2-Bromo-2',6'-dichloro-acetophenone (from Example C(52)) and 1-acetyl-4-(4-isothiocyanato-phenyl)-piperazine gave a crude product that precipitated from hexanes to provide a cream solid in 37% yield, mp 265–267° C.

$^1$H NMR (DMSO-$d_6$): δ 10.60 (1H, bs), 8.02 (2H, bs), 7.50 (2H, d, J=1.9 Hz), 7.42 (1H, m), 7.38 (2H, bs), 6.98 (2H, d, J=9.0 Hz), 3.60 (4H, s), 3.20–3.10 (4H, m), 2.00 (3H, s).

IR (KBr): 3377, 3166, 1601, 1542, 11425 cm⁻¹.
HRFABMS: Calcd. for C$_{22}$H$_{22}$Cl$_2$N$_5$O$_2$S (MH⁺): 490.0871. Found: 490.0858.
Anal. Calcd. for C$_{22}$H$_{21}$Cl$_2$N$_5$O$_2$S.0.16H$_2$O.0.1C$_6$H$_{14}$: C, 54.08; H, 4.56; Cl, 14.13; N, 13.95; S, 6.39. Found: C, 53.88; H, 4.32; Cl, 14.46; N, 14.28; S, 6.54.

Example C(98)

2-[4-(1-Acetyl-piperazine-4-yl)-phenylamino]-4-amino-thiazol-5-yl-(3-methyl-thiophen-2-yl)-methanone

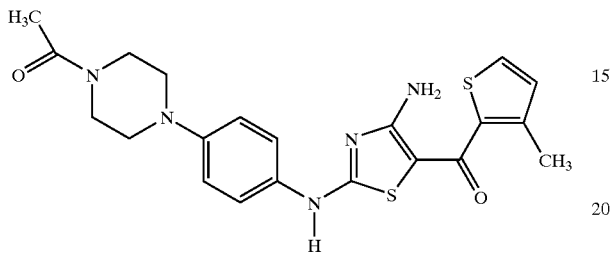

The title compound was prepared in a manner like that described for Example C(1). 1-Acetyl-4-(4-isothiocyanato-phenyl)-piperazine (from Example C(97)) and 2-bromoacetyl-3-methyl-thiophene (from Example C(19)) provided a yellow solid in 37% yield, mp 290–292° C.
¹H NMR (DMSO-d$_6$): δ 10.60 (1H, bs), 8.10 (2H, bs), 7.48 (1H, d, J=5.0 Hz), 7.40 (2H, d, J=8.7 Hz), 6.96–7.04 (2H, m), 3.60 (4H, s), 3.18 (2H, bs), 3.12 (2H, bs), 2.40 (3H, s), 2.02 (3H, s).
IR (KBr): 3377, 3166, 1633, 1601, 1542, 1425, 1225 cm⁻¹.
Anal. Calcd. for C$_{21}$H$_{23}$N$_5$O$_2$S.1H$_2$O: C, 56.89; H, 5.27; N, 15.80; S, 14.46. Found: C, 56.98; H, 5.27; N, 15.72; S, 14.35.

Example C(99)

4-[4-Amino-5-(2-fluoro-6-trifluoromethyl-benzoyl)-thiazol-2-ylamino]-benzenesulfonamide

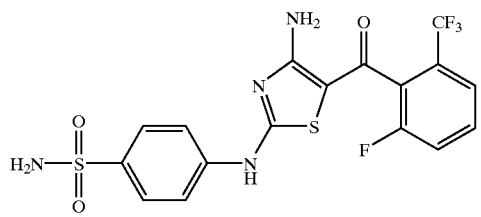

2-Bromo-2'-fluoro-6'-trifluoromethyl-acetophenone, which has the structural formula

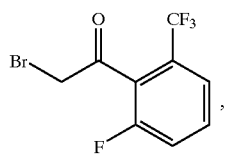

was prepared in a manner analogous to 2-bromo-2'-iodo-acetophenone, see Example C(12). 2'-Fluoro-6'-(trifluoromethyl)-acetophenone (745 mg, 3.61 mmol) provided 1.05 g of yellow oil, which was used without further purification.

¹H NMR (CDCl$_3$): δ 7.69–7.52 (2H, m), 7.44–7.35 (1H, m), 4.42 (3H, s).

The title compound was prepared in a manner analogous to that used in Example C(1). 4-Isothiocyanato-benzenesulfonamide and crude 2-bromo-2'-fluoro-6'-trifluoromethyl-acetophenone provided a light yellow solid in 21% yield, mp 290–292° C.
¹H NMR (DMSO-d$_6$): δ 11.15 (1H, s), 8.20 (2H, bs), 7.83–7.68 (7H, m), 7.31 (2H, s).
Anal. Calcd. for C$_{17}$H$_{12}$N$_4$O$_3$S$_2$F$_4$: C, 44.35; H, 2.63; N, 12.17; S, 13.93. Found: C, 44.42; H, 2.64; N, 12.13; S, 13.94.

Example C(100)

{4-Amino-2-[4-(4-methyl-piperazin-1-yl)-phenylamino]-thiazol-5-yl}-(2-fluoro-6-trifluoromethyl-phenyl)-methanone

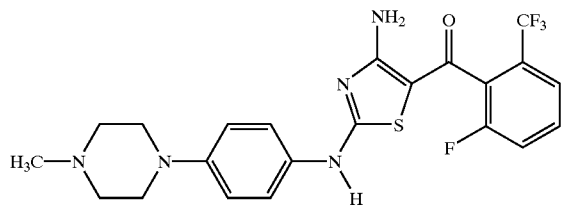

The title compound was prepared in a manner analogous to that used in Example C(1). 1-(4-Isothiocyanato-phenyl)-4-methyl-piperazine (from Example C(70)) and 2-bromo-2'-fluoro-6'-trifluoromethyl-acetophenone (from Example C(99)) produced a crude product that recrystallized from EtOH to provide a yellow powder in 74% yield, mp 155–158° C.
¹H NMR (DMSO-d$_6$): δ 10.62 (1H, s), 8.06 (2H, bs), 7.72–7.62 (3H, m), 7.10 (2H, d, J=8.7 Hz), 6.93 (2H, d, J=8.7 Hz), 3.11 (4H, bs), 2.45 (4H, bs), 2.22 (3H, s).
HRFABMS (MH⁺): Calcd.: 480.1481. Found: 480.1468.
Anal. Calcd. for C$_{22}$H$_{21}$N$_5$OSF$_4$.1.0EtOH: C, 54.84; H, 5.18; N, 13.33; S, 6.10. Found: C, 55.11; H, 5.11; N, 13.31; S, 6.00.

Example C(101)

4-Amino-2-[4-(1-tert-butoxycarbonyl-piperazine-4-yl)-phenylamino]-thiazol-5-yl-(2,6-difluorophenyl)-methanone

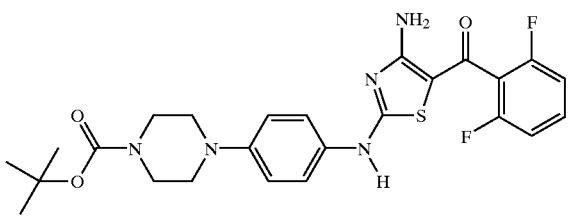

1-tert-Butoxycarbonyl-4-(4-nitro-phenyl)-piperazine, which has the structural formula

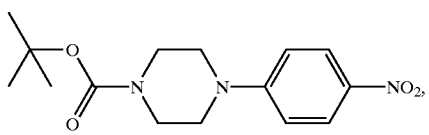

was first prepared as follows. To a suspension of 1-(4-nitro-phenyl)-piperazine (2.00 g, 9.65 mmol) in dioxane (30 mL) was added diisopropylethylamine (1.48 mL, 10.6 mmol) and di-t-butyl dicarbonate (2.10 g, 9.65 mmol). After 12 hours, the mixture was poured into H$_2$O (100 mL) and extracted with EtOAc (2×50 mL). The combined organic layers were dried over MgSO$_4$, filtered, and concentrated in vacuo to give a yellow solid, which recrystallized from EtOAc/hexane to afford 2.2 g of yellow needles. This material was used without further purification.

$^1$H NMR (CDCl$_3$): δ 8.20 (2H, d, J=9.3 Hz), 6.82 (2H, d, J=9.3 Hz), 3.58–3.64 (4H, m), 3.28–3.44 (4H, m), 1.54 (9H, s).

1-(4-Amino-phenyl)-4-tert-butoxycarbonyl-piperazine, which has the structural formula

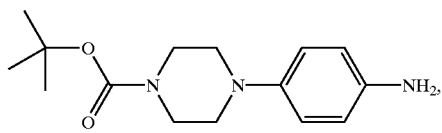

was prepared in a manner analogous to 4-(4-methyl-piperazin-1-yl)-aniline for Example C(70). 1-tert-Butoxycarbonyl-4-(4-nitro-phenyl)-piperazine furnished a pale brown gel in 100% crude yield, which was used without further purification.

$^1$H NMR (CDCl$_3$): δ 6.84 (2H, d, J=8.7 Hz), 6.67 (2H, d, J=8.8 Hz), 3.58 (4H, dd, J=5.1, 5.0 Hz), 2.97 (4H, dd, J=5.2, 4.8 Hz), 1.52 (9H, s).

1-tert-Butoxycarbonyl-4-(4-isothiocyanato-phenyl)-piperazine, which has the structural formula

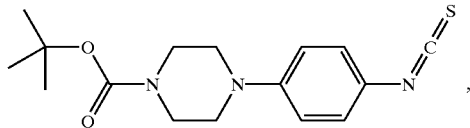

was prepared in a manner analogous to 1-(4-isothiocyanato-phenyl)-1H-imidazole for Example C(41). 1-(4-Amino-phenyl)-4-tert-butoxycarbonyl-piperazine afforded cream-colored needles in 87% yield, which were used without further purification.

$^1$H NMR (CDCl$_3$): δ 7.18 (2H, d, J=9.0 Hz), 6.82 (2H, d, J=9.0 Hz), 3.64 (4H, t, J=5.3 Hz), 3.24 (4H, t, J=5.3 Hz), 1.54 (9H, s).

The title compound was prepared in a manner analogous to that used in Example C(1). 1-tert-Butoxycarbonyl-4-(4-isothiocyanato-phenyl)-piperazine and 2-bromo-2',6'-difluoro-acetophenone (from Example C(79)) gave a crude product which recrystallized from EtOH to furnish a yellow solid in 67% yield, mp 140–143° C.

$^1$H NMR (DMSO-d$_6$): δ 10.67 (1H, s), 8.13 (2H, bs), 7.59–7.45 (1H, m), 7.35 (2H, d, J=9.0 Hz), 7.23–7.13 (2H, m), 6.96 (2H, d, J=9.0 Hz), 3.46 (4H, bs), 3.07 (4H, bs), 1.43 (9H, s).

HRFABMS (MH$^+$): Calcd.: 516.1881. Found: 516.1900.

Anal. Calcd. for C$_{25}$H$_{27}$N$_5$O$_3$SF$_2$.0.8H$_2$O.0.8EtOH: C, 56.56; H, 5.57; N, 12.99; S, 5.95. Found: C, 56.34; H, 5.54; N, 12.89; S, 5.83.

Example C(102)

4-[4-Amino-5-(2,6-difluoro-benzoyl)-thiazol-2-ylamino]-benzamide

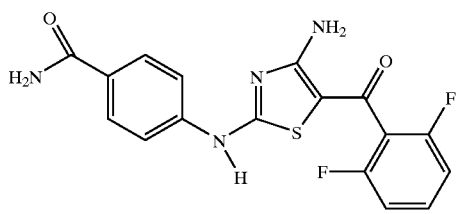

4-Isothiocyanato-benzamide, which has the structural formula

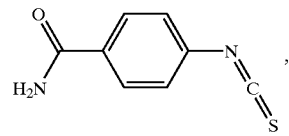

was first prepared according to a method from McKee et al., J. Am. Chem. Soc., vol. 48 (1946), pp. 2506–2507. To a solution of 4-aminobenzamide (5.00 g, 36.7 mmol) in water (60 mL) and 38% aq HCl (15 mL) was added thiophosgene (3.08 mL, 40.4 mmol). After approximately 30 min, the resultant white precipitate was filtered off, washed with water, and dried under high vacuum to obtain 4.66 g (78% yield) of white powder, which was used without further purification.

$^1$H NMR (DMSO-d$_6$): δ 8.08 (1H, bs), 7.94 (2H, d, J=8.7 Hz), 7.53 (2H, d, J=8.7 Hz), 7.51 (1H, bs).

The title compound was prepared in a manner analogous to that used in Example C(1). 4-Isothiocyanato-benzamide and 2-bromo-2',6'-difluoro-acetophenone (from Example C(79)) provided a yellow solid in 26% yield, mp 297–298° C.

$^1$H NMR (DMSO-d$_6$): δ 11.07 (1H, s), 8.22 (2H, bs), 7.91 (1H, s), 7.88 (2H, d, J=8.7 Hz), 7.66 (2H, d, J=8.7 Hz), 7.62–7.50 (1H, m), 7.31 (1H, s), 7.27–7.18 (2H, m).

Anal. Calcd. for C$_{17}$H$_{12}$N$_4$O$_2$SF$_2$: C, 54.54; H, 3.23; N, 14.97; S, 8.57. Found: C, 54.27; H, 3.27; N, 14.68; S, 8.35.

Example C(103)

tert-Butyl({4-[4-Amino-5-(2,6-difluoro-benzoyl)-thiazol-2-ylamino]-phenyl}-methyl-amino)-acetate

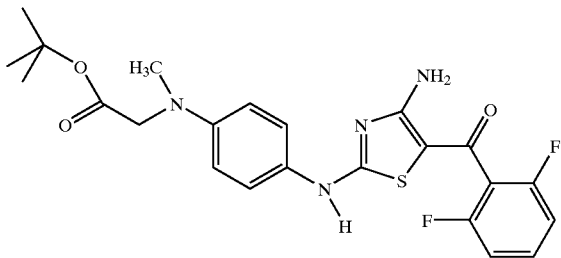

tert-Butyl[methyl-(4-nitro-phenyl)-amino]-acetate, which has the structural formula

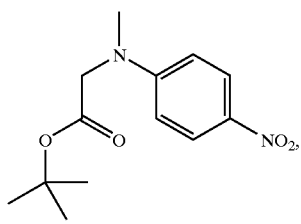

was first prepared as follows. To a solution of sarcosine t-butyl ester hydrochloride (2.0 g, 11 mmol) in DMSO (6 mL) was added 4-fluoro-nitrobenzene (1.6 g, 11 mmol) and triethylamine (3.4 mL, 24 mmol). The resultant mixture was heated at 100° C. for 12 hours. The resultant yellow suspension was allowed to cool, diluted with $H_2O$ (100 mL), and extracted with ether (2×100 mL). The combined organic layers were dried over $MgSO_4$, filtered, and concentrated in vacuo to give yellow needles, which recrystallized from ether/hexane to give 2.0 g of yellow needles, which were used without further purification.

$^1$H NMR ($CDCl_3$): δ 8.18 (2H, d, J=9.3 Hz), 6.62 (2H, d, J=9.7 Hz), 4.08 (2H, s), 3.20 (3H, s), 1.42 (9H, s).

tert-Butyl[(4-amino-phenyl)-methyl-amino]-acetate, which has the structural formula

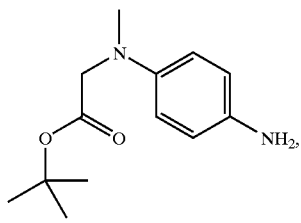

was prepared in a manner analogous to 4-(4-methyl-piperazin-1-yl)-aniline for Example C(70). tert-Butyl [methyl-(4-nitro-phenyl)-amino]-acetate provided a red oil in 95% crude yield, which was used without further purification.

$^1$H NMR ($CDCl_3$): δ 6.60–6.80 (4H, m), 4.08 (2H, s), 3.20 (2H, bs), 3.80 (2H, s), 2.82 (3H, s), 1.42 (9H, s).

tert-Butyl[(4-isothiocyanato-phenyl)-methyl-amino]-acetate, which has the structural formula

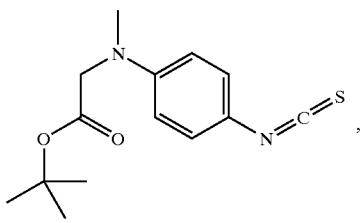

was prepared in a manner analogous to 1-(4-isothiocyanato-phenyl)-1H-imidazole for Example C(41). tert-Butyl[(4-amino-phenyl)-methyl-amino]-acetate furnished a pale brown solid in 98% yield, which was used without further purification.

$^1$H ($CDCl_3$): δ 7.10 (2H, d, J=9.1 Hz), 6.52 (2H, d, J=9.1 Hz), 3.90 (2H, s), 2.92 (3H, s), 1.30 (9H, s).

The title compound was prepared in a manner like that described for Example C(1). tert-Butyl[(4-isothiocyanato-phenyl)-methyl-amino]-acetate and 2-bromo-2',6'-difluoro-acetophenone (from Example C(79)) provided a cream powder in 34% yield, mp 200.0–200.5° C.

$^1$H NMR (DMSO-$d_6$): δ 7.44–7.56 (1H, m), 7.10–7.30 (4H, m), 6.62 (2H, d, J=9.0 Hz), 4.08 (2H, s), 2.95 (3H, s), 1.32 (9H, s).

IR (KBr): 3248, 3142, 2978, 1725, 1619, 1537, 1466, 1231 cm$^{-1}$.

Anal. Calcd. for $C_{23}H_{24}F_2N_4O_3S$: C, 58.22; H, 5.10; N, 11.81; S, 6.76. Found: C, 58.27; H, 5.11; Cl, N, 11.53; S, 6.63.

Example C(104)

4-Amino-2-[4-(1-tert-butoxycarbonyl-piperazine-4-yl)-phenylamino]-thiazol-5-yl-(3-methyl-thiophen-2-yl)-methanone

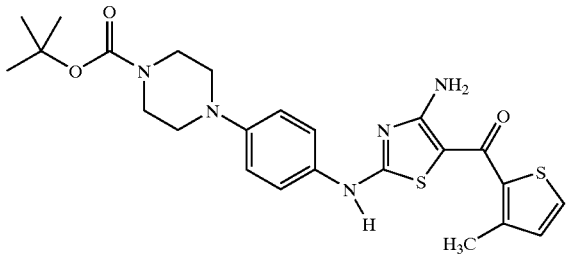

The title compound was prepared in a manner like that described for Example C(1). 1-tert-Butoxycarbonyl-4-(4-isothiocyanato-phenyl)-piperazine (from Example C(101)) and 2-bromoacetyl-3-methyl-thiophene (from Example C(19)) gave, after recrystallization with EtOAc/hexane, 387 mg (52% yield) of a yellow solid, mp 175–176° C.

$^1$H NMR ($CDCl_3$): δ 7.00–6.85 (4H, m), 3.62 (4H, dd, J=5.3, 5.0 Hz), 3.18 (4H, dd, J=5.3, 5.0 Hz), 2.48 (3H, s), 1.42 (9H, s).

IR (KBr): 3260, 2978, 1725, 1684, 1601, 1531, 1419, 1231 cm$^{-1}$.

Anal. Calcd. for $C_{24}H_{29}N_5O_3S_2$: C, 57.68; H, 5.85; N, 14.02; S, 12.83. Found: C, 57.74; H, 5.82; Cl, N, 13.95; S, 12.95.

Example C(105)

4-Amino-2-[4-(1-tert-butoxycarbonyl-piperazine-4-yl)-phenylamino]-thiazol-5-yl-(2,6-dichlorophenyl)-methanone

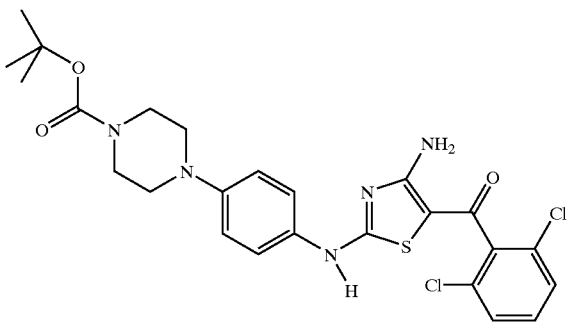

The title compound was prepared in a manner like that described for Example C(1). 1-tert-Butoxycarbonyl-4-(4-isothiocyanato-phenyl)-piperazine (from Example C(101)) and 2-bromo-2',6'-dichloro-acetophenone (from Example C(52)) afforded a crude product, which was purified via flash column chromatography with MeOH:CH$_2$Cl$_2$ (2.5:97.5) as eluant and azeotroped with hexanes to give a yellow solid in 90% yield, mp 165–167° C.

$^1$H NMR (CDCl$_3$): δ 7.22 (2H, d, J=9.0 Hz), 6.92 (2H, d, J=9.0 Hz), 3.60 (4H, m), 3.18 (4H, m), 1.42 (9H, s).

IR (KBr): 3401, 3271, 2966, 1689, 1607, 1542, 1460, 1225 cm$^{-1}$.

HRFABMS: Calcd. for C$_{25}$H$_{28}$N$_5$O$_3$ClS (MH$^+$): 548.1290. Found: 548.1270.

Anal. Calcd. for C$_{25}$H$_{27}$N$_5$O$_3$Cl$_2$S.0.1C$_6$H$_{14}$: C, 55.23; H, 5.07; N, 12.58; Cl, 12.74; S, 5.76. Found: C, 55.34; H, 5.28; N, 12.29; Cl, 12.48; S, 5.58.

Example C(106)

(3-Acetamido-2,6-dichloro-phenyl)-[4-amino-2-(4-tert-butoxycarbonyl-piperazin-1-yl)-amino-thiazol-5-yl]-methanone

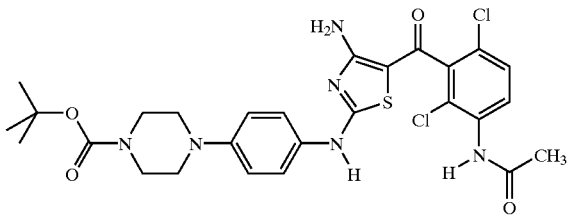

The title compound was prepared in a manner like that described for Example C(1). 1-tert-Butoxycarbonyl-4-(4-isothiocyanato-phenyl)-piperazine (from Example C(101)) and N-(3-bromoacetyl-2,4-dichloro-phenyl)-acetamide (from Example C(82)) provided a pale yellow solid in 57% yield, mp 248–250° C.

$^1$H NMR (CDCl$_3$): δ 7.20 (2H, d, J=9.0 Hz), 6.92 (2H, d, J=9.0 Hz), 3.54–3.66 (4H, m), 3.12–3.22 (4H, m), 2.28 (3H, s), 1.42 (9H, s).

IR (KBr): 3377, 3271, 3177, 2978, 1672, 1548, 1437, 1290, 1231 cm$^{-1}$.

HRFABMS: Calcd. for C$_{27}$H$_{31}$Cl$_2$N$_6$O$_4$S (MH$^+$): 605.1505. Found: 605.1528.

Anal. Calcd. for C$_{27}$H$_{30}$Cl$_2$N$_6$O$_4$S.1.3H$_2$O: C, 51.56; H, 5.22; N, 13.36; Cl, 11.27; S, 5.10. Found: C, 51.50; H, 5.18; Cl, 11.15; N, 13.19; S, 4.99.

Example C(107)

4-[4-Amino-5-(2,4,6-trichloro-benzoyl)-thiazol-2-yl-amino]-benzenesulfonamide

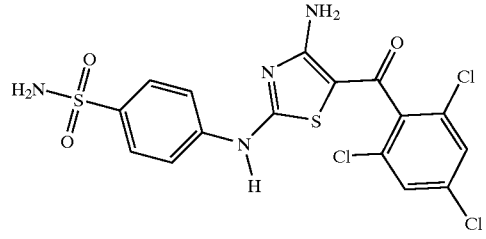

2,4,6-Trichloroacetophenone, which has the structural formula

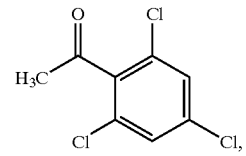

was first prepared as follows. Adapted from a procedure by Reynolds et al., Org. Syn. Coll., vol. IV (1963), pp. 708–710. To Mg turnings (283 mg, 11.3 mmol) and EtOH (0.25 mL) was added CCl$_4$ (11 µL). The ensuing reaction subsided, before a solution of diethyl malonate (1.71 mL, 11.33 mmol) in EtOH (0.91 mL) was added at a rate to sustain reaction. After 30 min, the mixture was refluxed to consume Mg for one hour, then allowed to cool. The solid mass was suspended in ether (25 mL) and a solution of 2,4,6-trichlorobenzoyl chloride (2.50 g, 10.3 mL) in ether (5 mL) was added cautiously. After 3 days, a solution of H$_2$SO$_4$ (0.6 mL) in water (10 mL) was carefully added to dissolve any solids, and extracted with ether (2×10 mL). The extracts were dried over MgSO4 and evaporated to a cloudy oil, which was placed in HOAc (3 mL), H$_2$O (2 mL) and H$_2$SO$_4$ (0.33 mL), and heated to reflux. After 7.5 hours, the mixture was allowed to cool overnight. The mixture was made alkaline with 1N NaOH (35 mL) and extracted with ether (3×10 mL). The combined ethereal layers were dried with MgSO$_4$ and evaporated to give 1.80 g (78%) of a white solid that was used without further purification (previously described in Baker et al., J. Chem. Soc. (1941), pp. 796–802).

2-Bromo-2',4',6'-trichloroacetophenone, which has the structural formula

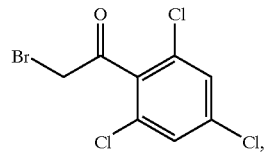

was prepared in a manner analogous to 2-bromo-2'iodo-acetophenone for Example C(12). Crude 2',4',6'-trichloroacetophenone afforded 1.27 g (94%) of gold crystals that were used without further purification (previously described in Baker et al., J. Chem. Soc. (1941), pp. 796–802).

¹H NMR: δ 7.42 (2H, s), 4.42 (s, 2H).

The title compound was prepared essentially as described for Example C(1), except that excess potassium t-butoxide (2.2 equivalents) was employed. 4-Isothiocyanato-benzenesulfonamide and 2-bromo-2',4',6'-trichloroacetophenone provided a dark brown gum, which was purified via column chromatography with 10% MeOH/CHCl₃ and precipitated from MeOH/CHCl₃ to obtain 96 mg (21%) of an amorphous, pale yellow solid.

¹H NMR (CD₃OD): δ 7.87 (4H, dd, J=14.6, 9.0 Hz), 7.60 (2H, s).

IR (KBr): 3312, 1593, 1545, 1459, 1421, 1161 cm⁻¹.

ESIMS (MH⁺): 477/479/481. (M⁻): 475/477/479.

Anal. Calcd for C₁₆H₁₁Cl₃N₄O₃S₂: C, 40.22; H, 2.32; N, 11.73; Cl, 22.26; S, 13.42. Found: C, 40.12; H, 2.34; N, 11.56; Cl, 22.41; S, 13.43.

Example C(108)

4-[4-Amino-5-(2,6-difluoro-benzoyl)-thiazol-2-ylamino]-N-methyl-benzenesulfonamide

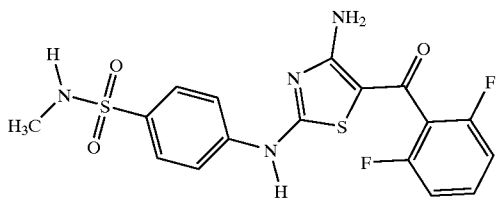

4-Amino-N-methyl-benzenesulfonamide, which has the structural formula

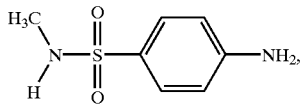

was first made as follows. N-Methyl-4-nitro-benzenesulfonamide (2.58 g, 11.9 mmol; Khanna et al., *J. Med. Chem.*, vol. 40 (1997), pp. 1619–1633) and 10% Pd/C (250 mg) in MeOH (60 mL) was stirred under hydrogen atmosphere for 2 hours and filtered. The filtrate was concentrated in vacuo to provide 2.17 g (98% yield) of colorless crystalline flakes, which by ¹H NMR matched that reported in the literature (Khanna et al., *J. Med. Chem.*, vol. 40 (1997), pp. 1619–1633) and was used without further purification.

4-Isothiocyanato-N-methyl-benzenesulfonamide, which has the structural formula

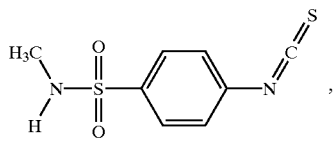

was prepared in a manner analogous to 4-isothiocyanato-benzamide of Example C(102). 4-Amino-N-methyl-benzenesulfonamide (2.17 g, 11.7 mmol) gave 2.10 g (79% yield) of white fluffy powder, which was used without further purification.

¹H NMR (DMSO-d₆): δ 7.83 (2H, d, J=8.4 Hz), 7.65 (2H, d, J=8.4 Hz), 7.61 (1H, q, J=4.9 Hz), 2.43 (3H, d, J=4.9 Hz).

The title compound was prepared in a manner analogous to that used in Example C(1). 4-Isothiocyanato-N-methyl-benzenesulfonamide and 2-bromo-2',6'-difluoro-acetophenone (from Example C(79)) provided a crude product, which was extracted with 10% i-PrOH/CHCl₃ and purified via column chromatography with 5% MeOH/CHCl₃ to afford an amorphous yellow powder in 41% yield, that decomposed above 200° C.

¹H NMR (DMSO-d₆): δ 11.23 (1H, s), 8.33 (2H, bs), 7.81 (2H, d, J=8.5 Hz), 7.54 (2H, d, J=8.5 Hz), 7.63–7.41 (1H, m), 7.39 (1H, q, J=5.0 Hz), 7.23 (2H, t, J=7.1 Hz), 2.41 (3H, d, J=5.0 Hz).

HRFABMS (MH⁺): Calcd.: 425.0554. Found: 425.0566; Anal. Calcd. for C₁₇H₁₄N₄O₃S₂F₂.0.5CH₃OH: C, 47.72; H, 3.66; N, 12.72; S, 14.56. Found C, 47.56; H, 3.52; N, 12.72; S, 14.77.

Example C(109)

4-[4-Amino-5-(2,6-difluoro-benzoyl)-thiazol-2-ylamino]-N,N-dimethyl-benzenesulfonamide

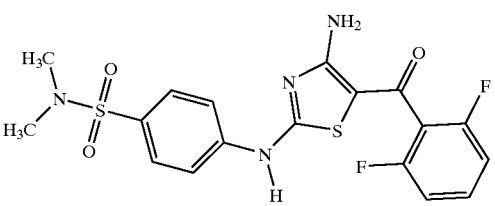

4-Amino-N,N-dimethyl-benzenesulfonamide, which has the structural formula

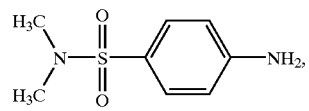

was next prepared as follows. Crude N,N-dimethyl-4-nitro-benzenesulfonamide (3.89 g, 16.9 mmol; Khanna et al., *J. Med. Chem.*, vol. 40 (1997), pp. 1619–1633), 10% Pd/C (800 mg), MeOH (80 mL), and THF (200 mL) were stirred under hydrogen for 6 hours and filtered. The filtrate was concentrated in vacuo to furnish 3.68 g of yellow solid, which was identical by ¹H NMR spectrum to previous description by Khanna et al., *J. Med. Chem.*, vol. 40 (1997), pp. 1619–1633 and was used without further purification.

4-Isothiocyanato-N,N-dimethyl-benzenesulfonamide, which has the structural formula

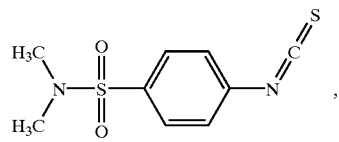

was next made as follows. To a solution of 4-amino-N,N-dimethyl-benzenesulfonamide (2.0 g, 10 mmol) in acetone (50 mL) at 5–10° C. were added simultaneously a solution of thiophosgene (0.91 mL, 12 mmol) in acetone (20 mL) and 25% aq Na₂CO₃ (10 mL). After 5 min at 5–8° C., the mixture was allowed to warm and was stirred at ambient temperature for a half hour. The solvent was evaporated and water (70 mL) was added. The resultant light-yellow precipitate was filtered off, washed with water, and dried under vacuum to afford 2.35 g (97% yield) of white powder, which was used without further purification.

¹H NMR (DMSO-d₆): δ 7.82 (2H, d, J=8.4 Hz), 7.69 (2H, d, J=8.4 Hz), 2.63 (6H, s).

The title compound was prepared in a manner analogous to that used in Example C(1). 4-Isothiocyanato-N,N-dimethyl-benzenesulfonamide and 2-bromo-2',6'-difluoro-acetophenone (from Example C(79)) provided a crude brown solid that recrystallized from EtOH to give light-brown crystals in 52% yield, mp 240–242° C.

¹H NMR (DMSO-d₆): δ 11.24 (1H, s), 8.14 (2H, bs), 7.84 (2H, d, J=8.8 Hz), 7.72 (2H, d, J=8.8 Hz), 7.62–7.49 (1H, m), 7.23 (1H, d, J=7.9 Hz), 7.20 (1H, d, J=8.0 Hz), 2.59 (6H, s).

Anal. Calcd. for $C_{18}H_{16}N_4O_3S_2F_2$: C, 49.3 1; H, 3.68; N, 12.78; S, 14.63. Found: C, 49.29; H, 3.71; N, 12.68; S, 14.50.

Example C(110)

(4-Amino-2-{4-[(2-dimethylamino-ethyl)-methyl-amino]-phenylamino}-thiazol-5-yl)-(2,6-difluoro-phenyl)-methanone

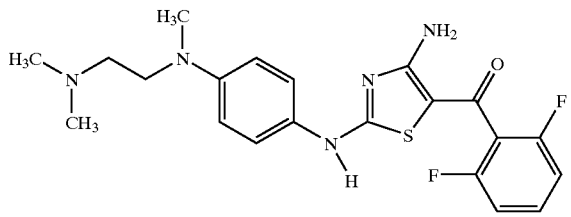

N-(4-Nitrophenyl)-N,N'-trimethyl-ethane-1,2-diamine, which has the structural formula

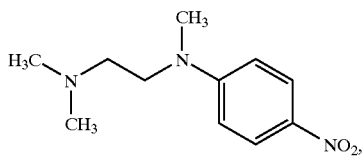

was first prepared in a manner analogous to tert-butyl [methyl-(4-nitro-phenyl)-amino]-acetate for Example C(103). 4-Fluoronitrobenzene and N,N,N'-trimethyl-ethylendiamine gave a brown oil in 87% crude yield, which was used without any further purification.

¹H NMR (CDCl₃): δ 8.14 (2H, d, J=9.6 Hz), 6.64 (2H, d, J=9.3 Hz), 3.58 (2H, t, J=7.5 Hz), 3.12 (3H, s) 2.52 (2H, t, J=7.5 Hz), 2.32 (6H, s).

N-(4-Aminophenyl)-N,N'-ethane-1,2-diamine, which has the structural formula

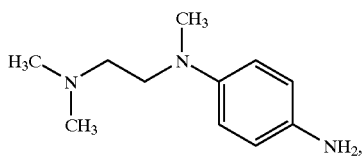

was prepared in a manner analogous to 4-(4-methyl-piperazin-1-yl)-aniline for Example C(70). N-(4-nitrophenyl)-N,N,N'-trimethyl-ethane-1,2-diamine furnished a reddish-brown oil in 92% crude yield which was used without further purification.

¹H NMR (CDCl₃): δ 6.62 (4H, s), 3.30 (2H, dd, J=7.6, 7.4 Hz), 2.85 (3H, s), 2.47 (2H, dd, J=7.7, 7.2 Hz), 2.32 (6H, s).

N-(4-Isothiocyanato-phenyl)-N,N',N'-trimethyl-ethane-1,2-diamine, which has the structural formula

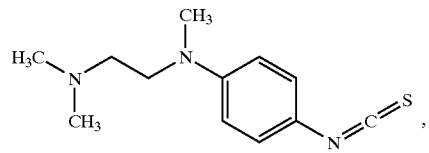

was prepared in a manner analogous to 1-(4-isothiocyanato-phenyl)-1H-imidazole for Example C(41). N-(4-Aminophenyl)-N,N',N'-ethane-1,2-diamine provided a brown oil in 75% crude yield, which was used without further purification.

¹H NMR (CDCl₃): δ 7.13 (2H, d, J=8.8 Hz), 7.01 (2H, d, J=8.2 Hz), 3.99 (2H, dd, J=7.6, 7.1 Hz), 3.15 (1H, bs), 3.02 (3H, s), 2.80 (6H, s).

The title compound was prepared in a manner like that described for Example C(1). N-(4-Isothiocyanato-phenyl)-N,N',N'-trimethyl-ethane-1,2-diamine and 2-bromo-2',6'-difluoro-acetophenone (from Example C(79)) afforded a crude product, which was purified via flash column chromatography with a stepwise gradient of MeOH:CH₂Cl₂ (2.5:97.5–10:90) to provide a yellow solid in 55% yield, mp 96–98° C.

¹H NMR (DMSO-d₆): δ 7.42–7.55 (1H, m), 7.10–7.24 (4H, m), 6.64 (2H, d, J=9.0 Hz), 2.90 (3H, s), 2.38 (2H, dd, J=7.2, 6.5 Hz), 2.18 (6H, s).

IR (KBr): 3394, 3180, 2948, 2828, 1620, 1546, 1523, 1466 cm⁻¹.

HRFABMS: Calcd. for $C_{21}H_{24}F_2N_5OS$ (MH⁺): 432.1670. Found: 432.1658.

Anal. Calcd. for $C_{21}H_{23}F_2N_5OS \cdot 0.4H_2O$: C, 57.49; H, 5.47; N, 15.96; S, 7.31. Found: C, 57.36; H, 5.45; N, 15.77; S, 7.27.

Example C(111)

2-[4-(1-Acetyl-piperazin-4-yl)-phenylamino]-4-amino-thiazol-5-yl-(2,6-difluorophenyl)-methanone

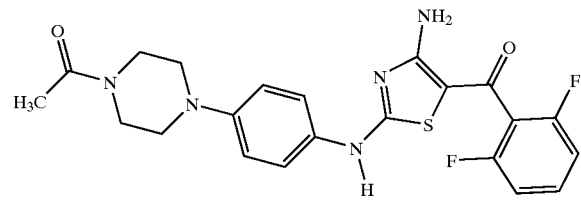

The title compound was prepared in a manner like that described for Example C(1). 1-Acetyl-4-(4-isothiocyanato-phenyl)-piperazine (from Example C(97)) and 2-bromo-2',6'-difluoro-acetophenone (from Example C(79)) provided 320 mg (66% yield) of a cream-colored solid, mp 298° C.

¹H NMR (DMSO-d₆): δ 7.44–7.58 (1H, m), 7.36 (2H, bd, J=7.2 Hz), 7.18 (2H, dd, J=8.1, 7.5 Hz), 6.95 (2H, d, J=9.0 Hz), 3.58 (4H, bs), 3.00–3.20 (4H, m), 2.05 (3H, s);

IR (KBr): 3389, 3154, 1607, 1601, 1542, 1419, 1231 cm⁻¹.

HRFABMS: Calcd. for $C_{22}H_{21}F_2N_5OSNa$ (M+Na⁺): 480.1282. Found: 480.1266.

Anal. Calcd. for $C_{22}H_{21}N_5O_2F_2S \cdot 0.3H_2O$: C, 57.08; H, 4.70; N, 15.13; S, 6.93; Found: C, 56.95; H, 4.74; N, 15.16; S, 6.82.

Example C(112)

2-[4-(1-Acetyl-piperazin-4-yl)-phenylamino]-4-amino-thiazol-5-yl-(2,5-dimethyl-thiophen-3-yl)-methanone

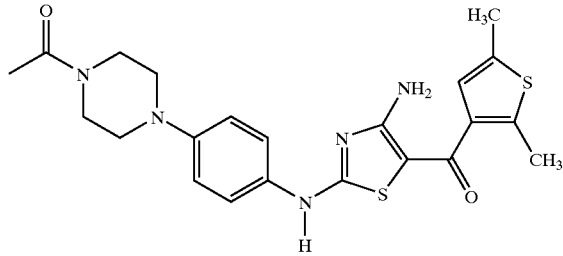

The title compound was prepared in a manner like that described for Example C(1). 1-Acetyl-4-(4-isothiocyanatophenyl)-piperazine (from C(97)) and 3-bromoacetyl-2,5-dimethyl-thiophene (from Example C(50)) provided 200 mg (53% yield) of a pale cream-colored solid, mp 282–283° C.

$^1$H NMR (DMSO-d$_6$): δ 7.42 (2H, d, J=9.0 Hz), 6.98 (2H, d, J=9.0 Hz), 6.82 (1H, s), 3.60 (4H, bs), 3.02–3.20 (4H, m), 2.46 (3H, s), 2.38 (3H, s), 2.05 (3H, s).

IR (KBr): 3401, 3166, 1637, 1601, 1542, 1425, 1231 cm$^{-1}$.

HRFABMS: Calcd. for $C_{22}H_{26}N_5O_2S_2$ (MH$^+$): 456.1528. Found: 456.1510.

Anal. Calcd. for $C_{22}H_{25}N_5O_2S_2$: C, 57.87; H, 5.74; N, 15.34; S, 14.05. Found: C, 57.85; H, 5.53; N, 15.23; S, 14.20.

Example C(113)

4-[4-Amino-5-(2-fluoro-6-trifluoromethyl-benzoyl)-thiazol-2-ylamino]-benzamide

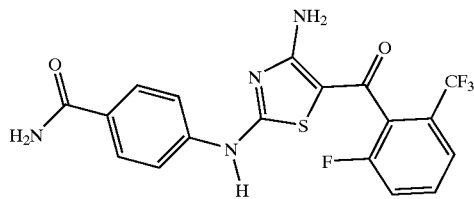

The title compound was prepared in a manner analogous to that used in Example C(1). 4-Isothiocyanato-benzamide (from Example C(102)) and 2-bromo-2'-fluoro-6'-trifluoromethyl-acetophenone (from Example C(99)) provided a crude product, which was purified via column chromatography with a stepwise gradient of 8–10% EtOH/CHCl$_3$ to afford an amorphous yellow solid in 14% yield that decomposed above 145° C.

$^1$H NMR (DMSO-d$_6$): δ 8.30 (1H, bs), 8.10 (1H, bs), 7.94–7.82 (3H, m), 7.74–7.62 (5H, m), 7.30 (1H, s).

HRFABMS (MH$^+$): Calcd.: 425.0695. Found: 425.0709.

Anal. Calcd. for $C_{18}H_{12}N_4O_2SF_4$·0.9EtOH: C, 51.05; H, 3.76; N, 12.03; S, 6.88. Found: C, 51.14; H, 3.78; N, 12.36; S, 6.79.

Example C(114)

4-[4-Amino-5-(3-methyl-thiophene-2-carbonyl)-thiazol-2-ylamino]-N-methyl-benzenesulfonamide

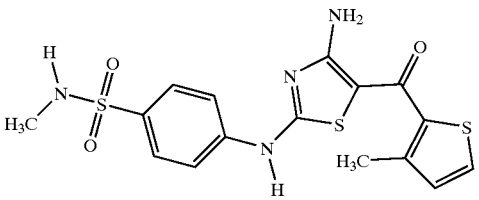

The title compound was prepared in a manner analogous to that used in Example C(1). 4-Isothiocyanato-N-methyl-benzenesulfonamide (from Example C(108)) and 2-bromoacetyl-3-methyl-thiophene (from Example C(19)) provided a yellow solid in 57% yield, mp 197.0–199.5° C.

$^1$H NMR (DMSO-d$_6$): δ 11.19 (1H, s), 8.24 (2H, bs), 7.86 (2H, d, J=8.7 Hz), 7.75 (2H, d, J=8.7 Hz), 7.65 (1H, d, J=5.0 Hz), 7.36 (1H, q, J=6.1 Hz), 7.03 (1H, d, J=5.0 Hz), 2.42 (3H, S), 2.41 (3H, d, J=6.1 Hz).

HRFABMS (MH$^+$): Calcd.: 409.0463. Found: 409.0474.

Anal. Calcd. for $C_{16}H_{16}N_4O_3S_3$·0.4H$_2$O: C, 46.23; H, 4.07; N, 13.48; S, 23.14. Found: C, 46.28; H, 3.98; N, 13.38; S, 23.08.

Example C(115)

4-[4-Amino-5-(2,4,6-trifluoro-benzoyl)-thiazol-2-yl-amino]-benzenesulfonamide

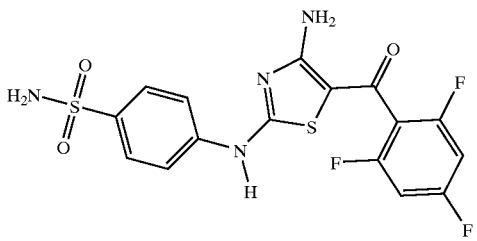

2-Chloro-2',4',6'-trifluoroacetophenone, which has the structural formula

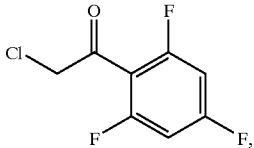

was first prepared as follows. To a mechanically stirred solution of 1,3,5-trifluorobenzene (5.17 mL, 50.0 mmol) in dichloroethane (12.5 mL) was added gradually AlCl$_3$ (13.4 g, 115 mmol) over 15 min. time period with caution. Violent bumping and HCl gas evolution was observed. The mixture was carefully heated to reflux, and chloroacetyl chloride (6.20 g, 4.37 mL, 55.0 mmol) was added dropwise over 45 min. time period. After 6 hours at reflux, the mixture was allowed to cool over 12 hours, then carefully poured onto an ice/water slush (~200 mL) and extracted with ether (3×50 mL). The combined ethereal layers were washed with 10% aq. HCl (2×30 mL), 1N aq. NaOH (3×30 mL), and brine (25 mL), dried over MgSO$_4$ and evaporated to give 5.28 g (51%)

of a yellow solid that was used without further purification. (An analytical sample crystallized from ether/hexane to give yellow microcrystals, mp 43–45° C.).

$^1$H NMR (CDCl$_3$): δ 6.81 (2H, t, J=8.4 Hz), 4.54 (2H, s).

IR (KBr): 1721, 1637, 1616, 1447, 1201, 1128, 1045 cm$^{-1}$.

Anal. Calcd. for C$_8$H$_4$ClF$_3$O: C, 46.07; H, 1.93; Cl, 17.00. Found: C, 45.92; H, 1.95; Cl, 16.97.

The title compound was prepared essentially as described for Example C(1), except that excess potassium t-butoxide (2.2 equivalents) was employed. 4-Isothiocyanato-benzenesulfonamide and 2-chloro-2',4',6'-trifluoroacetophenone gave a red-brown solid, which was purified via column chromatography with 5% MeOH/CH$_2$Cl$_2$ as eluant. Precipitation with trace hexane in MeOH/CH$_2$Cl$_2$ gave 70 mg (33%) of yellow amorphous powder that decomposed above 148° C.

$^1$H NMR (CD$_3$OD): δ 7.91 (1H, s), 7.86 (4H, dd, J=14.9, 6.9 Hz), 6.99 (2H, dd, J=9.0, 7.5 Hz).

IR (KBr): 3278, 1602, 1549, 1425, 1155 cm$^{-1}$.

HRFABMS. Calcd for C$_{16}$H$_{12}$F$_3$N$_4$O$_3$S$_2$ (MH$^+$): 429.0303. Found: 429.0315.

Anal. Calcd for C$_{16}$H$_{11}$F$_3$N$_4$O$_3$S$_2$·1.1H$_2$O: C, 42.87; H, 2.97; N, 12.50; S, 14.31. Found: C, 42.98; H, 2.73; N, 12.12; S, 14.48.

Example C(116)

{4-Amino-2-[4-(4-methyl-piperazine-1-sulfonyl)-phenylamino]-thiazol-5-yl}-(2,6-difluoro-phenyl)-methanone

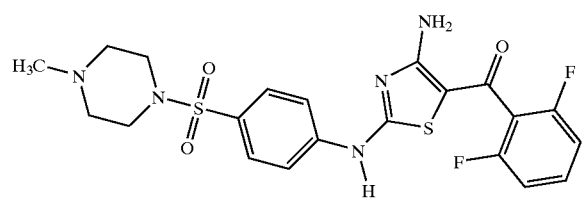

1-Methyl-4-(4-nitro-benzenesulfonyl)-piperazine, which has the structural formula

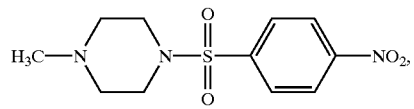

was prepared in a manner analogous to that used for N-methyl-4-nitro-benzenesulfonamide for Example C(108) (Khanna et al., *J. Med. Chem.*, vol. 40 (1997), pp. 1619–1633). 4-Nitrobenzenesulfonyl chloride and 1-methylpiperazine gave 5.1 g (88% yield) of yellow solid, which was used without further purification.

4-(4-Methyl-piperazine-1-sulfonyl)-aniline, which has the structural formula

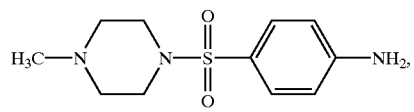

was prepared in a manner analogous to that used for N-methyl-4-amino-benzenesulfonamide for Example C(108). 1-Methyl-4-(4-nitro-benzenesulfonyl)-piperazine provided a gray solid in 99% yield, which was used in the next step without further purification.

$^1$H NMR (DMSO-d$_6$): δ 7.37 (2H, d, J=8.8 Hz), 6.67 (2H, d, J=8.8 Hz), 6.16 (2H, bs), 3.30 (4H, bs), 3.03 (4H, bs), 2.58 (3H, s).

1-(4-Isothiocyanato-benzenesulfonyl)-4-methyl-piperazine, which has the structural formula

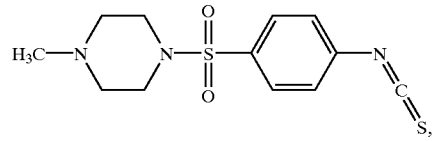

was made in a manner analogous to 4-isothiocyanato-benzamide for Example C(102). 4-(4-Methyl-piperazine-1-sulfonyl)-aniline provided 1.1 g (94% yield) of white crystals which were used without further purification.

$^1$H NMR (CDCl$_3$): δ 7.74 (2H, d, J=8.6 Hz), 7.35 (2H, d, J=8.6 Hz), 3.27 (4H, bs), 2.77 (4H, bs), 2.47 (3H, s).

The title compound was prepared in a manner analogous to that used in Example C(1). 1-(4-Isothiocyanato-benzenesulfonyl)-4-methyl-piperazine and 2-bromo-2',6'-difluoro-acetophenone (from Example C(79)) provided a yellow solid in 69% yield, mp 172–174° C.

$^1$H NMR (DMSO-d$_6$): δ 11.23 (1H, bs), 8.21 (2H, bs), 7.84 (2H, d, J=8.8 Hz), 7.69 (2H, d, J=8.8 Hz), 7.62–7.49 (1H, m), 7.22 (1H, d, J=7.8 Hz), 7.19 (1H, d, J=8.1 Hz), 2.87 (4H, t, J=4.5 Hz), 2.35 (4H, t, J=4.5 Hz), 2.13 (3H, s).

HRFABMS (MH$^+$): Calcd.: 494.1132. Found: 494.1120.

Anal. Calcd. for C$_{21}$H$_{21}$N$_5$O$_3$S$_2$F$_2$·0.1H$_2$O·0.5CH$_3$OH: C, 50.50; H, 4.57; N, 13.70; S, 12.54. Found: C, 50.34; H, 4.39; N, 13.51; S, 12.63.

Example C(117)

(4-Amino-2-{4-[(2-dimethylamino-ethyl)-methyl-amino]-phenylamino}-thiazol-5-yl)-(3-methyl-thiophen-2-yl)-methanone

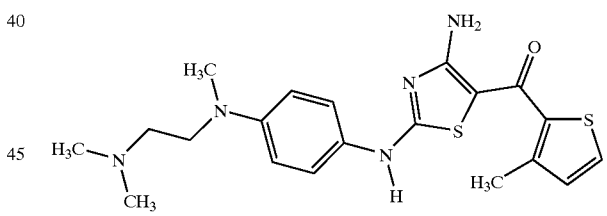

The title compound was prepared in a manner like that described for Example C(1). N-(4-Isothiocyanato-phenyl)-N,N',N'-trimethyl-ethane-1,2-diamine (from Example C(110)) and 2-bromoacetyl-3-methyl-thiophene (from Example C(19)) gave, after purification via flash column chromatography with MeOH:CH$_2$Cl$_2$ (5:95) as eluant, a yellow foam in 70% yield.

$^1$H NMR (DMSO-d$_6$): δ 7.22 (1H, d, J=5.0 Hz), 7.16 (2H, d, J=9.0 Hz), 6.72 (1H, d, J=5.0 Hz), 6.58 (2H, d, J=9.0 Hz), 3.44 (2H, dd, J=7.7, 7.4 Hz), 3.00 (3H, s), 2.42 (3H, s), 2.3 (6H, s).

IR (KBr): 3377, 3269, 2937, 2821, 1609, 1543, 1518, 1423 cm$^{-1}$.

HRFABMS: Calcd. for C$_{20}$H$_{26}$Cl$_2$N$_5$OS$_2$ (MH$^+$): 416.1579. Found: 416.1594.

Anal. Calcd. for C$_{20}$H$_{25}$Cl$_2$N$_5$OS$_2$·1H$_2$O: C, 55.40; H, 6.28; N, 16.15; S, 14.71. Found: C, 55.43; H, 5.94; N, 16.37; S, 14.57.

Example C(118)

4-{4-[4-Amino-5-(2,6-difluoro-benzoyl)-thiazol-2-ylamino]-phenyl}-1-methyl-piperazin-2-one

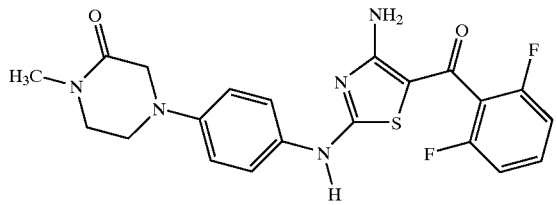

4-(4-Nitro-phenyl)-piperazin-2-one, which has the structural formula

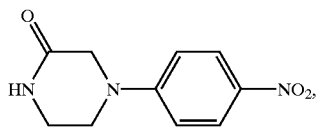

was first prepared in a manner analogous to tert-butyl [methyl-(4-nitro-phenyl)-amino]-acetate for Example C(103). Piperazin-2-one (Aspinall et al., *J. Amer. Chem. Soc.*, vol. 62 (1940), pp. 1202–1204) and 4-fluoronitrobenzene furnished a yellow solid in 63% yield, which was used without any further purification.

$^1$H NMR (CDCl$_3$): δ 8.10 (2H, d, J=8.8 Hz), 6.80 (2H, d, J=9.2 Hz), 6.38 (1H, bs), 4.10 (2H, s), 3.74–2.52 (4H, m).

1-Methyl-4-(4-nitro-phenyl)-piperazin-2-one, which has the structural formula

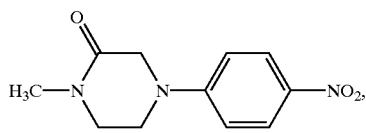

was next prepared as follows. To a suspension of 4-(4-nitro-phenyl)-piperazin-2-one (500 mg, 2.26 mmol) in THF (5 mL) was added NaH (60 mg, 2.5 mmol). The mixture was cooled to 0° C., iodomethane (162 uL, 2.59 mmol) was added, and then the mixture was allowed to warm to ambient temperature. After 12 hours, the solvent was removed in vacuo to give a yellow gum, which was treated with H$_2$O. The resultant yellow precipitate was filtered off, washed with H$_2$O, and dried under high vacuum for several hours to afford 420 mg (79% yield).

$^1$H NMR (CDCl$_3$): δ 8.18 (2H, d, J=9.4 Hz), 6.78 (2H, d, J=9.4 Hz), 4.08 (2H, s), 3.68 (2H, dd, J=4.7, 3.6 Hz), 3.54 (2H, dd, J=4.9, 3.7 Hz), 3.02 (3H, s).

4-(4-Amino-phenyl)-1-methyl-piperazin-2-one, which has the structural formula

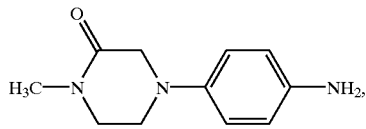

was prepared in a manner analogous to 4-(4-methyl-piperazin-1-yl)-aniline for Example C(70). 1-Methyl-4-(4-nitro-phenyl)-piperazin-2-one provided a brown gum, which was used without any further purification.

$^1$H NMR (CDCl$_3$): δ 6.78 (2H, d, J=9.0 Hz), 6.60 (2H, d, J=9.0 Hz), 3.76 (2H, s), 3.44 (2H, dd, J=5.8, 4.9 Hz), 3.20 (2H, dd, J=4.9, 4.0 Hz), 3.02 (3H, s).

4-(4-Isothiocyanato-phenyl)-1-methyl-piperazin-2-one, which has the structural formula

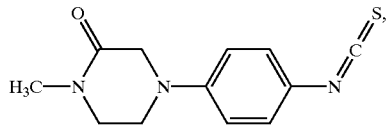

was prepared in a manner analogous to 1-(4-isothiocyanato-phenyl)-1H-imidazole for Example C(41). 4-(4-Amino-phenyl)-1-methyl-piperazin-2-one gave a cream-colored powder in 85% yield, which was used without further purification.

$^1$H NMR (CDCl$_3$): δ 7.18 (2H, d, J=9.0 Hz), 6.80 (2H, d, J=9.0 Hz), 3.90 (2H, s), 3.50 (4H, bs), 3.70 (3H, s).

The title compound was prepared in a manner like that described for Example C(1). 2-bromo-2',6'-difluoro-acetophenone (from Example C(79)) and 4-(4-isothiocyanato-phenyl)-1-methyl-piperazin-2-one provided a yellow solid in 77% yield, mp >300° C.

$^1$H NMR (DMSO-d$_6$): δ 7.60–7.70 (1H, m), 7.48 (2H, bd, J=8.3 Hz), 7.31 (2H, t, J=7.9 Hz), 7.09 (2H, d, J=9.0 Hz), 3.88 (2H, s), 3.58 (4H, bd, J=4.4 Hz), 3.02 (3H, s).

Anal. Calcd. for C$_{21}$H$_{19}$F$_2$N$_5$O$_2$S: C, 56.88; H, 4.32; N, 15.79; S, 7.23. Found: C, 56.81; H, 4.42; N, 15.83; S, 7.31.

Example C(119)

[4-Amino-2-(4-thiomorpholin-4-yl-phenylamino)-thiazol-5-yl]-(2,6-difluoro-phenyl)-methanone

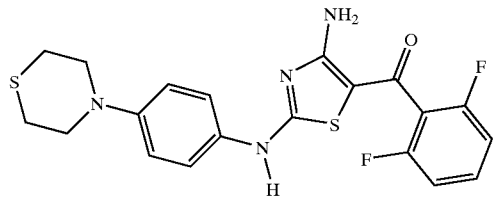

4-Thiomorpholin-4-yl-aniline, which has the structural formula

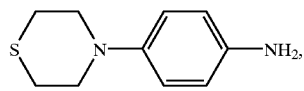

was first prepared as follows. 4-(4-Nitro-phenyl)-thiomorpholine (1.50 g, 6.70 mmol; Beach et al., *J. Chem. Soc. Perkin Trans.* 2 (1984), pp. 217–221) and 10% Pd/C (200 mg of wet DeGussa type, 50% by wt.) was stirred in ethyl acetate (20 mL) and MeOH (20 mL) under hydrogen overnight and filtered. The filtrate was concentrated in vacuo to give 1.28 g (98% yield) of white crystalline flakes, which were used without further purification.

4-(4-Isothiocyanato-phenyl)-thiomorpholine, which has the structural formula

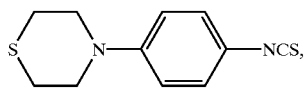

was prepared in a manner analogous to 4-isothiocyanato-N,N-dimethyl-benzenesulfonamide for Example C(109). 4-Thiomorpholin-4-yl-aniline provided a yellow powder in 83% yield.

$^1$H NMR (CDCl$_3$): δ 7.13 (2H, d, J=9.1 Hz), 6.79 (2H, d, J=9.1 Hz), 3.59 (4H, ddd, J=5.2, 5.0, 2.6 Hz), 2.72 (4H, ddd, J=5.2, 5.0, 2.6 Hz).

The title compound was prepared in a manner analogous to that used in Example C(1). 4-(4-Isothiocyanato-phenyl)-thiomorpholine and 2-bromo-2',6'-difluoro-acetophenone (from Example C(79)) provided a yellow powder in 51% yield, mp 128–130° C.

$^1$H NMR (DMSO-d$_6$): δ 10.64 (1H, s), 8.12 (2H, bs), 7.56–7.44 (1H, m), 7.30 (2H, d, J=9.0 Hz), 7.18 (1H, d, J=7.7 Hz), 7.15 (1H, d, J=8.1 Hz), 6.91 (2H, d, J=9.0 Hz), 3.47 (2H, dd, J=5.1, 5.0 Hz), 2.65 (2H, dd, J=5.1, 5.0 Hz).

HRFABMS (MH$^+$): Calcd.: 433.0968. Found: 433.0980.

Anal. Calcd. for C$_{20}$H$_{18}$N$_4$OS$_2$F$_2$.0.2H$_2$O: C, 55.08; H, 4.25; N, 12.85; S, 14.71. Found: C, 55.02; H, 4.14; N, 12.72; S, 14.53.

Example C(120)

4-{4-[4-Amino-5-(2,6-difluoro-benzoyl)-thiazol-2-ylamino]-phenyl}-piperazin-2-one

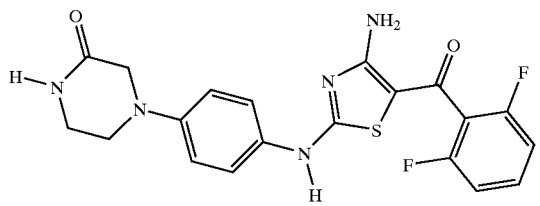

4-(4-Amino-phenyl)-piperazin-2-one, which has the structural formula

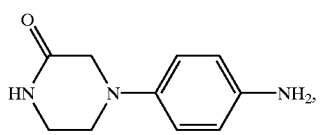

was prepared in a manner analogous to 4-(4-methyl-piperazin-1-yl)-aniline for Example C(70). 4-(4-Nitro-phenyl)-piperazin-2-one (from Example C(115)) gave a pale brown oil in 100% crude yield, which was used without any further purification.

$^1$H NMR (CD$_3$OD): δ 7.02 (2H, d, J=8.7 Hz), 6.91 (2H, d, J=8.8 Hz), 3.81 (2H, s), 3.59 (2H, dd, J=5.9, 4.8 Hz), 3.46 (2H, dd, J=5.9, 4.8 Hz).

4-(4-Isothiocyanato-phenyl)-piperazin-2-one, which has the structural formula

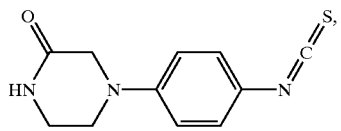

was prepared in a manner analogous tol-(4-isothiocyanato-phenyl)-1H-imidazole for Example C(41). 4-(4-Amino-phenyl)-piperazin-2-one provided a cream-colored solid, which was used without further purification.

$^1$H NMR (CDCl$_3$): δ 9.00 (1H, bs), 8.20 (2H, d, J=9.0 Hz), 7.80 (2H, d, J=9.0 Hz), 4.50 (2H, s), 4.00–4.30 (4H, m).

The title compound was prepared in a manner like that described for Example C(1). 2-bromo-2',6'-difluoro-acetophenone (from Example C(79)) and 4-(4-isothiocyanato-phenyl)-piperazin-2-one provided a yellow solid in 56% yield, mp 280–282° C.

$^1$H NMR (DMSO-d$_6$): δ 9.12 (3H, bs), 8.32–8.44 (1H, m), 8.18 (2H, bd, J=6.9 Hz), 8.05 (2H, t, J=8.2 Hz), 7.78 (2H, d, J=9.0 Hz), 4.52 (2H, s).

HRFABMS: Calcd. for C$_{20}$H$_{18}$F$_2$N$_5$O$_2$S (MH$^+$): 430.1149. Found: 430.1138.

Anal. Calcd. for C$_{20}$H$_{17}$F$_2$N$_5$O$_2$S.0.3H$_2$O: C, 55.24; H, 4.08; N, 16.11; S, 7.37. Found: C, 55.24; H, 4.10; N, 15.87; S, 7.34.

Example C(121)

{4-Amino-2-[4-(4-cyclopropylmethyl-piperazin-1-yl)-phenylamino]-thiazol-5-yl}-(2,6-difluoro-phenyl)-methanone

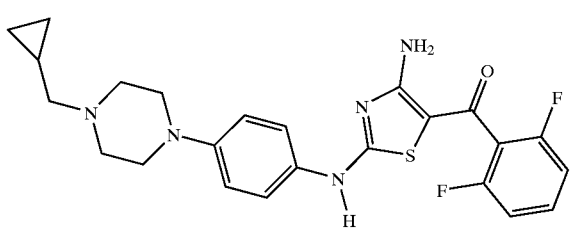

1-Cyclopropylmethyl-4-(4-nitro-phenyl)-piperazine, which has the structural formula

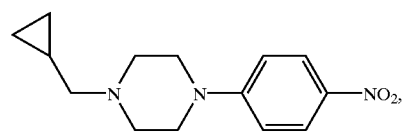

was first prepared as follows. To a suspension of 1-(4-nitro-phenyl)-piperazine (2.50 g, 12.1 mmol) in DMF (10 mL) was added anhydrous Na$_2$CO$_3$ (639 mg, 6.03 mmol) and bromomethylcyclopropane (585 μL, 6.03 mmol). The mixture was heated at 100° C. overnight, then allowed to cool and diluted with H$_2$O (30 mL). The separated aqueous layer was extracted with CHCl$_3$ (3×50 mL). The combined organic layers were dried over Na$_2$SO$_4$, filtered, and concentrated under reduced pressure to give an orange-brown solid, which was purified via flash column chromatography with 2.5% MeOH/CH$_2$Cl$_2$ as eluant to give 2.65 g (84% yield) of a yellow solid. This material was used without any further purification.

¹H NMR (CDCl₃): δ 8.10 (2H, d, J=10.7 Hz), 7.11 (2H, d, J=9.5 Hz), 3.45 (4H, dd, J=5.3, 5.1 Hz), 2.65 (4H, dd, J=5.3, 5.1 Hz), 2.29 (2H, d, J=6.6 Hz), 0.84–0.98 (1H, m), 0.50–0.58 (2H, m), 0.10–0.15 (2H, m).

4-(4-Cyclopropylmethyl-piperazin-1-yl)-aniline, which has the structural formula

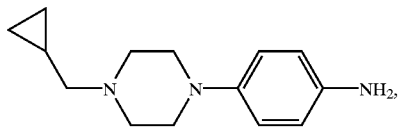

was prepared in a manner analogous to 4-(4-methyl-piperazin-1-yl)-aniline for Example C(70). 1-Cyclopropylmethyl-4-(4-nitro-phenyl)-piperazine furnished a red solid in 99% crude yield, which was used without further purification.

¹H NMR (CDCl₃): δ 6.85 (2H, d, J=9.9 Hz), 6.62 (2H, d, J=8.8 Hz), 3.42 (2H, bs), 3.10 (4H, dd, J=5.1, 4.8 Hz), 2.69 (4H, dd, J=5.1, 4.9 Hz), 2.30 (2H, d, J=6.5 Hz), 0.90–0.98 (1H, m), 0.50–0.56 (2H, m), 0.10–0.15 (2H, m).

1-Cyclopropylmethyl-4-(4-isothiocyanato-phenyl)-piperazine, which has the structural formula

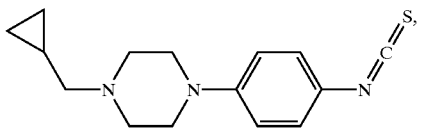

was prepared in a manner analogous to 1-(4-isothiocyanato-phenyl)-1H-imidazole for Example C(41). 4-(4-Cyclopropylmethyl-piperazin-1-yl)-aniline gave a dark-brown oil in 95% crude yield, which was used without further purification.

¹H NMR (CDCl₃): δ 6.80 (2H, d, J=9.0 Hz), 6.68 (2H, d, J=9.1 Hz), 3.08 (4H, bs), 2.55 (4H, bs), 2.10 (2H, d, J=6.2 Hz), 0.65–0.80 (1H, m), 0.42 (2H, d, J=8.0 Hz), 0.00 (2H, d, J=4.6 Hz).

The title compound was prepared in a manner like that described for Example C(1). 1-Cyclopropylmethyl-4-(4-isothiocyanato-phenyl)-piperazine and 2-bromo-2',6'-difluoro-acetophenone (from Example C(79)) provided, after crystallization from EtOH, a yellow solid in 17% yield, mp 215–218° C.

¹H NMR (DMSO-d₆): δ 10.60 (1H, s), 8.04 (2H, bs), 7.46–7.56 (1H, m), 7.18–7.20 (2H, m), 7.08 (2H, dd, J=8.0, 7.7 Hz), 6.82 (2H, d, J=9.1 Hz), 2.98–3.03 (4H, m), 2.47 (4H, bs), 2.12 (2H, d, J=6.6 Hz), 0.72–0.78 (1H, m), 0.34–0.42 (2H, m), 0.00–0.12 (2H, m).

IR (KBr): 2917, 1620, 1513, 1428 cm⁻¹.

HRFABMS: Calcd. for C₂₄H₂₅F₂N₅OSCs (M+Cs⁺): 602.0802. Found: 602.0818.

Anal. Calcd. for C₂₄H₂₅F₂N₅OS·0.5H₂O·0.1EtOH: C, 60.16; H, 5.55; N, 14.49; S, 6.64. Found: C, 59.94; H, 5.24; N, 14.19; S, 6.92.

Example C(122)

[4-Amino-2-(4-pyridin-4-yl-phenylamino)-thiazol-5-yl]-(2,6-difluoro-phenyl)-methanone

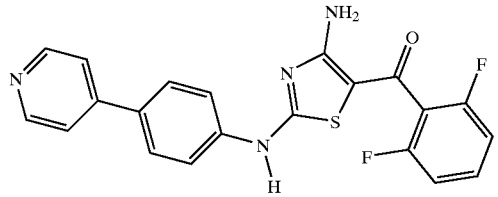

4-Pyridin-4-yl-aniline, which has the structural formula

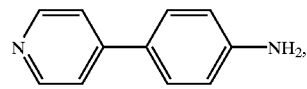

was first prepared as follows. A mixture of 4-(4-nitro-phenyl)-pyridine (600 mg, 3.0 mmol; Wang et al., *J. Phys. Chem.*, vol. 99 (1995), pp. 6876–6888) and 10% Pd/C (100 mg) in EtOH (20 mL) was stirred under a hydrogen atmosphere overnight. The catalyst was filtered off and the filtrate concentrated in vacuo to provide 510 mg (100% yield) of white solid.

¹H NMR (CDCl₃): δ 8.59 (2H, dd, J=6.2, 1.6 Hz), 7.51 (2H, d, J=8.6 Hz), 7.46 (2H, dd, J=6.2, 1.6 Hz), 6.79 (2H, d, J=8.6 Hz).

4-(4-Isothiocyanato-phenyl)-pyridine, which has the structural formula

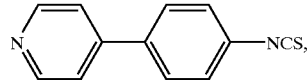

was prepared as follows. To 4-pyridin-4-yl-aniline (200 mg, 1.18 mmol) in THF (35 mL) at 0° C. was added in succession Et₃N (0.33 mL, 2.4 mmol) and thiophosgene (99 μl, 1.29 mmol) dropwise. After 20 min. at 0° C., then ambient temperature for 10 min., the solvent was evaporated. The residue was suspended in water, filtered, washed with minimal water, and dried under vacuum to give a brown solid, 240 mg (96%), which was used without further purification.

¹H NMR (CDCl₃): δ 8.62 (2H, d, J=6.3 Hz), 7.57 (2H, d, J=8.6 Hz), 7.45 (2H, d, J=6.3 Hz), 7.27 (2H, d, J=8.6 Hz).

The title compound was prepared in a manner analogous to that used in Example C(1). 4-(4-Isothiocyanato-phenyl)-pyridine and 2-bromo-2',6'-difluoro-acetophenone (from Example C(79)) provided, after recrystallization from EtOH, a brown powder in 64% yield, mp >300° C.

¹H NMR (DMSO-d₆): δ 11.08 (1H, s), 8.61 (2H, d, J=6.0 Hz), 8.25 (2H, bs), 7.85 (2H, d, J=8.8 Hz), 7.73 (2H, d, J=8.8 Hz), 7.71 (2H, d, J=6.0 Hz), 7.61–7.49 (1H, m), 7.23 (1H, d, J=7.7 Hz), 7.20 (1H, d, J=8.1 Hz).

HRFABMS (MH⁺): Calcd.: 409.0935. Found: 409.0921.

Anal. Calcd. for C₂₁H₁₄N₄OSF₂·0.4H₂O·0.3EtOH: C, 60.41; H, 3.90; N, 13.05; S, 7.47. Found: C, 60.51; H, 3.65; N, 12.69; S, 7.86.

Example C(123)

{4-Amino-2-[4-(4-carbamoyl-piperazin-1-yl)-phenylamino]-thiazol-5-yl}-(2,6-difluoro-phenyl)-methanone

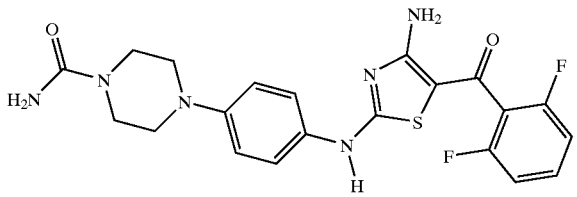

1-Carbamoyl-4-(4-nitro-phenyl)-piperazine, which has the structural formula

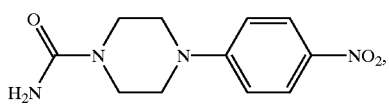

was first obtained according to a procedure from Cain et al., *J. Med. Chem.*, vol. 20 (1977), pp. 987–996, wherein 1-(4-nitrophenyl)piperazine was treated with potassium cyanate to provide a white solid, 705 mg (99%), which was used without further purification.

$^1$H NMR (CDCl$_3$): δ 6.71 (2H, d, J=8.6 Hz), 6.50 (2H, d, J=8.6 Hz), 5.97 (2H, bs), 4.58 (2H, bs), 3.39 (4H, dd, J=5.1, 4.9 Hz), 2.82 (4H, dd, J=5.1, 4.9 Hz).

1-(4-Amino-phenyl)-4-carbamoyl-piperazine, which has the formula

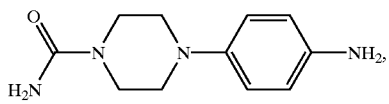

was next prepared as follows. A mixture of 4-(4-nitro-phenyl)-piperazine-1-carboxylic acid amide (760 mg, 3.22 mmol), 10% Pd/C (120 mg), MeOH (20 mL), and THF (20 mL) was stirred under hydrogen for 2 hours. The catalyst was filtered off and the filtrate concentrated in vacuo to provide a white solid, 705 mg (99%), which was used without further purification.

$^1$H NMR (CDCl$_3$): δ 6.71 (2H, d, J=8.6 Hz), 6.50 (2H, d, J=8.6 Hz), 5.97 (2H, bs), 4.58 (2H, bs), 3.39 (4H, dd, J=5.1, 4.9 Hz), 2.82 (4H, dd, J=5.1, 4.9 Hz).

1-Carbamoyl-4-(4-isothiocyanato-phenyl)-piperazine, which has the structural formula

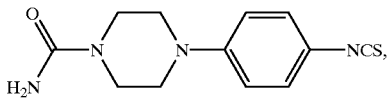

was prepared as follows. To a suspension of 1-(4-amino-phenyl)-4-carbamoyl-piperazine (300 mg, 1.36 mmol) in THF (30 mL) at −35° C. was successively added triethylamine (0.38 mL, 2.73 mmol) and thiophosgene (104 μl, 1.36 mmol) dropwise. The solvent was evaporated and the tarry residue diluted with water. The resultant light brown solid was filtered off, washed with a small amount of water, and dried under vacuum to afford a brown powder, 337 mg (94% yield), which was used without further purification.

$^1$H NMR (CDCl$_3$): δ 7.08 (2H, d, J=9.0 Hz), 6.76 (2H, d, J=9.0 Hz), 4.45 (2H, bs), 3.50 (4H, dd, J=5.4, 5.0 Hz), 3.15 (4H, dd, J=5.4, 5.0 Hz).

The title compound was prepared in a manner analogous to that used in Example C(1). 1-Carbamoyl-4-(4-isothiocyanato-phenyl)-piperazine and 2-bromo-2',6'-difluoro-acetophenone (from Example C(79)) provided a light-gray powder in 45% yield, mp 278.5–279° C.

$^1$H NMR (DMSO-d$_6$): δ 10.69 (1H, s), 8.16 (2H, bs), 7.63–7.51 (1H, m), 7.38 (2H, d, J=9.0 Hz), 7.25 (1H, d, J=7.8 Hz), 7.21 (1H, d, J=7.9 Hz), 7.02 (2H, d, J=9.0 Hz), 6.09 (2H, bs), 3.48 (2H, t, J=4.7 Hz), 3.11 (2H, t, J=4.7 Hz).

HRFABMS (M+Na$^+$): Calcd.: 81.1234. Found: 481.1246.

Anal. Calcd. for C$_{21}$H$_{20}$N$_6$O$_2$SF$_2$.0.5H$_2$O: C, 53.95; H, 4.53; N, 17.98; S, 6.86. Found: C, 53.92; H, 4.35; N, 17.64; S, 6.64.

Example C(124)

{4-Amino-2-[4-(3R,4-dimethyl-piperazin-1-yl)-phenylamino]-thiazol-5-yl}-(2,6-difluoro-phenyl)-methanone

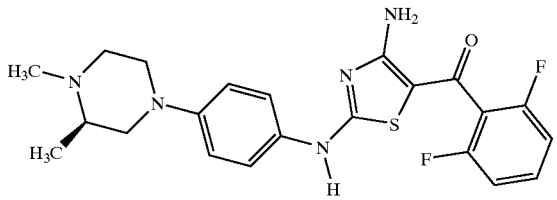

3R-Methyl-1-(4-nitro-phenyl)-piperazine, which has the structural formula

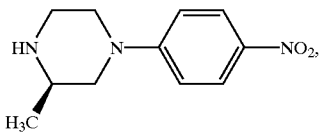

was made first as follows. (R)-(−)-2-Methylpiperazine (186 mg, 1.86 mmol), 1-fluoro-4-nitrobenzene (131 mg, 0.93 mmol), Et$_3$N (0.26 mL, 1.86 mmol), and acetonitrile (2 mL) was refluxed overnight and then concentrated in vacuo. The residue was suspended in water and the resultant solid was filtered off, washed with minimal water, and dried under vacuum to provide a bright yellow solid 128 mg (62% yield), which was used without further purification.

$^1$H NMR (CDCl$_3$): δ 8.12 (2H, d, J=9.5 Hz), 6.82 (2H, d, J=9.5 Hz), 3.80–3.71 (2H, m), 3.18–3.08 (1H, m), 3.04–2.88 (3H, m), 2.58 (1H, dd, J=12.3, 12.3 Hz), 1.16 (3H, d, J=6.3 Hz).

1,2R-Dimethyl-4-(4-nitro-phenyl)-piperazine, which has the structural formula

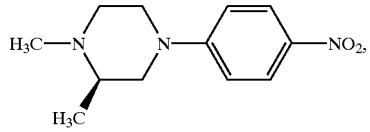

was prepared as follows. A mixture of 3R-methyl-1-(4-nitro-phenyl)-piperazine (124 mg, 0.56 mmol), sodium formate (93 mg, 1.37 mmol), formic acid (1.5 mL), and formalin (1.5 mL) was stirred at 80° C. overnight, cooled, poured into ice/water, and extracted with CHCl₃. The organic layer washed with brine, dried over Na₂SO₄, and concentrated to give 116 mg (71% yield) of yellow crystals, which were used without further purification.

$^1$H NMR (CDCl₃): δ 8.12 (2H, d, J=9.4 Hz), 6.82 (2H, d, J=9.4 Hz), 3.76 (1H, d, J=12.4 Hz), 3.67 (1H, d, J=12.4 Hz), 3.14 (1H, ddd, J=12.4, 11.7, 1.5 Hz), 2.90 (1H, d, J=11.7 Hz), 2.74 (1H, dd, J=11.7, 10.9 Hz), 2.40 (1H, m), 2.34 (3H, s), 2.22 (1H, m), 1.16 (3H, d, J=6.3 Hz).

4-(3R,4-Dimethyl-piperazin-1-yl)-aniline, which has the structural formula

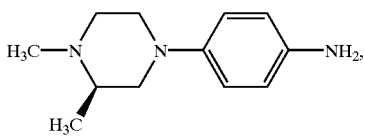

was made as follows. A mixture of 1,2R-dimethyl-4-(4-nitro-phenyl)-piperazine (168 mg, 0.71 mmol), 10% Pd/C (30 mg), and MeOH (10 mL) was stirred under hydrogen for 1.5 hours. The catalyst was filtered off and the filtrate concentrated in vacuo to provide a cloudy yellow oil, which was used without further purification.

$^1$H NMR (CDCl₃): δ 6.91 (2H, d, J=8.8 Hz), 6.75 (2H, d, J=8.8 Hz), 3.66–3.32 (4H, m), 3.05–2.89 (2H, m), 2.63–2.48 (2H, m), 2.44–2.36 (1H, m), 2.44 (3H, s), 1.22 (3H, d, J=6.1 Hz).

4-(4-Isothiocyanato-phenyl)-1,2R-dimethyl-piperazine, which has the structural formula

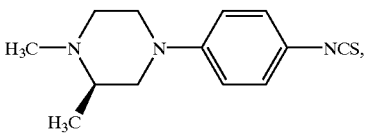

was prepared as follows. To 4-(3R,4-dimethyl-piperazin-1-yl)-aniline (0.71 mmol) in THF (15 mL) at −35° C. was added in succession Et₃N (0.20 mL, 1.43 mmol) and thiophosgene (58 μl, 0.75 mmol) dropwise. The solvent was evaporated and the residue partitioned with CHCl₃ and water. The organic layer was dried with NASO₄ and concentrated to furnish a brown powder, 184 mg, which contained trace Et₃N by NMR, but was sufficient for use without further purification.

$^1$H NMR (CDCl₃): δ 7.12 (2H, d, J=9.1 Hz), 6.82 (2H, d, J=9.1 Hz), 3.58–3.46 (2H, m), 3.13–3.03 (2H, m), 2.89–2.75 (1H, m), 2.65–2.41 (2H, m), 2.49 (3H, s), 1.27 (3H, d, J=6.3 Hz).

The title compound was prepared in a manner analogous to that used in Example C(1). 4-(4-Isothiocyanato-phenyl)-1,2R-dimethyl-piperazine and 2-bromo-2',6'-difluoro-acetophenone (from Example C(79)) provided a yellow powder in 57% yield, mp 115–118° C.

$^1$H NMR (DMSO-d₆): δ 10.65 (1H, bs), 8.15 (2H, bs), 7.62–7.50 (1H, m), 7.35 (2H, d, J=9.0 Hz), 7.23 (1H, d, J=7.7 Hz), 7.20 (1H, d, J=8.0 Hz), 6.97 (2H, d, J=9.0 Hz), 3.59–3.49 (2H, m), 3.34 (3H, s), 2.90–2.72 (2H, m), 2.40 (1H, t, J=10.9 Hz), 2.28–2.05 (2H, m), 1.09 (3H, d, J=6.2 Hz).

HRFABMS (MH⁺): Calcd.: 444.1670. Found: 444.1656.

Anal. Calcd. for C₂₂H₂₃N₅OSF₂.0.8H₂O.0.6t-BuOH: C, 58.33; H, 6.14; N, 13.94; S, 6.38. Found: C, 58.38; H, 5.92; N, 13.89; S, 6.33.

Example C(125)

{4-Amino-2-[4-(3S,4-dimethyl-piperazin-1-yl)-phenylamino]-thiazol-5-yl}-(2,6-difluoro-phenyl)-methanone

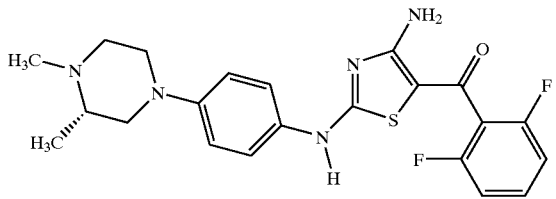

4-(4-Isothiocyanato-phenyl)-1,2S-dimethyl-piperazine, which has the structural formula

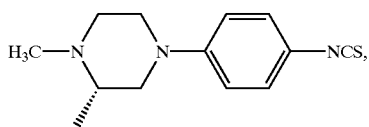

was prepared according to the route employed for its enantiomer, 4-(4-isothiocyanato-phenyl)-1,2R-dimethyl-piperazine for Example C(124). The resultant yellow powder displayed a comparable NMR spectrum and was used without further purification.

The title compound was prepared in a manner analogous to that used in Example C(1). 4-(4-Isothiocyanato-phenyl)-1,2S-dimethyl-piperazine and 2-bromo-2',6'-difluoro-acetophenone (from Example C(79)) provided a yellow powder in 77% yield, mp 110–116° C.

$^1$H NMR (DMSO-d₆): δ 10.65 (1H, bs), 8.15 (2H, bs), 7.62–7.50 (1H, m), 7.35 (2H, d, J=9.0 Hz), 7.23 (1H, d, J=7.7 Hz), 7.20 (1H, d, J=8.0 Hz), 6.97 (2H, d, J=9.0 Hz), 3.59–3.49 (2H, m), 3.34 (3H, s), 2.90–2.72 (2H, m), 2.40 (1H, t, J=10.9 Hz), 2.28–2.05 (2H, m), 1.09 (3H, d, J=6.2 Hz).

IR (KBr): 3386, 3274, 3168, 2970, 2807, 1620, 1589, 1547, 1517, 1464, 1429, 1238, 1001 cm⁻¹.

HRFABMS (MH⁺): Calcd.: 444.1670. Found: 444.1659.

Anal. Calcd. for C₂₂H₂₃N₅OSF₂.0.7H₂O.0.2t-BuOH: C, 58.15; H, 5.65; N, 14.87; S, 6.81. Found: C, 58.06; H, 5.61; N, 14.58; S, 6.90.

Example C(126)

(4-Amino-2-{4-[(3-dimethylamino-propyl)-methyl-amino]-phenylamino}-thiazol-5-yl)-(2,6-difluoro-phenyl)-methanone

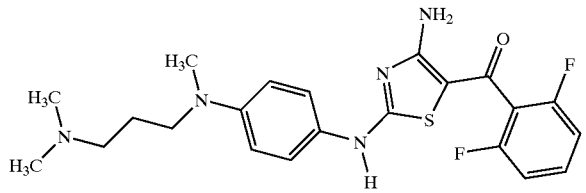

N-(4-Nitrophenyl)-N,N',N'-trimethyl-propane-1,3-diamine, which has the structural formula

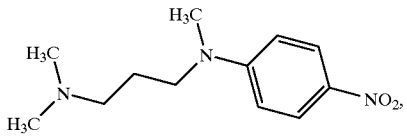

was first prepared in a manner analogous to tert-butyl [methyl-(4-nitro-phenyl)-amino]-acetate for Example C(103). 4-Fluoronitrobenzene and N,N,N'-trimethyl-propanediamine gave a yellow oil, which was heated up to 280° C. at 1 torr to remove starting materials, furnishing an orange oil, 4.26 g (85% crude yield), which was used without any further purification.

$^1$H NMR (CDCl$_3$): δ 8.10 (2H, ddd, J=9.5, 8.2, 5.3 Hz), 6.64 (2H, ddd, J=9.5, 8.2, 5.3 Hz), 3.50 (2H, t, J=7.2 Hz), 3.08 (3H, s), 2.07 (3H, t, J=6.8 Hz), 2.23 (6H, s), 1.72–1.82 (2H, m).

N-(4-Aminophenyl)-N,N',N'-propane-1,3-diamine, which has the structural formula

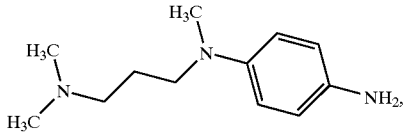

was prepared as follows. A mixture of N-(4-nitrophenyl)-N,N',N'-trimethyl-propane-1,3-diamine (1.72 g, 7.25 mmol), tin(II)chloride dihydrate (8.05 g, 36.2 mmol), dioxane (25 mL), and ethanol (5 mL) was heated at reflux for 3.5 hours, then allowed to cool. To the resultant mixture was added sat aq. Na$_2$CO$_3$ until no gas evolution was observed. Celite was added to ease subsequent filtering. The solids were rinsed with MeOH, and the filtrate was concentrated under reduced pressure and extracted with 10% MeOH/CHCl$_3$ (4x). The combined extracts were washed with brine, dried over NASO$_4$, and evaporated to give a black oil, which was purified via column chromatography with alumina (neutral, activity I) and 1% MeOH/CH$_2$Cl$_2$ as eluant to afford 0.39 g (26%) of a darkening brown oil that was used without further purification.

$^1$H NMR (CDCl$_3$): δ 6.67 (4H, dd, J=9.0, 8.6 Hz), 3.22 (2H, t, J=7.2 Hz), 2.82 (3H, s), 2.31 (2H, t, J=7.5 Hz), 2.23 (6H, s), 1.70 (2H, p, J=7.4 Hz).

N-(4-Isothiocyanato-phenyl)-N,N',N'-trimethyl-propane-1,3-diamine, which has the structural formula

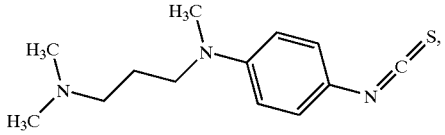

was prepared in a manner analogous to 4-(4-isothiocyanato-phenyl)-1,2R-dimethyl-piperazine for Example C(124). N-(4-Aminophenyl)-N,N',N'-propane-1,3-diamine provided a black oil in 86% crude yield, which was used without further purification.

$^1$H NMR (CDCl$_3$): δ 7.09 (2H, d, J=9.0 Hz), 6.59 (2H, d, J=9.0 Hz), 3.38 (2H, J=7.2 Hz), 2.94 (3H, s), 2.36 (2H, t, J=7.2 Hz), 2.29 (6H, s), 1.78 (2H, p, J=7.2 Hz).

IR (KBr): 2127, 1605, 1514, 1379 cm$^{-1}$.

The title compound was prepared in a manner like that described for Example C(1). N-(4-Isothiocyanato-phenyl)-N,N',N'-trimethyl-propane-1,3-diamine and 2-bromo-2',6'-difluoro-acetophenone (from Example C(79)) afforded a brown oil, which was purified via flash column chromatography with a stepwise gradient of 7–14% MeOH/CHCl$_3$ and precipitated from CH$_2$Cl$_2$/hex to provide an amorphous yellow solid in 51% yield, mp 115–120° C. (decomp).

$^1$H NMR (DMSO-d$_6$): δ 10.50 (1H, bs), 8.05 (2H, bs), 7.50 (1H, ddd, J=15.3, 8.4, 6.7 Hz), 7.10–7.35 (4H, m), 6.68 (2H, d, J=9.1 Hz), 2.84 (3H, s), 2.27 (2H, t, J=7.2 Hz), 2.16 (6H, s), 1.61 (2H, p, J=7.3 Hz).

IR (KBr): 3393, 3279, 3165, 2951, 1619, 1545, 1524, 1462, 1436 cm$^{-1}$.

HRFABMS: Calcd. for C$_{22}$H$_{26}$F$_2$N$_5$OS (MH$^+$): 446.1826. Found: 446.1810.

Anal. Calcd. for C$_{21}$H$_{23}$F$_2$N$_5$OS.0.8H$_2$O.0.4C$_6$H$_{14}$: C, 59.28; H, 6.56; N, 14.16; S, 6.49. Found: C, 59.37; H, 6.31; N, 13.76; S, 6.26.

Example C(127)

(2,6-Difluoro-phenyl)-{2-[4-(4-pyridin-4-yl-piperazin-1-yl)-phenylamino]-thiazol-5-yl}-methanone

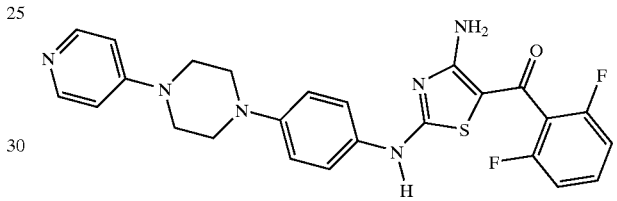

1-(4-Nitro-phenyl)-4-pyridin-4-yl-piperazine, which has the structural formula

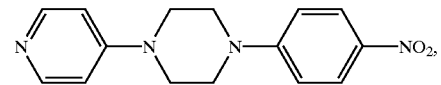

was prepared in a manner analogous to tert-butyl[methyl-(4-nitro-phenyl)-amino]-acetate for Example C(103). 4-Fluoronitrobenzene and 1-(4-pyridyl)piperazine (Ratous et. al., J. Med. Chem., vol. 8 (1965), pp. 104–107) gave a brown powder in 27% yield, which was used without further purification.

$^1$H NMR (CD$_3$OD): δ 8.20 (2H, d, J=5.0 Hz), 8.08 (2H, d, J=9.4 Hz), 7.04 (2H, d, J=9.5 Hz), 3.62–3.68 (4H, m), 3.50–3.56 (4H, m).

4-(4-Pyridin-4-yl-piperazin-1-yl)-aniline, which has the structural formula

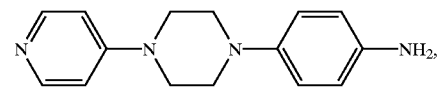

was prepared in a manner analogous to 4-(4-methyl-piperazin-1-yl)-aniline for Example C(70). 1-(4-Nitrophenyl)-4-pyridin-4-yl-piperazine afforded a brown powder in 100% crude yield, which was used without further purification.

$^1$H NMR (CD$_3$OD): δ 8.16 (2H, d, J=6.7 Hz), 6.90 (4H, bd, J=8.9 Hz), 6.74 (2H, d, J=6.6 Hz), 3.56 (4H, dd, J=5.3, 5.0 Hz), 3.14 (4H, dd, J=5.0, 4.2 Hz).

1-(4-Isothiocyanato-phenyl)-4-pyridin-4-yl-piperazine, which has the structural formula

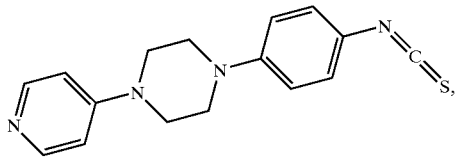

was prepared as follows. To a solution of 4-(4-pyridin-4-yl-piperazin-1-yl)-aniline (2.00 g, 7.86 mmol) in 10% aq HCl (10 mL) was added thiophosgene (720 μL, 9.43 mmol). After 0.5 hour, the resultant yellow precipitate was filtered off, washed with sat aq NaHCO$_3$ and H$_2$O, and dried under high vacuum to give 1.9 g (82% yield) of a yellow powder, which was used without further purification.

$^1$H NMR (DMSO-d$_6$): δ 6.73 (4H, d, J=8.8 Hz), 6.51 (4H, d, J=8.8 Hz), 3.32 (4H, bs), 3.29 (4H, bs).

The title compound was prepared in a manner like that described for Example C(1). 1-(4-Isothiocyanato-phenyl)-4-pyridin-4-yl-piperazine and 2-bromo-2',6'-difluoroacetophenone (from Example C(79)) provided, after recrystallization with trace DMSO in MeOH/CHCl$_3$, a pale tan powder in 30% yield, mp 155–157° C.

$^1$H NMR (DMSO-d$_6$): δ 8.16 (2H, d, J=6.0 Hz), 8.04 (1H, bs), 7.40–7.52 (1H, m), 7.32 (2H, d, J=8.7 Hz), 7.15 (2H, t, J=7.7 Hz), 6.96 (2H, d, J=9.0 Hz), 6.85 (2H, d, J=5.5 Hz), 3.60 (4H, bs).

HRFABMS: Calcd. for C$_{25}$H$_{23}$F$_2$N$_6$OS (MH$^+$): 493.1622. Found: 493.1606.

Anal. Calcd. for C$_{25}$H$_{22}$F$_2$N$_6$OS.0.7MeOH.0.1CHCl$_3$.0.1 DMSO: C, 58.40; H, 4.81; N, 15.72; S, 6.60. Found: C, 58.38; H, 4.50; N, 15.37; S, 7.00.

Example C(128)

{4-Amino-2-[4-(1-methyl-[1,4]-diazepan-4-yl)-phenylamino]-thiazol-5-yl}-(2,6-difluoro-phenyl)-methanone

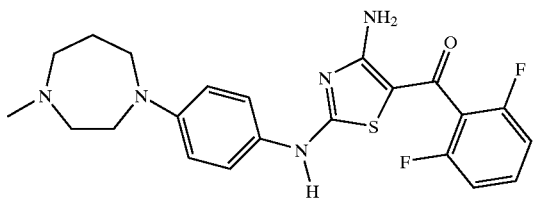

1-Methyl-4-(4-nitro-phenyl)-[1,4]diazepane, which has the structural formula

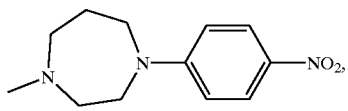

was prepared in a manner analogous to tert-butyl[methyl-(4-nitro-phenyl)-amino]-acetate for Example C(103). 1-Methyl-homopiperazine provided a yellow powder in 93% yield, which was used without further purification.

$^1$H NMR (CDCl$_3$): δ 8.12 (2H, d, J=9.5 Hz), 6.64 (2H, d, J=9.5 Hz), 3.56–3.70 (4H, m), 2.74 (2H, dd, J=4.9, 3.3 Hz), 2.58 (2H, dd, J=5.6, 5.4 Hz), 2.40 (3H, s), 2.00–2.08 (2H, m).

4-(4-Methyl-[1,4]diazepan-1-yl)-aniline, which has the structural formula

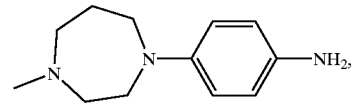

was prepared in a manner analogous to 4-(4-methyl-piperazin-1-yl)-aniline for Example C(70). 1-Methyl-4-(4-nitro-phenyl)-[1,4]diazepane furnished a purple oil in 100% crude yield, which was used immediately without further purification.

$^1$H NMR (CDCl$_3$): δ 6.68 (2H, d, J=12.2 Hz), 6.60 (2H, d, J=6.8 Hz), 3.52 (2H, dd, J=4.8, 4.7 Hz), 3.43 (2H, t, J=6.3 Hz), 2.71 (2H, dd, J=4.9, 4.7 Hz), 2.58 (2H, dd, J=5.5, 5.4 Hz), 2.38 (3H, s), 1.95–2.04 (1H, m).

1-(4-Isothiocyanato-phenyl)-4-methyl-[1,4]diazepane, which has the structural formula

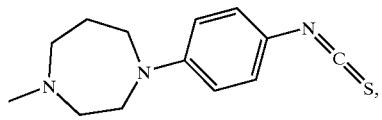

was prepared in a manner analogous to 1-(4-isothiocyanato-phenyl)-1H-imidazole for Example C(41). 4-(4-Methyl-[1,4]diazepan-1-yl)-aniline gave a crude product that was extracted with CHCl$_3$ to eventually afford a black oil in 85% crude yield. This material was used immediately without any further purification.

$^1$H NMR (CDCl$_3$): δ 7.02 (2H, d, J=9.0 Hz), 6.56 (2H, d, J=9.0 Hz), 3.54 (2H, dd,J=4.8, 4.8 Hz), 3.45 (2H, t, J=6.3 Hz), 2.67 (2H, dd, J=4.9, 4.8 Hz), 2.53 (2H, dd, J=5.6, 5.4 Hz), 2.36 (3H, s), 1.97 (2H, p, J=5.7 Hz).

The title compound was prepared in a manner like that described for Example C(1). 1-(4-Isothiocyanato-phenyl)-4-methyl-[1,4]diazepane and 2-bromo-2',6'-difluoro-acetophenone (from Example C(79)) provided, after crystallization from boiling EtOH, a light-tan powder in 26% yield, mp 138–140° C.

$^1$H NMR (DMSO-d$_6$): δ 8.05 (1H, s), 7.42–7.52 (1H, m), 7.10–7.22 (4H, m), 6.64 (2H, d, J=9.1 Hz), 3.36–3.52 (4H, m), 2.58 (2H, dd, J=4.8, 4.7 Hz), 2.42 (2H, dd, J=5.6, 5.4 Hz), 2.25 (3H, s), 1.82–1.92 (2H, m).

HRFABMS: Calcd. for C$_{22}$H$_{24}$F$_2$N$_5$OS (MH$^+$): 444.1670. Found: 444.1656.

Anal. Calcd. for C$_{22}$H$_{23}$F$_2$N$_5$OS.0.5H$_2$O.0.8EtOH: C, 57.92; H, 5.93; N, 14.31; S, 6.55. Found: C, 58.05; H, 5.69; N, 14.15; S, 6.55.

Example C(129)

3-({4-[4-Amino-5-(2,6-difluorobenzoyl)-thiazol-2-yl-amino]-phenyl}-methylamino)-propionitrile

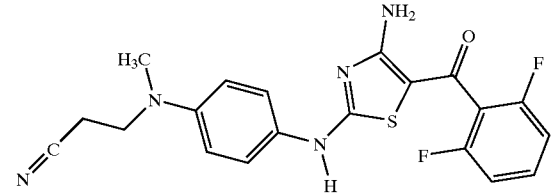

3-[Methyl-(4-nitro-phenyl)-amino]-propionitrile, which has the structural formula

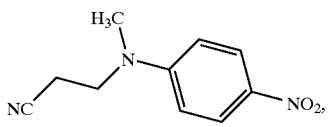

was prepared as follows. Benzyltrimethylammonium hydroxide (7.23 mL of a 40% solution in MeOH) was added to a suspension of N-methyl-4-nitroaniline (5.00 g, 32.9 mmol) and acrylonitrile (7.23 mL) in dioxane (80 mL). The resultant solution was heated at 55° C. for 3.5 hours, then poured into water, and extracted with 20% isopropanol in chloroform. The separated organic layer was washed with water, dried over $K_2CO_3$, and concentrated to a suspension of yellow solid, which was diluted with ether. The solid was filtered off and dried under vacuum to obtain 6.15 g (91% yield) of yellow solid, which was used without further purification.

$^1$H NMR (CDCl$_3$): δ 8.17 (2H, d, J=9.4 Hz), 6.66 (2H, d, J=9.4 Hz), 3.82 (2H, t,J=6.7 Hz), 3.19 (3H, s), 2.66 (2H, t, J=6.7 Hz).

3-[(4-Amino-phenyl)-methyl-amino]-propionitrile, which has the structural formula

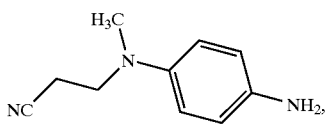

was prepared in a manner analogous to 4-(3S,4-dimethyl-piperazin-1-yl)-phenylamine for Example C(134). 3-[Methyl-(4-nitro-phenyl)-amino]-propionitrile gave a brown oil in 100% yield, which was used without further purification.

$^1$H NMR (CDCl$_3$): δ 6.68 (4H, s), 3.57 (2H, t, J=7.0 Hz), 2.90 (3H, s), 2.51 (2H, t, J=7.0 Hz).

3-[(4-Isothiocyanato-phenyl)-methyl-amino]-propionitrile, which has the structural formula

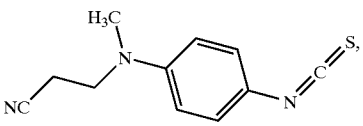

was prepared in a manner analogous to 4-(4-isothiocyanato-phenyl)-1,2S-dimethyl-piperazine for Example C(134). 3-[(4-Amino-phenyl)-methyl-amino]-propionitrile gave a brown solid in 95% yield, which was used without further purification.

$^1$H NMR (CDCl$_3$): δ 7.15 (2H, d, J=9.1 Hz), 6.62 (2H, d, J=9.1 Hz), 3.72 (2H, t, J=6.8 Hz), 3.05 (3H, s), 2.58 (2H, t, J=6.8 Hz).

The title compound was prepared in a manner analogous to that used in Example C(1). 3-[4-(4-Isothiocyanato-phenyl)-methylamino]-propionitrile and 2-bromo-2',6'-difluoro-acetophenone (from Example C(79)) provided an amorphous yellow powder in 66% yield, mp 120–130° C. (decomp).

$^1$H NMR (DMSO-d$_6$): δ 10.52 (1H, bs), 8.10 (2H, bs), 7.49 (1H, ddd, J=15.3, 8.2, 6.7 Hz), 7.26 (2H, bd, J=8.2 Hz), 7.15 (2H, dd, J=8.1, 7.7 Hz), 6.76 (2H, d, J=9.1 Hz), 3.63 (2H, t, J=6.7 Hz), 2.91 (3H, s), 2.69 (2H, t, J=6.7 Hz).

IR (KBr): 3417, 3309, 1618, 1548, 1523, 1463, 1436, 1376, 1356, 1234, 1001 cm$^{-1}$.

HRFABMS Calcd. for $C_{20}H_{17}N_5OSF_2Na$ (M+Na$^+$): 436.1020. Found: 436.1030.

Anal. Calcd. for $C_{20}H_{17}N_5OSF_2 \cdot 0.2H_2O \cdot 0.45$t-BuOH: C, 58.13; H, 4.90; N, 15.55; S, 7.12. Found: C, 57.88; H, 4.79; N, 15.16; S, 6.95.

Example C(130)

2-[4-Amino-2-(4-nitro-phenylamino)-thiazole-5-carbonyl]-phenyl Benzoate

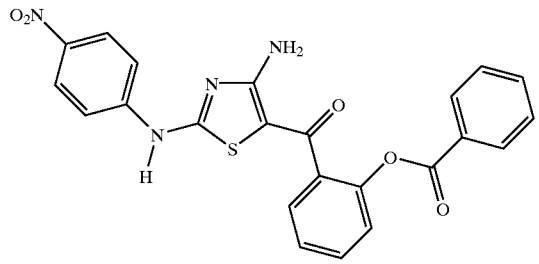

The title compound was prepared essentially as described for Example C(1). In addition, two other reaction products were isolated after flash column chromatography and identified: characteristics for (Z)- and (E)-4-(2-hydroxy-phenyl)-3-(4-nitro-phenyl)-3H-thiazol-2-ylidene-cyanamide follow below. 4-Nitro-phenyl isothiocyanate and 2'-benzoyloxy-2-bromo-acetophenone provided title compound as a yellow solid, mp 258–260° C.

$^1$H NMR (DMSO-d$_6$): δ 11.35 (1H, s), 8.23 (2H, d, J=9.3 Hz), 7.98–8.04 (4H, m), 7.85 (2H, d, J=9.2 Hz), 7.35–7.67 (1H, m), 7.52–7.63 (4H, m), 7.39–7.45 (2H, m). $^{13}$C NMR (MeOH-d$_4$): δ 181.5, 166.4, 164.4, 147.2, 145.8, 142.0, 135.2, 134.3, 131.2, 130.0, 129.3, 129.2, 128.3, 126.5, 125.6, 123.9, 118.3.

Anal. Calcd. for $C_{23}H_{16}N_4O_5S$: C, 59.99; H, 3.50; N, 12.17; S, 6.96. Found: C, 58.25; H, 3.54; N, 11.77; S, 6.94.

Earlier-eluting component, (Z)-4-(2-hydroxy-phenyl)-3-(4-nitro-phenyl)-3H-thiazol-2-ylidene-cyanamide, which has the structural formula

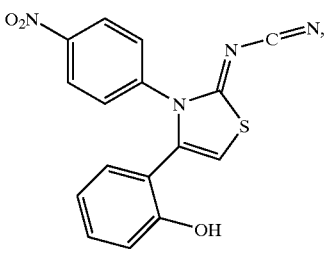

was isolated as a yellow amorphous solid.

$^1$H NMR (DMSO-d$_6$): δ 9.79 (1H, s), 8.18 (2H, d, J=9.0 Hz), 7.55 (2H, d, J=9.0 Hz), 7.26 (1H, dd, J=7.5, 1.5 Hz), 7.17 (1H, ddd, J=7.5, 7.4, 1.5 Hz), 7.05 (1H, s), 6.79 (1H, dd, J=7.6, 7.4 Hz), 6.65 (1H, d, 8.2 Hz). $^{13}$C NMR (MeOH-d$_4$): δ 176.8, 157.9, 150.3, 143.6, 141.7, 134.4, 134.2, 132.0, 126.0, 122.1, 119.5, 119.3, 117.9, 107.3.

HRFABMS: Calcd. for $C_{16}H_{10}N_4O_3S$ (MH$^+$): 339.0552. Found: 339.0550.

A later-eluting component, (E)-4-(2-hydroxy-phenyl)-3-(4-nitro-phenyl)-3H-thiazol-2-ylidene-cyanamide, which has the structural formula

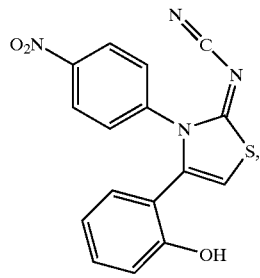

was isolated as a yellow amorphous solid.

$^1$H NMR (DMSO-d$_6$): δ 13.2 (1H, s), 8.25 (2H, d, J=9.2 Hz), 7.75 (1H, dd, J=7.8, 1.5 Hz), 7.55 (1H, ddd, J=8.6, 7.5, 1.1 Hz), 7.41 (1H, ddd, J=8.6, 7.5, 1.1 Hz), 7.25 (1H, dd, J=8.1, 1.0 Hz), 7.13 (1H, d, 9.2 Hz), 7.01 (1H, s). $^{13}$C NMR (MeOH-d$_4$): δ 174.8, 162.1, 152.2, 143.6, 134.0, 131.4, 129.9, 126.4, 126.2, 122.0, 121.5, 117.8, 105.6. ESIMS: Calcd. for C$_{16}$H$_{10}$N$_4$O$_3$S (MH$^+$): 339. Found: 339.

Example C(131)

(4-Amino-2-{4-[4-(2,2,2-trifluoro-ethyl)-piperazin-1-yl]-phenylamino}-thiazol-5-yl)-(2,6-difluoro-phenyl)-methanone

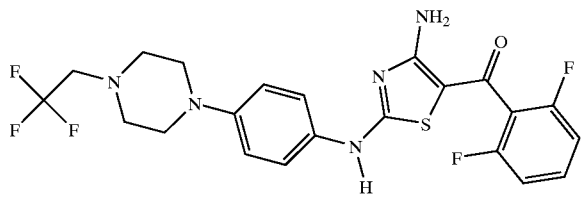

1-(4-Nitro-phenyl)-4-(2,2,2-trifluoro-ethyl)-piperazine, which has the structural formula

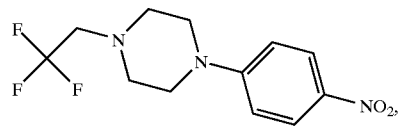

was first prepared in a manner analogous to tert-butyl [methyl-(4-nitro-phenyl)-amino]-acetate for Example C(103). 1-(4-Nitro-phenyl)-piperazine and 1,1,1-trifluoro-2-iodo-ethane gave a yellow-orange solid in 33% crude yield.

$^1$H NMR (CDCl$_3$): δ 8.13 (2H, d, J=9.2 Hz), 6.82 (2H, d, J=9.2 Hz), 3.51–3.38 (4H, m), 3.10–2.99 (2H, m), 2.87–2.77 (4H, m).

4-[4-(2,2,2-Trifluoro-ethyl)-piperazin-1-yl]-aniline, which has the structural formula

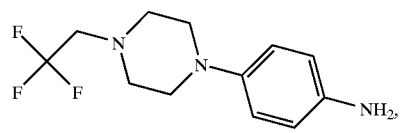

was next prepared in a manner analogous to 4-(4-methyl-piperazin-1-yl)-aniline for Example C(70). 1-(4-Nitro-phenyl)-4-(2,2,2-trifluoro-ethyl)-piperazine gave a pale-brown solid in 100% crude yield.

$^1$H NMR (CDCl$_3$): δ 6.83 (2H, d, J=8.8 Hz), 6.68 (2H, d, J=8.8 Hz), 3.40 (2H, bs), 3.11–3.06 (6H, m), 2.86 (4H, dd, J=5.1, 4.7 Hz).

1-(4-Isothiocyanato-phenyl)-4-(2,2,2-trifluoro-ethyl)-piperazine, which has the structural formula

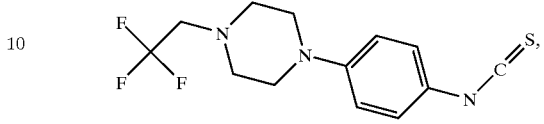

was prepared in a manner analogous to 1-(4-isothiocyanato-phenyl)-4-methyl-piperazine for Example C(70) from 4-[4-(2,2,2-trifluoro-ethyl)-piperazin-1-yl]-aniline, providing a brown powder in 89% yield.

$^1$H NMR (CDCl$_3$): δ 7.15 (2H, d, J=9.1 Hz), 6.85 (2H, d, J=9.0 Hz), 3.25 (4H, dd, J=4.9, 5.2 Hz), 3.05 (2H, q, J=9.5 Hz), 2.86 (4H, dd, J=5.1, 4.8 Hz).

The title compound was prepared in a manner like that described for Example C(1). 1-(4-isothiocyanato-phenyl)-4-(2,2,2-trifluoro-ethyl)-piperazine and 2-bromo-2',6'-difluoroacetophenone (from Example C(79)) provided, after purification via column chromatography with 5% MeOH/CHCl$_3$ as eluant, a yellow powder in 63% yield, mp 99–102° C.

$^1$H NMR (DMSO-d$_6$): δ 8.12 (1H, bs), 7.58–7.46 (1H, m), 7.30 (2H, bd, J=7.4 Hz), 7.18 (2H, dd, J=7.8, 7,7 Hz), 6.92 (2H, d, J=8.9 Hz), 3.24 (2H, q, J=10.3 Hz), 3.12 (4H, dd, J=4.1, 5.0 Hz), 2.76 (4H, bd, J=4.6 Hz).

IR (KBr): 3394, 3276, 3178, 3058, 2954, 2829, 1617, 1588, 1547, 1462, 1426, 1231 cm$^{-1}$.

Anal. Calcd. for C$_{22}$H$_{20}$F$_2$N$_5$OS.0.15CHCl$_3$: C, 51.62; H, 3.94; N, 13.59; S, 6.22. Found: C, 51.68; H, 3.93; N, 13.39; S, 6.03.

Example C(131)

(4-Amino-2-{4-[4-(2,2,2-trifluoroethyl)-piperazin-1-yl]-phenylamino}-thiazol-5-yl)-(2,6-difluoro-phenyl)-methanone

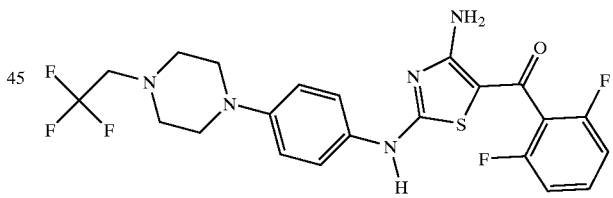

1-(4-Nitro-phenyl)-4-(2,2,2-trifluoro-ethyl)-piperazine, which has the structural formula

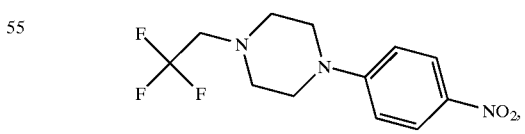

was first prepared in a manner analogous to tert-butyl [methyl-(4-nitro-phenyl)-amino]-acetate for Example C(103). 1-(4-Nitro-phenyl)-piperazine and 1,1,1-trifluoro-2-iodo-ethane gave a yellow-orange solid in 33% crude yield.

$^1$H NMR (CDCl$_3$): δ 8.13 (2H, d, J=9.2 Hz), 6.82 (2H, d, J=9.2 Hz), 3.51–3.38 (4H, m), 3.10–2.99 (2H, m), 2.87–2.77 (4H, m).

4-[4-(2,2,2-Trifluoro-ethyl)-piperazin-1-yl]-aniline, which has the structural formula

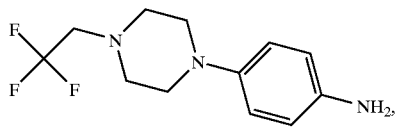

was next prepared in a manner analogous to 4-(4-methyl-piperazin-1-yl)-aniline for Example C(70). 1-(4-Nitro-phenyl)-4-(2,2,2-trifluoro-ethyl)-piperazine gave a pale-brown solid in 100% crude yield.

$^1$H NMR (CDCl$_3$): δ 6.83 (2H, d, J=8.8 Hz), 6.68 (2H, d, J=8.8 Hz), 3.40 (2H, bs), 3.11–3.06 (6H, m), 2.86 (4H, dd, J=5.1, 4.7 Hz).

1-(4-Isothiocyanato-phenyl)-4-(2,2,2-trifluoro-ethyl)-piperazine, which has the structural formula

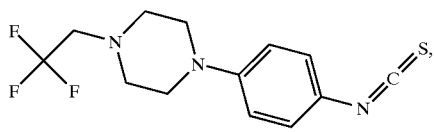

was prepared in a manner analogous to 1-(4-isothiocyanato-phenyl)-4-methyl-piperazine for Example C(70) from 4-[4-(2,2,2-trifluoro-ethyl)-piperazin-1-yl]-aniline, providing a brown powder in 89% yield.

$^1$H NMR (CDCl$_3$): δ 7.15 (2H, d, J=9.1 Hz), 6.85 (2H, d, J=9.0 Hz), 3.25 (4H, dd,J=4.9, 5.2 Hz), 3.05 (2H, q, J=9.5 Hz), 2.86 (4H, dd, J=5.1, 4.8 Hz).

The title compound was prepared in a manner like that described for Example C(1). 1-(4-isothiocyanato-phenyl)-4-(2,2,2-trifluoro-ethyl)-piperazine and 2-bromo-2',6'-difluoroacetophenone (from Example C(79)) provided, after purification via column chromatography with 5% MeOH/CHCl$_3$ as eluant, a yellow powder in 63% yield, mp 99–102° C.

$^1$H NMR (DMSO-d$_6$): δ 8.12 (1H, bs), 7.58–7.46 (1H, m), 7.30 (2H, bd, J=7.4 Hz), 7.18 (2H, dd, J=7.8, 7,7 Hz), 6.92 (2H, d, J=8.9 Hz), 3.24 (2H, q, J=10.3 Hz), 3.12 (4H, dd, J=4.1, 5.0 Hz), 2.76 (4H, bd, J=4.6 Hz).

IR (KBr): 3394, 3276, 3178, 3058, 2954, 2829, 1617, 1588, 1547, 1462, 1426, 1231 cm$^{-1}$.

Anal. Calcd. for C$_{22}$H$_2$OF$_2$N$_5$OS.0.15CHCl$_3$: C, 51.62; H, 3.94; N, 13.59; S, 6.22. Found: C, 51.68; H, 3.93; N, 13.39; S, 6.03.

Example D(1)

(3-Amino-phenyl)-(4-amino-2-phenylamino-thiazol-5-yl)-methanone

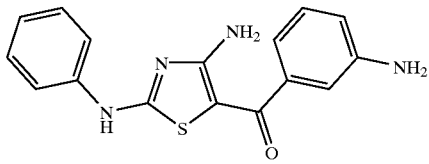

A mixture of the title compound from Example A(1) ((4-amino-2-phenylamino-thiazol-5-yl)-(3-nitrophenyl)-methanone, 520 mg, 1.53 mmol) and 10% palladium on carbon (80 mg) in THF (10 mL) was stirred under a hydrogen atmosphere overnight. The catalyst was filtered off and the filtrate concentrated in vacuo to give 470 mg of a crude solid that recrystallized from ethyl acetate/benzene to provide 100 mg (19% yield) of light yellow powder, mp 162–164° C.

$^1$H NMR (DMSO-d$_6$): δ 10.75 (1H, s), 8.42 (2H, bs), 8.15 (2H, bs), 7.60 (2H, d, J=7.8 Hz), 7.34 (2H, d, J=7.8 Hz), 7.23 (1H, t, J=7.8 Hz), 7.14 (1H, s), 7.07 (1H, d, J=7.8 Hz), 7.05 (1H, t, J=7.8 Hz), 6.91 (1H, d, J=7.8 Hz).

FABMS (MH$^+$): 311.

Anal. Calcd. for C$_{16}$H$_{14}$N$_4$OS.H$_2$O.C$_6$H$_6$: C, 59.30; H, 4.98; N, 16.66; S, 9.54. Found: C, 59.02; H, 4.61; N, 16.34; S, 9.25.

Example D(2)

(4-Amino-phenyl)-(4-amino-2-phenylamino-thiazol-5-yl)-methanone

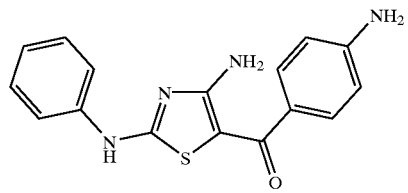

The title compound was prepared in a manner like that described for Example D(1). Catalytic reduction of the title compound of Example A(2) ((4-nitro-phenyl)-(4-amino-2-phenylamino-thiazol-5-yl)-methanone) provided, after recrystallization from ethanol, 410 mg (90% yield) of red amorphous powder, mp >300° C.

$^1$H NMR (DMSO-d$_6$): δ 10.85 (1H, bs), 8.44–8.20 (2H, bs), 8.36 (1H, d, J=8.7 Hz), 8.17 (1H, d, J=8.7 Hz), 7.89 (1H, d, J=15.9 Hz), 7.86 (1H, d, J=15.9 Hz), 7.62 (2H, d, J=7.8 Hz), 7.37 (2H, t, J=7.8 Hz), 7.09 (1H, t, J=7.8 Hz).

FABMS (MH$^+$): 311.

Anal. Calcd. for C$_{16}$H$_{14}$N$_4$OS.0.5H$_2$O: C, 60.17; H, 4.73; N, 17.54; S, 10.04. Found: C, 60.09; H, 4.73; N, 17.58; S, 9.93.

Example D(3)

[4-Amino-2-(4-dimethylamino-phenylamino)-thiazol-5-yl]-(2-amino-phenyl)-methanone

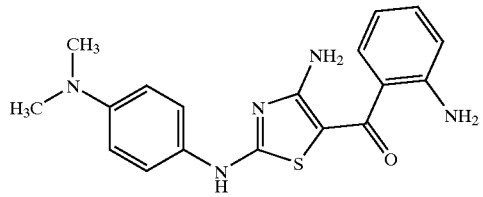

The title compound was prepared essentially as described for Example D(1). Catalytic reduction of the title compound of Example C(4) gave 26 mg (30% yield) of an amorphous solid.

$^1$H NMR (DMSO-d$_6$): δ 10.38 (1H, s), 8.06 (2H, bs), 7.31 (2H, d, J=9.0 Hz), 7.30 (1H, d, J=7.5 Hz), 7.08 (1H, t, J=7.5 Hz), 6.72 (2H, d, J=9.0 Hz), 6.68 (1H, d, J=7.5 Hz), 6.51 (1H, t, J=7.5 Hz), 5.75 (2H, s), 2.88 (6H, s).

FABMS (MH$^+$): 354.

Anal. Calcd. for C$_{18}$H$_{19}$N$_5$OS.0.5H$_2$O.0.3MeOH: C, 59.07; H, 5.74; N, 18.82; S, 8.62. Found: C, 59.24; H, 5.56; N, 18.51; S, 8.36.

Example D(4)

[4-Amino-2-(4-amino-phenylamino)-thiazol-5-yl]-phenyl-methanone

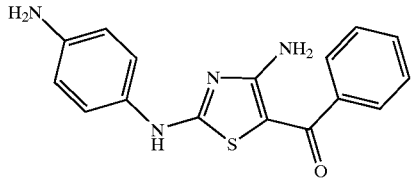

The title compound was prepared in a manner similar to that described for Example D(1). Catalytic reduction of the title compound from Example A(8) (i.e., [4-amino-2-(4-nitro-phenylamino)-thiazol-5-yl]-phenyl-methanone, 450 mg, 1.32 mmol) gave, after recrystallization from ethanol, 120 mg (29% yield) of orange powder, mp 167–169° C.

$^1$H NMR (DMSO-$d_6$): δ 10.38 (1H, s), 8.15 (2H, bs), 7.64–7.55 (2H, m), 7.47–7.38 (3H, m), 7.10 (2H, d, J=8.6 Hz), 6.55 (2H, d, J=8.6 Hz), 5.20 (2H, bs).

FABMSH (MH$^+$): 311.

Anal. Calcd. for $C_{16}H_{14}N_4OS \cdot H_2O$: C, 56.96; H. 5.08; N. 16.61; S. 9.50. Found: C, 56.94; H. 5.07; N. 16.60; S. 9.64.

Example D(5)

4-[4-Amino-5-(3-amino-5-amino-thiophene-2-carbonyl)-thiazol-2-ylamino]-benzenesulfonamide

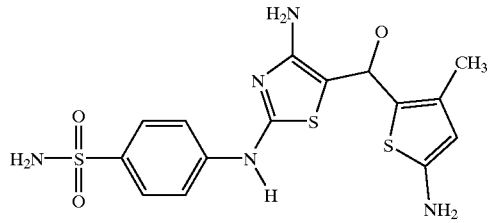

The title compound was prepared in a manner analogous to that used in Example D(1). The title compound of Example C(95) was hydrogenated and recrystallized from EtOH to provide a brown powder in 96% yield, mp 268–271° C.

$^1$H NMR (DMSO-$d_6$): δ 10.97 (1H, s), 7.91 (2H, s), 7.82 (2H, d, J=9.1 Hz), 7.78 (2H, d, J=9.1 Hz), 7.28 (2H, s), 6.43 (2H, s), 5.81 (1H, s), 2.34 (3H, s).

FABMS (MH$^+$): 410.

Anal. Calcd. for $C_{15}H_{15}N_5O_3S_3 \cdot 0.1H_2O \cdot 0.3EtOH$: C, 44.07; H, 4.03; N, 16.47; S, 22.63. Found: C, 44.23; H, 3.93; N, 16.07; S, 23.01.

Example E(1)

4-[4-Amino-5-(2-nitro-benzoyl)-thiazol-2-ylamino]-benzoic Acid

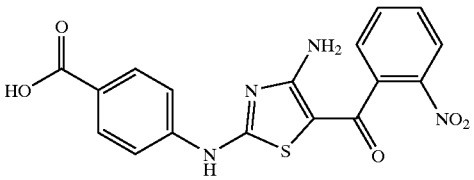

To a suspension of the title compound of Example A(5) (i.e., ethyl 4-[4-amino-5-(2-nitro-benzoyl)-thiazol-2-ylamino]-benzoate, 950 mg, 2.3 mmol), in methanol (15 mL) was added 3N NaOH (10 mL). After 30 minutes, the mixture was acidified to a pH of 4 with 1N HCl, whereupon a yellow precipitate formed. The mixture was diluted with water (100 mL). The solid was filtered off and rinsed with water. Recrystallization from ethanol provided 672 mg (76% yield) of yellow crystals, mp 289–292° C.

$^1$H NMR (DMSO-$d_6$): δ 12.75 (1H, s), 11.13 (1H, s), 8.12 (2H, bs), 8.08 (1H, d, J=7.8 Hz), 7.91 (2H, d, J=8.7 Hz), 7.82 (1H, td, J=8.4, 0.9 Hz), 7.78–7.68 (4H, m).

FABMS (MH$^+$): 385.

Anal. Calcd. for $C_{19}H_{18}N_4O_3S$: C, 53.12; H, 3.15; N, 14.58; S, 8.34. Found: C, 53.29; H, 3.25; N, 14.31; S, 8.11.

Example E(2)

4-[4-Amino-2-(4-sulfamoyl-phenylamino)-thiazole-5-carbonyl]-benzoic Acid

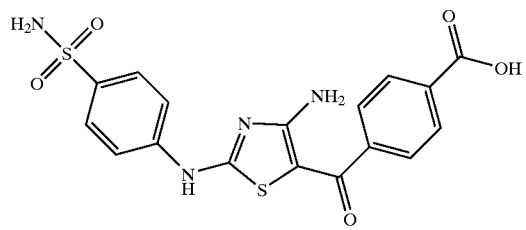

To a suspension of ethyl 4-[4-amino-2-(4-sulfamoyl-phenylamino)-thiazole-5-carbonyl]-benzoate (500 mg, 1.12 mmol; Example C(34)) in MeOH (10 mL) was added 1N aq NaOH (3.4 mL, 3.4 mmol). After 4 hours, the resultant mixture was acidified with 1N aq HCl to pH 3 and filtered. The isolated brown solid crystallized in EtOH to provide 330 mg (70% yield) of light brown crystals, mp 298.5–300° C.

$^1$H NMR (DMSO-$d_6$): δ 13.15 (1H, s), 11.14 (1H, s), 8.31 (2H, bs), 8.02 (2H, d, J=8.1 Hz), 7.78 (4H, s), 7.77 (2H, d, J=8.1 Hz), 7.26 (2H, s).

HRFABMS (M+Na$^+$): Calcd.: 441.0303. Found: 441.0320.

Anal. Calcd. for $C_{17}H_{14}N_4O_5S_2 \cdot 0.4H_2O$: C, 47.97; H, 3.50; N, 13.16; S, 15.07. Found: C, 48.04; H, 3.48; N, 12.98; S, 15.18.

Example F

2-[4-Amino-2-(4-methoxy-phenylamino)-thiazole-5-carbonyl]-benzonitrile

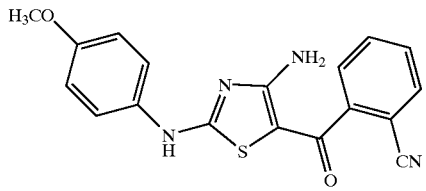

To a solution of the compound of Example C(12) (2.00 g, 4.43 mmol) in pyridine (5 mL) was added copper(I)cyanide (709 mg, 8.86 mmol), and the mixture was heated to reflux. After 2 hours, the resultant mixture was allowed to cool, acidified with 1N aqueous HCl, and extracted with 20% MeOH/CHCl$_3$. The CHCl$_3$ extracts were combined, washed with H$_2$O and brine, dried over Na$_2$SO$_4$, and evaporated to provide a dark-brown viscous oil, which was purified via preparative thin-layer chromatography with 5% MeOH/CH$_2$Cl$_2$ and precipitated from EtOH to furnish 255 mg (61% yield) of yellow amorphous solid that decomposed at 110–116° C.

$^1$H NMR (DMSO-d$_6$): δ 10.70 (1H, s), 8.24 (2H, bs), 7.91 (1H, d, J=7.8 Hz), 7.80–7.66 (2H, m), 7.61 (1H, td, J=7.8, 1.2 Hz), 7.42 (2H, d, J=9.0 Hz), 6.92 (2H, d, J=9.0 Hz), 3.72 (3H, s).

FABMS (MH$^+$): 351.

Anal. Calcd. for C$_{18}$H$_{14}$N$_4$O$_2$S.0.25H$_2$O.0.2EtOH: C, 60.69; H, 4.35; N, 15.39; S, 8.81. Found: C, 60.84; H, 4.24; N, 15.07; S, 9.02.

Example G

[4-Amino-2-(1H-benzoimidazol-6-ylamino)-thiazol-5-yl]-(3-amino-2,6-dichloro-phenyl)-methanone

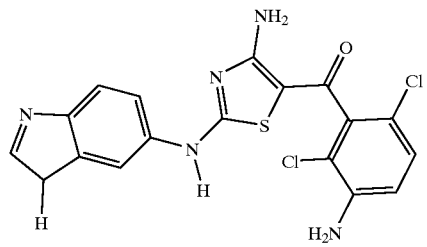

The title compound of Example C(82), N-{3-[4-amino-2-(1H-benzoimidazol-6-ylamino)-thiazole-5-carbonyl]-2,4-dichloro-phenyl}-acetamide (100 mg, 0.220 mmol), was placed in 6N aq. HCl (4 mL) and stirred at ambient temperature for 24 hours. The mixture was brought to pH 7 with 2N aq NaOH and the resultant pale yellow precipitate was filtered off, washed with H$_2$O, recrystallized from MeOH/H$_2$O, and dried under high vacuum. A yellow solid was obtained in 36% yield, mp 235–237° C.

$^1$H NMR (DMSO-d$_6$): δ 8.16 (1H, bs), 7.86 (2H, bs), 7.38–7.62 (1H, m), 7.18 (1H, d, J=8.5 Hz), 7.02 (1H, d, J=8.8 Hz), 6.68 (1H, d, J=8.7 Hz), 5.50 (1H, bs).

IR (KBr): 3177, 1614, 1543, 1443, 1308 cm$^{-1}$.

FABMS (MH$^+$): 419.

Anal. Calcd. for C$_{17}$H$_{12}$Cl$_2$N$_6$OS.0.8H$_2$O.0.1MeOH: C, 46.42; H, 3.81; N, 18.04; S, 6.88. Found: C, 46.37; H, 3.45; Cl, 15.29; N, 17.84; S, 6.77.

Example H(1)

[4-Amino-2-(4-piperazin-1-yl-phenylamino)-thiazol-5-yl]-(3-methyl-thiophen-2-yl)-methanone Trihydrochloride

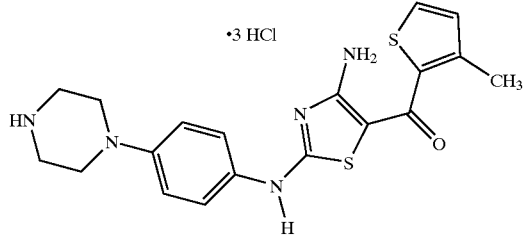

The title compound was prepared as follows. To a solution of the title compound of Example C(104) (100 mg, 0.20 mmol) in a mixture of THF (1 mL) and MeOH (0.5 mL) was added a solution of 4N HCl in dioxane (200 μL, 0.80 mmol). The resultant suspension was heated at reflux for 2 hours. The suspension was allowed to cool and filtered. The isolated solid was washed with anhydrous ether and dried to provide a yellow solid in 97% yield, mp 198–200° C.

$^1$H NMR (DMSO-d$_6$): δ 10.80 (1H, m), 9.22 (1H, bs), 7.60 (1H, d, J=5.0 Hz), 7.42 (1H, d, J=8.7 Hz), 6.98–7.08 (3H, m), 3.38 (4H, d, J=4.4 Hz), 3.22 (4H, s), 2.18 (3H, s).

IR (KBr): 3177, 1614, 1543, 1443, 1308 cm$^{-1}$.

HRFABMS: Calcd. for C$_{19}$H$_{22}$N$_5$OS$_2$ (MH$^+$): 400.1266. Found: 400.1254.

Anal. Calcd. for C$_{19}$H$_{21}$N$_5$OS$_2$.0.6H$_2$O.3HCl: C, 43.91; H, 4.89; N, 13.47; S, 12.34. Found: C, 43.61; H, 4.97; N, 13.12; S, 12.16.

Example H(2)

(3-Amino-2,6-dichloro-phenyl)-[4-amino-2-(4-piperazin-1-yl-phenylamino)-thiazol-5-yl]-methanone Trihydrochloride

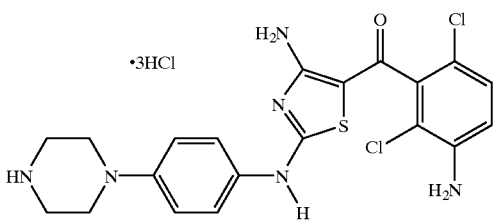

The title compound was prepared in a manner like that described for Example H(1). The title compound of Example C(106) provided a yellow solid in 48% yield, mp >280° C.

$^1$H NMR (DMSO-d$_6$): δ 8.88 (1H, bs), 8.00 (1H, bs), 7.40(2H, bs), 7.18 (1H, d, J=8.7 Hz), 6.98 (2H, d, J=8.4 Hz), 6.80 (1H, d, J=8.7 Hz), 3.38 (4H, s), 3.12 (4H, s).

IR (KBr): 3406, 1618, 1560, 1458, 1308 cm$^{-1}$.

HRFABMS: Calcd. for C$_{20}$H$_{21}$Cl$_2$N$_6$OS (MH$^+$): 463.0875. Found: 463.0862.

Anal. Calcd. for C$_{20}$H$_{20}$Cl$_2$N$_6$OS.3HCl.0.5dioxane: C, 42.84; H, 4.41; Cl, 28.74; N, 13.62; S, 5.20. Found: C, 42.96; H, 4.47; Cl, 28.58; N, 13.53; S, 5.15.

Example H(3)

[4-Amino-2-(4-piperazin-1-yl-phenylamino)-thiazol-5-yl]-(2,6-dichloro-phenyl)-methanone

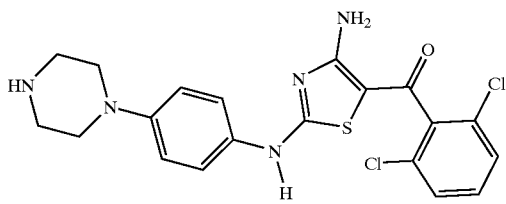

The title compound was prepared in a manner like that described for Example H(1). The title compound of Example C(105) provided a yellow solid in 44% yield, mp 298–300° C.

$^1$H NMR (DMSO-d$_6$): δ 7.60–7.50 (5H, m), 7.08 (2H, d, J=7.8 Hz), 3.44 (4H, bs).

IR (KBr): 3395, 2959, 1618, 1513, 1425 cm$^{-1}$.

HRFABMS: Calcd. for C$_{20}$H$_{20}$Cl$_2$N$_5$OS (MH$^+$): 448.0766. Found: 448.0749.

Anal. Calcd. for C$_{20}$H$_{19}$Cl$_2$N$_5$OS.1.2H$_2$O.09HCl: C, 47.78; H, 4.47; Cl, 20.45; N, 13.93; S, 6.38. Found: C, 47.99; H, 4.38; Cl, 20.57; N, 13.56; S, 6.24.

Example J(1)

[4-Amino-2-(4-piperazin-1-yl-phenylamino)-thiazol-5-yl]-(2,4,6-trichloro-phenyl)-methanone

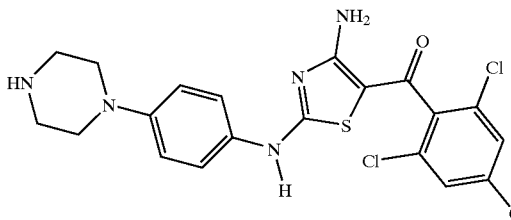

{4-Amino-2-[4-(4-t-butoxycarbonyl-piperazin-1-yl)-phenylamino]-thiazol-5-yl}-(2,4,6-trichloro-phenyl)-methanone, which has the structural formula

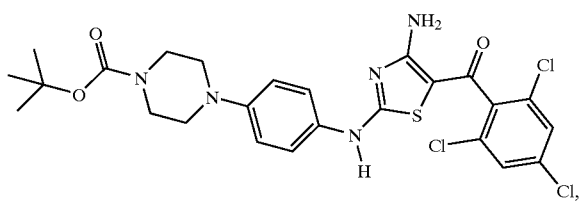

was prepared essentially as described for Example C(1). 1-t-Butoxycarbonyl-4-(4-isothiocyanato-phenyl)-piperazine (from Example C(101)) and 2-bromo-2',4',6'-trichloroacetophenone (from Example C(107)) gave a black tar, which precipitated from EtOH to give 144 mg (50%) of yellow amorphous powder, mp 192–193° C. (d).

$^1$H NMR (DMSO-d$_6$): δ 7.78 (2H, s), 7.33 (2H, bm), 6.98 (2H, d, J=9.0 Hz), 3.15–3.05 (4H, m), 1.45 (s, 9H).

IR (KBr): 3389, 3276, 3166, 1676, 1608, 1577, 1544, 1461, 1421, 1366, 1235, 1202, 1164 cm$^{-1}$.

HRFABMS: Calcd for C$_{25}$H$_{26}$Cl$_3$N$_5$O$_3$SCs (M+Cs$^+$): 715.9847. Found: 715.9822.

Anal. Calcd for C$_{25}$H$_{26}$Cl$_3$N$_5$O$_3$S.0.75H$_2$O.0.4EtOH: C, 50.40; H, 4.90; N, 11.39; Cl, 17.30; S, 5.22. Found: C, 50.69; H, 5.16; N, 10.98; Cl, 17.70; S, 4.90.

The title compound was prepared as follows. {4-Amino-2-[4-(4-tert-butoxycarbonyl-piperazin-1-yl)-phenylamino]-thiazol-5-yl}-(2,4,6-trichloro-phenyl)-methanone (50 mg, 0.086 mmol) was stirred in trifluoroacetic acid (TFA; 0.5 mL) at 0° C. After 20 min at 0° C., a minimal amount of water was added, and sat aq NaHCO$_3$ was used for neutralization. The resultant suspension was filtered to obtain a yellow paste, which gave a suspension with MeOH/CHCl$_3$ and led to isolation of 22 mg (42%) of yellow amorphous powder.

$^1$H NMR (DMSO-d$_6$): δ 7.80 (2H, s), 7.38 (2H, d, J=9.0 Hz), 7.01 (2H, d, J=9.0 Hz).

IR (KBr): 3396, 3284, 3178, 1676, 1614, 1543, 1461, 1423, 1202, 1137 cm$^{-1}$.

HRFABMS: Calcd for C$_{20}$H$_{18}$Cl$_3$N$_5$OS (MH$^+$): 484.0346. Found: 484.0333.

Anal. Calcd for C$_{20}$H$_{18}$Cl$_3$N$_5$OS.0.8MeOH.0.8CHCl$_3$: C, 42.96; H, 3.67; N, 11.60. Found: C, 42.87; H, 3.45; N, 11.27.

Example J(2)

[4-Amino-2-(4-piperazin-1-yl-phenylamino)-thiazol-5-yl]-(2,6-difluoro-phenyl)-methanone

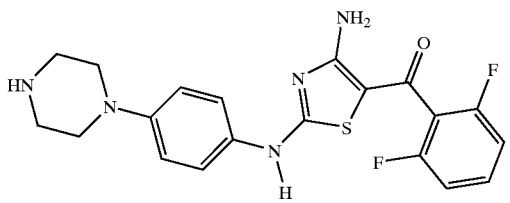

The title compound was prepared essentially as described for Example J(1). To the title compound of Example C(101) (250 mg, 0.48 mmol) in CH$_2$Cl$_2$ at 0° C. was added TFA (5 mL). After 20 min at 0° C., the resultant clear solution was concentrated in vacuo to a residue which was suspended in a minimal amount of water, cooled to 0° C., and basified with sat. Na$_2$CO$_3$ to pH 9. The solid was collected and recrystallized from EtOH to obtain 116 mg (58% yield) of yellow solid, mp 190–193° C.

$^1$H NMR (DMSO-d$_6$): δ 8.13 (2H, bs), 7.52 (1H, p, J=7.3 Hz), 7.36 (2H, d, J=8.7 Hz), 7.19 (2H, t, J=8.7 Hz), 6.99 (2H, t, d=8.7 Hz), 3.24 (4H, bs), 3.13 (4H, bs).

HRFABMS (MH$^+$): Calcd.: 416.1357. Found: 416.1370.

Anal. Calcd. for C$_{20}$H$_{19}$N$_5$OSF$_2$.0.7H$_2$O.0.7CF$_3$COOH: C, 49.96; H, 4.11; N, 13.49; S, 6.17. Found: C, 50.16, H, 4.33; N, 13.14; S, 6.06.

Example J(3)

[4-Amino-2-(4-piperazin-1-yl-phenylamino)-thiazol-5-yl]-(2,4,6-trifluoro-phenyl)-methanone

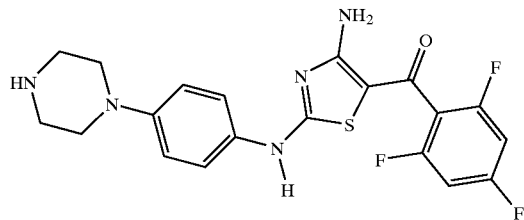

{4-Amino-2-[4-(4-t-butoxycarbonyl-piperazin-1-yl)-phenylamino]-thiazol-5-yl}-(2,4,6-trifluoro-phenyl)-methanone, which has the structural formula

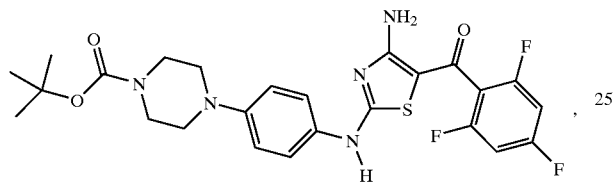

was prepared essentially as described for Example C(1). 1-tert-Butoxycarbonyl-4-(4-isothio-cyanato-phenyl)-piperazine (from Example C(101)) and 2'-bromo-2,4,6-trifluoroacetophenone (from Example C(115)) gave a yellow solid, which crystallized from EtOH to give 200 mg (80%) of yellow amorphous powder that darkened at 125–130° C., mp 132–135° C. (decomposed).

$^1$H NMR (CD$_3$CN): δ 8.69 (1H, bs), 7.46 (2H, d, J=9.0 Hz), 7.20–7.10 (4H, m), 3.74–3.62 (4H, m), 3.28–3.20 (4H, m), 1.60 (s, 9H).

IR (KBr): 3389, 3282, 3178, 1686, 1637, 1604, 1546, 1427, 1366, 1343, 1233, 1168, 1121, 1035, 999 cm$^{-1}$.

HRFABMS: Calcd for C$_{25}$H$_{27}$F$_3$N$_5$O$_3$S (MH$^+$): 534.1787. Found: 534.1772.

Anal. Calcd for C$_{25}$H$_{26}$F$_3$N$_5$O$_3$S.1H$_2$O.0.5EtOH: C, 54.35; H, 5.44; N, 12.19; S, 5.58. Found: C, 54.26; H, 5.07; N, 11.92; S, 5.50.

The title compound was prepared essentially as described for Example J(1) to give a brown solid, which was purified via column chromatography with 10% MeOH/CHCl$_3$ as eluant to provide 57 mg (60%) of a yellow-orange amorphous solid that decomposed above 205° C.

$^1$H NMR (CD$_3$CN): δ 7.78 (2H, s), 7.42 (2H, d, J=9.0 Hz), 7.01 (2H, d, J=9.0 Hz), 3.30–3.18 (4H, m), 3.14–3.02 (4H, m).

IR (KBr): 33406, 1603, 1544, 1430, 1237, 1120, 1034 cm$^{-1}$.

HRFABMS: Calcd for C$_{20}$H$_{18}$F$_3$N$_5$OS (MH$^+$): 434.1262. Found: 434.1274.

Anal. Calcd for C$_{20}$H$_{18}$F$_3$N$_5$OS.0.7MeOH.0.7CHCl$_3$: C, 47.65; H, 4.02; N, 12.98; S, 5.94. Found: C, 47.84; H, 3.64; N, 12.59; S, 5.69.

Example J(4)

4-[4-Amino-5-(2,6-difluoro-benzoyl)-thiazol-2-ylamino]-N-piperidin-4-ylmethyl-benzenesulfonamide

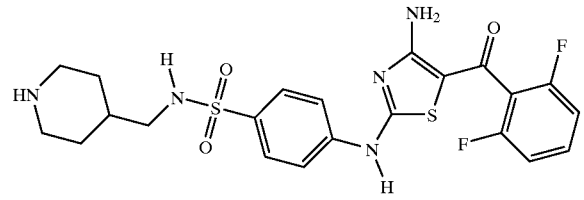

N-tert-Butoxycarbonyl-4-carbamoyl-piperidine, which has the structural formula

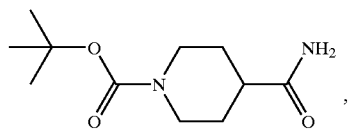

was made as follows. To isonipecotamide (5.00 g, 39.0 mmol) in dioxane (100 mL) was added di-tert-butyl dicarbonate (8.51 g, 39.0 mmol) and N,N-diisopropylethylamine (6.0 mL, 42.9 mmol). The mixture was allowed to stir overnight, then evaporated under reduced pressure to dryness. The residue was partitioned between CHCl$_3$ and 1N HCl. The organic layer was washed with water and brine, dried over Na$_2$SO$_4$, and concentrated to give 8.3 g (93% yield) of white solid, which was used without further purification.

$^1$H NMR (CDCl$_3$): δ 5.53 (2H, bs), 4.03 (2H, d, J=13.7 Hz), 2.33 (2H, tt, J=11.8, 3.7 Hz), 2.08 (2H, bs), 1.89 (2H, dd, J=13.7, 3.7 Hz), 1.69 (1H, dd, J=11.8, 4.4 Hz), 1.65–1.57 (1H, m), 1.44 (9H, s).

4-Aminomethyl-N-tert-butoxycarbonyl-piperidine, which has the structural formula

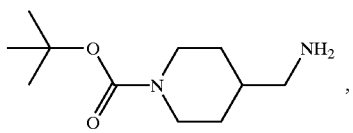

was made as follows. To N-tert-butoxycarbonyl-4-carbamoyl-piperidine (15.6 mmol) in THF (40 mL) at −78° C. under Ar was added LiAlH$_4$ (592 mg, 15.6 mmol). The mixture was allowed to warm to ambient temperature slowly and after a half hour, recooled to −78° C., quenched with ethyl acetate, and partitioned between EtOAc and 2N NaOH. The organic layer was separated, dried over K$_2$CO$_3$, and concentrated to give 1.98 g (59% yield) of yellow slurry, which was used without further purification.

N-tert-Butoxycarbonyl-4-[(4-nitro-benzenesulfonylamino)-methyl]-piperidine, which has the structural formula

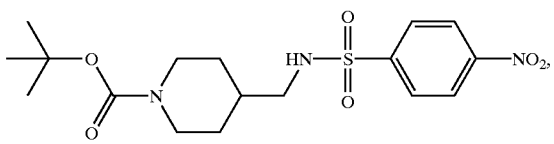

was made as follows. 4-nitrobenzenesulfonyl chloride (2.05 g, 9.24 mmol) was added to a solution of 4-aminomethyl-N-tert-butoxycarbonyl-piperidine (1.98 g, 9.24 mmol) in THF (20 mL) at ambient temperature. The mixture was refluxed for 1 hour, concentrated in vacuo, and partitioned between $CH_2Cl_2$ and 1N HCl. The organic layer was washed with brine, dried over $Na_2SO_4$, passed through a pad of silica gel, and concentrated to give 1.71 g (46% yield) of yellow solid, which was used without further purification.

4-[(4-Amino-benzenesulfonylamino)-methyl]-N-tert-butoxycarbonyl-piperidine, which has the structural formula

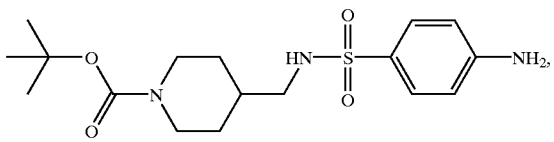

was prepared as follows. N-tert-Butoxycarbonyl-4-[(4-nitro-benzenesulfonylamino)-methyl]-piperidine (1.70 g, 4.26 mmol), 10% Pd/C (250 mg), MeOH (10 mL), and THF (10 mL) was stirred under hydrogen for 2 hours and filtered. The filtrate was concentrated to a residue that was purified via column chromatography with 5% $MeOH/CHCl_3$ as eluant, producing 1.39 g (88% yield) of white solid, which was used without further purification. N-tert-Butoxycarbonyl-4-[(4-isothiocyanato-benzenesulfonylamino)-methyl]-piperidine, which has the structural formula

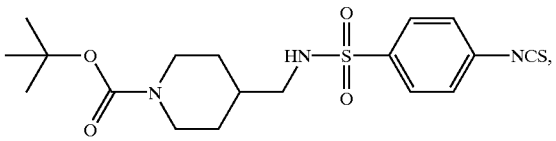

was prepared in a manner analogous to 1-(4-isothiocyanato-phenyl)-morpholine for Example C(54). 4-[(4-Amino-benzenesulfonylamino)-methyl]-N-tert-butoxycarbonyl-piperidine provided a yellow solid in 39% yield, which was used without further purification.

4-{[4-(5-Acetyl-4-amino-thiazol-2-ylamino)-benzenesulfonylamino]-methyl}-N-tert-butoxycarbonyl-piperidine, which has the structural formula

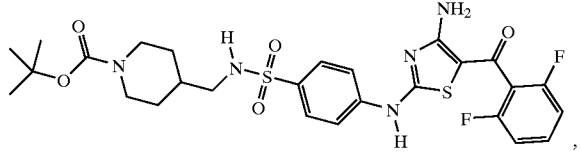

was prepared in a manner analogous to that used in Example C(1). N-tert-Butoxycarbonyl-4-[(4-isothiocyanato-benzenesulfonylamino)-methyl]-piperidine and 2-bromo-2',6'-difluoro-acetophenone (from Example C(79)) provided a yellow solid in 50% yield.

$^1$H NMR (DMSO-$d_6$): δ 11.22 (1H, s), 8.20 (2H, bs), 7.84–7.73 (3H, m), 7.62–7.54 (2H, m), 7.24 (2H, dd, J=7.8, 7.7 Hz), 3.89 (2H, d, J=12.8 Hz), 3.35 (2H, s), 2.52 (2H, d, J=1.2 Hz), 1.60 (2H, d, J=10.1 Hz), 1.56–1.42 (1H, m), 1.39 (9H, s), 0.91 (2H, d, J=12.8 Hz).

The title compound was prepared in a manner analogous to that used in Example J(1). 4-{[4-(5-Acetyl-4-amino-thiazol-2-ylamino)-benzenesulfonylamino]-methyl}-N-tert-butoxycarbonyl-piperidine provided a brown solid in 28% yield.

$^1$H NMR (DMSO-$d_6$): δ 8.11 (2H, bs), 7.70 (4H, bs), 7.58–7.42 (1H, m), 7.20 (1H, d, J=7.8 Hz), 7.15 (1H, d, J=7.8 Hz), 3.80 (2H, bs), 3.05 (2H, d, J=10.0 Hz), 2.60 (2H, d, J=6.8 Hz), 1.65 (2H, d, J=12.2 Hz), 1.52 (1H, bs), 1.07 (2H, d, J=10.0 Hz).

HRFABMS (MH$^+$): Calcd.: 507.1210. Found: 507.1206.

Anal. Calcd. for $C_{22}H_{23}N_5O_3S_2F_2 \cdot 0.1CH_3OH \cdot 0.2CF_3COOH$: C, 50.65; H, 4.73; N, 13.12; S, 12.02. Found: C, 50.92; H, 4.46; N, 12.87; S, 12.18.

Example J(5)

{4-Amino-2-[4-(cis-3,5-dimethyl-piperazin-1-yl)-phenylamino]-thiazol-5-yl}-(2,6-difluoro-phenyl)-methanone

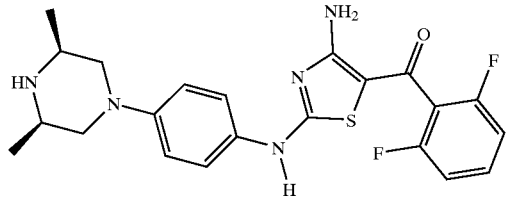

2,6-cis-dimethyl-4-(4-nitro-phenyl)-piperazine, which has the structural formula

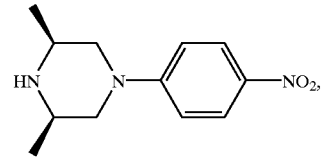

was first prepared essentially as described for 3R-methyl-1-(4-nitro-phenyl)-piperazine for Example C(124). cis-2,6-Dimethylpiperazine gave 2.19 g (100% yield) of yellow powder mp 130–131.5° C., which was used without further purification.

$^1$H NMR (CDCl$_3$): δ 8.03 (2H, d, J=9.5 Hz), 7.02 (2H, d, J=9.5 Hz), 3.88 (2H, dd, J=12.4, 2.0 Hz), 2.82–2.68 (2H, m), 2.44–2.33 (3H, m), 1.03 (6H, d, J=6.3 Hz).

IR (KBr): 1596, 1509, 1482, 1316, 1252, 1193, 1119, 1101 cm$^{-1}$.

Anal. Calcd. for $C_{12}H_{17}N_3O_2$: C, 61.26; H, 7.28; N, 17.86. Found: C, 61.25; H, 7.42, N, 17.84.

1-tert-Butoxycarbonyl-2,6-dimethyl-4-(4-nitro-phenyl)-piperazine, which has the structural formula

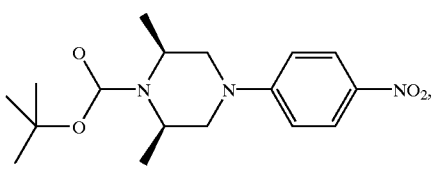

was prepared as follows. To 2,6-cis-dimethyl-4-(4-nitro-phenyl)-piperazine (1.00 g, 4.25 mmol) in dioxane (20 mL) was added di-tert-butyl dicarbonate (1.12 g, 5.12 mmol) and N,N-diisopropylethylamine (1.37 mL, 9.76 mmol). After 3 hours at 80° C., the mixture was allowed to cool and evaporated to dryness. The solid was suspended in water, filtered off, washed with water, and dried under vacuum to give 1.40 g (98% yield) a yellow powder, which was used without further purification.

$^1$H NMR (CDCl$_3$): δ 8.12 (2H, ddd, J=7.3, 2.1, 2.1 Hz), 6.80 (2H, ddd, J=7.3, 2.1, 2.1 Hz), 4.30 (2H, ddd, J=13.2, 6.8, 4.5 Hz), 3.71 (d, 2H, J=13.2 Hz), 3.22 (dd, 2H, J=12.8, 4.5 Hz), 1.49 (9H, s), 1.29 (6H, d, J=6.8 Hz).

IR (KBr): 1689, 1594, 1489, 1400, 1322, 1257, 1057 cm$^{-1}$.

1-(4-Amino-phenyl)-4-tert-butoxycarbonyl-3,5-dimethyl-piperazine, which has the structural formula

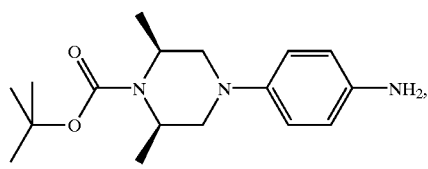

was prepared as follows. Hydrogenation of crude 1-tert-butoxycarbonyl-2,6-dimethyl-4-(4-nitro-phenyl)-piperazine (1.48 g, 4.41 mmol) in THF (20 mL) and MeOH (20 mL) with 10% Pd/C as catalyst gave 1.12 g (83% yield) of a clear sticky oil, which was used without further purification.

$^1$H NMR (CDCl$_3$): δ 8.13 (2H, d, J=9.4 Hz), 6.81 (2H, d, J=9.4 Hz), 4.30 (2H, ddd, J=13.2, 6.8, 4.5 Hz), 3.71 (2H, d, J=13.2 Hz), 3.21 (2H, dd, J=13.2, 4.5 Hz), 1.49 (9H, s), 1.29 (6H, d, J=6.8 Hz).

1-(tert-Butoxycarbonyl)-2,6-cis-dimethyl-4-(4-isothiocyanato-phenyl)-piperazine, which has the structural formula

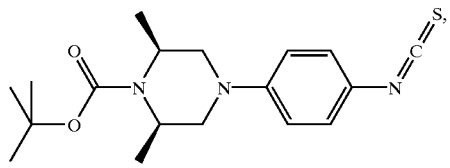

was prepared in a manner analogous to 4-(4-isothiocyanatophenyl)-morpholine for Example C(54). 1-(4-Amino-phenyl)-4-tert-butoxycarbonyl-3,5-dimethyl-piperazine provided a clear sticky foam that recrystallized from cold ether/hexanes to furnish pale tan crystals in 68% yield, mp 97–98° C.

$^1$H NMR (CDCl$_3$): δ 6.74 (2H, d, J=8.7 Hz), 6.67 (2H, d, J=8.7 Hz), 4.20–4.08 (2H, m), 3.08 (2H, d, J=11.6 Hz), 2.71 (2H, dd, J=11.6, 3.9 Hz), 1.41 (9H, s), 1.28 (6H, d, J=6.8 Hz).

IR (KBr): 2175, 2135, 1691, 1507, 1395, 1341, 1246, 1177, 1098 cm$^{-1}$.

Anal. calcd for C$_{18}$H$_{25}$N$_3$O$_2$S: C, 62.21; H, 7.25; N, 12.09; S, 9.23. Found: C, 62.31; H, 7.32; N, 11.96; S, 9.39.

4-Amino-2-[4-(1-tert-butoxycarbonyl-2,6-cis-dimethyl-piperazine-4-yl)-phenylamino]-thiazol-5-yl-(2,6-difluorophenyl)-methanone, which has the structural formula

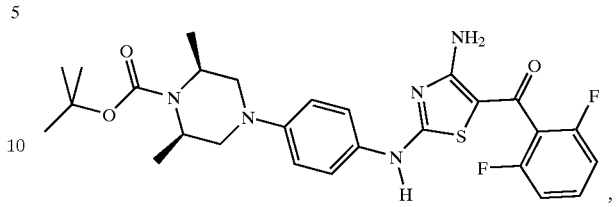

was prepared in a manner analogous to that used in Example C(1). 1-(tert-Butoxycarbonyl)-2,6-cis-dimethyl-4-(4-isothiocyanato-phenyl)-piperazine and 2-bromo-2',6'-difluoro-acetophenone (from Example C(79)) provided a yellow solid in 51% yield, which was used without further purification.

$^1$H NMR (DMSO-d$_6$): δ 10.66 (1H, s), 8.12 (2H, bs), 7.56–7.44 (1H, m), 7.38 (2H, d, J=9.0 Hz), 7.18 (1H, d, J=7.7 Hz), 7.15 (1H, d, J=8.1 Hz), 6.95 (2H, d, J=9.0 Hz), 4.14–4.03 (2H, m), 3.49–3.41 (2H, m), 2.75 (2H, dd, J=12.2, 4.4 Hz), 1.42 (9H, S), 1.24 (6H, d, J=6.7 Hz).

FABMS (M+Na$^+$): 566.

The title compound was prepared in a manner analogous to that used in Example J(1). 4-Amino-2-[4-(1-tert-butoxycarbonyl-2,6-dimethyl-piperazine-4-yl)-phenylamino]-thiazol-5-yl-(2,6-difluorophenyl)-methanone provided a brown powder in 52% yield, mp 293–294.5° C.

$^1$H NMR (DMSO-d$_6$): δ 8.11 (2H, bs), 7.56–7.44 (1H, m), 7.26 (2H, d, J=9.0 Hz), 7.18 (1H, d, J=7.7 Hz), 7.14 (1H, d, J=8.1 Hz), 6.89 (2H, d, J=9.0 Hz), 3.48 (2H, dd, J=10.9, 2.2 Hz), 2.88–2.76 (2H, m), 2.07 (4H, t, J=10.9 Hz), 1.00 (6H, d, J=6.3 Hz).

HRFABMS (MH$^+$): Calcd.: 444.1670. Found: 444.1658.

Anal. Calcd. for C$_{22}$H$_{23}$N$_5$OSF$_2$.0.4H$_2$O: C, 58.63; H, 5.32; N, 15.54; S, 7.11. Found: C, 58.64; H, 5.40; N, 15.23; S, 6.96.

Example J(6)

{4-Amino-2-[4-(3,3-dimethyl-piperazin-1-yl)-phenylamino]-thiazol-5-yl}-(2,6-difluoro-phenyl)-methanone

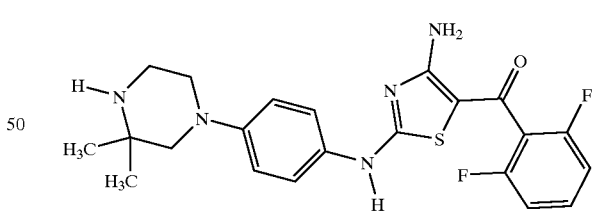

2,2-Dimethyl-4-(4-nitro-phenyl)-piperazine, which has the structural formula

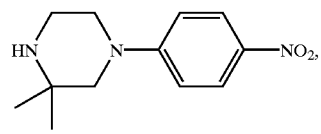

was first prepared as follows. Crude 2,2-dimethylpiperazine (10.0 mmol; Chu et al., *Can. J. Chem.*, vol. 70 (1992), pp. 1328–1337), 4-fluoro-nitrobenzene (5.0 mmol, 706 mg), and K₂CO₃ (8.3 g, 60.0 mmol) in DMSO (10 mL) was heated at 100° C. for 4 hours, cooled, diluted with water (100 mL), and extracted with ether:ethyl acetate (200:50 mL). The organic layer was washed with water (3×) and brine, and concentrated to provide 1.17 g (100% yield) of yellow solid, which was used without further purification.

$^1$H NMR (CDCl$_3$): δ 8.13 (2H, d, J=9.5 Hz), 6.80 (2H, d, J=9.5 Hz), 3.38 (2H, dd, J=5.5, 5.0 Hz), 3.20 (2H, s), 3.07 (2H, dd, J=5.5, 5.0 Hz), 1.21 (6H, s).

1-tert-Butoxycarbonyl-2,2-dimethyl-4-(4-nitro-phenyl)-piperazine, which has the structural formula

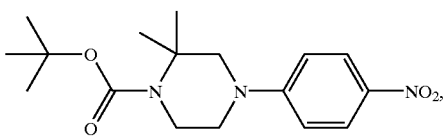

was prepared in a manner analogous to 1-(4-amino-phenyl)-4-(tert-butoxycarbonyl)-2,6-dimethyl-piperazine for Example J(5). 2,2-Dimethyl-4-(4-nitro-phenyl)-piperazine provided a bright yellow solid in 99% yield, which was used without further purification.

$^1$H NMR (CDCl$_3$): δ 8.15 (2H, d, J=9.4 Hz), 6.64 (2H, d, J=9.4 Hz), 3.90 (2H, dd, J=6.0, 5.5 Hz), 3.54 (2H, dd, J=6.0, 5.5 Hz), 3.53 (2H, s), 1.51 (9H, s), 1.44 (6H, s).

1-(4-Amino-phenyl)-4-(tert-butoxycarbonyl)-3,3-dimethyl-piperazine, which has the structural formula

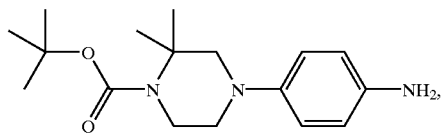

was prepared as follows. 1-tert-Butoxycarbonyl-2,2-dimethyl-4-(4-nitro-phenyl)-piperazine (700 mg, 2.09 mmol) and 10% Pd/C (100 mg) in THF (15 mL) and MeOH (15 mL) was stirred under hydrogen for 2 hours and filtered. The filtrate was concentrated in vacuo to give a light brown slurry, which was used without further purification.

$^1$H NMR (CDCl$_3$): δ 6.69–5.65 (4H, m), 3.67 (2H, dd, J=5.8, 5.4 Hz), 3.21–3.14 (2H, m), 3.01 (2H, s), 1.49 (9H, s), 1.43 (6H, s).

1-(tert-Butdxycarbonyl)-2,2-dimethyl-4-(4-isothiocyanato-phenyl)-piperazine, which has the structural formula

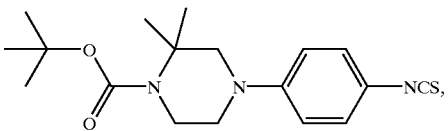

was prepared analogous to 4-isothiocyanato-benzamide for C(102). 1-(4-Amino-phenyl)-4-(tert-butoxycarbonyl)-3,3-dimethyl-piperazine provided a white solid in 80% yield, which was used without further purification.

$^1$H NMR (CDCl$_3$): δ 7.15 (2H, d, J=9.0 Hz), 6.63 (2H, d, J=9.0 Hz), 3.85 (2H, dd, J=5.9, 5.5 Hz), 3.42 (2H, dd, J=5.9, 5.5 Hz), 3.37 (2H, s), 1.57 (9H, s), 1.44 (6H, s).

4-Amino-2-[4-(1-tert-butoxycarbonyl-2,2-dimethyl-piperazine-4-yl)-phenylamino]-thiazol-5-yl-(2,6-difluorophenyl)-methanone, which has the structural formula

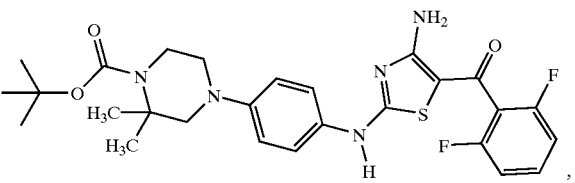

was prepared in a manner analogous to that used in Example C(1). 1-(tert-Butoxycarbonyl)-2,2-dimethyl-4-(4-isothiocyanato-phenyl)-piperazine and 2-bromo-2',6'-difluoro-acetophenone (from Example C(79)) provided a yellow powder in 60% yield, which was used without further purification.

$^1$H NMR (DMSO-d$_6$): δ 10.58 (1H, s), 8.13 (2H, bs), 7.61–7.48 (1H, m), 7.40–7.15 (5H, m), 6.79 (2H, d, J=9.1 Hz), 3.74 (2H, dd, J=5.8, 5.3 Hz), 3.41–3.30 (4H, m), 1.48 (9H, s), 1.39 (6H, s).

The title compound was prepared in a manner analogous to that used in Example J(1). 4-Amino-2-[4-(1-tert-butoxycarbonyl-2,2-dimethyl-piperazine-4-yl)-phenylamino]-thiazol-5-yl-(2,6-difluorophenyl)-methanone provided a yellow solid in 51% yield, mp 205–210° C.

$^1$H NMR (DMSO-d$_6$): δ 8.15 (2H, bs), 7.63–7.54 (1H, m), 7.35 (2H, d, J=9.0 Hz), 7.25 (1H, d, J=7.7 Hz), 7.22 (1H, d, J=8.1 Hz), 6.98 (2H, d, J=9.0 Hz), 3.10–3.04 (2H, m), 3.02–2.95 (2H, m), 2.92 (2H, s), 1.21 (6H, s).

IR (KBr): 3276, 2961, 1620, 1590, 1546, 1516, 1464, 1429, 1364, 1257, 1232, 1002 cm$^{-1}$.

HRFABMS (MH$^+$): Calcd.: 444.1670. Found: 444.1657.

Anal. Calcd. for C$_{22}$H$_{23}$N$_5$OSF$_2$.0.7CH$_3$OH: C, 58.5 1; H, 5.58; N, 15.03; S, 6.88. Found: C, 58.601; H, 5.68; N, 14.87; S, 6.76.

Example K

{4-Amino-2-[4-(4-pyridin-2-yl-piperazin-1-yl)-phenylamino]-thiazol-5-yl}-(2,6-difluoro-phenyl)-methanone

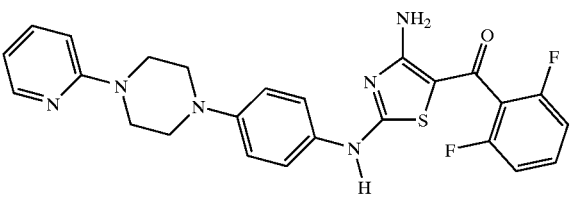

1-(4-Nitro-phenyl)-4-pyridin-2-yl-piperazine, which has the structural formula

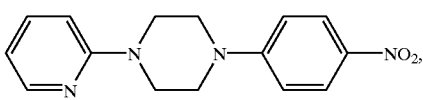

was first prepared in a manner analogous to tert-butyl [methyl-(4-nitro-phenyl)-amino]-acetate for Example C(103). 1-Pyridin-2-yl-piperazine and 4-fluoronitrobenzene gave a yellow solid in 85% yield.

$^1$H NMR (CDCl$_3$): δ 8.13–8.28 (3H, m), 7.50–7.58 (2H, m), 7.52 (1H, ddd, J=15.7, 7.3, 2.0 Hz), 6.88 (2H, d, J=9.4 Hz), 6.70 (2H, dd, J=7.4, 5.1 Hz), 3.78 (4H, dd, J=7.4, 5.0 Hz), 3.62 (4H, dd, J=5.7, 3.3 Hz).

4-(1-Pyridin-2-yl-piperazin-4-yl)-aniline, which has the structural formula

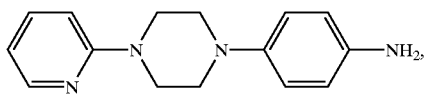

was prepared in a manner analogous to 4-(4-methyl-piperazin-1-yl)-aniline for Example C(70). 1-(4-Nitrophenyl)-4-pyridin-2-yl-piperazine afforded a gray solid in 94% crude yield, which was used without further purification.

$^1$H NMR (CDCl$_3$): δ 8.22 (1H, bd, J=3.5 Hz), 7.52 (1H, ddd, J=17.6, 7.2, 1.9 Hz), 6.88 (2H, d, J=8.7 Hz), 6.62–6.78 (4H, m), 3.72 (4H, dd, J=5.2, 5.0 Hz), 3.48 (2H, bs), 3.18 (4H, t, J=5.2, 5.0 Hz).

1-(4-Isothiocyanato-phenyl)-4-pyridin-2-yl-piperazine, which has the structural formula

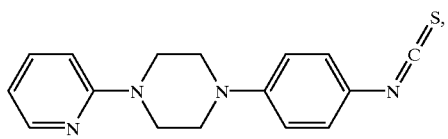

was prepared in a manner analogous to 1-(4-isothiocyanato-phenyl)-4-pyridin-4-yl-piperazine for Example C(127). 4-(4-Pyridin-2-yl-piperazin-1-yl)-aniline gave 2.2 g (95% yield) of a yellow solid, which was used without any further purification.

$^1$H NMR (CDCl$_3$): δ 8.26 (1H, bd, J=6.3 Hz), 7.91 (1H, ddd, J=18.1, 7.1, 1.8 Hz), 7.18 (2H, d, J=9.0 Hz), 6.82–7.00 (4H, m), 4.10 (4H, dd, J=5.3, 5.1 Hz), 3.48 (4H, dd, J=5.3, 5.2 Hz).

The title compound was prepared as follows. To a solution of 1-(4-isothiocyanato-phenyl)-4-pyridin-2-yl-piperazine (250 mg, 0.84 mmol) in dry MeOH (4 mL) was added cyanamide (35 mg, 0.84 mmol) and a fresh solution of NaOH (67 mg, 1.67 mmol) in dry MeOH (4 mL). After 1 hour, 2-bromo-2',6'-difluoro-acetophenone (from Example C(79); 178 mg, 0.76 mmol) was added. The next day, the resultant yellow suspension was filtered. The solid was washed with H$_2$O and dried under high vacuum to afford a yellow solid in 86% yield, mp 138–140° C.

$^1$H NMR (DMSO-d$_6$): δ 8.12 (2H, dd, J=6.5, 1.7 Hz), 7.42–7.60 (2H, m), 7.32 (2H, bd, J=8.5 Hz), 7.08 (2H, t, J=9.0 Hz), 6.98 (2H, d, J=9.0 Hz), 6.88 (2H, d, J=8.7 Hz), 6.64 (1H, dd, J=7.0, 5.0 Hz), 3.62 (4H, t, J=4.7 Hz), 3.20 (4H, t, J=4.7 Hz).

IR (KBr): 3369, 3180, 2835, 1620, 1597, 1546, 1466, 1433, 1232 cm$^{-1}$.

HRFABMS: Calcd. for C$_{25}$H$_{23}$F$_2$N$_6$OS (MH$^+$): 493.1622. Found: 493.1608.

Anal. Calcd. for C$_{25}$H$_{22}$F$_2$N$_6$OS.0.9H$_2$O: C, 58.90; H, 4.90; N, 16.49; S, 6.29. Found: C, 58.91; H, 4.64; N, 16.55; S, 6.24.

Example L

{4-Amino-2-[4-(4-carboxamido-piperidin-1-yl)-phenylamino]-thiazol-5-yl}-(2,6-difluoro-phenyl)-methanone

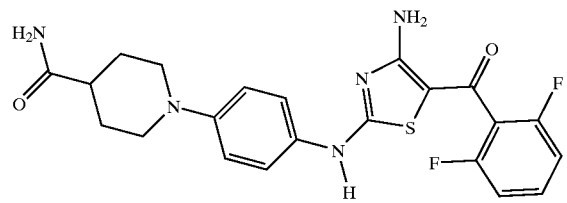

4-Carboxamido-1-(4-nitro-phenyl)-piperidine, which has the structural formula

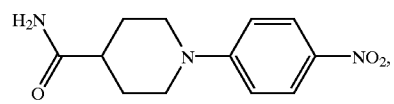

was prepared in a manner analogous to tert-butyl[methyl-(4-nitro-phenyl)-amino]-acetate for Example C(103). 4-Fluoronitrobenzene and isonipecotamide gave a yellow powder in 98% crude yield, which was used without further purification.

$^1$H NMR (CD$_3$OD): δ 8.22 (2H, d, J=9.5 Hz), 7.12 (2H, d, J=9.5 Hz), 4.20 (2H, d, J=12.5 Hz), 3.16 (2H, ddd, J=25.6, 13.3, 2.7 Hz), 2.62–2.70 (1H, m), 2.02 (2H, bd, J=10.3 Hz), 1.85–1.95 (2H, m).

1-(4-Amino-phenyl)-4-carboxamido-piperidine, which has the structural formula

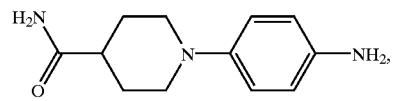

was prepared in a manner analogous to 4-(4-methyl-piperazin-1-yl)-aniline for Example C(70). 4-Carboxamido-1-(4-nitro-phenyl)-piperidine gave a pale yellow powder in 100% crude yield, which was used without further purification.

$^1$H NMR (CD$_3$OD): δ 6.60 (2H, bs), 6.42 (2H, bs), 3.22 (2H, bs), 2.38 (2H, bs), 2.02 (1H, bs), 1.72–1.92 (4H, m).

4-Carboxamido-1-(4-isothiocyanato-phenyl)-piperidine, which has the structural formula

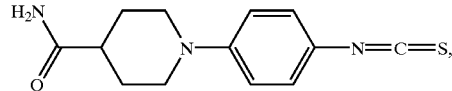

was prepared in a manner analogous to 1-(4-isothiocyanato-phenyl)-4-pyridin-2-yl-piperazine for Example K(1). 1-(4-Amino-phenyl)-4-carboxamido-piperidine to give a cream-colored powder in 93% yield, which was used without further purification.

$^1$H NMR (CDCl$_3$): δ 7.14 (2H, d, J=9.0 Hz), 6.86 (2H, d, J=9.0 Hz), 5.50 (1H, bs), 5.30 (1H, bs), 3.74 (2H, d, J=12.8 Hz), 2.82 (2H, ddd, J=24.3, 12.5, 2.8 Hz), 2.30–2.40 (1H, m), 1.80–2.08 (4H, m).

The title compound was prepared as follows. To a solution of 4-carboxamido-1-(4-isothiocyanato-phenyl)-piperidine (198 mg, 0.76 mmol) in MeOH (3 mL) was added cyanamide (32 mg, 0.76 mmol) and a solution of sodium methoxide in MeOH (1.65 mL of 0.5 N, 0.83 mmol). After 30 min, 2-bromo-2',6'-difluoro-acetophenone (162 mg, 0.69 mmol; from Example C(79)) was added. After 2 hours, H$_2$O was added. The yellow precipitate was filtered off, washed with water, and recrystallized from boiling MeOH to give 200 mg (63% in yield) of an amorphous yellow powder, mp >300° C.

$^1$H NMR (DMSO-d$_6$): δ 7.46–7.58 (1H, m), 7.28 (2H, dd, J=8.8, 7.5 Hz), 7.16 (3H, dd, J=8.0, 7.7 Hz), 6.82 (2H, d, J=9.1 Hz), 3.68 (2H, bd, J=12.6 Hz), 3.64 (2H, ddd, J=23.7, 12.1, 2.8 Hz), 2.04–2.18 (1H, m), 1.52–1.82 (4H, m).

HRFABMS: Calcd. for. C$_{22}$H$_{21}$F$_2$N$_5$O$_2$SNa (M+Na$^+$): 480.1282. Found: 480.1266.

Anal. Calcd. for C$_{22}$H$_{21}$F$_2$N$_5$O$_2$S.0.2H$_2$O: C, 57.31; H, 4.68; N, 15.19; S, 6.95. Found: C, 57.25; H, 4.63; N, 15.31; S, 7.01.

Example M

1-{4-[4-Amino-5-(2,6-difluoro-benzoyl)-thiazol-2-ylamino]-phenyl}-piperidine-4-carboxylic Acid

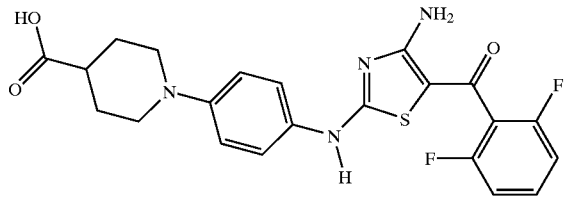

1-(4-Nitrophenyl)-piperidine-4-carboxylic acid, which has the structural formula

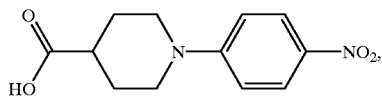

was prepared in a manner analogous to tert-butyl[methyl-(4-nitro-phenyl)-amino]-acetate for Example C(103). 4-Fluoronitrobenzene and isonipecotic acid afforded a yellow powder in 89% crude yield, which was used without further purification.

$^1$H NMR (CDCl$_3$): δ 8.00 (2H, d, J=10.8 Hz), 6.71 (2H, d, J=10.7 Hz), 3.80 (1H, t, J=3.9 Hz), 3.72 (1H, t, J=3.8 Hz), 2.98 (2H, ddd, J=24.3, 11.1, 3.0 Hz), 2.48–2.60 (1H, m), 1.88–2.02 (2H, m), 1.68–1.82 (2H, m).

Benzyl 1-(4-nitrophenyl)-piperidine-4-carboxylate, which has the structural formula

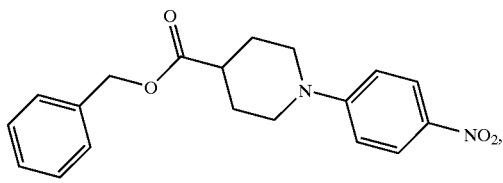

was prepared as follows. To a suspension of 1-(4-nitrophenyl)-piperidine-4-carboxylic acid (500 mg, 2.01 mmol) in acetonitrile (10 mL) was added K$_2$CO$_3$ (612 mg, 4.44 mmol) and benzyl bromide (265 μL, 2.22 mmol). The resultant mixture was heated at reflux for 2 hours, allowed to cool, and diluted with H$_2$O. The aqueous layer was extracted with ether (2×50 mL). The combined organic layers were dried over MgSO$_4$, filtered, and concentrated in vacuo to give 470 mg (64% in crude yield) of a yellow solid, which was used without further purification.

$^1$H NMR (CDCl$_3$): δ 8.13 (2H, d, J=9.4 Hz), 7.30–7.42 (5H, m), 6.83 (2H, d, J=9.4 Hz), 5.18 (2H, s), 3.92 (2H, dd, J=3.9, 3.5 Hz), 3.10 (2H, ddd, J=24.5, 13.7, 2.9 Hz), 2.62–2.70 (1H, m), 2.08 (2H, dd, J=13.5, 3.5 Hz), 1.84–1.94 (2H, m).

Benzyl 1-(4-aminophenyl)-piperidine-4-carboxylate, which has the structural formula

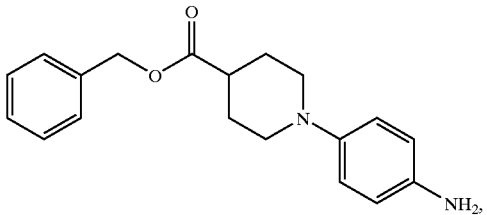

was prepared as follows. To a solution of benzyl 1-(4-nitrophenyl)-piperidine-4-carboxylate (400 mg, 1.18 mmol) in dioxane (5 mL) and ethanol (1 mL) was added tin(II) chloride dihydrate (1.06 g, 4.70 mmol). The resultant solution was heated at reflux for 4 hours, allowed to cool, and to aggregate solids, a small amount of Celite added. The mixture was brought to pH 8 with saturated aq NaHCO$_3$ and filtered. The filtrate was diluted with H$_2$O (50 mL) and extracted with 5% MeOH in CHCl$_3$ (2×50 mL). The combined organic layers were dried over MgSO$_4$, filtered, and concentrated in vacuo to furnish 400 mg (100% crude yield) of a cream-colored powder, which was used without further purification.

$^1$H NMR (CDCl$_3$): δ 7.30 (5H, bs), 6.58 (2H, d, J=8.8 Hz), 6.42 (2H, d, J=8.8 Hz), 4.94 (2H, s), 3.28 (1H, dd, J=3.6, 3.1 Hz), 3.18 (1H, dd, J=3.6, 3.0 Hz), 2.46 (2H, ddd, J=23.2, 11.8, 2.8 Hz), 2.14–2.28 (1H, m), 1.60–1.88 (4H, m).

Benzyl 1-(4-isothiocyanatophenyl)-piperidine-4-carboxylate, which has the structural formula

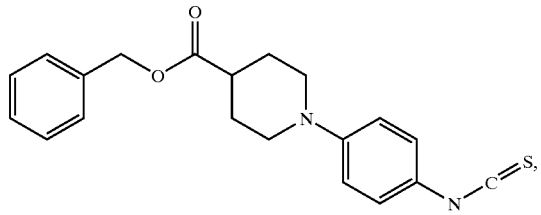

was prepared as follows. To a solution of benzyl 1-(4-aminophenyl)-piperidine-4-carboxylate (400 mg, 1.29 mmol) in THF (5 mL) at −35° C. was added in succession Et$_3$N (435 μL, 3,12 mmol) and thiophosgene (108 μL, 1.42 mmol). The resultant mixture was allowed to warm to ambient temperature, stirred for 0.5 hour, diluted with H$_2$O (50 mL), and extracted with CHCl$_3$ (2×50 mL). The combined organic layers were dried over MgSO$_4$, filtered, and concentrated under reduced pressure to give 400 mg (92% in yield) of a yellow powder, which was used without further purification.

$^1$H NMR (CD$_3$OD): δ 8.10 (2H, d, J=9.5 Hz), 7.38 (5H, d, J=4.5 Hz), 6.92 (2H, d, J=9.5 Hz), 5.18 (2H, s), 4.00 (1H, t, J=3.4 Hz), 3.96 (1H, dd, J=3.5, 3.2 Hz), 3.13 (2H, ddd, J=24.9, 13.8, 2.9 Hz), 2.71–2.77 (1H, m), 2.05 (2H, dd, J=14.1, 3.4 Hz), 1.74–1.83 (2H, m).

Benzyl 1-{4-[4-amino-5-(2,6-difluorobenzoyl)-thiazol-2-ylamino]-phenyl}-piperidine-4-carboxylate, which has the structural formula

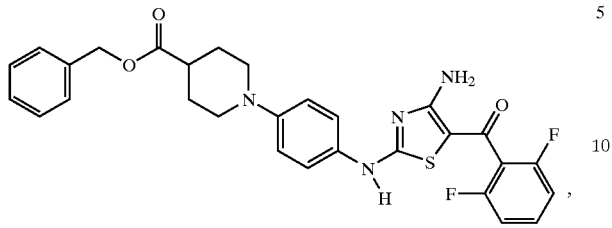

was prepared as prepared in a manner like that described for the title compound of Example C(1). Benzyl 1-(4-isothiocyanato-phenyl)-piperidine-4-carboxylate and 2-bromo-2',6'-difluoro-acetophenone (from Example C(79)) provided brown powder in 82% yield, and was used without further purification.

$^1$H NMR (DMSO-d$_6$): δ 7.30 (1H, m), 7.18 (2H, d, J=8.9 Hz), 6.92 (2H, d, J=9.0 Hz), 4.96 (2H, s), 3.62 (2H, bd, J=9.2 Hz), 2.80 (2H, ddd, J=26.4, 14.1, 2.6 Hz), 2.36–2.58 (1H, m), 2.04 (2H, bd, J=3.1 Hz), 1.80–1.92 (2H, m).

The title compound was prepared as follows. To a mixture of benzyl 1-{4-[4-amino-5-(2,6-difluoro-benzoyl)-thiazol-2-ylamino]-phenyl}-piperidine-4-carboxylate (150 mg, 0.27 mmol) in ethanol (10 mL) was added 20% palladium(II) hydroxide on carbon (60 mg). The resultant mixture stirred under a hydrogen atmosphere for 48 hours. The catalyst was filtered onto a pad of Celite and rinsed with ethanol. The filtrate was concentrated under reduced pressure, and minimal ethyl acetate and CHCl$_3$ were added to induce precipitation. The solid was filtered off, washed with ethyl acetate, and dried to give 40 mg (30%) of a pale blue amorphous powder, mp 275–277° C., which was used without further purification.

$^1$H NMR (DMSO-d$_6$): δ 8.10 (1H, bs), 7.46–7.58 (1H, m), 7.30 (2H, bd, J=7.5 Hz), 7.16 (2H, dd, J=8.0, 7.9 Hz), 6.92 (2H, d, J=9.1 Hz), 3.58 (2H, bd, J=12.6 Hz), 2.52 (2H, dd, J=11.2, 10.4 Hz), 2.32–2.40 (1H, m), 1.88 (2H, bd, J=16.1 Hz), 1.58–1.70 (2H, m).

Anal. Calcd. for C$_{22}$H$_{20}$F$_2$N$_4$O$_3$S·0.9H$_2$O·0.1CHCl$_3$: C, 54.55; H, 4.54; N, 11.51; S, 6.59. Found: C, 54.55; H, 4.30; N, 11.13; S, 6.40.

Example N(1)

[4-Amino-2-(4-nitro-phenylamino)-thiazol-5-yl]-(2-hydroxy-phenyl)-methanone

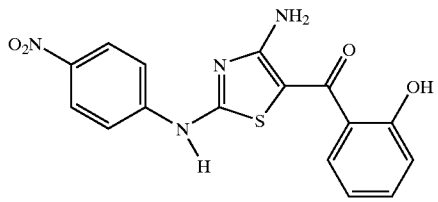

And Example N(2): N-[5-(2-Hydroxy-benzoyl)-2-(4-nitro-phenylamino)-thiazol-4-yl]-benzamide

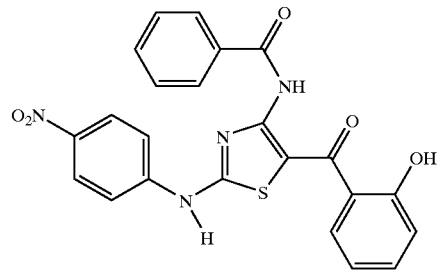

Both title compounds were obtained from the same experiment. The title compound of Example C(130) stirred in a mixture of 2.5% aq. KOH (5 eq) in tetrahydrofuran for one hour. The crude product mixture was separated via flash column chromatography with 5% MeOH/CH$_2$Cl$_2$ to furnish the two title compounds, as yellow amorphous solids in 30 and 50% yields, respectively, of Examples N(1) and N(2).

For Example N(1): [4-Amino-2-(4-nitro-phenylamino)-thiazol-5-yl]-(2-hydroxy-phenyl)-methanone:

$^1$H NMR (DMSO-d$_6$): δ 11.40 (1H, s), 11.00 (1H, s), 8.24 (4H, d, J=9.3 Hz), 7.89 (2H, d, J=9.3 Hz), 7.47 (1H, d, J=6.9 Hz), 7.34 (1H, dd, J=7.9, 7.7 Hz), 6.92 (2H, d, J=7.8 Hz).

HRFABMS: Calcd. for C$_{16}$H$_{12}$N$_4$O$_4$S (MH$^+$): 357.0658. Found: 357.0660.

For Example N(2): N-[5-(2-Hydroxy-benzoyl)-2-(4-nitro-phenylamino)-thiazol-4-yl]-benzamide:

$^1$H NMR (DMSO-d$_6$): δ 11.80 (1H, s), 11.60 (1H, s), 10.30 (1H, s), 8.27 (2H, d, J=9.2 Hz), 8.00 (2H, d, J=9.2 Hz), 7.92 (2H, d, J=7.1 Hz), 7.56–7.68 (3H, m), 7.43 (1H, dd, J=7.6, 1.6 Hz), 7.34 (1H, ddd, J=8.5, 7.0, 1.6 Hz), 6.94 (1H, d, J=8.2 Hz), 6.89 (1H, dd, J=7.6, 7.5 Hz).

ESIMS: Calcd. for C$_{23}$H$_{16}$N$_4$O$_5$S (MH$^+$): 461. Found: 461.

Other compounds may be made in accordance with the invention in manners similar to those described above. Additional exemplary compounds of the invention are identified in Tables I, II, and III below, which provide results of biochemical and biological assays.

BIOCHEMICAL AND BIOLOGICAL EVALUATION

Cyclin-dependent kinase activity was measured by quantifying the enzyme-catalyzed, time-dependent incorporation of radioactive phosphate from [$^{32}$P]ATP or [$^{33}$P]ATP into a protein substrate. Unless noted otherwise, assays were performed in 96-well plates in a total volume of 50 μL, in the presence of 10 mM HEPES (N-[2-hydroxyethyl]piperazine-N'-[2-ethanesulfonic acid]) (pH 7.4), 10 mM MgCl$_2$, 25 μM adenosine triphosphate (ATP), 1 mg/mL ovalbumin, 5 μg/mL leupeptin, 1 mM dithiothreitol, 10 mM β-glycerophosphate, 0.1 mM sodium vanadate, 1 mM sodium fluoride, 2.5 mM ethylene glycol-bis(β-aminoethyl ether)-N,N,N'N'-tetraacetic acid (EGTA), 2% (v/v) dimethylsulfoxide, and 0.03–0.4 μCi [$^{32/33}$P]ATP per reaction. Reactions were initiated with enzyme, incubated at 30° C., and terminated after 20 minutes by the addition of ethylenediaminetetraacetic acid (EDTA) to 250 mM. The phosphorylated substrate was then captured on a nitrocellulose or phosphocellulose membrane using a 96-well filtration manifold, and unincorporated radioactivity was removed by repeated washing with 0.85% phosphoric acid. Radioactivity was quantified by exposing the dried membranes to a phosphorimager.

Apparent $K_i$ values were measured by assaying enzyme activity in the presence of different inhibitor compound concentrations and subtracting the background radioactivity measured in the absence of enzyme. The kinetic parameters (kcat, Km for ATP) were measured for each enzyme under the usual assay conditions by determining the dependence of initial rates on ATP concentration. Inhibition data were fit to an equation for competitive inhibition using Kaleidagraph (Synergy Software), or were fit to an equation for competitive tight-binding inhibition using the software KineTic (BioKin, Ltd.).

Inhibition of CDK4/Cyclin D Retinoblastoma Kinase Activity

A complex of human CDK4 and cyclin D3, or a complex of cyclin D1 and a fusion protein of human CDK4 and gluathione-S-transferase (GST-CDK4), or a complex of human CDK4 and genetically truncated (1–264) cyclin D3, was purified using traditional biochemical chromatographic techniques from insect cells that had been co-infected with the corresponding baculovirus expression vectors (see e.g., Meijer and Kim, "Chemical Inhibitors of Cyclin-Dependent Kinases," *Methods in Enzymol,.* vol. 283 (1997), pp. 113–128.). The enzyme complex (5 or 50 nM) was assayed with 0.3–0.5 µg of purified recombinant retinoblastoma protein fragment (Rb) as a substrate. The engineered Rb fragment (residues 386–928 of the native retinoblastoma protein; 62.3 kDa) contains the majority of the phosphorylation sites found in the native 106-kDa protein, as well as a tag of six histidine residues for ease of purification. Phosphorylated Rb substrate was captured by microfiltration on a nitrocellulose membrane and quantified using a phosphorimager as described above. For measurement of tight-binding inhibitors, the enzyme complex concentration was lowered to 5 nM, and the assay duration was extended to 60 minutes, during which the time-dependence of product formation was linear.

Inhibition of CDK2/Cyclin A Retinoblastoma Kinase Activity

CDK2 was purified using published methodology (Rosenblatt et al., "Purification and Crystallization of Human Cyclin-dependent Kinase 2," *J. Mol. Biol.*, vol. 230, 1993, pp. 1317–1319) from insect cells that had been infected with a baculovirus expression vector. Cyclin A was purified from *E. coli* cells expressing full-length recombinant cyclin A, and a truncated cyclin A construct was generated by limited proteolysis and purified as described previously (Jeffrey et al., "Mechanism of CDK activation revealed by the structure of a cyclin A-CDK2 complex," *Nature*, vol. 376 (Jul. 27, 1995), pp. 313–320). Purified, proteolyzed cyclin A was included in the assay at a three- to five-fold molar excess to CDK2. Alternatively, a complex of CDK2 and proteolyzed cyclin A was prepared and purified by gel filtration. The substrate for this assay was the same Rb substrate fragment used for the CDK4 assays, and the methodology of the CDK2/cyclin A and the CDK4/cyclin D3 assays was essentially the same, except that CDK2 was present at 150 nM or 5 nM. $K_i$ values were measured as described above.

Inhibition of CDK1(cdc2)/Cyclin B Histone H1 Kinase Activity

The complex of human CDK1 (cdc2) and cyclin B was purchased from New England Biolabs (Beverly Mass.). Alternatively, a CDK1/glutathione-S-transferase-cyclin B1 complex was purified using glutathione affinity chromatography from insect cells that had been co-infected with the corresponding baculovirus expression vectors. The assay was executed as described above at 30° C. using 2.5 units of cdc2/cyclin B, 10 µg Histone H1 protein, and 0.1–0.3 µCi [$^{32/33}$P]ATP per assay. Phosphorylated histone substrate was captured by microfiltration on a phosphocellulose P81 membrane and quantified using a phosphorimager as described above. $K_i$ values were measured using the described curve-fitting programs.

Results of assays performed on compounds, which include the specific examples described above as well as additional examples designated by the prefix "I" (e.g., Examples I(1), I(2), etc.), where "*" denotes a compound having a known structure (i.e., the compound per se is known), are provided below in Tables I, II, and III. Unless indicated otherwise in a particular entry, the units and assays used are as indicated in the applicable column of the table. The abbreviation "N.I." indicates that no inhibition was observed at the concentration indicated.

TABLE I

| | | $K_i$ with CDKs | | |
| --- | --- | --- | --- | --- |
| Example | Structure | $K_i$ CDK 4/D (nM) | $K_i$ CDK 2/A (nM) | $K_i$ CDK 1/B (µM) |
| I(1)* | | 640$^a$; 102$^b$ | 460 | 0.5 |

TABLE I-continued

K_i with CDKs

| Example | Structure | $K_i$ CDK 4/D (nM) | $K_i$ CDK 2/A (nM) | $K_i$ CDK 1/B ($\mu$M) |
|---|---|---|---|---|
| I(2)* | 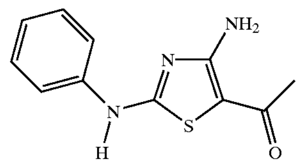 | 8000$^a$; ~30 $\mu$M$^b$ | 8700 | |
| I(3)* | 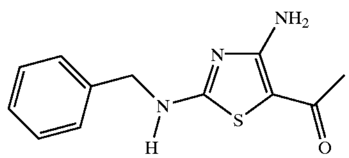 | >5 $\mu$M$^a$; >100 $\mu$M$^b$ | | |
| A(1) | 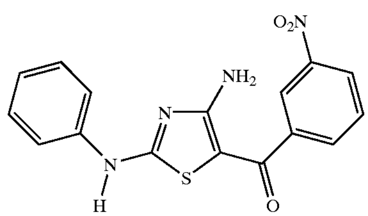 | 660$^a$; 770$^b$ | 1200 | |
| D(1) | 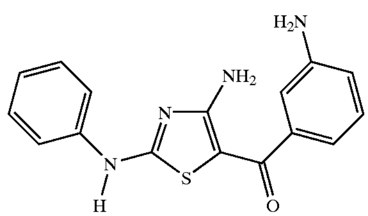 | 490$^b$ | 900 | |
| I(4)* | 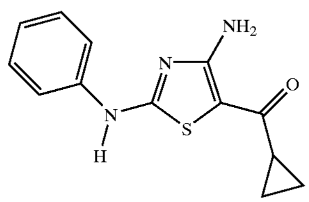 | 3.1 $\mu$M$^b$ | 4.3 $\mu$M | 3.9 |
| I(5)* | 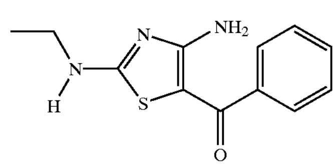 | 1100$^a$ 870$^b$ | 4600 | 4.5 |
| C(1) | 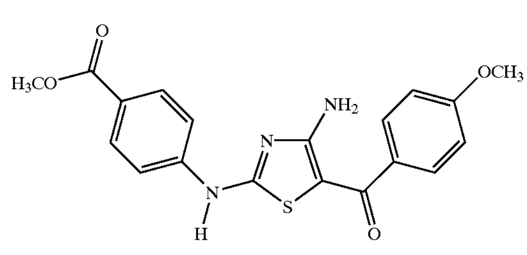 | N.I. at 10 $\mu$M$^a$ | N.I. at 10 $\mu$M | |

TABLE I-continued

K_i with CDKs

| Example | Structure | $K_i$ CDK 4/D (nM) | $K_i$ CDK 2/A (nM) | $K_i$ CDK 1/B (μM) |
|---|---|---|---|---|
| C(2) | 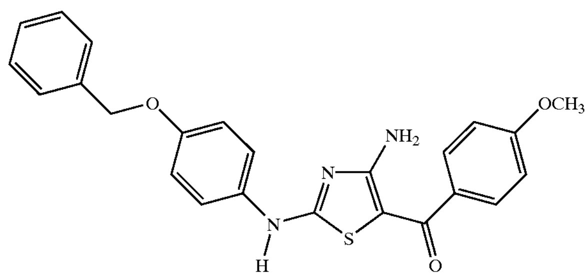 | >5000[a] | N.I. at 100 μM | |
| C(3) | 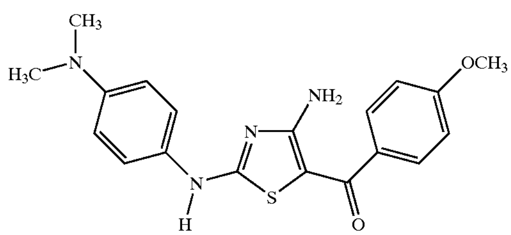 | 1200[a] | 4700 | |
| C(4) | 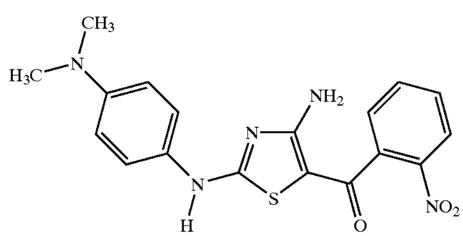 | 95[a] | 810 | 0.09 |
| A(2) | 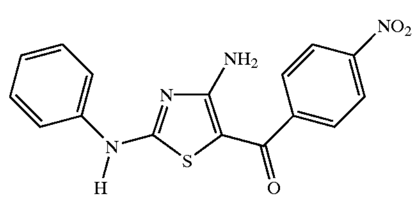 | ~300[a] | | |
| D(2) | 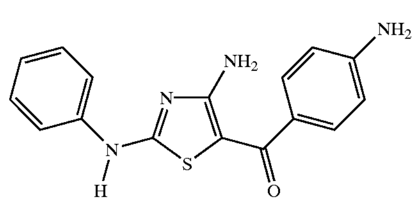 | >5000[a] | | |
| A(3) | 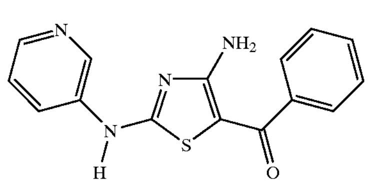 | 2000[a] | 6100 | 3.5 |

TABLE I-continued

$K_i$ with CDKs

| Example | Structure | $K_i$ CDK 4/D (nM) | $K_i$ CDK 2/A (nM) | $K_i$ CDK 1/B (μM) |
|---|---|---|---|---|
| C(5) | 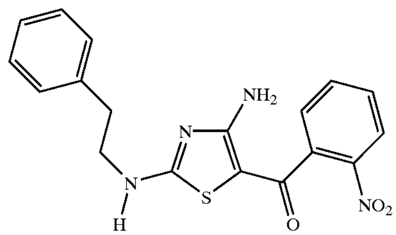 | 140[a] | 780 | 0.293 |
| C(6) | 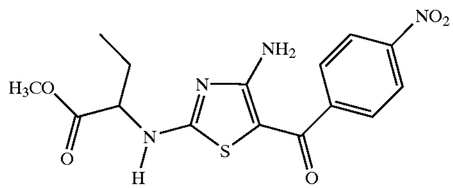 | >10 μM[a] | | |
| I(6) | 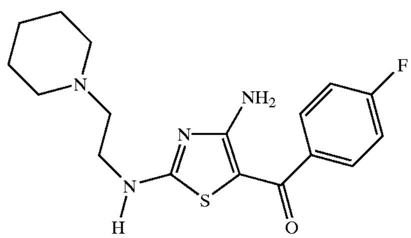 | none @ 10 μM[a] | | |
| D(3) | 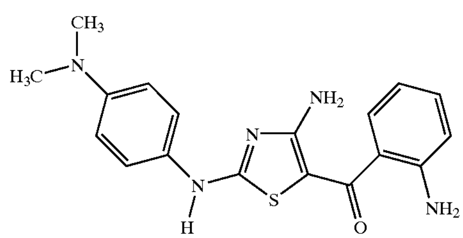 | 380[a] | | |
| I(7) | 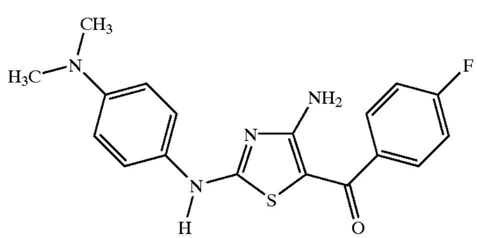 | ~1500[a] | | |
| I(8) | 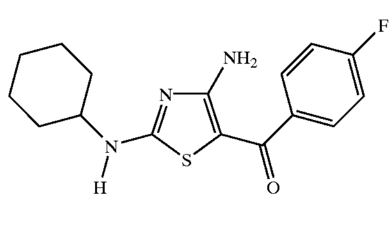 | 4300[a] | | |

TABLE I-continued

K_i with CDKs

| Example | Structure | $K_i$ CDK 4/D (nM) | $K_i$ CDK 2/A (nM) | $K_i$ CDK 1/B (μM) |
|---|---|---|---|---|
| I(9) | 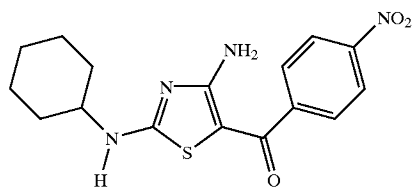 | 2500[a] | | |
| A(4) | 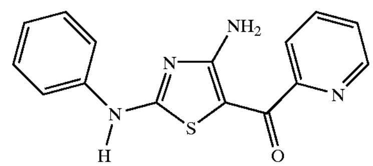 | 2000[a] | 3100 | 2.7 |
| I(10) | 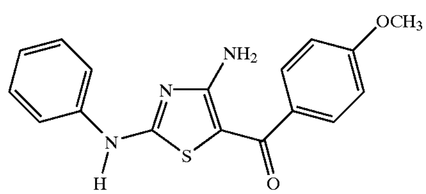 | >20 μM[a] | | |
| I(11) | 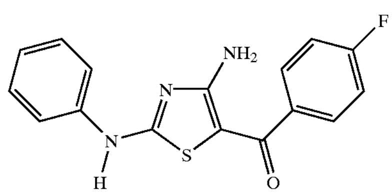 | 520[a] | | |
| I(12) | 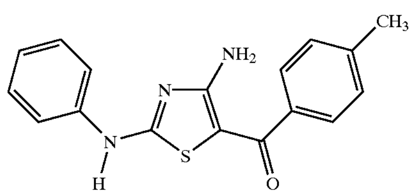 | 380[a] | 4170 | |
| I(13) | 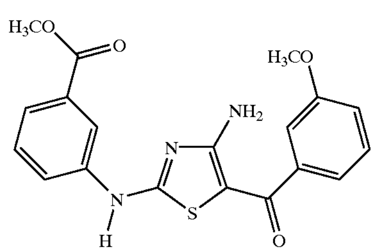 | 2400[a] | | |
| I(14) | 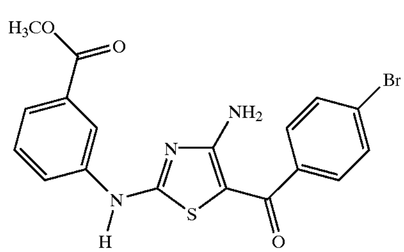 | >50 μM[a] | | |

TABLE I-continued

K$_i$ with CDKs

| Example | Structure | K$_i$ CDK 4/D (nM) | K$_i$ CDK 2/A (nM) | K$_i$ CDK 1/B ($\mu$M) |
|---|---|---|---|---|
| I(15) | 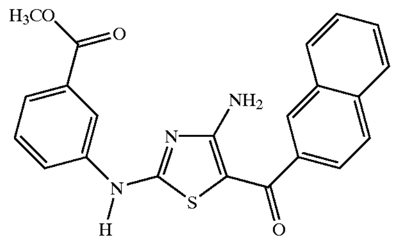 | 440[a] | | |
| I(16) | 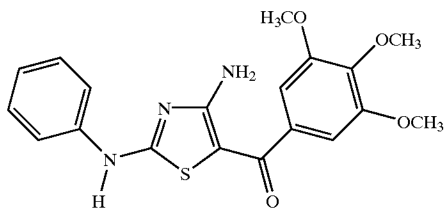 | 1880[a] | | |
| I(17) | 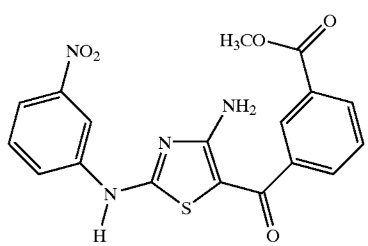 | <1000[a] | | |
| I(18) | 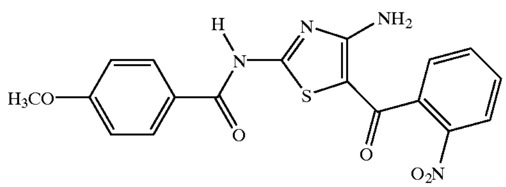 | >25 $\mu$M[a] | | |
| I(19) | 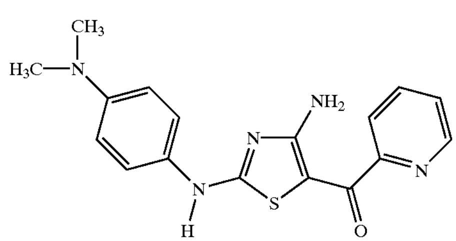 | 1600[a] | 4800 | none @ 100 $\mu$M |
| A(5) | 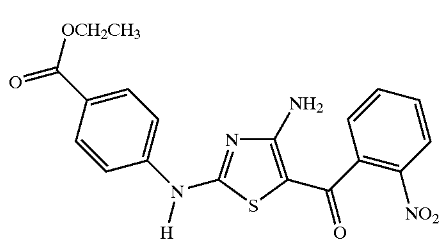 | 97[a] | 690 | 0.163 |

TABLE I-continued

K_i with CDKs

| Example | Structure | $K_i$ CDK 4/D (nM) | $K_i$ CDK 2/A (nM) | $K_i$ CDK 1/B (μM) |
|---|---|---|---|---|
| E(1) | 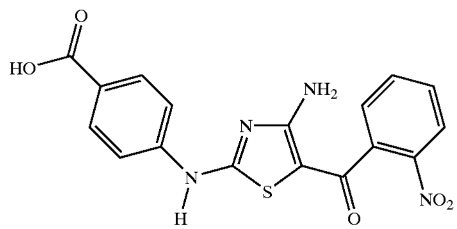 | 420[a] | 320 | 0.03 |
| A(6) | 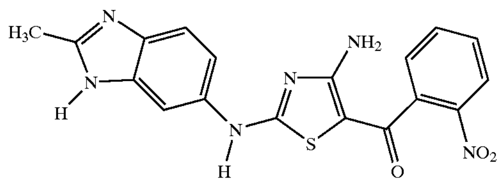 | 150[a] | 292 | 0.052 |
| A(7) | 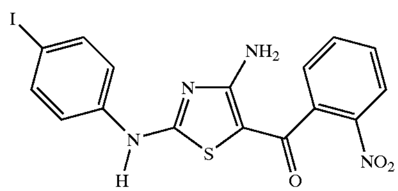 | 310[a] | | |
| A(8) | 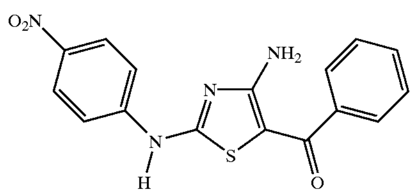 | >25 μM[a] | | |
| D(4) | 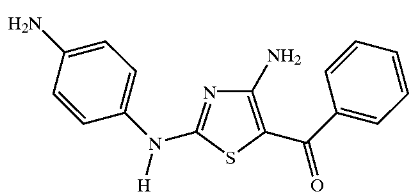 | 800[a] | | |
| A(9) | 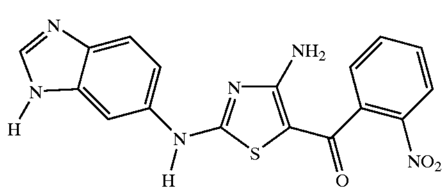 | 100[a] | 230 | 0.053 |
| A(10) | 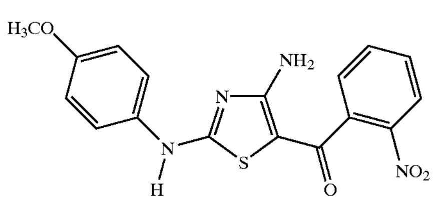 | 36[a] | 318 | 0.057 |

TABLE I-continued

K$_i$ with CDKs

| Example | Structure | K$_i$ CDK 4/D (nM) | K$_i$ CDK 2/A (nM) | K$_i$ CDK 1/B ($\mu$M) |
|---|---|---|---|---|
| I(20) | 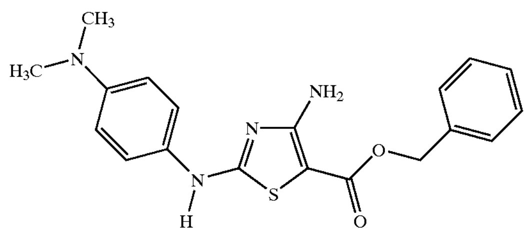 | none @ 25 $\mu$M[a] | | |
| I(21) | 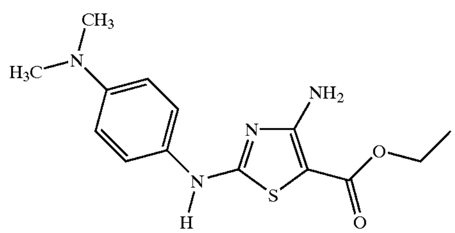 | none @ 25 $\mu$M[a] | | |
| I(22) | 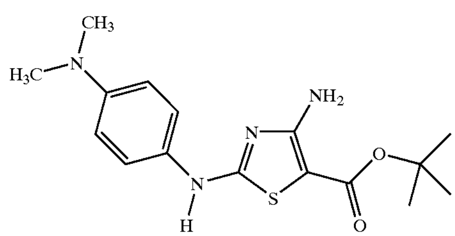 | none @ 25 $\mu$M[a] | none @ 100 $\mu$M | |
| I(23) | 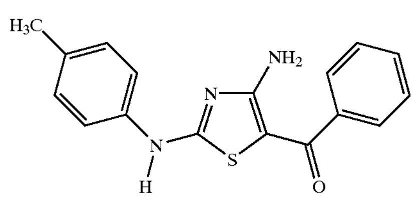 | 1500[a] | | |
| A(11) | 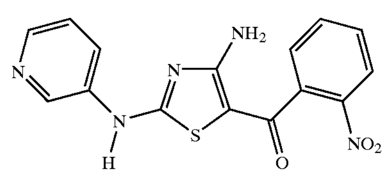 | 130[a] | | |
| I(24) | 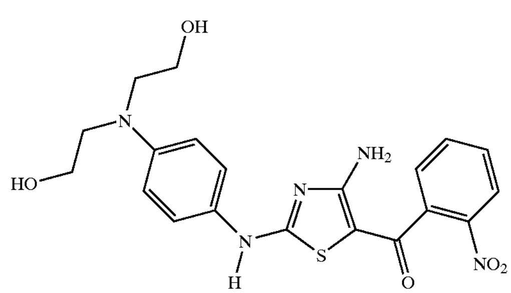 | N.I. at 25 $\mu$M[a] | | |

TABLE I-continued

K_i with CDKs

| Example | Structure | $K_i$ CDK 4/D (nM) | $K_i$ CDK 2/A (nM) | $K_i$ CDK 1/B (μM) |
|---|---|---|---|---|
| C(7) | 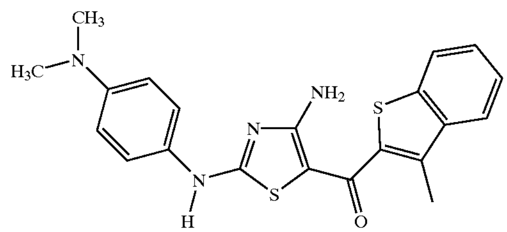 | 510[a] | | |
| C(9) | 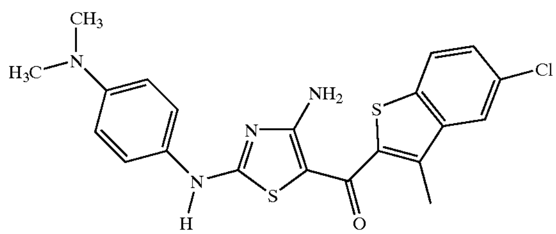 | 740[a] | | |
| C(10) | 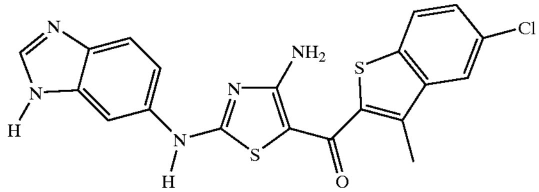 | 680[a] | | |
| C(8) | 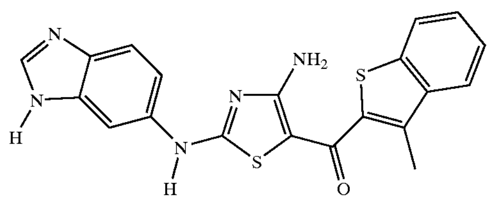 | 27[a] | 389 | 0.097 |
| C(11) | 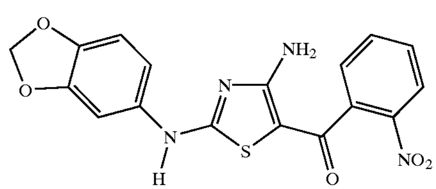 | 130[a] | | |
| C(12) | 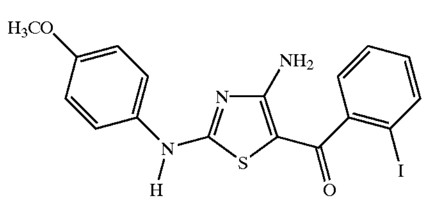 | 27[a] | 670 | |
| A(12) | 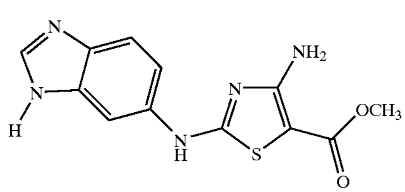 | 9400[a] | 4100 | |

TABLE I-continued

K<sub>i</sub> with CDKs

| Example | Structure | K<sub>i</sub> CDK 4/D (nM) | K<sub>i</sub> CDK 2/A (nM) | K<sub>i</sub> CDK 1/B (μM) |
|---|---|---|---|---|
| C(13) | 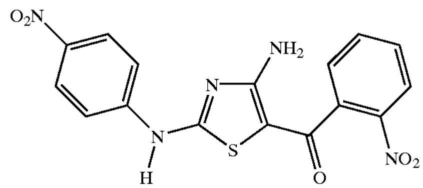 | 51<sup>a</sup> | | |
| C(14) | 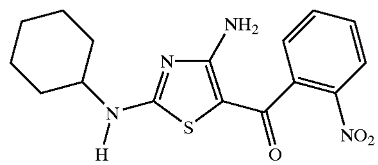 | 57<sup>a</sup> | | |
| C(15) | 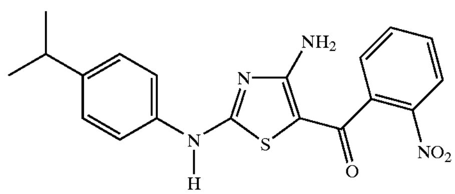 | 57<sup>a</sup> | | |
| C(16) | 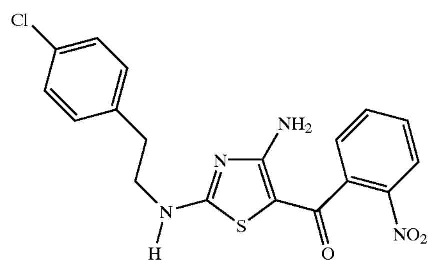 | 170<sup>a</sup> | | |
| C(25) | 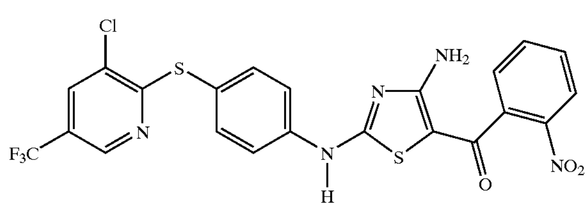 | 1300<sup>a</sup> | | |
| C(24) | 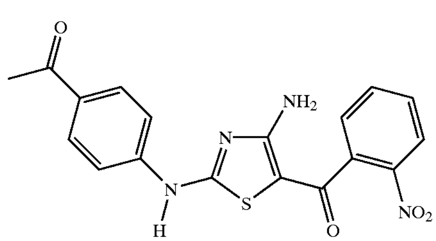 | 8<sup>a</sup> | 248 | 0.046 |
| C(22) | 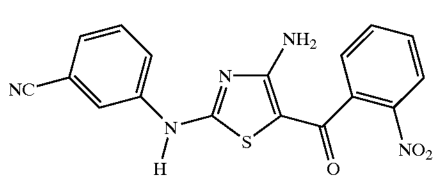 | 67<sup>a</sup> | | |

TABLE I-continued

K_i with CDKs

| Example | Structure | $K_i$ CDK 4/D (nM) | $K_i$ CDK 2/A (nM) | $K_i$ CDK 1/B (μM) |
|---|---|---|---|---|
| C(17) | 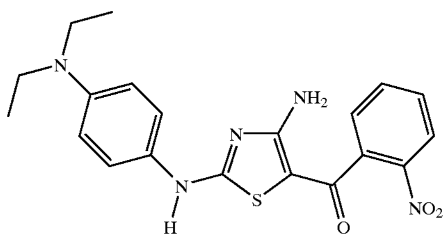 | 72[a] | | |
| C(18) | 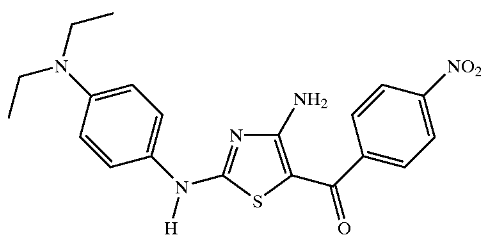 | 12900[a] | none @ 10 μM | |
| C(37) | 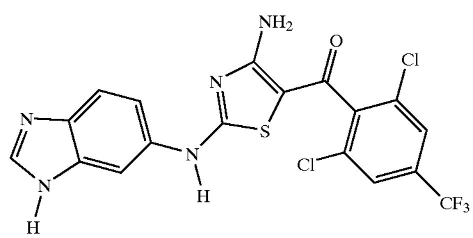 | 7[a] | 310 | 0.233 |
| C(23) | 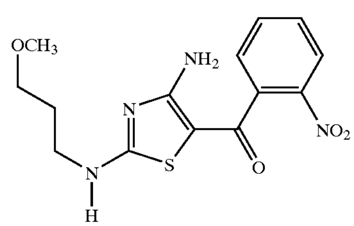 | 330[a] | | |
| C(19) | 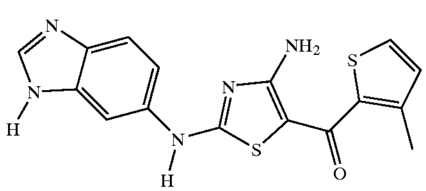 | 15.8[a] | 277 | |
| F | 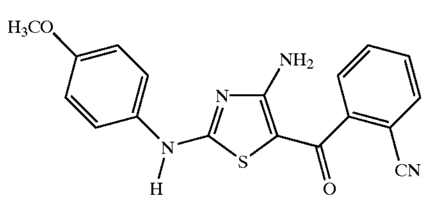 | 40.7[a] | 350 | 0.2 |

TABLE I-continued

K_i with CDKs

| Example | Structure | $K_i$ CDK 4/D (nM) | $K_i$ CDK 2/A (nM) | $K_i$ CDK 1/B ($\mu$M) |
|---|---|---|---|---|
| C(20) | 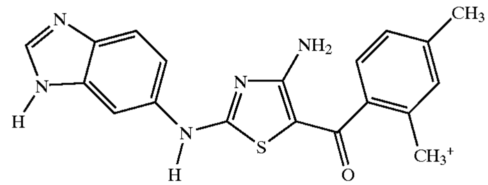 | 22[a] | 145 | |
| C(21) | 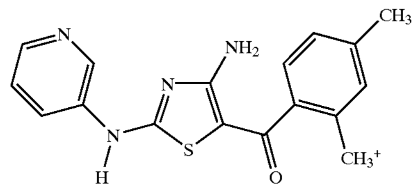 | 117[a] | 480 | |
| A(13) | 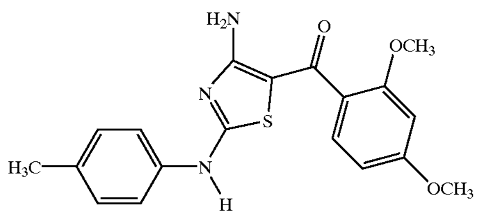 | 250[a] | | |
| A(14) | 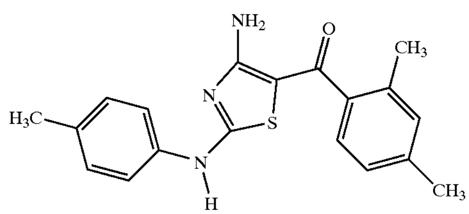 | 180[a] | | |
| C(36) | 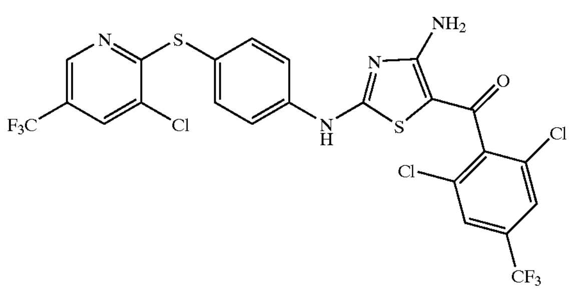 | 13900[a] | | |
| B | 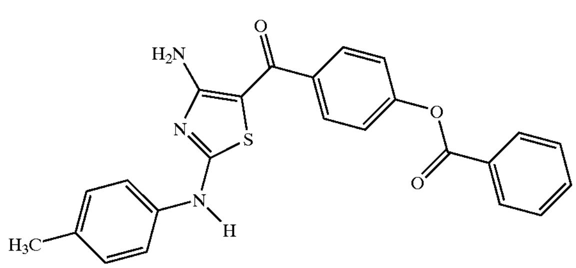 | N.I. at 100 $\mu$M[a] | | |

TABLE I-continued

K_i with CDKs

| Example | Structure | $K_i$ CDK 4/D (nM) | $K_i$ CDK 2/A (nM) | $K_i$ CDK 1/B (μM) |
|---|---|---|---|---|
| C(31) | 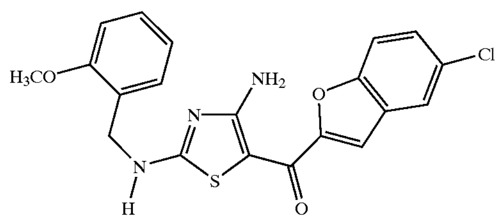 | N.I. at 100 μM[a] | | |
| C(32) | 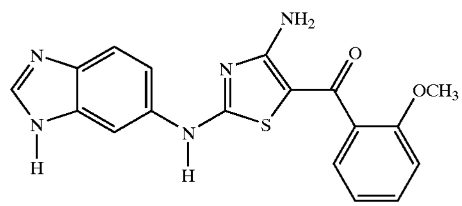 | 94[a] | | |
| C(33) | 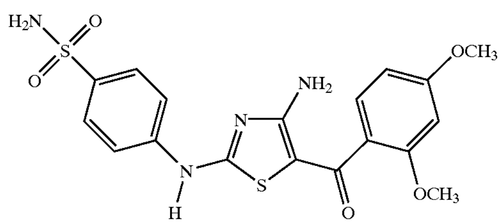 | 57[a] | 20 | |
| C(35) | 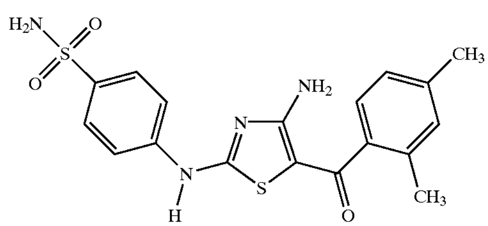 | 11[a] | 23 | |
| C(34) | 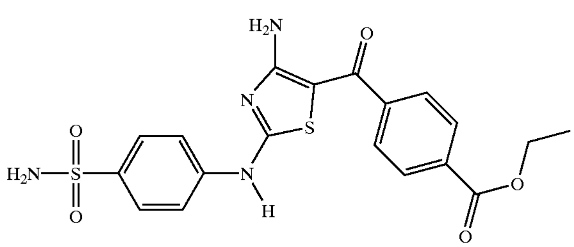 | 140[a] | 131 | |
| C(26) | 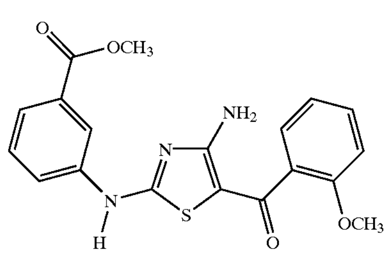 | 330[a] | | |

TABLE I-continued

K<sub>i</sub> with CDKs

| Example | Structure | $K_i$ CDK 4/D (nM) | $K_i$ CDK 2/A (nM) | $K_i$ CDK 1/B (μM) |
|---|---|---|---|---|
| C(27) | 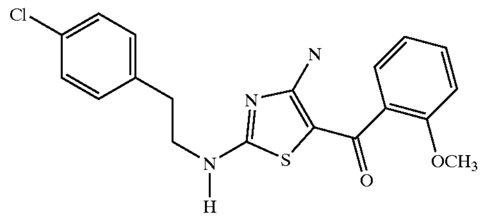 | 1020[a] | | |
| C(28) | 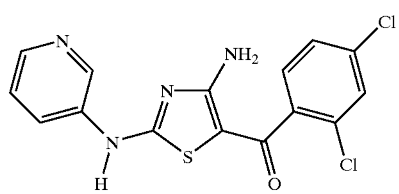 | 240[a] | | |
| C(29) | 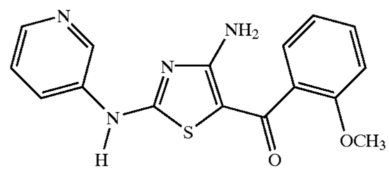 | 357[a] | | |
| C(30) | 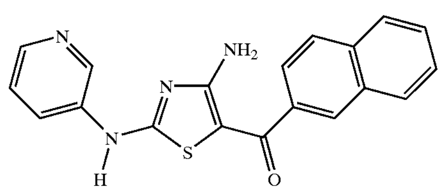 | 1400[a] | | |
| C(38) | 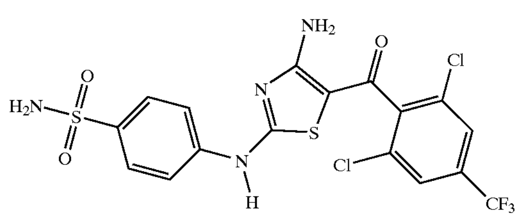 | 25[a] | 39 | |
| C(39) | 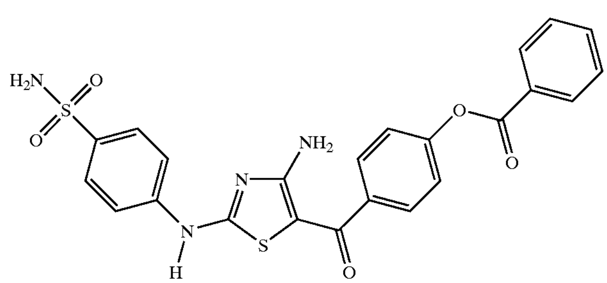 | >100 μM[a] | | |

TABLE I-continued

K_i with CDKs

| Example | Structure | $K_i$ CDK 4/D (nM) | $K_i$ CDK 2/A (nM) | $K_i$ CDK 1/B (μM) |
|---|---|---|---|---|
| E(2) | 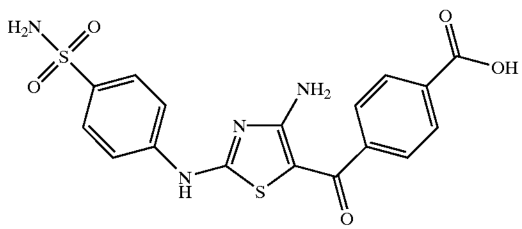 | 1170[a] | | |
| C(40) | 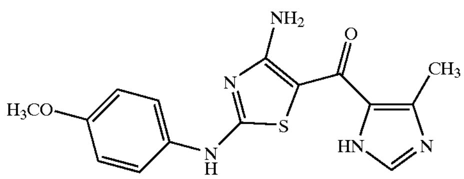 | 3840[a] | | |
| C(41) | 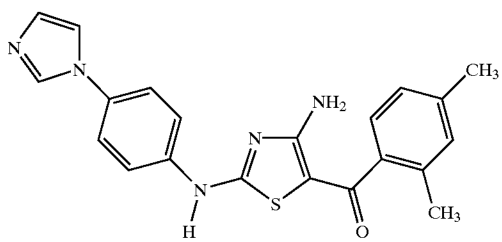 | 350[a] | 336 | |
| C(42) | 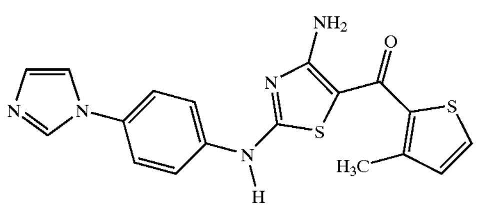 | 750[a] | 207 | |
| C(43) | 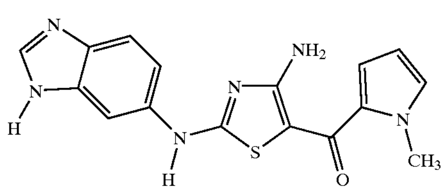 | 315[a] | | |
| C(44) | 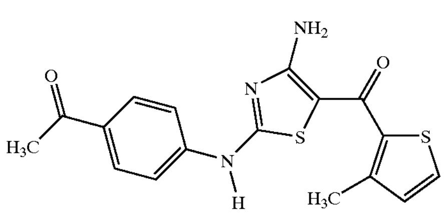 | ~128[a] | | |

TABLE I-continued

K$_i$ with CDKs

| Example | Structure | K$_i$ CDK 4/D (nM) | K$_i$ CDK 2/A (nM) | K$_i$ CDK 1/B (µM) |
|---|---|---|---|---|
| C(45) | 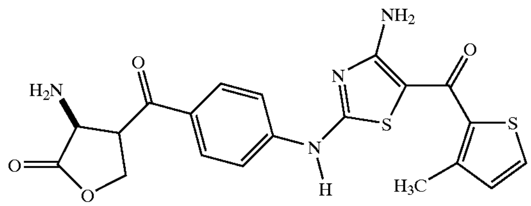 | 51[a] | 103 | 0.249 |
| C(46) | 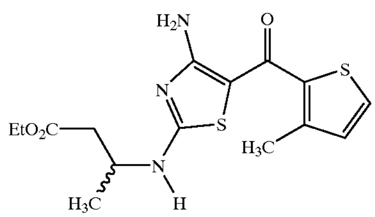 | 244[a] | 1790 | |
| C(47) | 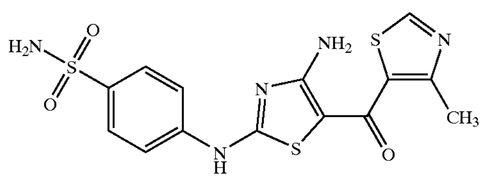 | 30[a] | 26 | |
| C(48) | 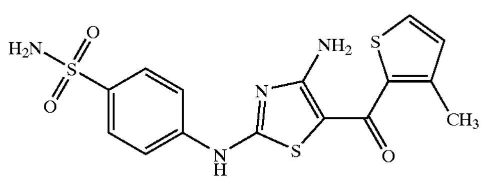 | 14[a] | 11.1 | 0.015 |
| C(49) | 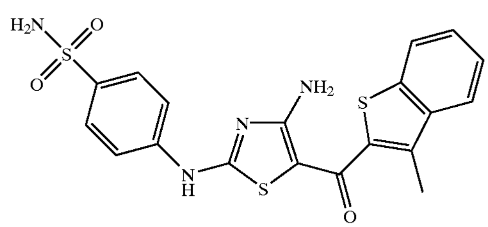 | 23[a] | 10 | 0.034 |
| C(50) | 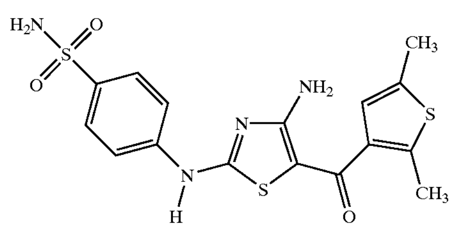 | 25.5[a] | 5.6 | 0.029 |
| C(51) | 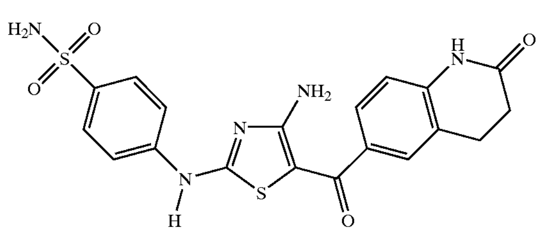 | 85[a] | 33.3 | |

TABLE I-continued
$K_i$ with CDKs
| Example | Structure | $K_i$ CDK 4/D (nM) | $K_i$ CDK 2/A (nM) | $K_i$ CDK 1/B ($\mu$M) |
|---|---|---|---|---|
| C(52) | 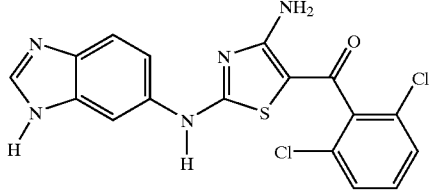 | 11[a] | 105 | |
| C(53) | 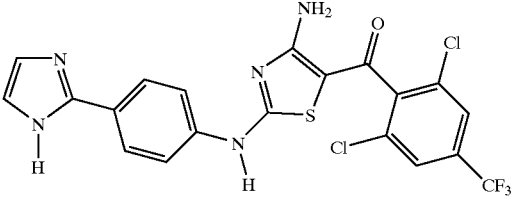 | 85[a] | 180 | |
| C(54) | 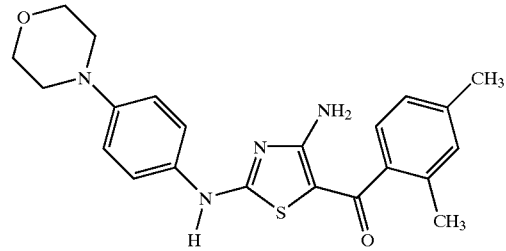 | 34[a] | 453 | |
| C(55) | 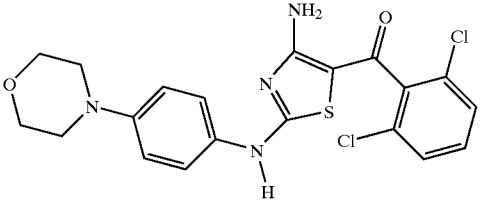 | 8.5[a] | 493 | 0.504 |
| C(56) | 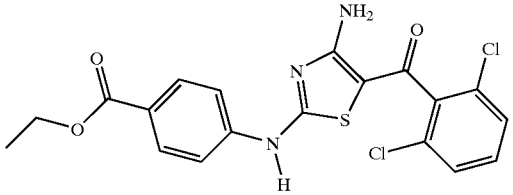 | 195[a] | 1020 | |
| C(57) | 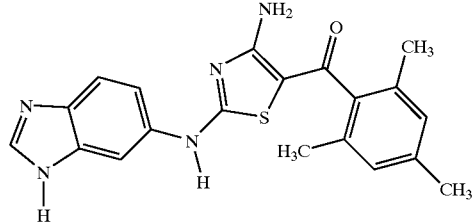 | 30[a] | 259 | |

TABLE I-continued

K_i with CDKs

| Example | Structure | $K_i$ CDK 4/D (nM) | $K_i$ CDK 2/A (nM) | $K_i$ CDK 1/B ($\mu$M) |
|---|---|---|---|---|
| C(58) | | 34[a] | 306 | |
| C(59) | | 100[a] | 135 | |
| C(60) | | 56[a] | 574 | |
| I(25) | | 639[a] | 280 | |
| C(61) | | 120[a] | 1200 | |
| C(62) | | 72[a] | 1710 | |

TABLE I-continued

K_i with CDKs

| Example | Structure | $K_i$ CDK 4/D (nM) | $K_i$ CDK 2/A (nM) | $K_i$ CDK 1/B (μM) |
|---|---|---|---|---|
| C(63) | 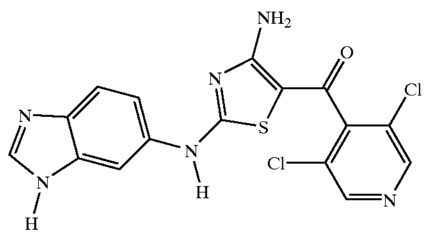 | 17[a] | 200 | 0.133 |
| C(64) | 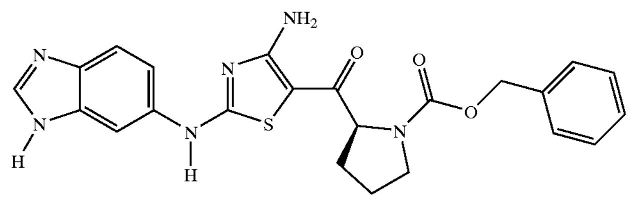 | 44000[a] | 42 μM | |
| C(65) | 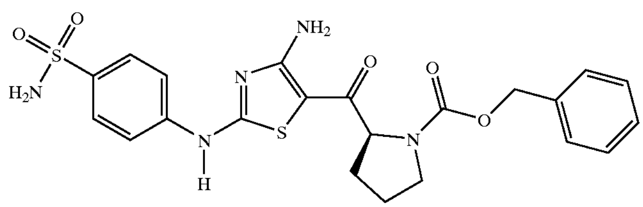 | 38000[a] | 14.3 μM | |
| C(66) | 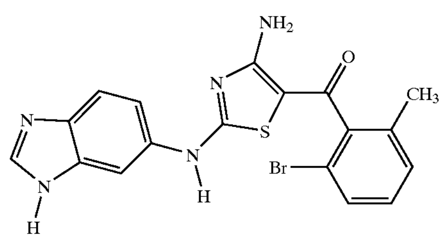 | 53[a] | 574 | |
| C(67) | 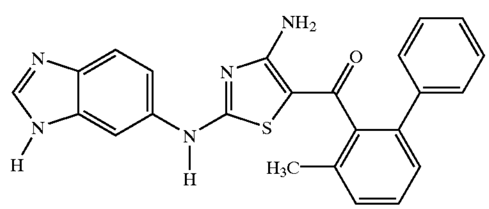 | 3170[a] | 13.2 μM | |
| C(68) | 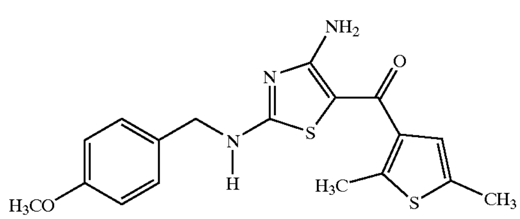 | >30 μM[a] | | |

TABLE I-continued

K$_i$ with CDKs

| Example | Structure | K$_i$ CDK 4/D (nM) | K$_i$ CDK 2/A (nM) | K$_i$ CDK 1/B (μM) |
|---|---|---|---|---|
| C(69) | 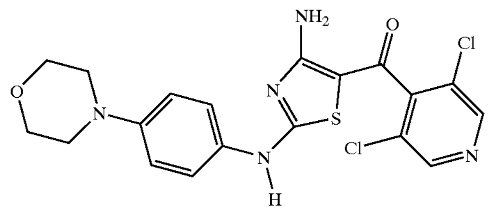 | 20[a] | 638 | |
| C(70) | 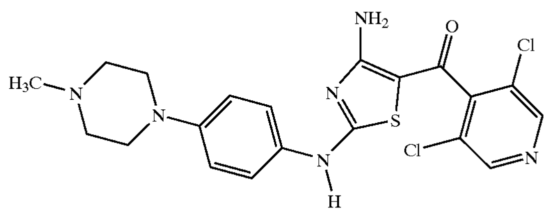 | 2.8[a] | 1120 | 1.37 |
| C(71) | 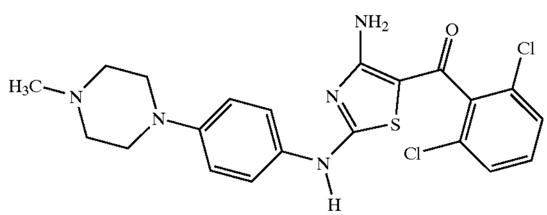 | 2[a] | 482 | 0.827 |
| C(72) | 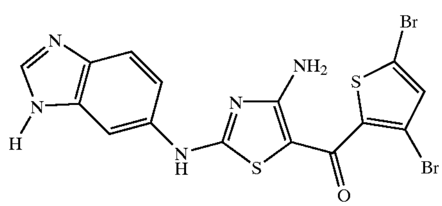 | 13.5[a] | 169 | |
| C(73) | 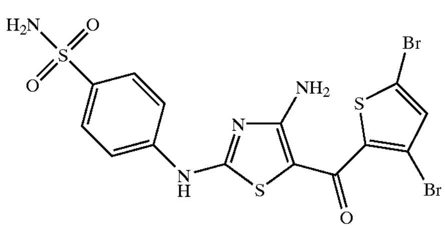 | 6.3[a] | 6.8 | 0.02 |
| C(74) | 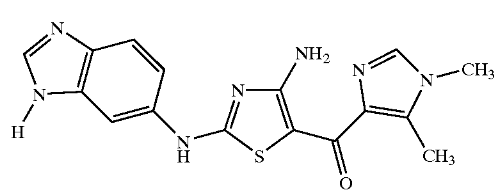 | 4800[a] | 10.6 μM | |

TABLE I-continued

K_i with CDKs

| Example | Structure | K_i CDK 4/D (nM) | K_i CDK 2/A (nM) | K_i CDK 1/B (μM) |
|---------|-----------|------------------|------------------|-------------------|
| C(75) | 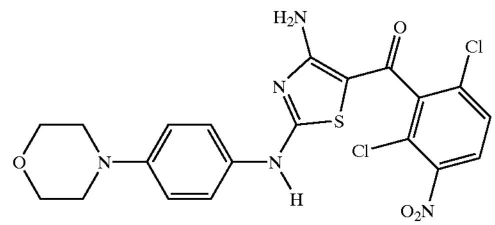 | 23[a] | 1080 | |
| C(76) | 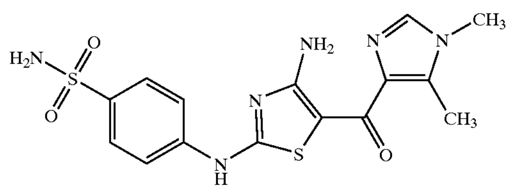 | 2000[a] | 507 | |
| C(77) | 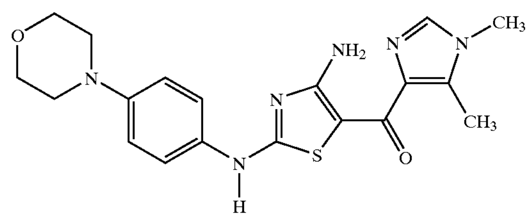 | 3000[a] | None @ 5 μM | |
| C(78) | 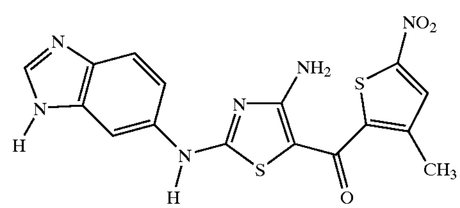 | 32[a] | 83 | |
| C(79) | 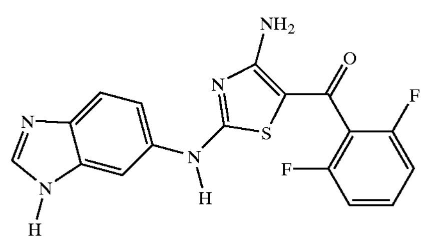 | 54[a] | 162 | |
| C(80) | 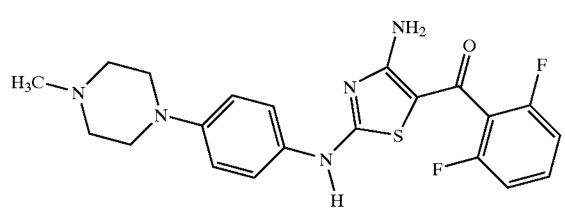 | 3.3[a] | 220 | 0.325 |

TABLE I-continued

K_i with CDKs

| Example | Structure | $K_i$ CDK 4/D (nM) | $K_i$ CDK 2/A (nM) | $K_i$ CDK 1/B (μM) |
|---|---|---|---|---|
| C(81) | 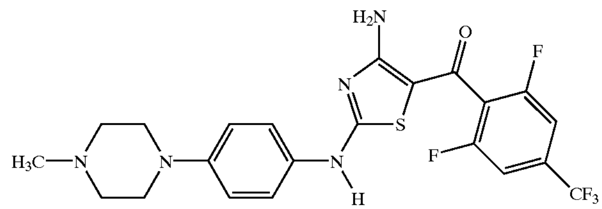 | 12.3[a] | 872 | 1.24 |
| C(82) | 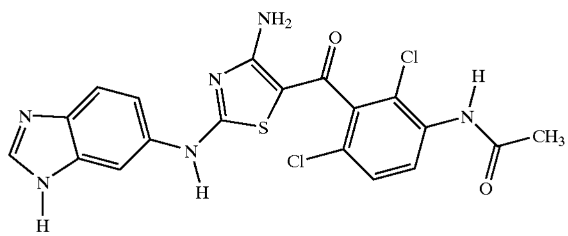 | 44.2[a] | 467 | |
| C(83) | 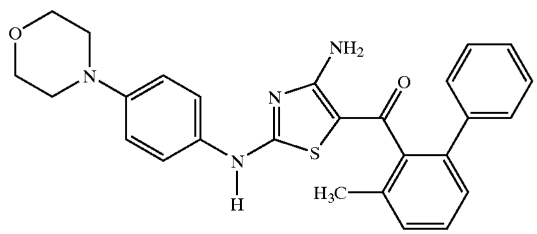 | 1800[a] | 32 μM | |
| C(84) | 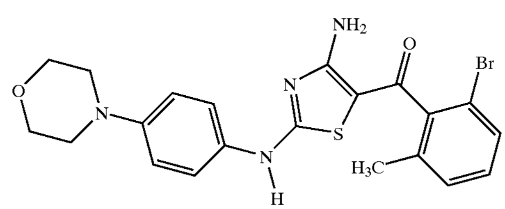 | 53[a] | 1040 | |
| C(85) | 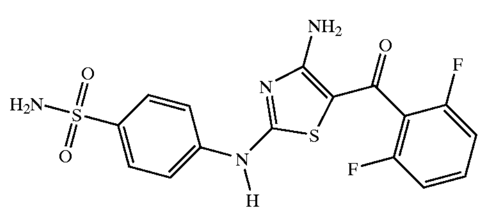 | 13[a] | 5.7 | 0.0022 |
| C(86) | 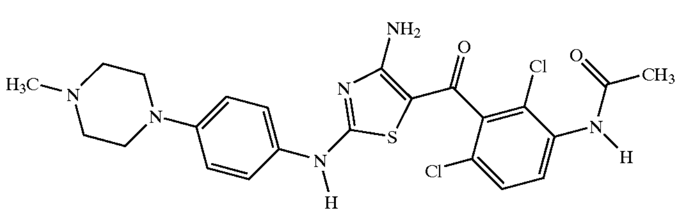 | 15[a] | 1100 | 1.31 |

TABLE I-continued

K$_i$ with CDKs

| Example | Structure | K$_i$ CDK 4/D (nM) | K$_i$ CDK 2/A (nM) | K$_i$ CDK 1/B (μM) |
|---|---|---|---|---|
| C(87) | 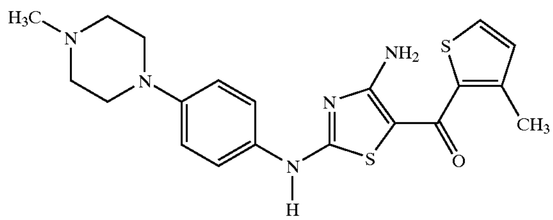 | 9[a] | 607 | 0.826 |
| C(88) | 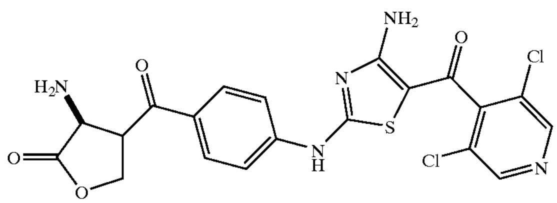 | 65[a] | 305 | |
| C(89) | 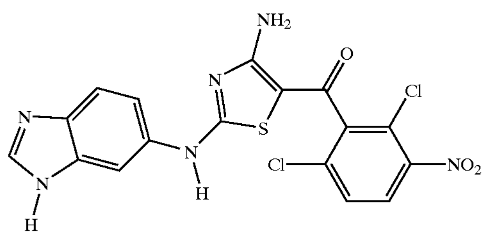 | 55[a] | 326 | |
| G | 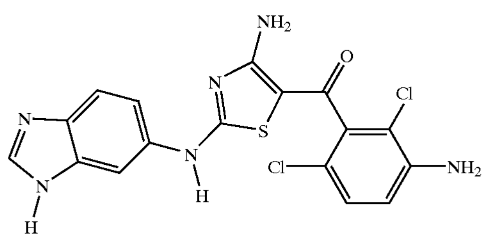 | 23[a] | 178 | |
| C(90) | 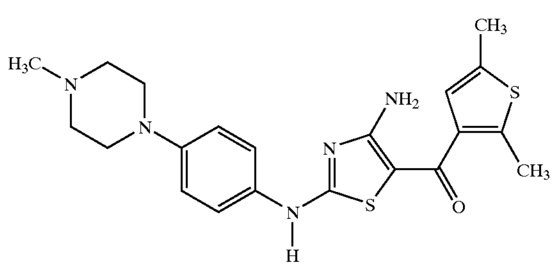 | 27[a] | 771 | |
| C(91) | 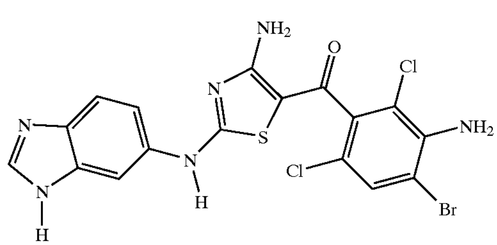 | 6.8[a] | 81 | |

TABLE I-continued

K$_i$ with CDKs

| Example | Structure | K$_i$ CDK 4/D (nM) | K$_i$ CDK 2/A (nM) | K$_i$ CDK 1/B (μM) |
|---|---|---|---|---|
| C(92) | 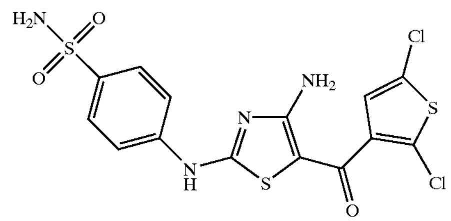 | 63[a] | 9.4 | |
| C(93) | 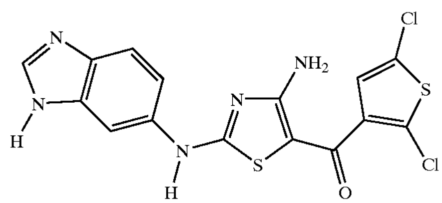 | 285[a] | 1040 | |
| C(94) | 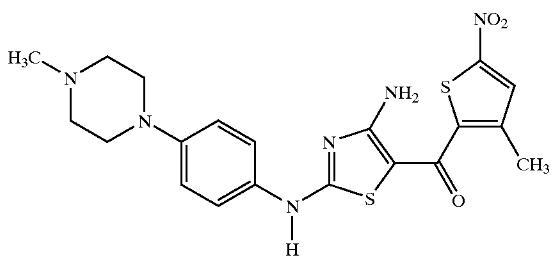 | 41[a] | 1040 | 1.41 |
| C(95) | 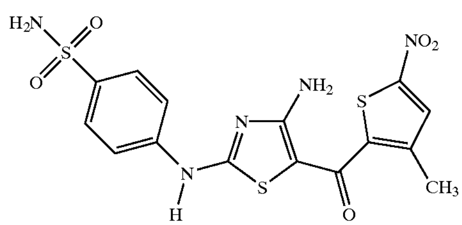 | 25[a] | <50 | 0.075 |
| D(5) | 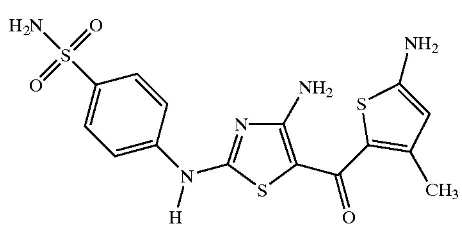 | 159[a] | 233 | |
| C(96) | 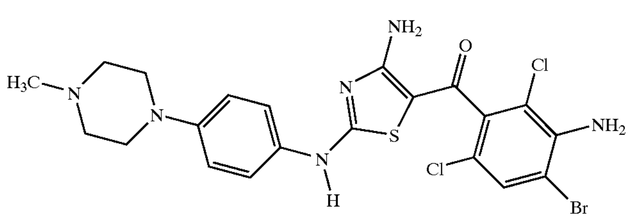 | 1.5[a] | 324 | 0.231 |

TABLE I-continued

K$_i$ with CDKs

| Example | Structure | K$_i$ CDK 4/D (nM) | K$_i$ CDK 2/A (nM) | K$_i$ CDK 1/B (μM) |
|---|---|---|---|---|
| H(1) | [structure: piperazine-phenyl-NH-aminothiazole-C(O)-3-methylthiophene · 3 HCl] | 8.2[a] | 370 | 0.681 |
| H(2) | [structure: piperazine-phenyl-NH-aminothiazole-C(O)-(2,6-dichloro-3-amino)phenyl · 3HCl] | 3.6[a] | 474 | 0.361 |
| C(97) | [structure: acetyl-piperazine-phenyl-NH-aminothiazole-C(O)-2,6-dichlorophenyl] | 8.5[a] | 392 | |
| C(98) | [structure: acetyl-piperazine-phenyl-NH-aminothiazole-C(O)-3-methylthiophene] | 27[a] | 565 | 0.72 |
| H(3) | [structure: piperazine-phenyl-NH-aminothiazole-C(O)-2,6-dichlorophenyl] | 2.4[a] | 405 | 0.472 |
| J(1) | [structure: piperazine-phenyl-NH-aminothiazole-C(O)-2,4,6-trichlorophenyl] | 2.3[a] | 452 | 0.732 |

TABLE I-continued

K<sub>i</sub> with CDKs

| Example | Structure | K<sub>i</sub> CDK 4/D (nM) | K<sub>i</sub> CDK 2/A (nM) | K<sub>i</sub> CDK 1/B (μM) |
|---|---|---|---|---|
| C(99) | 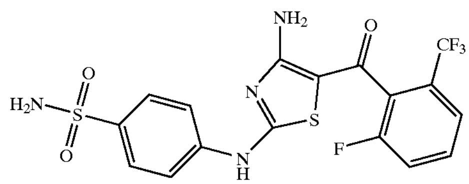 | 16.4[a] | 39.5 | 0.04 |
| C(100) | 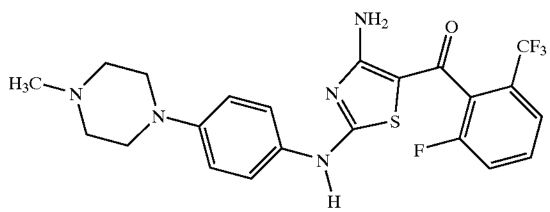 | 6.5[a] | 620 | 0.911 |
| C(101) | 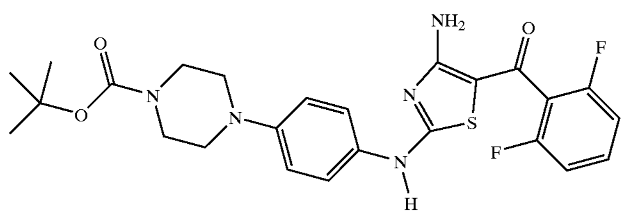 | 103[a] | 300 | 0.32 |
| C(102) | 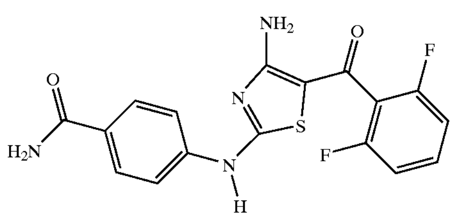 | 21[a] | 49 | 0.017 |
| C(103) | 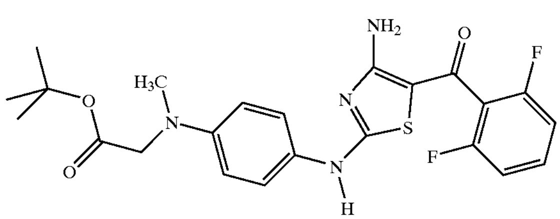 | 110[a] | 595 | |
| C(104) | 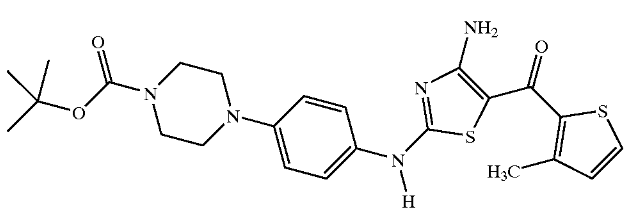 | 190[a] | 730 | |

TABLE I-continued

K_i with CDKs

| Example | Structure | $K_i$ CDK 4/D (nM) | $K_i$ CDK 2/A (nM) | $K_i$ CDK 1/B ($\mu$M) |
|---|---|---|---|---|
| C(105) | 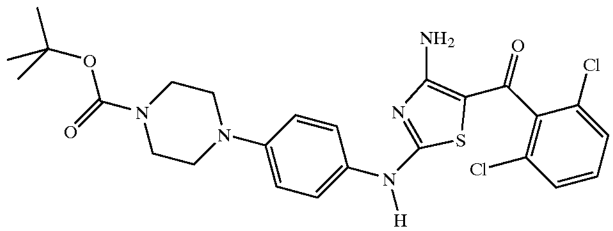 | 60[a] | 1060 | |
| C(106) | 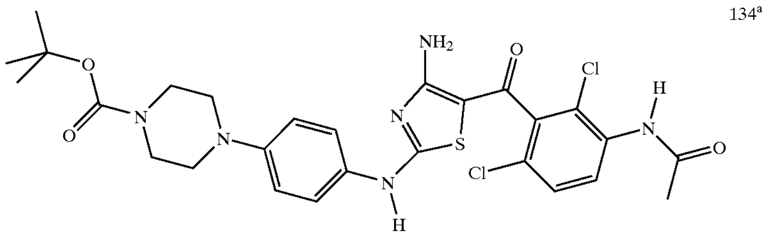 | 134[a] | 1460 | |
| J(2) | 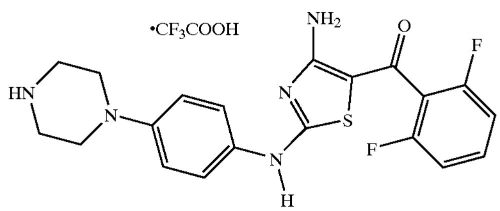 | 6.4[a] | 135 | 0.405 |
| C(107) | 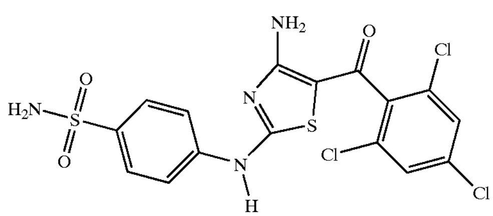 | 13.8[a] | 12.5 | |
| C(108) | 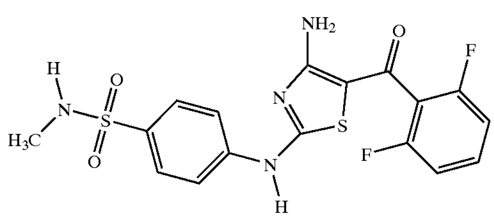 | 23[a] | 6.8 | 0.009 |
| C(109) | 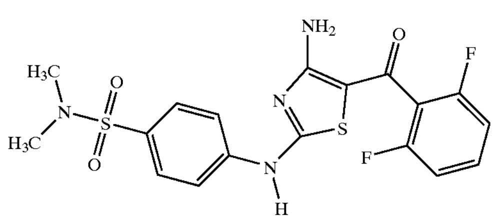 | 83[a] | 28 | 0.035 |

TABLE I-continued

K<sub>i</sub> with CDKs

| Example | Structure | $K_i$ CDK 4/D (nM) | $K_i$ CDK 2/A (nM) | $K_i$ CDK 1/B (μM) |
|---|---|---|---|---|
| C(110) | 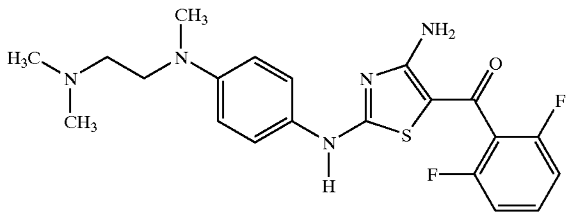 | 14[a] | 260 | 0.104 |
| C(111) | 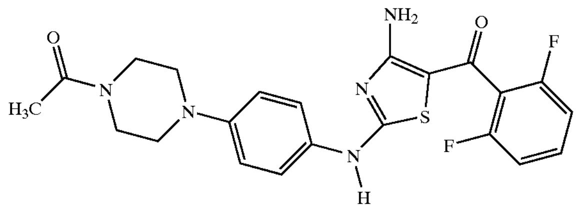 | 21[a] | 216 | |
| C(112) | 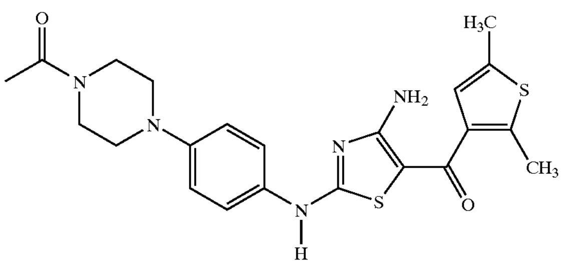 | 23[a] | 408 | |
| C(113) | 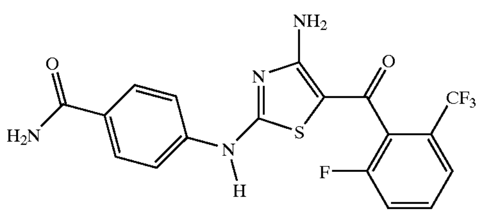 | 17.3[a] | 238 | |
| C(114) | 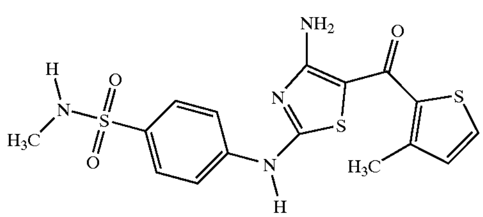 | 21[a] | 8.5 | 0.028 |
| C(115) | 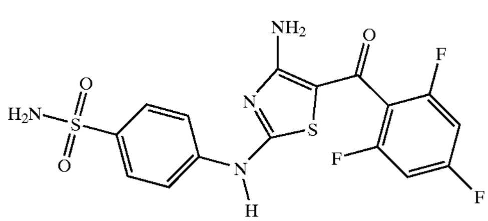 | 57[a] 55[c] | 18 | 0.05 |

TABLE I-continued

K$_i$ with CDKs

| Example | Structure | K$_i$ CDK 4/D (nM) | K$_i$ CDK 2/A (nM) | K$_i$ CDK 1/B (μM) |
|---|---|---|---|---|
| J(3) | 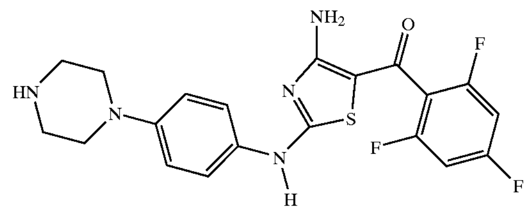 | 15[a] 19[c] | 572 | 2.0 |
| J(4) | 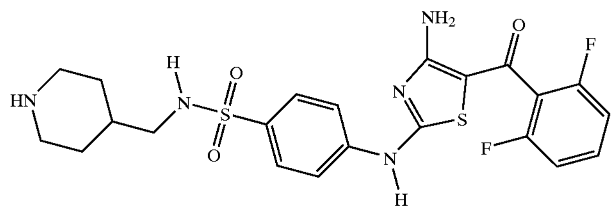 | 10.2[a] | 13.5 | 0.022 |
| C(116) | 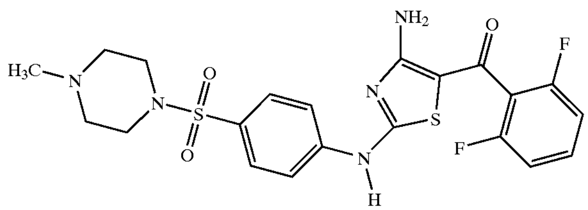 | 121[a] | 120 | 0.077 |
| J(5) | 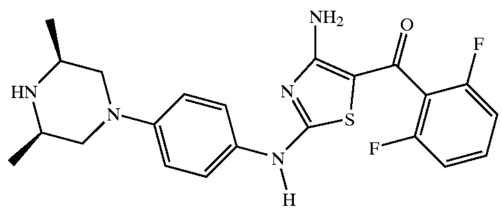 | 6.3[a] | 331 | 0.76 |
| C(117) | 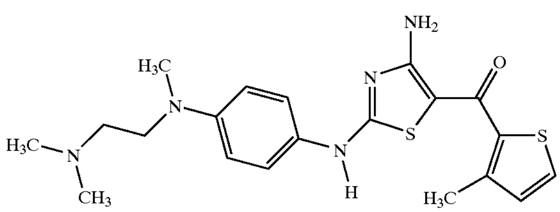 | 10[c] | 423 | 0.417 |
| C(118) | 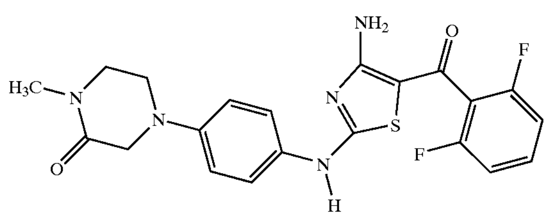 | 10.3[a] | 191 | 0.097 |

TABLE I-continued

K_i with CDKs

| Example | Structure | K_i CDK 4/D (nM) | K_i CDK 2/A (nM) | K_i CDK 1/B (μM) |
|---------|-----------|------------------|------------------|------------------|
| C(119) | 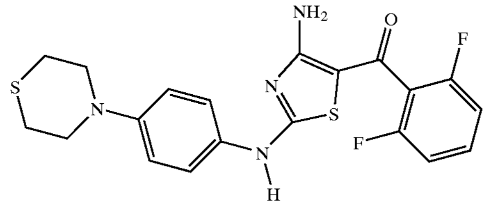 | 24[a] | 86 | 0.247 |
| C(120) | 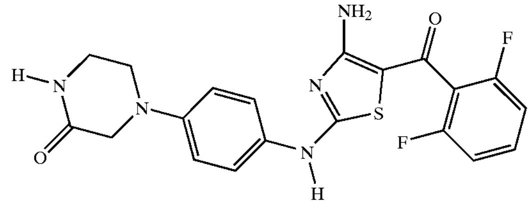 | 10.9[a] | 80 | 0.062 |
| C(121) | 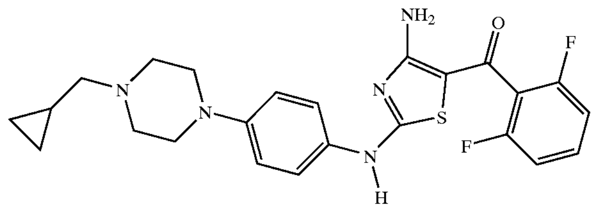 | 10.6[c] | 953 | |
| K | 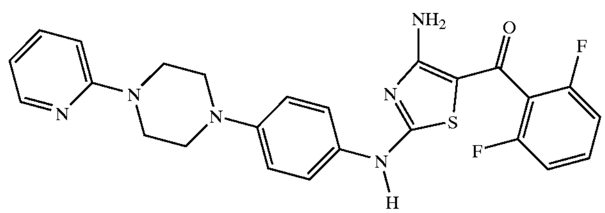 | 43[c] | 364 | |
| C(122) | 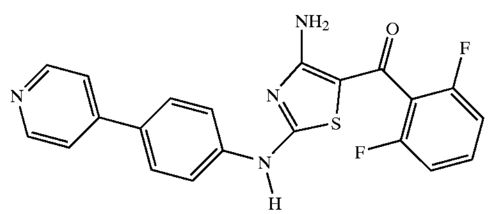 | 35[c] | 165 | |
| J(6) | 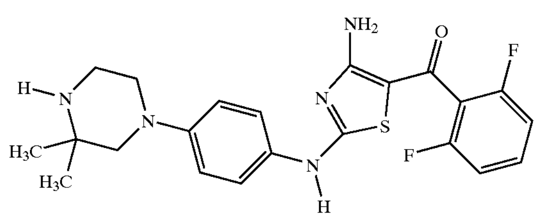 | 8.1[c] | 548 | 0.511 |

TABLE I-continued

K_i with CDKs

| Example | Structure | K_i CDK 4/D (nM) | K_i CDK 2/A (nM) | K_i CDK 1/B (μM) |
|---|---|---|---|---|
| C(123) | 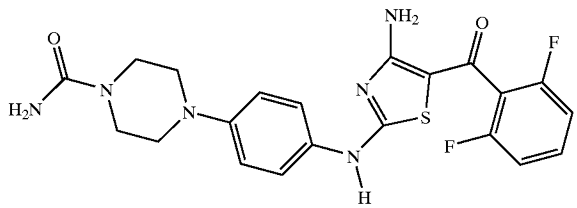 | 15.4[a] | 164 | |
| C(124) | 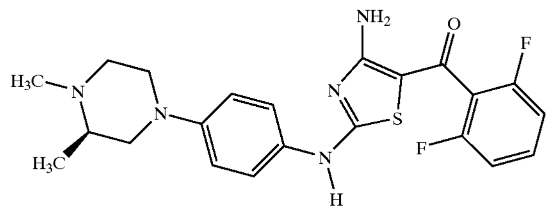 | 17[c] | 611 | 0.68 |
| C(125) | 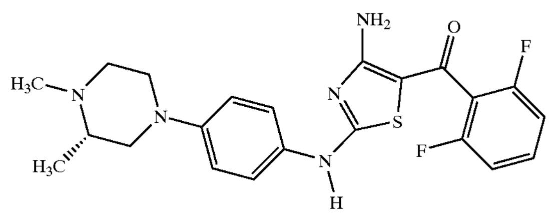 | 5.4[c] | 602 | 0.65 |
| L | 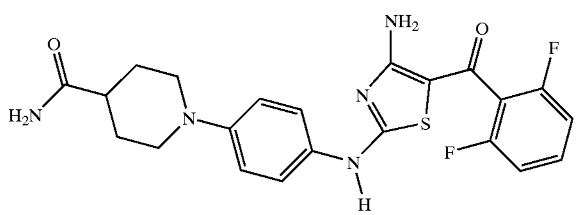 | 22[c] | | 0.193 |
| M | 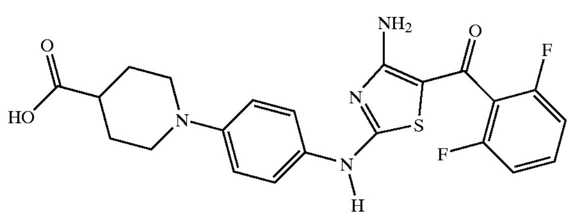 | 46[c] | 290 | |
| C(126) | 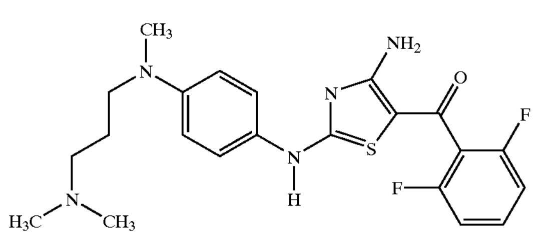 | 24[c] | 390 | |

TABLE I-continued

$K_i$ with CDKs

| Example | Structure | $K_i$ CDK 4/D (nM) | $K_i$ CDK 2/A (nM) | $K_i$ CDK 1/B (μM) |
|---|---|---|---|---|
| C(127) | 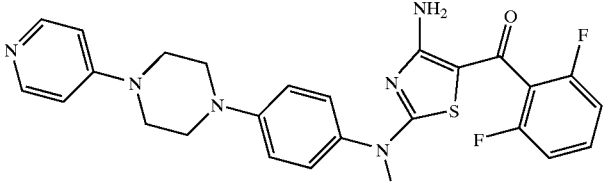 | 26[c] | 215 | |
| C(128) | 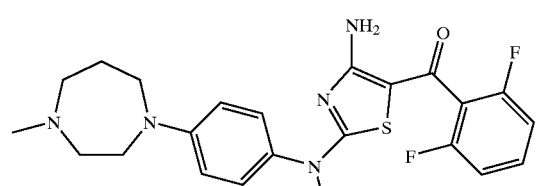 | 30[c] | 440 | |
| C(129) | 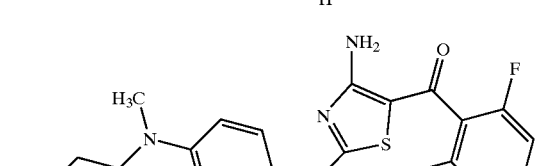 | 64[c] | 270 | |

[a] = D-type cyclin is D3;
[b] = D-type cyclin is D1;
[c] = D-type cyclin is truncated D3

Inhibition of Cell Growth: Assessment of Cytotoxicity

Inhibition of cell growth was measured using the tetrazolium salt assay, which is based on the ability of viable cells to reduce 3-(4,5-dimethylthiazol-2-yl)-2,5-[2H]-diphenyltetrazolium bromide (MTT) to formazan (Mossman, *Journal of Immunological Methods*, vol. 65 (1983), pp. 55–58). The water-insoluble purple formazan product was then detected spectrophotometrically. Various cell lines (HCT-116, Saos-2, U2-OS, SW480, COLO-205, RXF-393, M14, MDA-MB-468, and MCF7) were grown in 96-well plates. Cells were plated in the appropriate medium at a volume of 135 μl/well in either McCoy's 5A Medium (for Saos-2, U2-OS, SW480, and HCT-116 cells), RPMI (for COLO-205, RXF-393, M14 cells), or Minimum Essential Medium Eagle (for MDA-MB-468 and MCF7 cells). Plates were incubated for four hours before addition of inhibitor compounds. Different concentrations of inhibitor compounds were added in 0.5% (v/v) dimethylsulfoxide (15 μL/well), and cells were incubated at 37° C. (5% $CO_2$) for four to six days (depending on cell type). At the end of the incubation, MTT was added to a final concentration of 0.2 mg/mL, and cells were incubated for 4 hours more at 37° C. After centrifugation of the plates and removal of medium, the absorbance of the formazan (solubilized in dimethylsulfoxide) was measured at 540 nm. The concentration of inhibitor compound causing 50% inhibition of growth was determined from the linear portion of a semi-log plot of inhibitor concentration versus percentage inhibition. All results were compared to control cells treated only with 0.5% (v/v) dimethylsulfoxide.

TABLE II

$IC_{50}$ with Various Cancer Cell Lines in MTT Assay

Table II: $IC_{50}$, $IC_{90}$ (μM)

| Example Compound | HCT116 | U2-OS | Saos-2 | COLO-205 | M14 melanoma | RXF-393 | MCF-7 | MDA-MB-468 | SW-480 |
|---|---|---|---|---|---|---|---|---|---|
| A(1) | 2.5, 10 | | | | | | | | 4, 9 |
| C(4) | 0.7, 30 | | | | | | | | 0.4, 3 |
| A(3) | 41% @ 30 | | | | | | | | 15% @ 30 |
| C(5) | 6, 25 | | | | | | | | 3, 9 |

TABLE II-continued

IC$_{50}$ with Various Cancer Cell Lines in MTT Assay

Table II: IC$_{50}$, IC$_{90}$ ($\mu$M)

| Example Compound | HCT116 | U2-OS | Saos-2 | COLO-205 | M14 melanoma | RXF-393 | MCF-7 | MDA-MB-468 | SW-480 |
|---|---|---|---|---|---|---|---|---|---|
| A(4) | 29% @ 30 | | | | | | | | 0 @ 10, 66% @ 30 |
| I(19) | 16% @ 30 | | | | | | | | 22, (58% @ 30) |
| A(5) | 26, (85% @ 30) | | | | | | | | 1.7, 3 |
| E(1) | 17% @ 10 & 30 | | | | | | | | 23% @ 30 |
| A(6) | 20, 30 | | | | | | | | 5, 15 |
| A(9) | 20, 30 | | | | | | | | 4, 10 |
| A(10) | 0.95, 1.8 | 0.9, 1.6 | 1.3, 4.6 | | | | 0.65, 5.5 | 0.72, 1.7 | 0.7, 7.5 |
| C(8) | 18, >25 (88%) | 10, >25 (84%) | 6.2, 18.0 | | | | 15, >25 (82%) | 6.8, 15 | 8.3, 20.0 |
| C(12) | 2.0, 5.0 | 1.9, 6.0 | 2.1, 4.8 | | | | | | |
| C(24) | 0.7, 1.5 | 1.9, 3.0 | 1.4, 2.8 | | | | | | |
| C(37) | 10.0, 25.0 | 16.0, >25 (80%) | 14.0, >25 (70%) | | | | | | |
| C(19) | 9.0, 23.0 | 15.0, >25 (77%) | 7.0, 18.0 | | | | | | |
| F | 1.0, 2.6 | 1.0, 20.0 | 1.0, 1.6 | | | | | | |
| C(20) | 6.1, 25 | 6.5, >25 (74%) | 4.9, 13.0 | | | | | | |
| C(21) | 9.0, 22.0 | 22.0, >25 (57%) | 13.0, 23.0 | | | | | | |
| C(35) | 9.0, 19.0 | 12.0, 22.0 | 8.0, 20.0 | | | | | | |
| C(38) | 4.3, 19.0 | 11.0, >25 (87%) | 3.0, >25 (80%) | | | | | | |
| C(45) | 2.0, 8.0 | 5.5, 12.0 | 2.0, 10.0 | | | | | | |
| C(47) | 4.2, 7.8 | 10.0, 20.0 | 2.5, 5.1 | | | | | | |
| C(48) | 0.34, 0.70 | 1.0, 1.5 | 0.42, 0.75 | 0.29, 0.60 | 0.6, 1.8 | 0.8, 1.6 | 2.6, >25 (82%) | 0.26, 0.60 | |
| C(49) | 5.6, 12.0 | 14.0, 22.0 | 4.0, 20.0 | | | | | | |
| C(50) | 0.61, 1.6 | 2.0, 3.0 | 1.3, 2.8 | | | | 3.0, >25 (88%) | 0.48, 1.5 | |
| C(52) | 8.5, 17.0 | 15.0, 23.0 | 9.0, 22.0 | | | | | | |
| C(55) | 4.3, 17.0 | 18, >25 (74%) | 17, >25 (69%) | | | | | | |
| C(63) | 12.0, 22.0 | 16.0, >25 (84%) | 9.0, 20.0 | | | | | | |
| C(69) | 5.0, 15.0 | 14.0, 26.0 | 12.0, 26.0 | | | | | | |
| C(70) | 2.2, 5.9 | 5.0, 11.0 | 5.8, 12.0 | | | | | | |
| C(71) | 1.7, 4.4 | 3.3, 6.0 | 4.0, 7.0 | 1.2, >5.0 | 2.0, 1.8 | >5.0 | | | |
| C(73) | 1.4, 3.4 | 4.1, 9.5 | 1.3, 5.0 | | | | | | |
| C(80) | 0.4, 1.1 | 1.0, 2.3 | 0.9, 1.5 | 0.28, 1.0 | 0.92, 2.5 | 0.84, 1.3 | 0.4, 1.7 | 0.49, 1.3 | |
| C(81) | 10.0, 20.0 | 7.9, 12.0 | 13.0, 22.0 | >5.0 | 3.8, >5 | >5.0 | 3.9, 16.0 | 4.7, 9.3 | |
| C(82) | >25 (1%) | >25 (1%) | >25 (15%) | | | | | | |
| C(85) | 0.25, 0.56 | 1.7, 2.8 | 0.28, 0.67 | 0.24, 0.58 | 0.71, 2.2 | 1.2, 3.0 | 3.9, 13.0 | 0.22, 0.59 | |
| C(86) | 6.5, 17.0 | 14, 22 | 12, 22 | | | | | | |
| C(87) | 0.95, 2.9 | 1.8, 4.0 | 2.0, 4.0 | 0.39, 1.7 | 1.5, 4.2 | 1.5, 2.3 | | | |
| C(88) | 19, >25 (70%) | >25 (26%) | 22, >25 (56%) | | | | | | |
| C(91) | 4.7, 18.0 | 19.0, >25 | 5.9, 23.0 | | | | | | |
| C(94) | 1.3, 3.1 | 3.4, 6.0 | 2.2, 5.0 | | | | | | |
| C(95) | 1.5, 3.0 | 3.9, 5.8 | 1.8, 4.5 | | | | | | |
| D(5) | 1.9, 5.0 | >25 | 17.0, 25.0 | | | | | | |
| C(96) | 18.0, >25 (82%) | 8.0, 12.0 | 4.2, 10.0 | | | | | | |
| H(1) | 0.58, 1.4 | 0.85, 1.5 | 0.73, 1.4 | 0.2, 0.6 | 2.4, 9.0 | 0.46, 0.88 | | | |
| H(2) | 15.0, 25.0 | 16.0, 21.0 | 13.0, 22.0 | | | | | | |
| C(97) | 3.9, 11.0 | 10.0, 21.0 | 9.0, 20.0 | | | | | | |
| C(98) | 1.3, 2.9 | 2.4, 5.2 | 2.7, 5.3 | | | | | | |
| H(3) | 0.88, 2.4 | 3.5, 5.8 | 1.8, 3.0 | | | | | | |
| J(1) | 1.3, 3.0 | 3.5, 5.9 | 1.0, 5.9 | | | | | | |
| C(99) | 0.88, 2.7 | 4.0, 8.0 | 1.1, 2.9 | | | | | | |
| C(100) | 2.3, 6.1 | 12.0, 22.0 | 4.5, 10.0 | | | | | | |
| C(102) | 1.1, 2.4 | 3.1, 5.4 | 0.88, 2.2 | | | | | | |
| J(2) | 0.3, 0.73 | 1.7, 2.8 | 0.58, 1.3 | 0.9, 2.7 | 0.65, 2.0 | 0.55, 1.1 | 0.48, 1.7 | 0.34, 0.7 | |

TABLE II-continued

IC$_{50}$ with Various Cancer Cell Lines in MTT Assay

Table II: IC$_{50}$, IC$_{90}$ ($\mu$M)

| Example Compound | HCT116 | U2-OS | Saos-2 | COLO-205 | M14 melanoma | RXF-393 | MCF-7 | MDA-MB-468 | SW-480 |
|---|---|---|---|---|---|---|---|---|---|
| C(107) | 2.5, 7.0 | 7.9, 12.0 | 5.7, 12.0 | | | | | | |
| C(108) | 0.4, 1.4 | 1.4, 4.8 | 0.31, 3.2 | | | | | | |
| C(109) | 1.6, 3.0 | 4.7, 19.0 | 1.5, 14.0 | | | | | | |
| C(110) | 0.64, 1.7 | 0.7, 1.6 | 0.89, 1.8 | | | | 0.4, 1.7 | 0.44, 0.75 | |
| C(111) | 1.7, 3.8 | 3.0, 5.5 | 3.8, 5.9 | | | | | | |
| C(113) | 3.8, 8.0 | 8.0, 19.0 | 2.8, 9.0 | | | | | | |
| C(114) | 1.1, 2.8 | 3.0, 5.2 | 1.3, 4.8 | | | | | | |
| C(115) | 0.98, 2.1 | 2.7, 5.0 | 0.8, 2.2 | | | | | | |
| J(3) | 0.9, 2.8 | 2.9, 5.2 | 2.2, 4.9 | | | | | | |
| J(5) | 0.7, 1.6 | 1.0, 1.8 | 0.9, 1.5 | | | | | | |
| C(117) | 1.8, 2.9 | 0.9, 1.7 | 0.89, 1.5 | | | | | | |
| C(118) | 0.64, 1.4 | 2.4, 5.0 | 0.94, 1.5 | | | | | | |
| C(119) | 4.0, 7.0 | 7.8, 12.0 | 7.0, 13.0 | | | | | | |
| C(120) | 3.5, 6.0 | 5.7, 11.0 | 2.6, 5.2 | | | | | | |
| C(121) | 2.5, 5.3 | 6.0, 11.0 | 5.1, 12.0 | | | | | | |
| K | 3.5, 6.2 | 3.5, 6.0 | 6.0, 13.0 | | | | | | |
| C(122) | 1.7, 4.8 | 1.5, 4.7 | 3.7, 10.0 | | | | | | |
| J(6) | 0.26, 0.6 | 0.51, 1.3 | 0.47, 0.77 | | | | | | |
| C(123) | 2.7, 7.0 | 7.1, 12.0 | 2.9, 5.7 | | | | | | |
| C(124) | 0.54, 1.6 | 1.3, 2.5 | 0.98, 1.6 | | | | | | |
| C(125) | 0.62, 1.8 | 1.2, 2.3 | 0.9, 1.5 | | | | | | |
| L | >12.5 | | | | | | | | |
| M | >25 | | | | | | | | |
| C(126) | 0.6, 1.4 | | | | | | | | | pRb Immunoblotting

The ability of compounds to inhibit phosphorylation of the retinoblastoma protein (pRb) was assessed by western blot analysis. An anti-Rb antibody was used to measure the conversion of hyper-phosphorylated pRb to hypo-phosphorylated pRb. An anti-phospho-Rb (ser780) antibody was used to specifically measure dephosphorylation at serine 780, a site that has previously been shown to be phosphorylated by CDK4/cyclin D. Inhibition of pRb phosphorylation is indicated by a "+" in Table III below, and failure to inhibit pRb phosphorylation is indicated by a "−" in the table.

Human colon tumor cells (HCT-116 cells; 5×10$^6$) were plated on 100 mM dishes and allowed to grow overnight. Five micromolar of each compound was added for 12 hours. The cells were then collected and centrifuged. The cell pellets were lysed by the addition of 100 $\mu$L lysis buffer (50 mM HEPES (pH 7.0), 250 mM NaCl, 5 mM ethylenediaminetetraacetic acid, 0.1% Nonidet P-40, 1 mM dithiothreitol, 2 mM sodium pyrophosphate, 1 mM sodium orthovanadate, 1 $\mu$g/ml aprotonin, 1 $\mu$g/ml leupeptin, 50 $\mu$g/ml phenylmethylsulfonyl fluoride). Forty micrograms of protein were separated by sodium dodecyl sulfate-polyacrylamide gel electrophoresis (SDS-PAGE) on a 6% gel. The proteins were transferred to nitrocellulose and blocked with 5% blocking buffer in Tris-buffered saline overnight. The anti-Rb antibody (Pharmingen), the anti-phospho-Rb (Ser 780) antibody (MBL), and secondary antibody were incubated for 1 hour at room temperature followed by three wash steps in 0.01% Tween-20 in Tris-buffered saline. The Rb protein was detected using chemiluminescence according to the manufacturer (Amersham).

TABLE III

Inhibition of pRb Phosphorylation

| Example Compound | Inhibits pRb phosphorylation | Inhibits pRb (ser 780) phosphorylation |
|---|---|---|
| C(85) | + | + |
| J(2) | + | + |
| C(80) | + | + |
| C(48) | + | + |
| H(1) | + | + |
| C(50) | + | + |
| C(87) | + | + |
| C(73) | + | + |
| C(81) | + | + |
| C(94) | + | + |
| F | − | − |
| C(71) | + | + |

The examples above illustrate compounds according to Formula I and assays that may readily be performed to determine their activity levels against the various CDK/cyclin complexes. It will be apparent that such assays or other suitable assays known in the art may be used to select an inhibitor having a desired level of activity against a selected target.

While the invention has been illustrated by reference to specific and preferred embodiments, those skilled in the art will recognize that variations and modifications may be made through routine experimentation and practice of the invention. For example, those of ordinary skill in the art will recognize that variations or substitutions to the compounds of Formula I may be made without adversely affecting in a significant manner their efficacy in the pharmaceutical compositions. Thus, the invention is intended not to be limited by the foregoing description, but to be defined by the appended claims and their equivalents.

What is claimed is:

1. A compound of the Formula I:

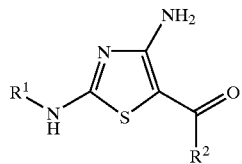

wherein:
- R¹ is a substituted or unsubstituted group selected from: $C_{1-6}$-alkyl; $C_{2-6}$-alkenyl; $C_{2-6}$-alkynyl; $C_{1-6}$alkoxyl; alkyl-hydroxy; carbocyclic or heterocyclic, monocyclic or fused or non-fused polycyclic, cycloalkyl; carbocyclic or heterocyclic, monocyclic or fused or non-fused polycyclic, aryl; carbonyl; ($C_{1-6}$-alkyl)-carbonyl; ($C_{1-6}$-alkyl)-aryl; ($C_{1-6}$-alkyl)-cycloalkyl; ($C_{1-6}$-alkyl)-($C_{1-6}$-alkoxyl); aryl-($C_{1-6}$-alkoxyl); thio; and sulfonyl; wherein when R¹ is substituted, each substituent independently is a halogen; haloalkyl; $C_{1-6}$-alkyl; $C_{2-6}$-alkenyl; $C_{2-6}$-alkynyl; hydroxyl; $C_{1-6}$-alkoxyl; amino; nitro; thio; imino, cyano; amido; phosphonate; phosphine; sulfonyl; sulfonamido; carbonyl; oxygen; carbocyclic or heterocyclic, monocyclic or fused or non-fused polycyclic, cycloalkyl; or carbocyclic or heterocyclic, monocyclic or fused or non-fused polycyclic, aryl; wherein when the substituent of the R¹ group is carbonyl, thio, sulfonyl, or oxygen, the substituent is further substituted with one or more halogen; haloalkyl; $C_{1-6}$-alkyl; $C_{2-6}$-alkenyl; $C_{2-6}$-alkynyl; hydroxyl; $C_{1-6}$-alkoxyl; amino; nitro; thio; imino, cyano; amido; phosphonate; phosphine; sulfonamido; carbocyclic or heterocyclic, monocyclic or fused or non-fused polycyclic, cycloalkyl; or carbocyclic or heterocyclic, monocyclic or fused or non-fused polycyclic, aryl; and
- R² is a carbocyclic or heterocyclic, monocyclic or fused or non-fused polycyclic, ring structure having a substituent at the position adjacent to the point of attachment, which ring structure is optionally further substituted, where each substituent of R² independently is a halogen; haloalyl; $C_{1-6}$-alkyl; $C_{2-6}$-alkenyl; $C_{2-6}$-alkynyl; hydroxyl; $C_{1-6}$-alkoxyl; amino, nitro, thio; imino; cyano; amido; phosphonate; phosphine; sulfonyl; sulfonamido; carbonyl; oxygen; carbocyclic or heterocyclic, monocyclic or fused or non-fused polycyclic, cycloalkyl; carbocyclic or heterocyclic, monocyclic or fused or non-fused polycyclic, aryl;

wherein when the substituent of the R² group is carbonyl, thio, sulfonyl, or oxygen, the substituent is further substituted with one or more halogen; haloalkyl; $C_{1-6}$alkyl; $C_{2-6}$-alkenyl; $C_{2-6}$-alkynyl; hydroxyl; $C_{1-6}$-alkoxyl; amino; nitro; thio; imino, cyano; amido; phosphonate; phosphine; sulfonamido; carbocyclic or heterocyclic, monocyclic or fused or non-fused polycyclic, cycloalkyl; or carbocyclic or heterocyclic, monocyclic or fused or non-fused polycyclic, aryl;

or a pharmaceutically acceptable salt of a compound of the Formula I, or pharmaceutically acceptable salt thereof.

2. A compound, or pharmaceutically acceptable salt thereof according to claim 1, wherein: when R¹ is substituted, each substituent independently is a halogen; haloalkyl; $C_{1-6}$-alkyl, $C_{2-6}$-alkenyl; $C_{2-6}$-alkynyl; hydroxyl; oxygen, $C_{1-6}$-alkoxyl; amino; nitro; thio; imino; cyano, amido; phosphonate; phosphine; carbonyl; sulfonyl; sulfonamido; and each substituent of R² independently is a halogen; haloalkyl; $C_{1-6}$-alkyl; $C_{2-6}$-alkenyl; $C_{2-6}$-alkynyl; hydroxyl; $C_{1-6}$alkoxyl; amino; nitro; thio; imino; cyano, amido; phosphonate; phosphine; sulfonamido; or carbonyl.

3. A compound, or pharmaceutically acceptable salt according to claim 1, wherein R¹ is a substituted phenyl group.

4. A compound, or pharmaceutically acceptable salt according to claim 1, wherein R¹ is phenyl substituted with an alkylamine or pyridine group.

5. A compound, or pharmaceutically acceptable salt according to claim 1, wherein R¹ is selected from the group consisting of:

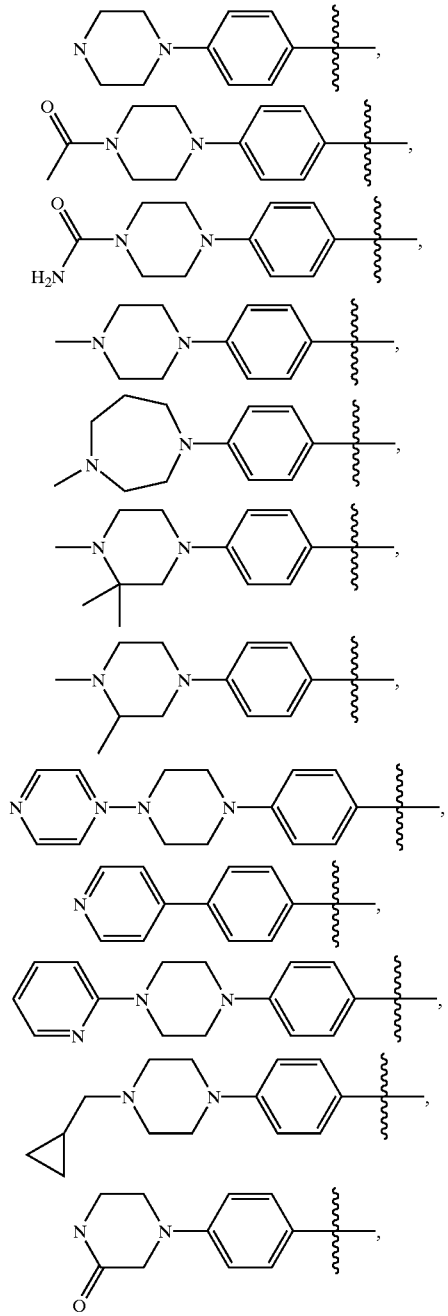

-continued

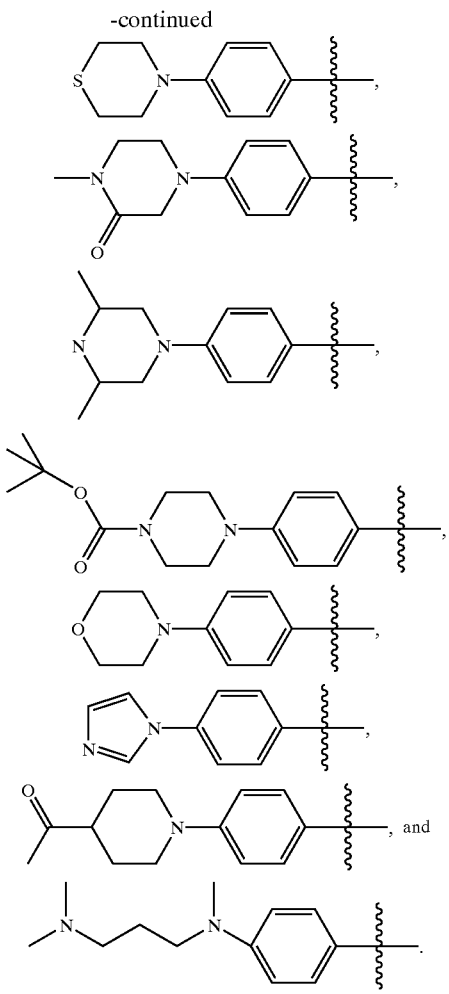

6. A compound, or pharmaceutically acceptable salt according to claim 1, wherein $R^1$ is phenyl substituted by optionally substituted carbonyl or sulfonamido.

7. A compound, or pharmaceutically acceptable salt according to claim 1, wherein $R^1$ is selected from the group consisting of:

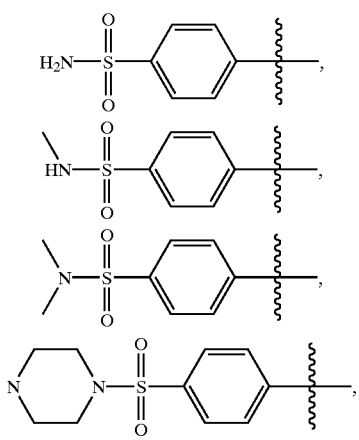

-continued

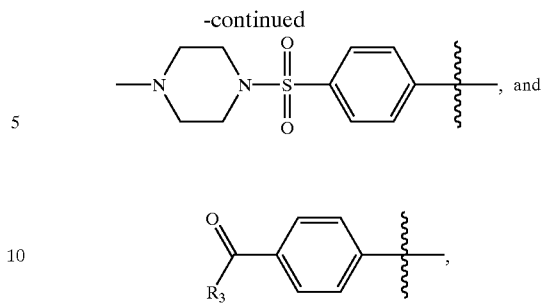

where $R^3$ is selected from the group consisting of $C_1$–$C_6$ alkyl, $C_1$–$C_6$ alkoxy, aryl, aryloxy, and amine.

8. A compound, or pharmaceutically acceptable salt according to claim 1, wherein $R^2$ is ortho-substituted phenyl or thienyl.

9. A compound, or pharmaceutically acceptable salt according to claim 8, wherein $R^2$ is o-halophenyl or o-dihalophenyl.

10. A compound, or pharmaceutically acceptable salt according to claim 9, wherein $R^2$ is o-difluorophenyl.

11. A compound according to claim 1 selected from the group consisting of:

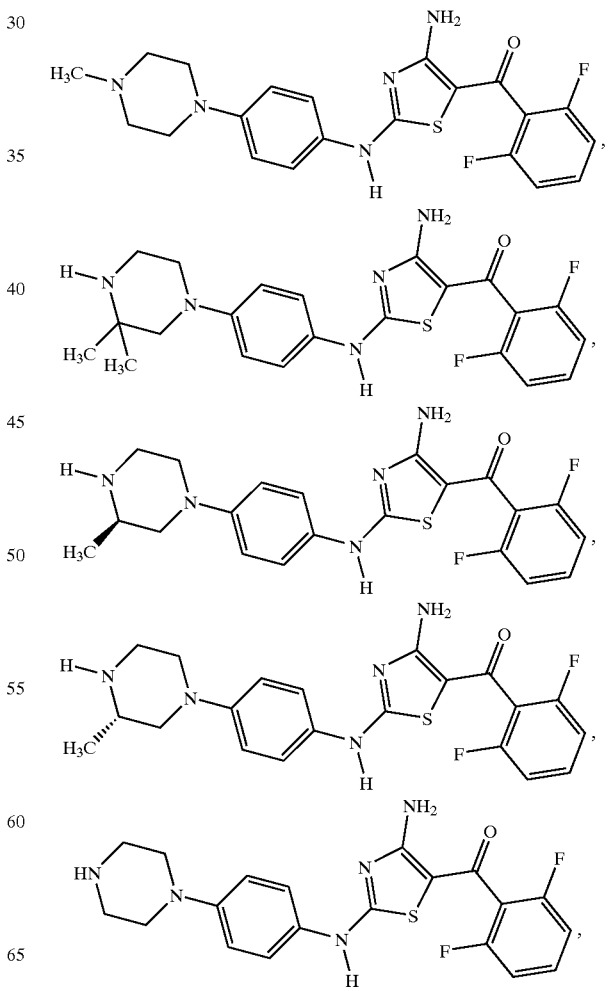

-continued
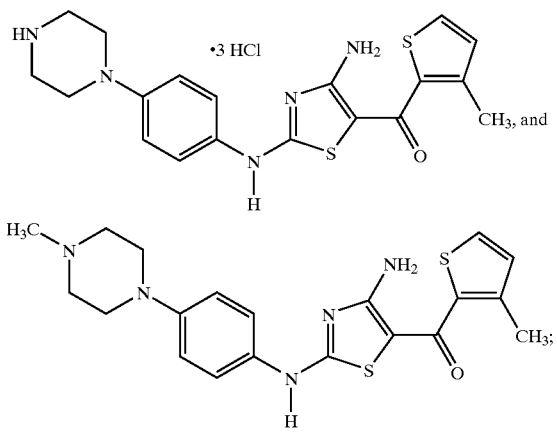
or a pharmaceutically acceptable salt of said compound.
12. A compound according to claim 1 selected from the group consisting of:
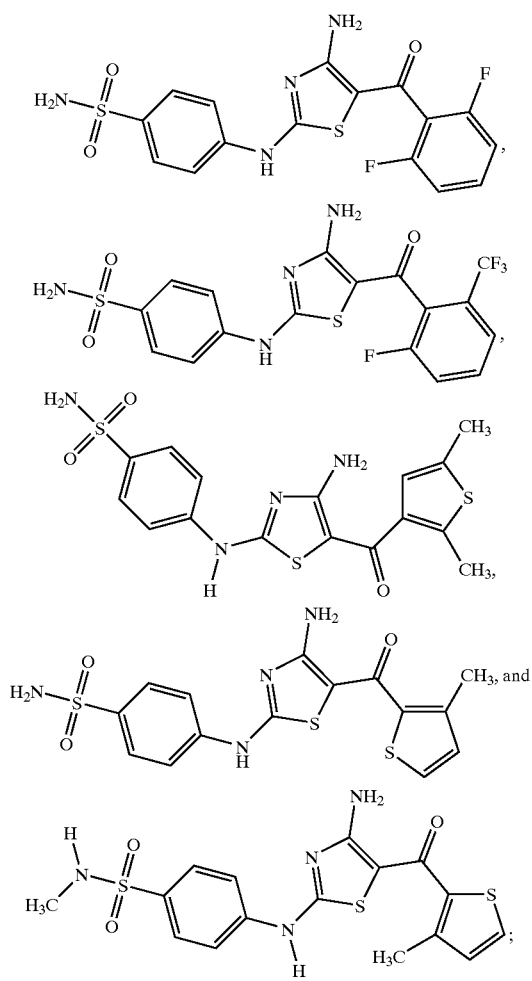
or a pharmaceutically acceptable salt of said compound.
13. A compound selected from the group consisting of:
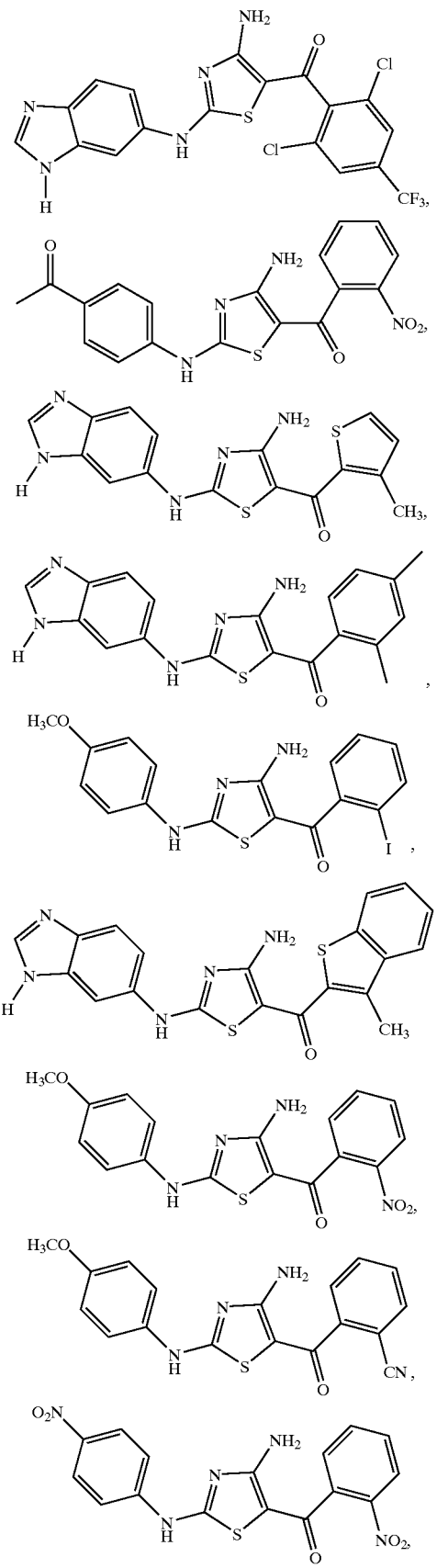

211
-continued
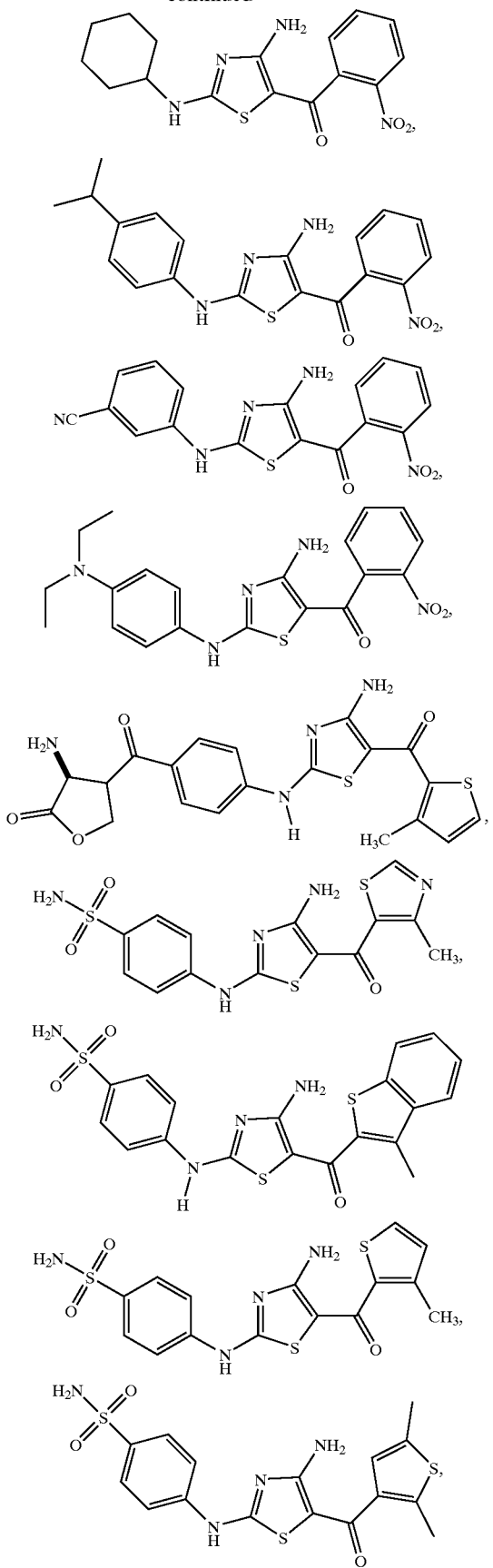
212
-continued
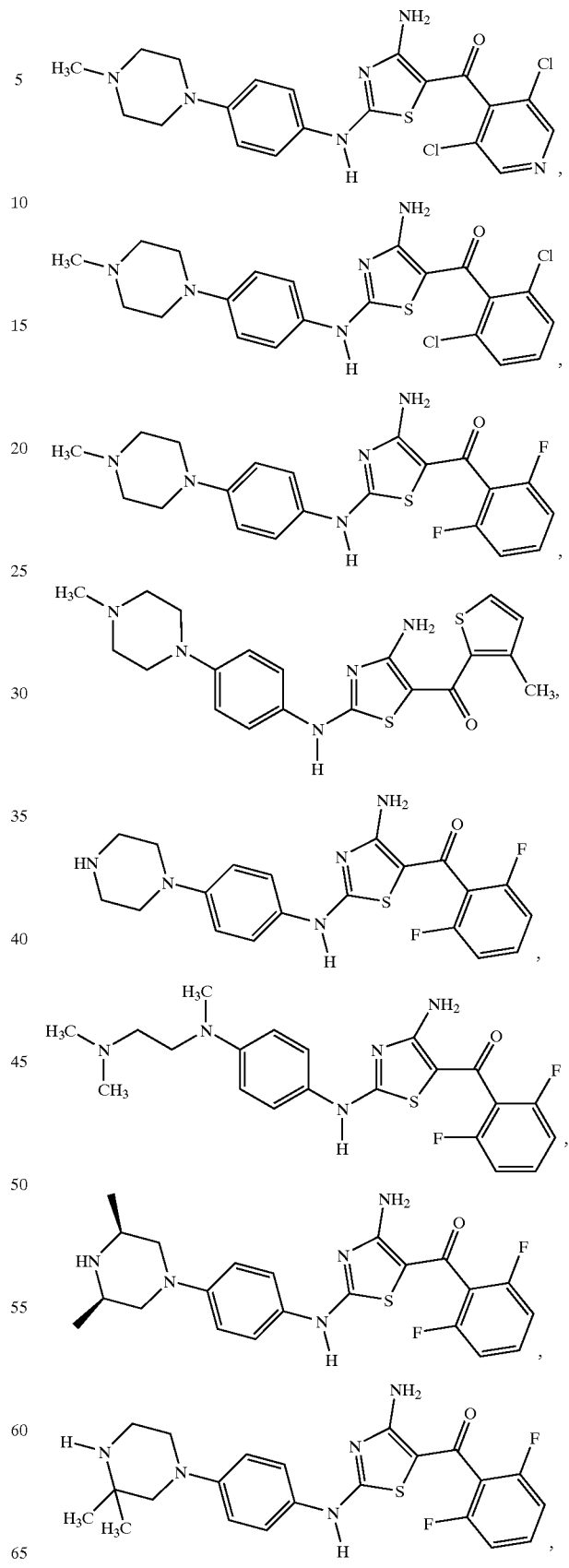

213
-continued

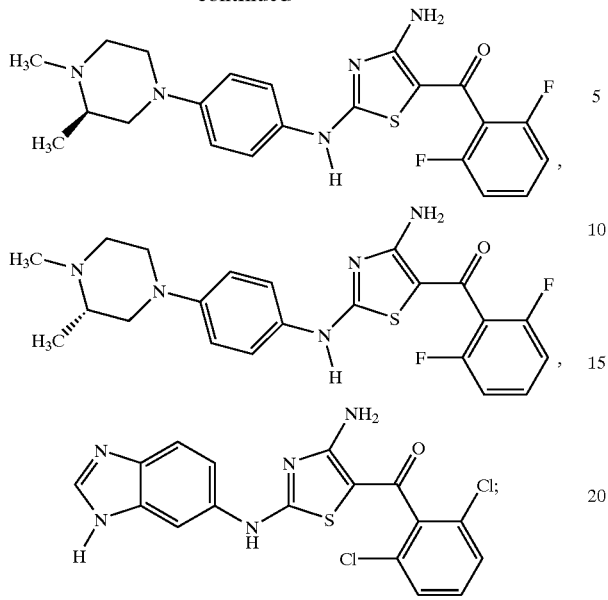

or a pharmaceutically acceptable salt of said compound.

14. A pharmaceutical composition comprising:
  (a) an amount of a cell-cycle control agent effective to inhibit CDK4 or a CDK4/cyclin complex, said cell-cycle control agent being selected from the group consisting of:
    (i) a compound of the Formula I:

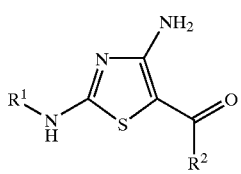

wherein:
  $R^1$ is a substituted or unsubstituted group selected from: $C_{1-6}$-alkyl; $C_{2-6}$-alkenyl; $C_{2-6}$-alkynyl; $C_{1-6}$-alkoxyl; alkyl-hydroxy; carbocyclic or heterocyclic, monocyclic or fused or non-fused polycyclic, cycloalkyl; carbocyclic or heterocyclic, monocyclic or fused or non-fused polycyclic, aryl; carbonyl; ($C_{1-6}$-alkyl)-carbonyl; ($C_{1-6}$-alkyl)-aryl; ($C_{1-6}$-alkyl)-cycloalkyl; ($C_{1-6}$-alkyl)-($C_{1-6}$-alkoxyl); aryl-($C_{1-6}$-alkoxyl); thio; and sulfonyl; wherein when $R^1$ is substituted, each substituent independently is a halogen; haloalkyl; $C_{1-6}$-alkyl; $C_{2-6}$-alkenyl; $C_{2-6}$-alkynyl; hydroxyl; $C_{1-6}$-alkoxyl; amino; nitro; thio; imino, cyano; amido; phosphonate; phosphine; sulfonyl; sulfonamido; carbonyl; oxygen; carbocyclic or heterocyclic, monocyclic or fused or non-fused polycyclic, cycloalkyl; or carbocyclic or heterocyclic, monocyclic or fused or non-fused polycyclic, aryl; wherein when the substituent of the $R^1$ group is carbonyl, thio, sulfonyl, or oxygen, the substituent is further substituted with one or more halogen; haloalkyl; $C_{1-6}$-alkyl; $C_{2-6}$-alkenyl; $C_{2-6}$-alkynyl; hydroxyl; $C_{1-6}$alkoxyl; amino; nitro; thio; imino, cyano; amido; phosphonate; phosphine; sulfonamido; carbocyclic or heterocyclic, monocyclic or fused or non-fused polycyclic, cycloalkyl; or carbocyclic or heterocyclic, monocyclic or fused or non-fused polycyclic, aryl; and

214

$R^2$ is a carbocyclic or heterocyclic, monocyclic or fused or non-fused polycyclic, ring structure having a substituent at the position adjacent to the point of attachment, which ring structure is optionally further substituted, where each substituent of $R^2$ independently is a halogen; haloalkyl; $C_{1-6}$-alkyl; $C_{2-6}$-alkenyl; $C_{2-6}$-alkynyl; hydroxyl; $C_{1-6}$-alkoxyl; amino, nitro, thio; imino; cyano; amido; phosphonate; phosphine; sulfonyl; sulfonamido; carbonyl; oxygen; carbocyclic or heterocyclic, monocyclic or fused or non-fused polycyclic, cycloalkyl; carbocyclic or heterocyclic, monocyclic or fused or non-fused polycyclic, aryl;
  wherein when the substituent of the $R^2$ group is carbonyl, thio, sulfonyl, or oxygen, the substituent is further substituted with one or more halogen; haloalkyl; $C_{1-6}$-alkyl; $C_{2-6}$-alkenyl; $C_{2-6}$-alkynyl; hydroxyl; $C_{1-6}$-alkoxyl; amino; nitro; thio; imino, cyano; amido; phosphonate; phosphine; sulfonamido; carbocyclic or heterocyclic, monocyclic or fused or non-fused polycyclic, cycloalkyl; or carbocyclic or heterocyclic, monocyclic or fused or non-fused polycyclic, aryl;
    (ii) a pharmaceutically acceptable salt of a compound of the Formula I; and
    (iii) a pharmaceutically acceptable salt thereof; and
  (b) a pharmaceutically acceptable carrier.

15. A method of treating a disease or disorder mediated by inhibition of CDK4 or a CDK4/cyclin complex, comprising administering to a subject in need of such treatment a cell-cycle control agent selected from the group consisting of:

compounds of the Formula I:

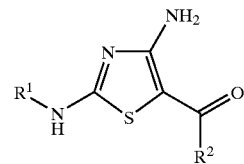

wherein:
  $R^1$ is a substituted or unsubstituted group selected from: $C_{1-6}$-alkyl; $C_{2-6}$-alkenyl; $C_{2-6}$-alkynyl; $C_{1-6}$-alkoxyl; alkyl-hydroxy; carbocyclic or heterocyclic, monocyclic or fused or non-fused polycyclic, cycloalkyl; carbocyclic or heterocyclic, monocyclic or fused or non-fused polycyclic, aryl; carbonyl; ($C_{1-6}$-alkyl)-carbonyl; ($C_{1-6}$-alkyl)aryl; ($C_{1-6}$-alkyl)-cycloalkyl; ($C_{1-6}$-alkyl)-($C_{1-6}$-alkoxyl); aryl-($C_{1-6}$-alkoxyl); thio; and sulfonyl; wherein when $R^1$ is substituted, each substituent independently is a halogen; haloalkyl; $C_{1-6}$-alkyl; $C_{2-6}$-alkenyl; $C_{2-6}$-alkynyl; hydroxyl; $C_{1-6}$-alkoxyl; amino; nitro; thio; imino, cyano; amido; phosphonate; phosphine; sulfonyl; sulfonamido; carbonyl; oxygen; carbocyclic or heterocyclic, monocyclic or fused or non-fused polycycle, cycloalkyl; or carbocyclic or heterocyclic, monocyclic or fused or non-fused polycyclic, aryl; wherein when the substituent of the $R^1$ group is carbonyl, thio, sulfonyl, or oxygen, the substituent is further substituted with one or more halogen; haloalkyl; $C_{1-6}$-alkyl; $C_{2-6}$-alkenyl; $C_{2-6}$-alkynyl, hydroxyl; $C_{1-6}$alkoxyl; amino; nitro; thio; imino, cyano; amido; phosphonate; phosphine; sulfonamido; carbocyclic or heterocyclic, monocyclic or fused or non-fused polycyclic, cycloalkyl; or carbocyclic or heterocyclic, monocyclic or fused or non-fused polycyclic, aryl; and $R^2$ is a carbocyclic or heterocyclic, monocyclic or fused or non-fused polycyclic, ring structure having a substituent at the position adjacent to the point of attachment, which ring structure is optionally further substituted, where each substituent of $R^2$ independently is a halogen; haloalkyl; $C_{1-6}$-alkyl; $C_{2-6}$-alkenyl, $C_{2-6}$-alkynyl; hydroxyl; $C_{1-6}$-alkoxyl; amino, nitro, thio; imino; cyano; amido; phosphonate; phosphine; sulfonyl; sulfonamido; carbonyl; oxygen; carbocyclic or heterocyclic, monocyclic or fused or non-fused polycyclic, cycloalkyl; carbocyclic or heterocyclic, monocyclic or fused or non-fused polycyclic, aryl;

wherein when the substituent of the $R^2$ group is carbonyl, thio, sulfonyl, or oxygen, the substituent is further substituted with one or more halogen; haloalkyl; $C_{1-6}$alkyl; $C_{2-6}$-alkenyl; $C_{2-6}$-alkynyl; hydroxyl; $C_{1-6}$-alkoxyl; amino; nitro; thio; imino, cyano; amido; phosphonate; phosphine; sulfonamido; carbocyclic or heterocyclic, monocyclic or fused or non-fused polycyclic, cycloalkyl; or carbocyclic or heterocyclic, monocyclic or fused or non-fused polycyclic, aryl;

pharmaceutically acceptable salts of compounds of the Formula I; and their pharmaceutically acceptable salts.

16. A compound of the Formula I:

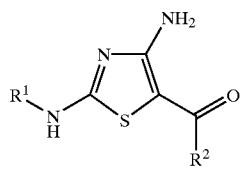

wherein:
$R^1$ is selected from:

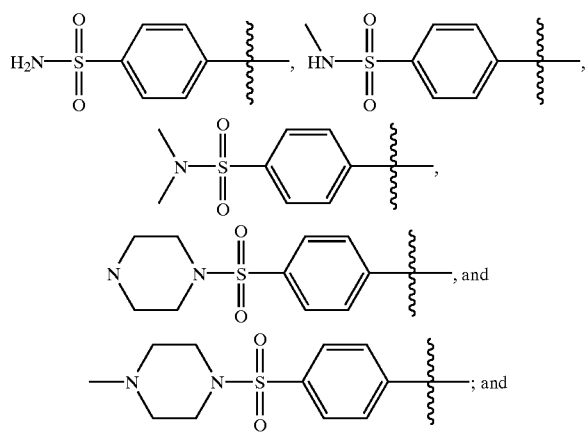

$R^2$ is a substituted or unsubstituted; carbocyclic or heterocyclic, monocyclic or fused or non-fused polycyclic, ring structure; where each optional substituent for $R^2$ is independently a halogen; oxygen; haloalkyl; $C_{1-6}$-alkyl; $C_{2-6}$-alkenyl; $C_{2-6}$-alkynyl; hydroxyl; $C_{1-6}$-alkoxyl; carbocyclic or heterocyclic, monocyclic or fused or non-fused polycyclic; cycloalkyl; carbocyclic or heterocyclic, monocyclic or fused or non-fused polycyclic; aryl; amino; nitro; thio; imino; cyano; amido; phosphonate; phosphine; sulfonyl; sulfonamido; or carbonyl;

wherein when the substituent of the $R^2$ group is carbonyl, thio, sulfonyl, or oxygen, the substituent is further substituted with one or more halogen; haloalkyl; $C_{1-6}$-alkyl; $C_{2-6}$-alkenyl; $C_{2-6}$-alkynyl; hydroxyl; $C_{1-6}$-alkoxyl; amino; nitro; thio; imino, cyano; amido; phosphonate; phosphine; sulfonamido; carbocyclic or heterocyclic, monocyclic or fused or non-fused polycyclic, cycloalkyl; or carbocyclic or heterocyclic, monocyclic or fused or non-fused polycyclic, aryl;

or a pharmaceutically acceptable salt of a compound of the Formula I, or pharmaceutically acceptable salt thereof.

17. A pharmaceutical composition comprising:
(a) an effective amount for inhibiting a CDK or a CDK/cyclin complex of a cell-cycle control agent selected from:
(i) compounds of the Formula I:

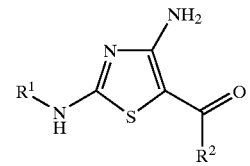

wherein:
$R^1$ is selected from:

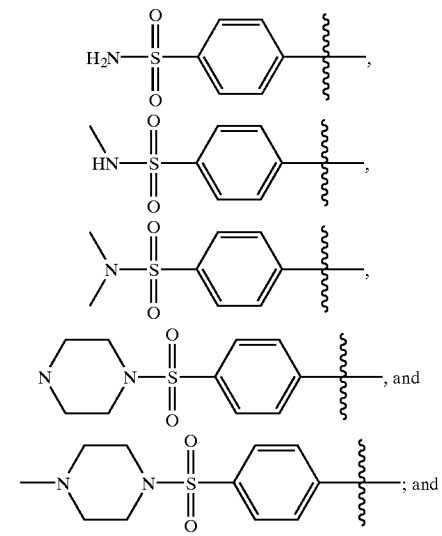

$R^2$ is a substituted or unsubstituted; carbocyclic or heterocyclic, monocyclic or fused or non-fused polycyclic, ring structure; where each optional substituent for $R^2$ is independently a halogen; oxygen; haloalkyl; $C_{1-6}$-alkyl; $C_{2-6}$-alkenyl; $C_{2-6}$-alkynyl; hydroxyl; $C_{1-6}$-alkoxyl; carbocyclic or heterocyclic, monocyclic or fused or non-fused polycyclic; cycloalkyl; carbocyclic or heterocyclic, monocyclic or fused or non-fused polycyclic; aryl; amino; nitro; thio; imino; cyano; amido; phosphonate; phosphine; sulfonyl; sulfonamido; or carbonyl;

wherein when the substituent of the $R^2$ group is carbonyl, thio, sulfonyl, or oxygen, the substituent is further substituted with one or more halogen; haloalkyl; $C_{1-6}$-alkyl; $C_{2-6}$-alkenyl; $C_{2-6}$-alkynyl; hydroxyl; $C_{1-6}$-alkoxyl; amino; nitro; thio; imino, cyano; amido; phosphonate; phosphine; sulfonamido; carbocyclic or heterocyclic, monocyclic or fused or non-fused polycyclic, cycloalkyl; or carbocyclic or heterocyclic, monocyclic or fused or non-fused polycyclic, aryl;

(ii) pharmaceutically acceptable salts of compounds of the Formula I; and (iii) pharmaceutically acceptable salts thereof; and a pharmaceutically acceptable carrier.

18. A compound having the formula or a pharmaceutically acceptable salt thereof.

19. The pharmaceutical composition according to claim 14, wherein when $R^1$ is substituted, each substituent independently is a halogen; haloalkyl; $C_{1-6}$-alkyl; $C_{2-6}$-alkenyl; $C_{2-6}$-alkynyl; hydroxyl; oxygen, $C_{1-6}$-alkoxyl; amino; nitro; thio; imino; cyano, amido; phosphonate; phosphine; carbonyl; sulfonyl; sulfonamido; and each substituent of $R^2$ independently is a halogen; haloalkyl; $C_{1-6}$alkyl; $C_{2-6}$-alkenyl; $C_{2-6}$-alkynyl; hydroxyl; $C_{1-6}$-alkoxyl; amino; nitro; thio; imino; cyano, amido; phosphonate; phosphine; sulfonyl; sulfonamido; or carbonyl.

20. The pharmaceutical composition according to claim 14, wherein the compound of Formula I is selected from the group consisting of:

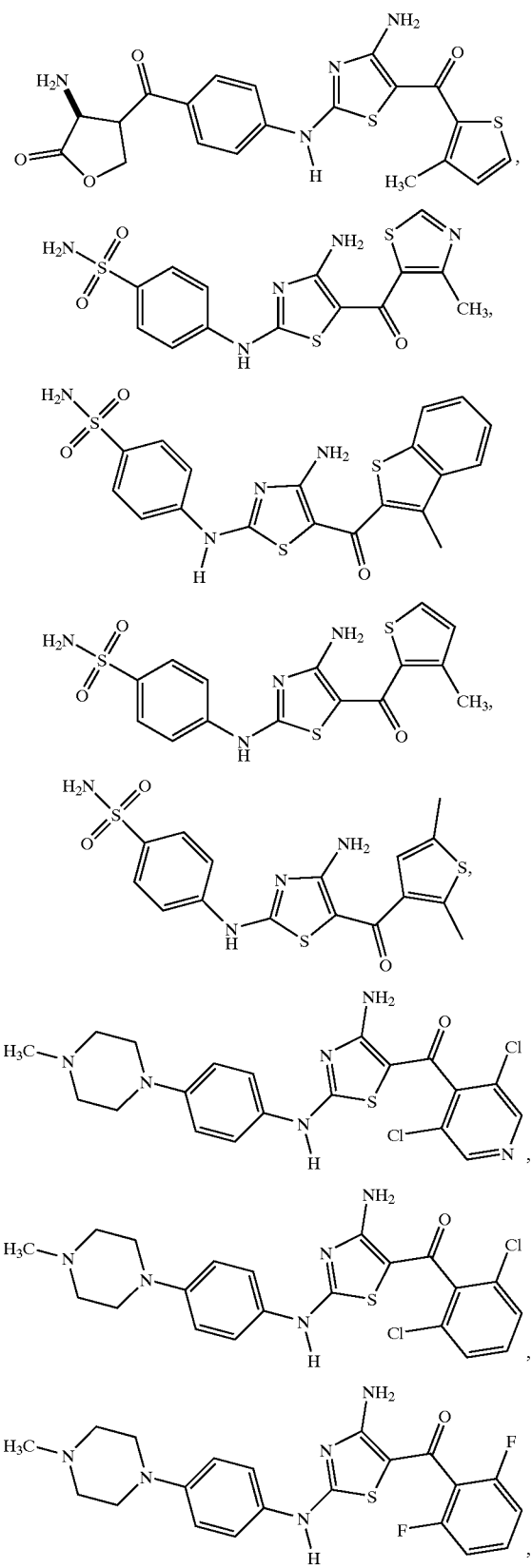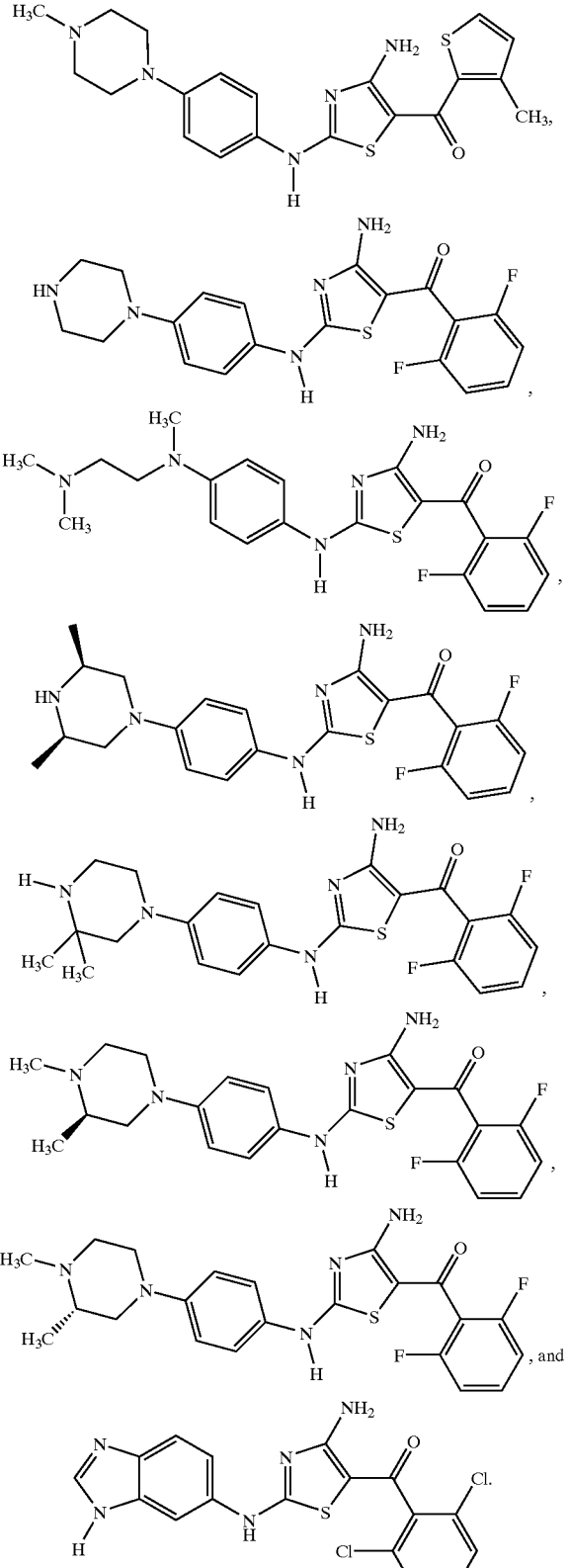
* * * * *